(12) United States Patent
Jin et al.

(10) Patent No.: US 9,156,822 B2
(45) Date of Patent: Oct. 13, 2015

(54) FUNCTIONALLY SELECTIVE LIGANDS OF DOPAMINE $D_2$ RECEPTORS

(75) Inventors: Jian Jin, Chapel Hill, NC (US); Bryan Roth, Durham, NC (US); Stephen Frye, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 150 days.

(21) Appl. No.: 13/807,347

(22) PCT Filed: Jul. 1, 2011

(86) PCT No.: PCT/US2011/042734
§ 371 (c)(1),
(2), (4) Date: Feb. 15, 2013

(87) PCT Pub. No.: WO2012/003418
PCT Pub. Date: Jan. 5, 2012

(65) Prior Publication Data
US 2013/0137679 A1    May 30, 2013

Related U.S. Application Data

(60) Provisional application No. 61/360,951, filed on Jul. 2, 2010.

(51) Int. Cl.
| | |
|---|---|
| *A61K 31/551* | (2006.01) |
| *C07D 401/02* | (2006.01) |
| *C07D 401/14* | (2006.01) |
| *C07D 403/02* | (2006.01) |
| *C07D 403/14* | (2006.01) |
| *C07D 417/02* | (2006.01) |
| *C07D 417/14* | (2006.01) |
| *C07D 471/04* | (2006.01) |
| *C07D 403/12* | (2006.01) |
| *C07D 215/20* | (2006.01) |
| *C07D 217/24* | (2006.01) |
| *C07D 231/56* | (2006.01) |
| *C07D 235/26* | (2006.01) |
| *C07D 277/62* | (2006.01) |
| *C07D 295/088* | (2006.01) |
| *C07D 401/12* | (2006.01) |
| *C07D 405/12* | (2006.01) |
| *C07D 413/12* | (2006.01) |
| *C07D 417/12* | (2006.01) |
| *A61K 31/454* | (2006.01) |
| *A61K 31/4725* | (2006.01) |
| *A61K 31/496* | (2006.01) |
| *A61K 31/4965* | (2006.01) |
| *A61K 31/538* | (2006.01) |
| *A61K 31/55* | (2006.01) |
| *A61K 45/00* | (2006.01) |
| *C07D 241/04* | (2006.01) |
| *C07D 405/14* | (2006.01) |
| *C07D 413/14* | (2006.01) |

(52) U.S. Cl.
CPC ............ *C07D 403/12* (2013.01); *A61K 31/454* (2013.01); *A61K 31/4725* (2013.01); *A61K 31/496* (2013.01); *A61K 31/4965* (2013.01); *A61K 31/538* (2013.01); *A61K 31/55* (2013.01); *A61K 45/00* (2013.01); *C07D 215/20* (2013.01); *C07D 217/24* (2013.01); *C07D 231/56* (2013.01); *C07D 235/26* (2013.01); *C07D 241/04* (2013.01); *C07D 277/62* (2013.01); *C07D 295/088* (2013.01); *C07D 401/12* (2013.01); *C07D 405/12* (2013.01); *C07D 405/14* (2013.01); *C07D 413/12* (2013.01); *C07D 413/14* (2013.01); *C07D 417/12* (2013.01); *C07D 471/04* (2013.01)

(58) Field of Classification Search
CPC .. A61K 31/551; C07D 401/02; C07D 401/14; C07D 403/02; C07D 403/14; C07D 417/02; C07D 417/14; C07D 471/04
USPC .......................................... 514/218; 540/575
See application file for complete search history.

(56) References Cited

U.S. PATENT DOCUMENTS

| | | | |
|---|---|---|---|
| 5,006,528 | A | 4/1991 | Oshiro et al. |
| 6,352,981 | B1 * | 3/2002 | Treiber et al. ................. 514/183 |
| 7,160,888 | B2 | 1/2007 | Johnson et al. |
| 7,491,726 | B2 | 2/2009 | Parthasaradhi et al. |
| 2006/0223820 | A1 | 10/2006 | Brand et al. |
| 2006/0270683 | A1 | 11/2006 | Lohray et al. |

FOREIGN PATENT DOCUMENTS

| | | |
|---|---|---|
| WO | WO 2005/019215 A1 | 3/2005 |
| WO | WO 2006/090272 A1 | 8/2006 |
| WO | WO 2006/090273 A2 | 8/2006 |
| WO | WO 2006/103559 A1 | 10/2006 |
| WO | WO 2008/020306 A2 | 2/2008 |
| WO | WO 2008/084324 A1 | 7/2008 |

OTHER PUBLICATIONS

CAPLUS printout of JP 56046812, JP 55162774, JP 55124766, and JP 55127371, 1980.*
Allen et al., "Discovery of β-Arrestin-Biased Dopamine $D_2$ Ligands for Probing Signal Transduction Pathways Essential for Antipsychotic Efficacy", *PNAS*, vol. 108, No. 45, Nov. 8, 2011, 18488-18493.
International Preliminary Report on Patentability Corresponding to International Application No. PCT/US2011/042734; Date of Mailing: Jan. 17, 2013; 7 Pages.
International Search Report and Written Opinion Corresponding to International Application No. PCT/US2011/042734; Date of Mailing: Mar. 27, 2012; 9 Pages.

* cited by examiner

*Primary Examiner* — Brenda Coleman
(74) *Attorney, Agent, or Firm* — Myers Bigel Sibley & Sajovec, P.A.

(57) ABSTRACT

The present invention relates to novel functionally selective ligands of dopamine $D_2$ receptors, including agonists, antagonists, and inverse agonists. The invention further relates to the use of these compounds for treating central nervous system disorders related to $D_2$ receptors.

11 Claims, 2 Drawing Sheets

FUNCTIONALLY SELECTIVE LIGANDS OF DOPAMINE D$_2$ RECEPTORS

STATEMENT OF PRIORITY

This application is a 35 U.S.C. §371 national phase application of PCT Application No. PCT/US2011/042734, filed Jul. 1, 2011 which claims the benefit of U.S. Provisional Application Ser. No. 61/360,951, filed Jul. 2, 2010, the entire contents of each of which is incorporated by reference herein.

STATEMENT OF GOVERNMENT SUPPORT

This invention was made with government support under Grant Nos. MH082441 awarded by the National Institutes of Health. The government has certain rights in the invention.

FIELD OF THE INVENTION

The present invention relates to novel functionally selective ligands of dopamine D$_2$ receptors, including agonists, antagonists, and inverse agonists. The invention further relates to the use of these compounds in research and for treating central nervous system disorders related to D$_2$ receptors.

BACKGROUND OF THE INVENTION

Classical notions of receptor pharmacology imply that when a ligand interacts with a receptor, only a unitary outcome is possible. According to these models of receptor pharmacology, a full or partial agonist can activate only a single signal transduction pathway while an antagonist can only block the actions of an agonist. The key theoretical construct underlying this model was the concept of intrinsic efficacy (Furchgott, *Advances in Drug Research* (Harper N and Simmonds A eds) Academic Press, New York., pp 21-55 (1966)). According to this conceptualization, a full agonist has maximum intrinsic efficacy and maximally stimulates all cellular responses induced by ligand binding. A partial agonist possesses a lower degree of intrinsic efficacy and partially activates all cellular responses induced by an agonist. Antagonists, according to this schema, are neutral entities which possess no intrinsic activity but are able to block the receptor and preclude activation by full or partial agonists (Furchgott, *Advances in Drug Research* (Harper N and Simmonds A eds) Academic Press, New York., pp 21-55 (1966)). An extension of this model has been that a single G-protein coupled receptor (GPCR) interacts with a single G protein subtype (e.g., Gi, Gs, Gq, Go and so on) and that full and partial agonists activate only a single transduction pathway.

For many decades, however, it has been clear that these simplistic notions of GPCR (also known as 7-transmembrane receptor or 7-TM) function cannot account for the myriad of actions induced by agonist or antagonist binding. This was first convincingly demonstrated for the serotonin (5-hydroxytryptamine; 5-HT) and dopamine (DA) families of receptors where it has been demonstrated that: (1) agonists differentially activate distinct signal transduction pathways (Beaulieu et al., *J. Neurosci.* 27:881 (2007); Berg et al., *Mol. Pharmacol.* 54:94 (1998); Ghosh et al., *J. Med. Chem.* 39:549 (1996); Kilts et al., *J. Pharmacol. Exp. Ther.* 301:1179 (2002); Mottola et al., *J. Pharmacol. Exp. Ther.* 301:1166 (2002); Parrish et al., *J. Neurochem.* 95:1575 (2005); Roth and Chuang, *Life Sci.* 41:1051 (1987); Urban et al., *J. Pharmacol. Exp. Ther.* 320:1 (2007)); (2) antagonists can possess negative intrinsic activity (e.g., function as inverse agonists) or be silent and thereby block the actions of an inverse agonist (e.g., neutral antagonists) (Barker et al., *J. Biol. Chem.* 269:11687 (1994); Burstein et al., *J. Pharmacol. Exp. Ther.* 315:1278 (2005); Chidiac et al., *Mol. Pharmacol.* 45:490 (1994); Gilliland and Alper, *Naunyn Schmiedebergs Arch. Pharmacol.* 361:498 (2000); Rauser et al., *J. Pharmacol. Exp. Ther.* 299:83 (2001)); (3) antagonists can also induce receptor down regulation (Peroutka and Snyder, *Science* 210:88 (1980)) and receptor internalization in vitro (Berry et al., *Mol. Pharmacol.* 50:306 (1996)) and in vivo (Gray and Roth, *Brain Res. Bull.* 56:441 (2001); Willins et al., *Ann. NY Acad. Sci.* 861: 121 (1998); Willins et al., *Neuroscience* 91:599 (1999))—properties typically associated with agonists.

The processes by which agonists and antagonists differentially modulate signaling pathways and receptor trafficking have been variously dubbed 'functional selectivity', 'biased agonism' or 'agonist-directed trafficking'. Currently, the preferred term for the process by which ligands can differentially activate signaling pathways mediated via a single GPCR is functional selectivity (Urban et al., *J. Pharmacol. Exp. Ther.* 320:1 (2007)). Functional selectivity has been demonstrated for more than a dozen GPCRs (reviewed in (Urban et al., *Neuropsychopharmacology* 32:67 (2007)) and is, likely, a ubiquitous phenomenon. In particular, functional selectivity has been widely observed among DA receptor subtypes.

It is desirable to identify novel, functionally selective ligands of dopamine D$_2$ receptors to elucidate the key signal transduction pathways essential for antipsychotic efficacy and the undesired ones associated with side-effects. Such compounds would also be useful agents for treating central nervous system (CNS) disorders including schizophrenia and depression.

SUMMARY OF THE INVENTION

The present invention relates to novel, functionally selective ligands of dopamine D$_2$ receptors. When evaluated in multiple D$_2$ binding and functional assays, the compounds of the invention showed different activity profiles ranging from full agonists to antagonists to inverse agonists. In particular, the compounds of the invention are β-arrestin biased and, in certain embodiments, also are inverse agonists of G$_i$-regulated pathways. These pharmacologically active compounds exhibit fewer side effects and are useful in research to study D$_2$ receptor function and its role in psychosis and for the treatment of CNS disorders.

Accordingly, as one aspect, the invention provides a compound of formula I:

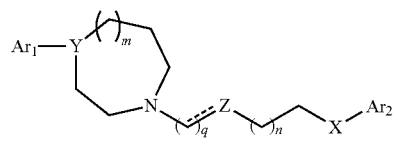

wherein m is 0 or 1;
n is 0, 1, or 2;
q is 1 or 2;
X is O, NH, or CH$_2$;
Y is N or CH;
Z is C, CH, CH$_2$, cycloalkyl, aryl, or heteroaryl;
===== is a single, double, or triple bond as valencies permit; and
Ar$_1$ and Ar$_2$ are independently an unsubstituted or substituted monocyclic or bicyclic aryl or heteroaryl;
or a pharmaceutically acceptable salt, prodrug, or optical isomer thereof.

In another aspect, the invention provides a compound of formula II:

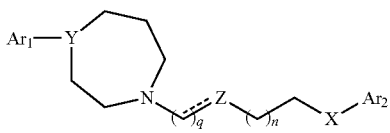

wherein n is 0, 1, or 2;
q is 1 or 2;
X is O, NH, or CH$_2$;
Y is N or CH;
Z is C, CH, CH$_2$, cycloalkyl, aryl, or heteroaryl;
===== is a single, double, or triple bond as valencies permit; and Ar$_1$ and Ar$_2$ are independently an unsubstituted or substituted monocyclic or bicyclic aryl or heteroaryl;

or a pharmaceutically acceptable salt, prodrug, or optical isomer thereof.

In a further aspect, the invention provides a compound of formula VI:

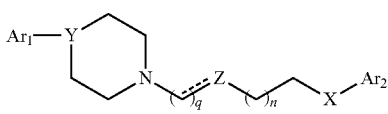

wherein n is 0, 1, or 2;
q is 1 or 2;
X is O, NH, or CH$_2$;
Y is N or CH;
Z is C, CH, CH$_2$, cycloalkyl, aryl, or heteroaryl;
===== is a single, double, or triple bond as valencies permit; and Ar$_1$ and Ar$_2$ are independently an unsubstituted or substituted monocyclic or bicyclic aryl or heteroaryl;

or a pharmaceutically acceptable salt, prodrug, or optical isomer thereof.

The invention further relates to a pharmaceutical composition comprising the compound of the invention and a pharmaceutically acceptable carrier.

The invention also relates to a method of modulating the activity of a D$_2$ dopamine receptor comprising contacting the receptor with a compound of the invention.

The invention additionally relates to a method of treating a central nervous system disorder associated with D$_2$ dopamine receptors in a subject (e.g., a psychiatric, neurological, pituitary, or endocrine disorder), comprising delivering to the subject a therapeutically effective amount of the compound of the invention.

The invention further relates to the use of a compound of the invention for treating a central nervous system disorder associated with D$_2$ dopamine receptors in a subject.

The invention further relates to the use of a compound of the invention for stimulating D$_2$ dopamine receptors in a β-arrestin biased manner.

The present invention is explained in greater detail in the drawings herein and the specification set forth below.

DETAILED DESCRIPTION OF THE INVENTION

Figure 1:
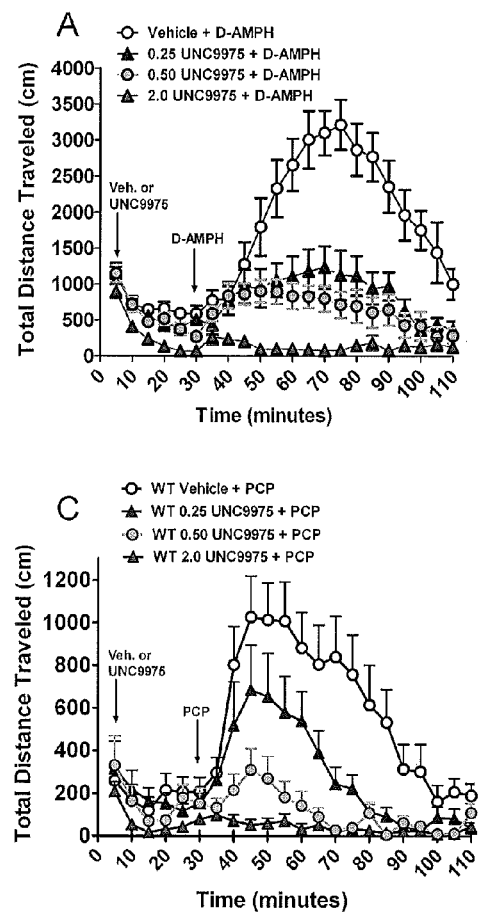
FIGS. 1A-1F show that UNC 9975 exhibits potent antipsychotic—like activity in mouse hyperlocomotion studies.
Figure 1:
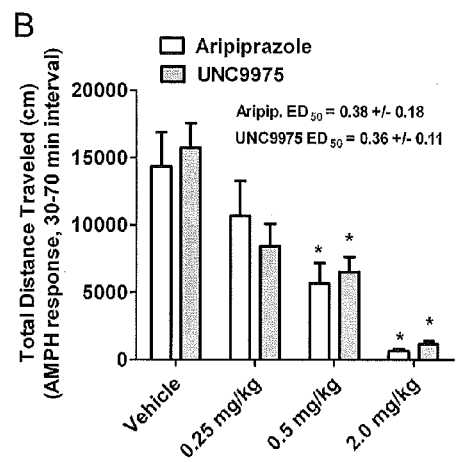
Figure 1:
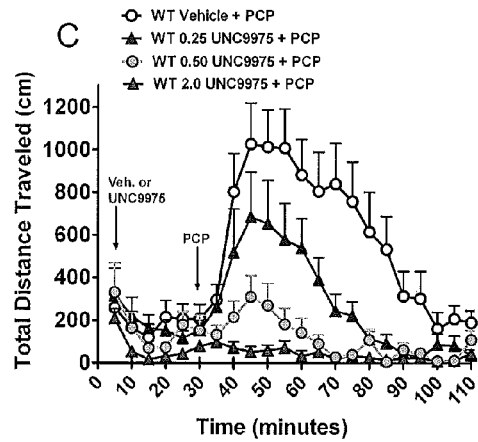
Figure 1:
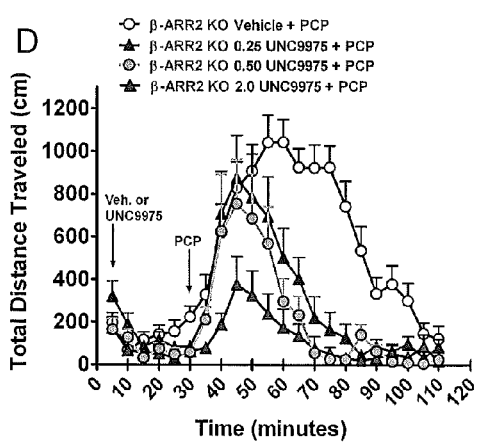
Figure 1:
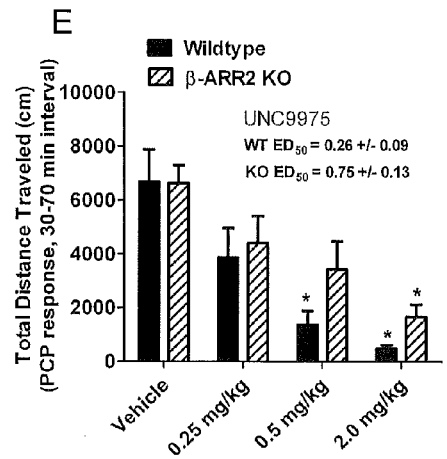
Figure 1:
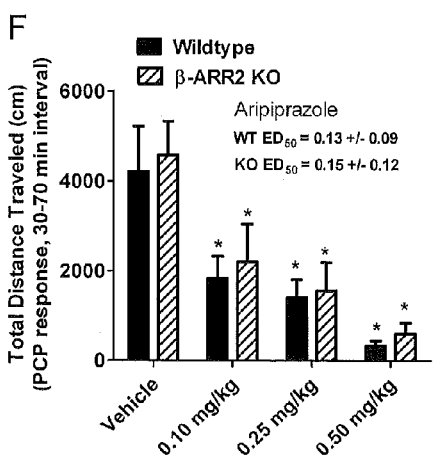

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety.

Definitions.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

A "central nervous system disorder associated with $D_2$ dopamine receptors" refers to any disorder in which modulation (either an increase or a decrease) of one or more activities of a $D_2$ dopamine receptor in a subject results in the treatment of one or more symptoms of the disorder in the subject.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; 21$^{st}$ ed. 2005). Exemplary pharmaceutically acceptable carriers for the compositions of this invention include, but are not limited to, sterile pyrogen-free water and sterile pyrogen-free physiological saline solution.

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The term "β-arrestin biased" refers to a compound that binds the $D_2$ dopamine receptor, is a partial or full agonist of the β-arrestin pathway, and is either neutral or an inverse agonist of the $G_i$-regulated cAMP pathway.

The term "neutral" refers to a compound that binds to a receptor but does not stimulate a particular receptor-linked pathway.

The term "inverse agonist" refers to a compound that binds to a receptor and reduces constitutive activity of a particular receptor-linked pathway.

The term "alkyl" denotes a straight or branched hydrocarbon chain containing 1-12 carbon atoms, e.g., 1-6 or 1-4 carbon atoms. Examples of alkyl groups include methyl, ethyl, propyl, isopropyl, butyl, isobutyl, tert-butyl, and the like.

By "substituted alkyl" is meant an alkyl in which an atom of the alkyl is substituted with, for example, a carbon, nitrogen, sulfur, oxygen, silicon, or halogen atom, or alternatively a nitrogen, sulfur, oxygen, or halogen atom. The term encompasses substituents on alkyl, alkenyl, alkynyl, and cycloalkyl groups.

Examples of substituents that can be attached to any atom of the alkyl group in a "substituted alkyl" include cyclyl groups, heterocyclyl groups; aryl groups, heteroaryl groups, amino groups, amido groups, nitro groups, cyano groups, azide groups, hydroxy groups, alkoxy groups, acyloxy groups, thioalkoxy groups, acyl thioalkoxy groups, halogen groups, sulfonate groups, sulfonamide groups, ester groups, carboxylic acids, oxygen (e.g., a carbonyl group), and sulfur (e.g., a thiocarbonyl group). Substituents also include any chemical functional group that imparts improved water-solubility to the molecule (e.g., carboxylic acid, carboxylic ester, carboxamido, morpholino, piperazinyl, imidazolyl, thiomorpholino, or tetrazolyl groups; both unsubstituted and substituted).

The term "cycloalkyl" denotes a monocyclic saturated carbocyclic group containing 3-8 carbon atoms, e.g., 3-6 carbon atoms. Examples of cycloalkyl groups include cyclopropyl, cyclobutyl, cyclopentyl, cyclohexyl, cycloheptyl, cyclooctyl, and the like.

The term "alkoxy" denotes an oxygen linked to an alkyl or substituted alkyl as defined above.

The terms "halo" and "halogen" refer to any radical of fluorine, chlorine, bromine or iodine.

The terms "ring" and "ring system" refer to a ring comprising the delineated number of atoms, said atoms being carbon or, where indicated, a heteroatom such as nitrogen, oxygen or sulfur. The ring itself, as well as any substituents thereon, can be attached at any atom that allows a stable compound to be formed.

The term "aryl" refers to an aromatic 5-8 membered monocyclic or 8-12 membered bicyclic ring system wherein 0, 1, 2, or 3 atoms of each ring can be substituted by a substituent. The term also includes aromatic bicyclic ring systems in which a hydrogen atom has been added to one, two, or three of the ring carbons in one of the rings (e.g., a partially saturated ring). Examples of aryl groups include phenyl, naphthyl and the like.

The term "heteroaryl" refers to an aromatic 5-8 membered monocyclic or 8-12 membered bicyclic ring system comprising 1-3 heteroatoms if monocyclic or 1-6 heteroatoms if bicyclic, said heteroatoms selected from O, N, or S, wherein 0, 1, 2 or 3 atoms of each ring can be substituted by a substituent. The term also includes aromatic bicyclic ring systems in which a hydrogen atom has been added to one, two, or three of the ring carbons in one of the rings (e.g., a partially saturated ring). Examples of heteroaryl groups include pyridyl, furyl or furanyl, benzofuranyl, imidazolyl, benzimidazolyl, pyrimidinyl, thiophenyl or thienyl, benzothiophenyl, quinolinyl, isoquinolinyl, dihydroquinolinyl, dihydroisoquinolinyl, naphthyridinyl, dihydronaphthyridinyl, quinazolinyl, indolyl, indazolyl, thiazolyl, benzothiazolyl, oxazinyl, benzooxazinyl, oxazolyl, benzooxazolyl, dihydrobenzodioxinyl, and the like.

Suitable substituents for aryl and heteroaryl groups are the same as the substituents for alkyl groups.

Compounds.

The present invention provides novel, functionally selective ligands of dopamine $D_2$ receptors. In particular, the compounds of the invention are β-arrestin biased. In certain embodiments, the compounds are at least partial agonists of the β-arrestin pathway. In other embodiments, the compounds are full agonists of the β-arrestin pathway. In further embodiments, the compounds also are neutral or inverse agonists of the $G_i$-regulated cAMP pathway. These compounds represent the first functionally selective β-arrestin-biased dopamine $D_2$ receptor ligands to exhibit antipsychotic activity in vivo.

In one aspect the invention provides a compound of formula I:

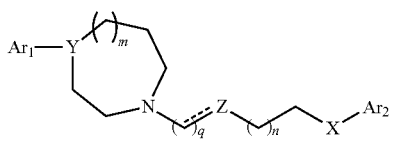

I wherein m is 0 or 1;
q is 1 or 2;
n is 0, 1, or 2;
X is O, NH, or $CH_2$;
Y is N or CH;
Z is C, CH, $CH_2$, cycloalkyl, aryl, or heteroaryl;
===== is optionally a single, double, or triple bond as valencies permit; and
$Ar_1$ and $Ar_2$ are independently an unsubstituted or substituted monocyclic or bicyclic aryl or heteroaryl;
or a pharmaceutically acceptable salt, prodrug, or optical isomer thereof.

In one embodiment, $Ar_2$ is an unsubstituted or substituted bicyclic aryl or heteroaryl. In another embodiment, Z is C, CH, $CH_2$, cycloalkyl, monocyclic aryl, or monocyclic heteroaryl. The bond indicated as ===== refers to the bond attached to Z and not to any other bond, e.g., not between the two carbon atoms that are present when q is 2.

In one aspect the compound of the invention has the structure of formula II:

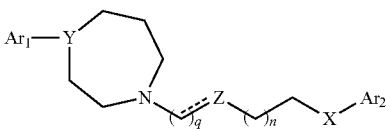

II wherein n is 0, 1, or 2;
q is 1 or 2;
X is O, NH, or $CH_2$;
Y is N or CH;
Z is C, CH, $CH_2$, cycloalkyl, aryl, or heteroaryl;
===== is optionally a single, double, or triple bond as valencies permit; and
$Ar_1$ and $Ar_2$ are independently an unsubstituted or substituted monocyclic or bicyclic aryl or heteroaryl;
or a pharmaceutically acceptable salt, prodrug, or optical isomer thereof.

In one embodiment, the compound of the invention has the structure of formula III:

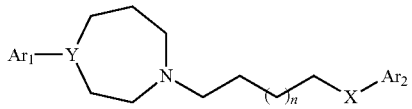

III wherein n is 0, 1, or 2;
X is O, NH, or $CH_2$;
Y is N or CH; and
$Ar_1$ and $Ar_2$ are independently an unsubstituted or substituted monocyclic or bicyclic aryl or heteroaryl;
or a pharmaceutically acceptable salt, prodrug, or optical isomer thereof.

In another embodiment, the compound has the structure of formula IV:

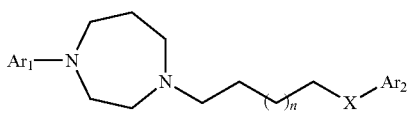

IV or a pharmaceutically acceptable salt, prodrug, or optical isomer thereof.

In one embodiment for the compound of formula II-IV, n is 1. In a further embodiment, n is 0. In another embodiment, X is O. In another embodiment, X is NH.

In one embodiment for the compound of formula II-IV, $Ar_1$ is selected from the group consisting of phenyl, substituted phenyl (e.g., chlorophenyl, dichlorophenyl, fluorophenyl, trifluoromethylphenyl, methylphenyl, cyanophenyl, methoxyphenyl, ethoxyphenyl, isopropoxyphenyl), 2,3-dihydro-1H-benzo[d]imidazolyl, benzo[d]oxazol-2(3H)-one, 1H-benzo[d]imidazolyl, benzo[d]oxazolyl, 1H-indazolyl, 1H-indazolyl, 1H-indolyl, benzofuranyl, benzo[b]thiophenyl, benzo[d]thiazolyl, naphthalenyl, isoquinolinyl, quinazolinyl, quinolinyl, and pyridinyl, or any subgroup selected from the list. In a further embodiment, $Ar_1$ is dichlorophenyl.

In one embodiment for the compound of formula II-IV, $Ar_2$ is selected from the group consisting of 3,4-dihydroquinolin-2(1H)-one, 3,4-dihydro-1,8-naphthyridin-2(1H)-one, quinolin-2(1H)-one, 3,4-dihydroisoquinolin-1(2H)-one, benzo[d]thiazole, 1H-benzo[d]imidazol-2(3H)-one, 1H-indazole, and benzo[d]oxazol-2(3H)-one, or any subgroup selected from the list.

In one embodiment for the compound of formula II-IV, $Ar_1$ is dichlorophenyl or methoxyphenyl and $Ar_2$ is quinolinone, dihydroquinolinone, naphthyridinone, or benzothiazole.

In one embodiment for the compound of formula II-IV, $Ar_1$ is dichlorophenyl, methoxyphenyl, ethoxyphenyl, or isopropyloxyphenyl and $Ar_2$ is quinolinone, dihydroquinolinone, naphthyridinone, benzothiazole, or benzoimidazolone.

In certain embodiments for the compound of formula II-IV, $Ar_2$ is not naphthyridinone, dihydronaphthyridinone, quinolinone, dihydroquinolinone, tetrahydropyridoazepinone, or isoindole.

In a further embodiment, Ar$_2$ is:

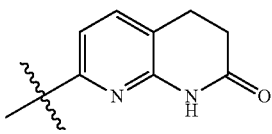 [SMILES: *c1ccc2c(n1)NC(=O)CC2]

In certain embodiments, the compounds of the invention have the structure of formula V:

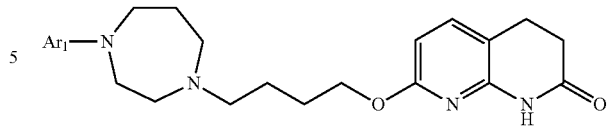

or a pharmaceutically acceptable salt, prodrug, or optical isomer thereof.

In one embodiment, the compound of formula II is selected from the group of compounds shown in Tables 1 and 2.

TABLE 1

| Compound Number | Structure | Name |
|---|---|---|
| 1 | 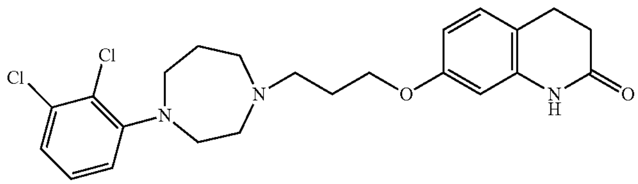 [SMILES: O=C1CCc2ccc(OCCCN3CCCN(c4cccc(Cl)c4Cl)CC3)cc2N1] | 7-(3-(4-(2,3-dichlorophenyl)-1,4-diazepan-1-yl)propoxy)-3,4-dihydroquinolin-2(1H)-one |
| 2 | 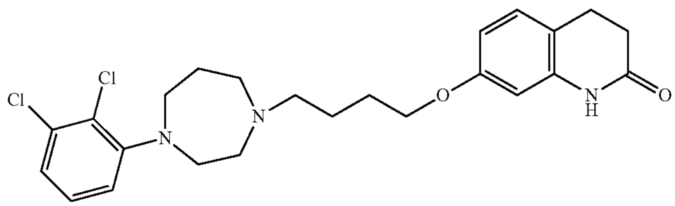 [SMILES: O=C1CCc2ccc(OCCCCN3CCCN(c4cccc(Cl)c4Cl)CC3)cc2N1] | 7-(4-(4-(2,3-dichlorophenyl)-1,4-diazepan-1-yl)butoxy)-3,4-dihydroquinolin-2(1H)-one |
| 3 | 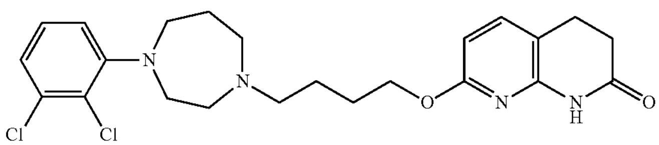 [SMILES: O=C1CCc2ccc(OCCCCN3CCCN(c4cccc(Cl)c4Cl)CC3)nc2N1] | 7-(4-(4-(2,3-dichlorophenyl)-1,4-diazepan-1-yl)butoxy)-3,4-dihydro-1,8-naphthyridin-2(1H)-one |
| 4 | 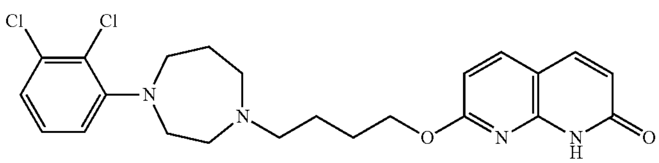 | 7-(4-(4-(2,3-dichlorophenyl)-1,4-diazepan-1-yl)butoxy)quinolin-2(1H)-one |
| 5 | 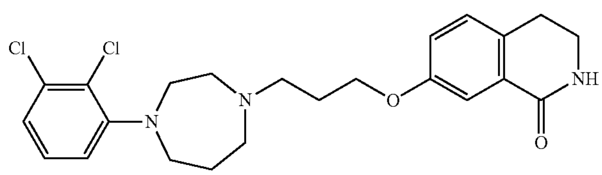 [SMILES: O=C1NCCc2ccc(OCCCN3CCCN(c4cccc(Cl)c4Cl)CC3)cc21] | 7-(3-(4-(2,3-dichlorophenyl)-1,4-diazepan-1-yl)propoxy)-3,4-dihydroisoquinolin-1(2H)-one |
| 6 | 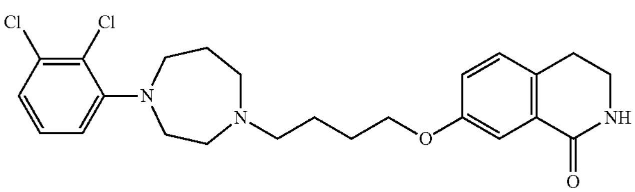 [SMILES: O=C1NCCc2ccc(OCCCCN3CCCN(c4cccc(Cl)c4Cl)CC3)cc21] | 7-(4-(4-(2,3-dichlorophenyl)-1,4-diazepan-1-yl)butoxy)-3,4-dihydroisoquinolin-1(2H)-one |
| 7 | 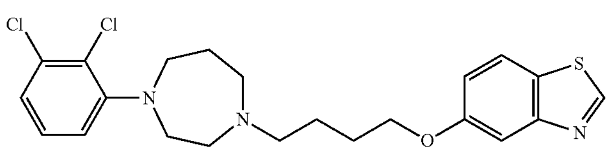 [SMILES: Clc1cccc(N2CCCN(CCCCOc3ccc4scnc4c3)CC2)c1Cl] | 5-(4-(4-(2,3-dichlorophenyl)-1,4-diazepan-1-yl)butoxy)benzo[d]thiazole |

TABLE 1-continued

| Compound Number | Structure | Name |
|---|---|---|
| 8 | 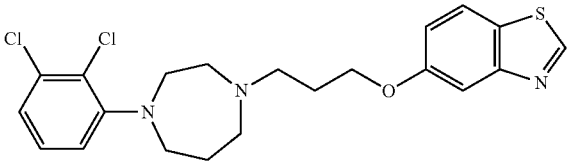 [SMILES: Clc1cccc(N2CCCN(CCCOc3ccc4scnc4c3)CC2)c1Cl] | 5-(3-(4-(2,3-dichlorophenyl)-1,4-diazepan-1-yl)propoxy)benzo[d]thiazole |
| 9 | 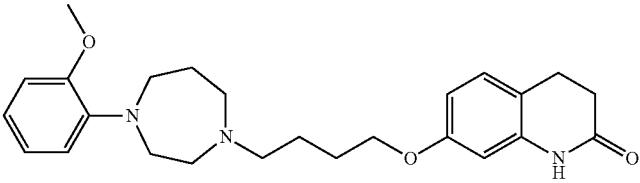 [SMILES: COc1ccccc1N1CCCN(CCCCOc2ccc3c(c2)NC(=O)CC3)CC1] | 7-(4-(4-(2-methoxyphenyl)-1,4-diazepan-1-yl)butoxy)-3,4-dihydroquinolin-2(1H)-one |
| 10 | 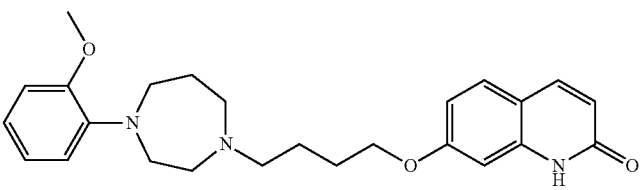 [SMILES: COc1ccccc1N1CCCN(CCCCOc2ccc3ccc(=O)[nH]c3c2)CC1] | 7-(4-(4-(2-methoxyphenyl)-1,4-diazepan-1-yl)butoxy)quinolin-2(1H)-one |
| 11 | 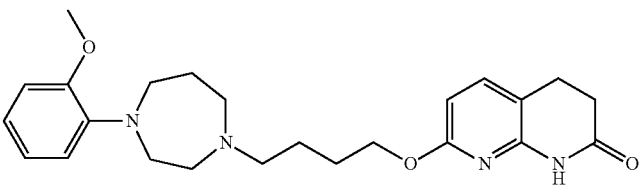 [SMILES: COc1ccccc1N1CCCN(CCCCOc2ccc3c(n2)NC(=O)CC3)CC1] | 7-(4-(4-(2-methoxyphenyl)-1,4-diazepan-1-yl)butoxy)-3,4-dihydro-1,8-naphthyridin-2(1H)-one |
| 12 | 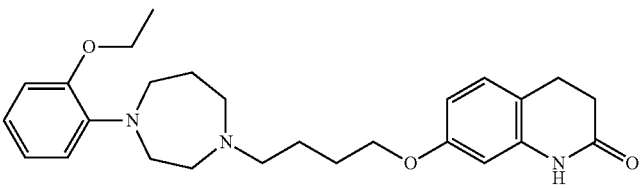 [SMILES: CCOc1ccccc1N1CCCN(CCCCOc2ccc3c(c2)NC(=O)CC3)CC1] | 7-(4-(4-(2-ethoxyphenyl)-1,4-diazepan-1-yl)butoxy)-3,4-dihydroquinolin-2(1H)-one |
| 13 | 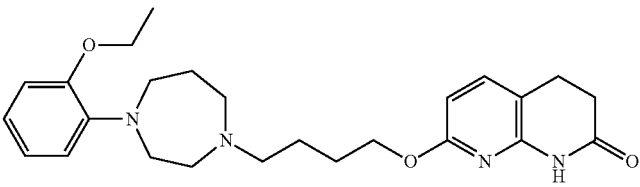 [SMILES: CCOc1ccccc1N1CCCN(CCCCOc2ccc3c(n2)NC(=O)CC3)CC1] | 7-(4-(4-(2-ethoxyphenyl)-1,4-diazepan-1-yl)butoxy)-3,4-dihydro-1,8-naphthyridin-2(1H)-one |
| 14 | 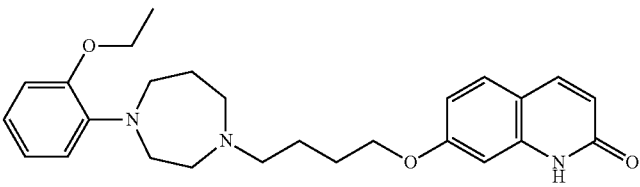 [SMILES: CCOc1ccccc1N1CCCN(CCCCOc2ccc3ccc(=O)[nH]c3c2)CC1] | 7-(4-(4-(2-ethoxyphenyl)-1,4-diazepan-1-yl)butoxy)quinolin-2(1H)-one |
| 15 | 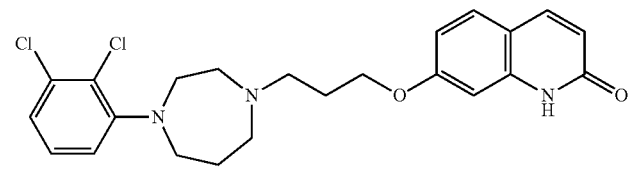 [SMILES: O=c1ccc2ccc(OCCCN3CCCN(c4cccc(Cl)c4Cl)CC3)cc2[nH]1] | 7-(3-(4-(2,3-dichlorophenyl)-1,4-diazepan-1-yl)propoxy)quinolin-2(1H)-one |

TABLE 1-continued

| Compound Number | Structure | Name |
|---|---|---|
| 16 | 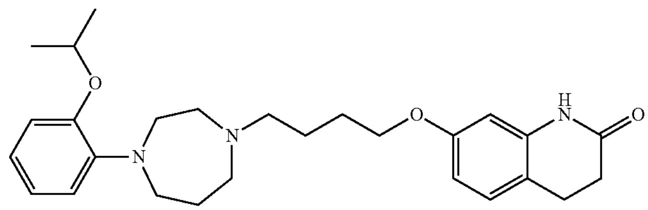 [SMILES: CC(C)Oc1ccccc1N1CCCN(CCCCOc2ccc3c(c2)NC(=O)CC3)CC1] | 7-(4-(4-(2-isopropoxyphenyl)-1,4-diazepan-1-yl)butoxy)-3,4-dihydroquinolin-2(1H)-one |
| 17 | 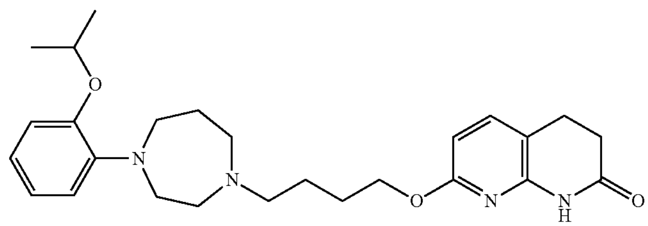 [SMILES: CC(C)Oc1ccccc1N1CCCN(CCCCOc2ccc3c(n2)NC(=O)CC3)CC1] | 7-(4-(4-(2-isopropoxyphenyl)-1,4-diazepan-1-yl)butoxy)-3,4-dihydro-1,8-naphthyridin-2(1H)-one |
| 18 | 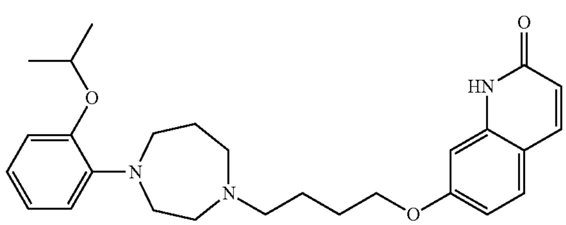 [SMILES: CC(C)Oc1ccccc1N1CCCN(CCCCOc2ccc3ccc(=O)[nH]c3c2)CC1] | 7-(4-(4-(2-isopropoxyphenyl)-1,4-diazepan-1-yl)butoxy)quinolin-2(1H)-one |
| 19 | 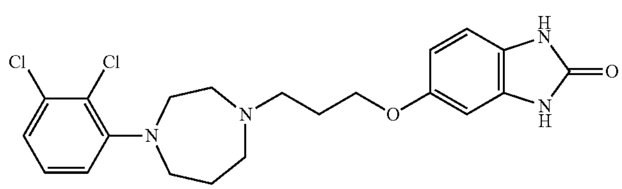 [SMILES: O=c1[nH]c2ccc(OCCCN3CCCN(c4cccc(Cl)c4Cl)CC3)cc2[nH]1] | 5-(3-(4-(2,3-dichlorophenyl)-1,4-diazepan-1-yl)propoxy)-1H-benzo[d]imidazol-2(3H)-one |
| 46 | 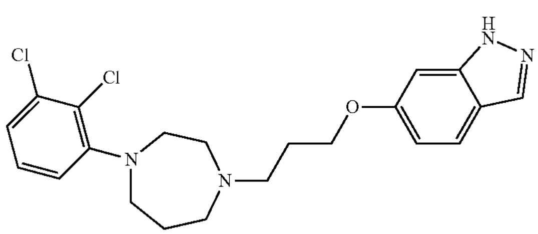 | 6-(3-(4-(2,3-dichlorophenyl)-1,4-diazepan-1-yl)propoxy)-1H-indazole |
| 47 | 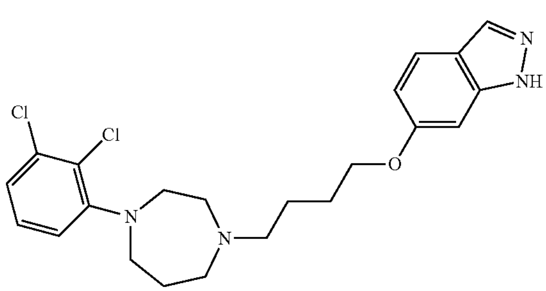 [SMILES: Clc1cccc(N2CCCN(CCCCOc3ccc4cn[nH]c4c3)CC2)c1Cl] | 6-(4-(4-(2,3-dichlorophenyl)-1,4-diazepan-1-yl)butoxy)-1H-indazole |

TABLE 2

| Compound Number | Structure | Name |
|---|---|---|
| 52 | 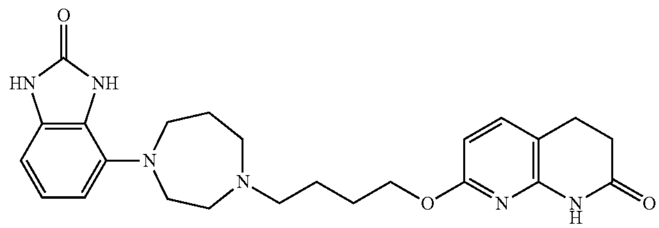 [SMILES: O=C1CCc2ccc(OCCCCN3CCCN(c4cccc5[nH]c(=O)[nH]c45)CC3)nc2N1] | 7-(4-(4-(2-oxo-2,3-dihydro-1H-benzo[d]imidazol-4-yl)-1,4-diazepan-1-yl)butoxy)-3,4-dihydro-1,8-naphthyridin-2(1H)-one |
| 53 | 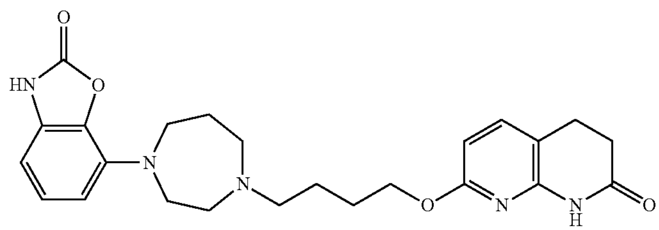 [SMILES: O=C1CCc2ccc(OCCCCN3CCCN(c4cccc5[nH]c(=O)oc45)CC3)nc2N1] | 7-(4-(4-(7-oxo-5,6,7,8-tetrahydro-1,8-naphthyridin-2-yloxy)butyl)-1,4-diazepan-1-yl)benzo[d]oxazol-2(3H)-one |
| 54 | 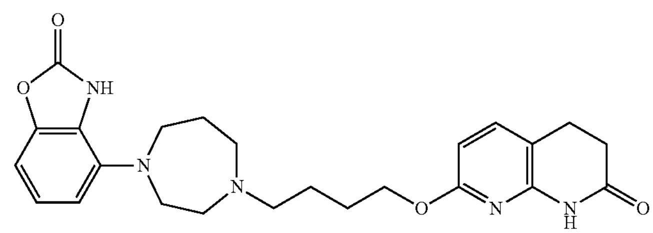 [SMILES: O=C1CCc2ccc(OCCCCN3CCCN(c4cccc5oc(=O)[nH]c45)CC3)nc2N1] | 4-(4-(4-(7-oxo-5,6,7,8-tetrahydro-1,8-naphthyridin-2-yloxy)butyl)-1,4-diazepan-1-yl)benzo[d]oxazol-2(3H)-one |
| 55 | 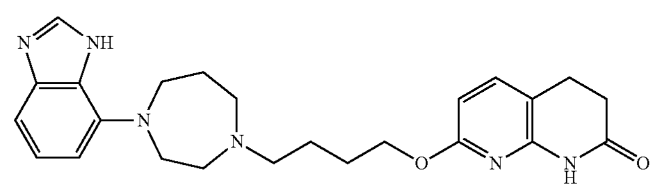 [SMILES: O=C1CCc2ccc(OCCCCN3CCCN(c4cccc5nc[nH]c45)CC3)nc2N1] | 7-(4-(4-(1H-benzo[d]imidazol-7-yl)-1,4-diazepan-1-yl)butoxy)-3,4-dihydro-1,8-naphthyridin-2(1H)-one |
| 56 | 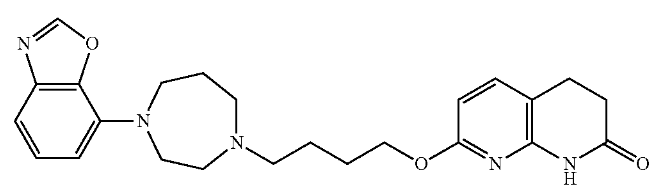 | 7-(4-(4-(benzo[d]oxazol-7-yl)-1,4-diazepan-1-yl)butoxy)-3,4-dihydro-1,8-naphthyridin-2(1H)-one |
| 57 | 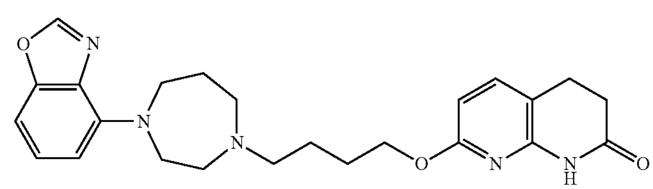 [SMILES: O=C1CCc2ccc(OCCCCN3CCCN(c4cccc5ocnc45)CC3)nc2N1] | 7-(4-(4-(benzo[d]oxazol-4-yl)-1,4-diazepan-1-yl)butoxy)-3,4-dihydro-1,8-naphthyridin-2(1H)-one |
| 58 | 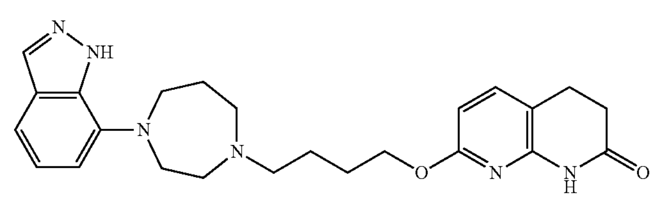 [SMILES: O=C1CCc2ccc(OCCCCN3CCCN(c4cccc5cn[nH]c45)CC3)nc2N1] | 7-(4-(4-(1H-indazol-7-yl)-1,4-diazepan-1-yl)butoxy)-3,4-dihydro-1,8-naphthyridin-2(1H)-one |

TABLE 2-continued

| Compound Number | Structure | Name |
|---|---|---|
| 59 | 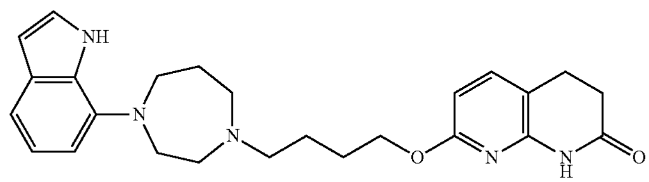 | 7-(4-(4-(1H-indol-7-yl)-1,4-diazepan-1-yl)butoxy)-3,4-dihydro-1,8-naphthyridin-2(1H)-one |
| 60 | 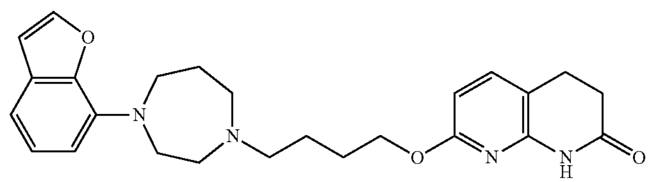 [SMILES: O=C1CCc2ccc(OCCCCN3CCCN(c4cccc5ccoc45)CC3)nc2N1] | 7-(4-(4-(benzofuran-7-yl)-1,4-diazepan-1-yl)butoxy)-3,4-dihydro-1,8-naphthyridin-2(1H)-one |
| 61 | 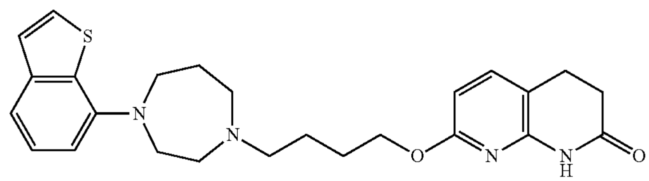 | 7-(4-(4-(benzo[b]thiophen-7-yl)-1,4-diazepan-1-yl)butoxy)-3,4-dihydro-1,8-naphthyridin-2(1H)-one |
| 62 | 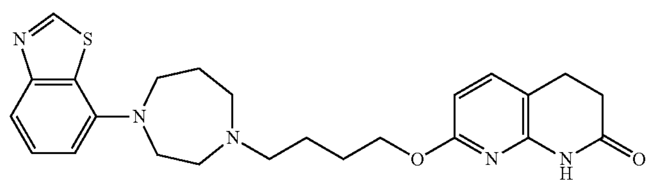 | 7-(4-(4-(benzo[d]thiazol-7-yl)-1,4-diazepan-1-yl)butoxy)-3,4-dihydro-1,8-naphthyridin-2(1H)-one |
| 63 | 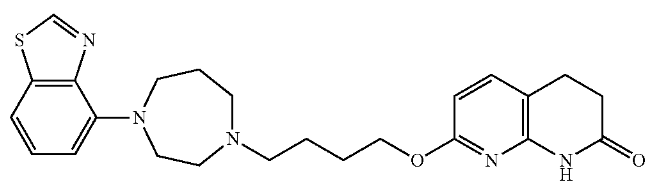 | 7-(4-(4-(benzo[d]thiazol-4-yl)-1,4-diazepan-1-yl)butoxy)-3,4-dihydro-1,8-naphthyridin-2(1H)-one |
| 64 | 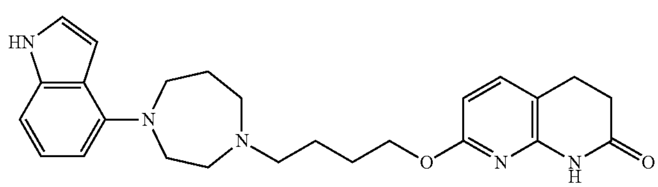 [SMILES: O=C1CCc2ccc(OCCCCN3CCCN(c4cccc5[nH]ccc45)CC3)nc2N1] | 7-(4-(4-(1H-indol-4-yl)-1,4-diazepan-1-yl)butoxy)-3,4-dihydro-1,8-naphthyridin-2(1H)-one |
| 65 | 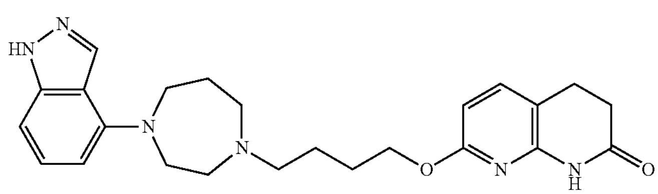 [SMILES: O=C1CCc2ccc(OCCCCN3CCCN(c4cccc5[nH]ncc45)CC3)nc2N1] | 7-(4-(4-(1H-indazol-4-yl)-1,4-diazepan-1-yl)butoxy)-3,4-dihydro-1,8-naphthyridin-2(1H)-one |
| 66 | 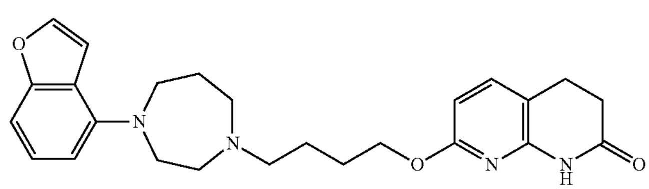 [SMILES: O=C1CCc2ccc(OCCCCN3CCCN(c4cccc5sccc45)CC3)nc2N1] | 7-(4-(4-(benzofuran-4-yl)-1,4-diazepan-1-yl)butoxy)-3,4-dihydro-1,8-naphthyridin-2(1H)-one |

TABLE 2-continued

| Compound Number | Structure | Name |
|---|---|---|
| 67 | 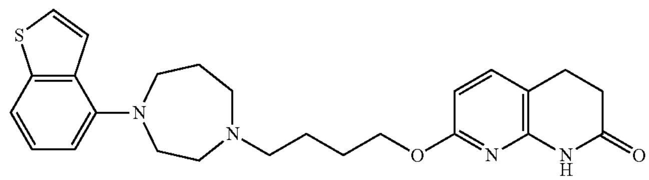 | 7-(4-(4-(benzo[b]thiophen-4-yl)-1,4-diazepan-1-yl)butoxy)-3,4-dihydro-1,8-naphthyridin-2(1H)-one |
| 68 | 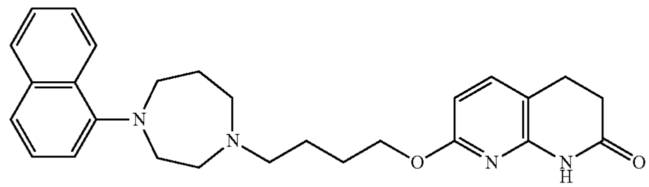 [SMILES: O=C1CCc2ccc(OCCCCN3CCCN(c4cccc5ccccc45)CC3)nc2N1] | 7-(4-(4-(naphthalen-1-yl)-1,4-diazepan-1-yl)butoxy)-3,4-dihydro-1,8-naphthyridin-2(1H)-one |
| 69 | 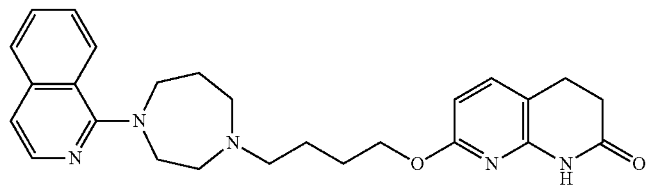 [SMILES: O=C1CCc2ccc(OCCCCN3CCCN(c4nccc5ccccc45)CC3)nc2N1] | 7-(4-(4-(isoquinolin-1-yl)-1,4-diazepan-1-yl)butoxy)-3,4-dihydro-1,8-naphthyridin-2(1H)-one |
| 70 | 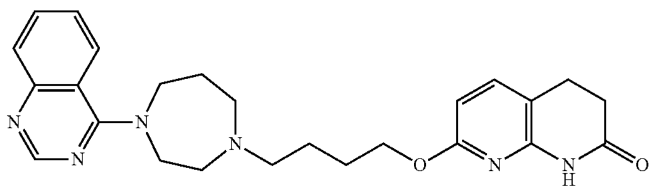 [SMILES: O=C1CCc2ccc(OCCCCN3CCCN(c4ncnc5ccccc45)CC3)nc2N1] | 7-(4-(4-(quinazolin-4-yl)-1,4-diazepan-1-yl)butoxy)-3,4-dihydro-1,8-naphthyridin-2(1H)-one |
| 71 | 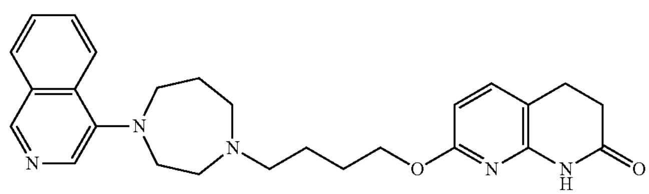 | 7-(4-(4-(isoquinolin-4-yl)-1,4-diazepan-1-yl)butoxy)-3,4-dihydro-1,8-naphthyridin-2(1H)-one |
| 72 | 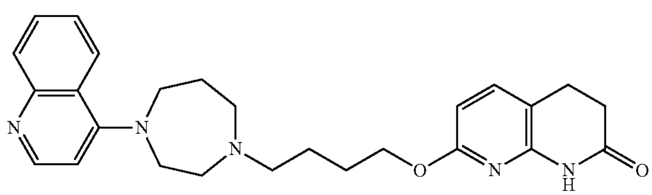 [SMILES: O=C1CCc2ccc(OCCCCN3CCCN(c4ccnc5ccccc45)CC3)nc2N1] | 7-(4-(4-(quinolin-4-yl)-1,4-diazepan-1-yl)butoxy)-3,4-dihydro-1,8-naphthyridin-2(1H)-one |
| 73 | 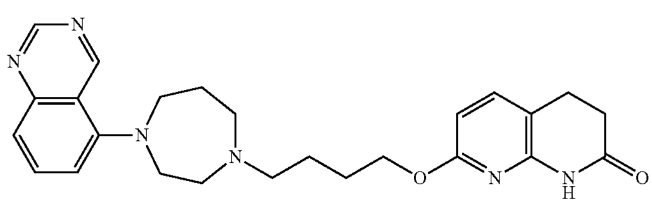 [SMILES: O=C1CCc2ccc(OCCCCN3CCCN(c4cccc5ncncc45)CC3)nc2N1] | 7-(4-(4-(quinazolin-5-yl)-1,4-diazepan-1-yl)butoxy)-3,4-dihydro-1,8-naphthyridin-2(1H)-one |
| 74 | 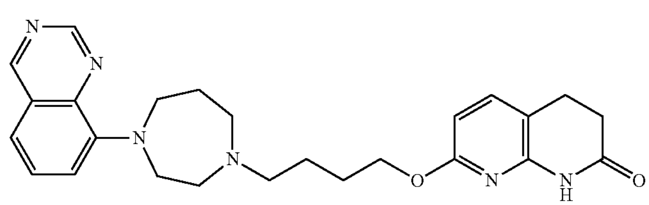 [SMILES: O=C1CCc2ccc(OCCCCN3CCCN(c4cccc5cncnc45)CC3)nc2N1] | 7-(4-(4-(quinazolin-8-yl)-1,4-diazepan-1-yl)butoxy)-3,4-dihydro-1,8-naphthyridin-2(1H)-one |

| Compound Number | Structure | Name |
|---|---|---|
| 75 | 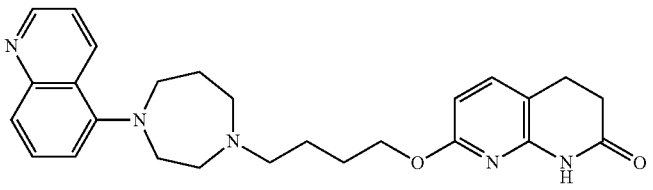 [SMILES: O=C1CCc2ccc(OCCCCN3CCCN(c4cccc5ncccc45)CC3)nc2N1] | 7-(4-(4-(quinolin-5-yl)-1,4-diazepan-1-yl)butoxy)-3,4-dihydro-1,8-naphthyridin-2(1H)-one |
| 76 | 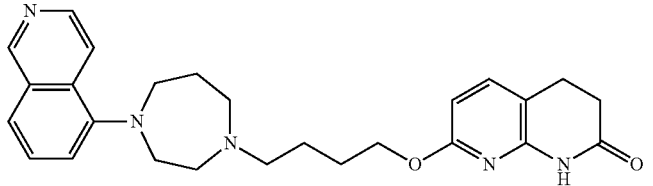 [SMILES: O=C1CCc2ccc(OCCCCN3CCCN(c4cccc5cnccc45)CC3)nc2N1] | 7-(4-(4-(isoquinolin-5-yl)-1,4-diazepan-1-yl)butoxy)-3,4-dihydro-1,8-naphthyridin-2(1H)-one |
| 77 | 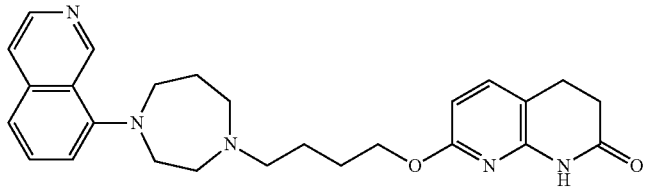 [SMILES: O=C1CCc2ccc(OCCCCN3CCCN(c4cccc5ccncc45)CC3)nc2N1] | 7-(4-(4-(isoquinolin-8-yl)-1,4-diazepan-1-yl)butoxy)-3,4-dihydro-1,8-naphthyridin-2(1H)-one |
| 78 | 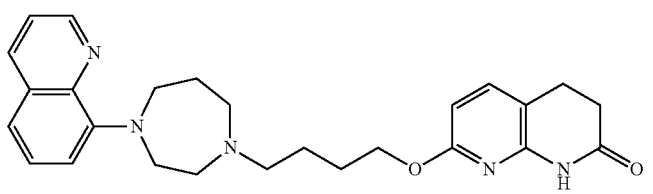 [SMILES: O=C1CCc2ccc(OCCCCN3CCCN(c4cccc5cccnc45)CC3)nc2N1] | 7-(4-(4-(quinolin-8-yl)-1,4-diazepan-1-yl)butoxy)-3,4-dihydro-1,8-naphthyridin-2(1H)-one |
| 79 | 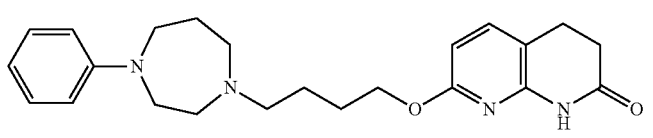 | 7-(4-(4-phenyl-1,4-diazepan-1-yl)butoxy)-3,4-dihydro-1,8-naphthyridin-2(1H)-one |
| 80 | 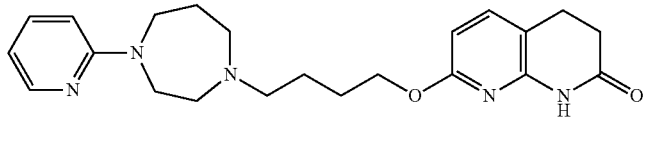 [SMILES: O=C1CCc2ccc(OCCCCN3CCCN(c4ccccn4)CC3)nc2N1] | 7-(4-(4-(pyridin-2-yl)-1,4-diazepan-1-yl)butoxy)-3,4-dihydro-1,8-naphthyridin-2(1H)-one |
| 81 | 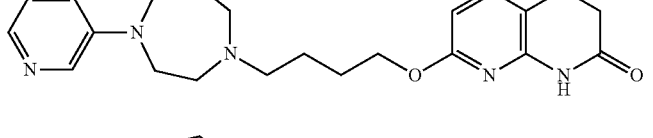 | 7-(4-(4-(pyridin-3-yl)-1,4-diazepan-1-yl)butoxy)-3,4-dihydro-1,8-naphthyridin-2(1H)-one |
| 82 | 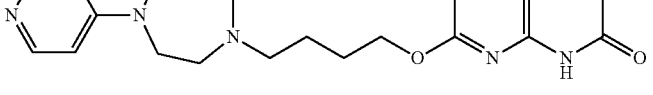 | 7-(4-(4-(pyridin-4-yl)-1,4-diazepan-1-yl)butoxy)-3,4-dihydro-1,8-naphthyridin-2(1H)-one |
| 83 | 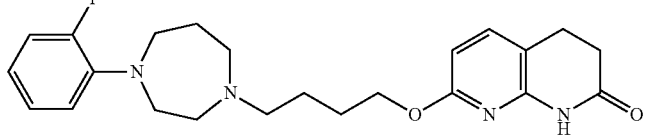 | 7-(4-(4-(2-fluorophenyl)-1,4-diazepan-1-yl)butoxy)-3,4-dihydro-1,8-naphthyridin-2(1H)-one |

TABLE 2-continued

| Compound Number | Structure | Name |
|---|---|---|
| 84 | 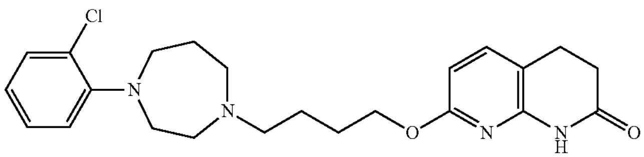 | 7-(4-(4-(2-chlorophenyl)-1,4-diazepan-1-yl)butoxy)-3,4-dihydro-1,8-naphthyridin-2(1H)-one |
| 85 | 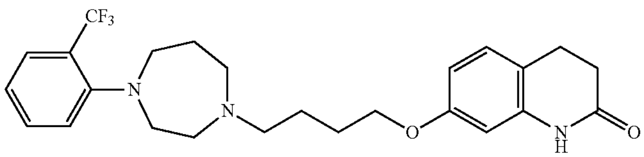 | 7-(4-(4-(2-(trifluoromethyl)phenyl)-1,4-diazepan-1-yl)butoxy)-3,4-dihydroquinolin-2(1H)-one |
| 86 | 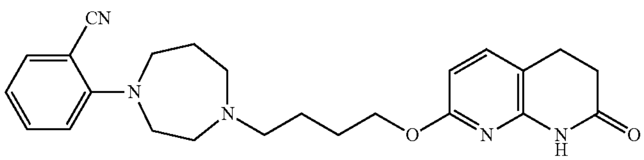 [SMILES: O=C1CCc2ccc(OCCCCN3CCCN(c4ccccc4Cl)CC3)nc2N1] | 2-(4-(4-(7-oxo-5,6,7,8-tetrahydro-1,8-naphthyridin-2-yloxy)butyl)-1,4-diazepan-1-yl)benzonitrile |
| 87 | 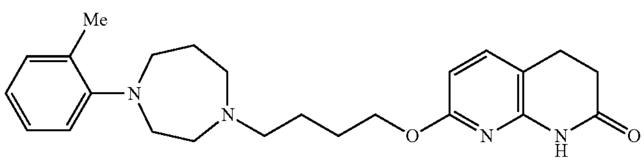 [SMILES: Cc1ccccc1N1CCCN(CCCCOc2ccc3c(n2)NC(=O)CC3)CC1] | 7-(4-(4-o-tolyl-1,4-diazepan-1-yl)butoxy)-3,4-dihydro-1,8-naphthyridin-2(1H)-one |
| 92 | 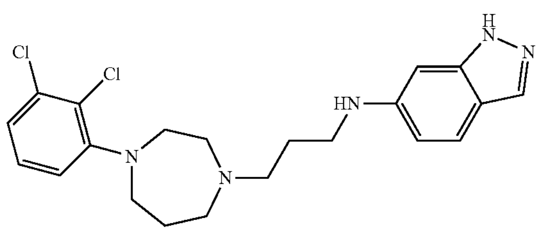 [SMILES: Clc1cccc(N2CCCN(CCCNc3ccc4cn[nH]c4c3)CC2)c1Cl] | N-(3-(4-(2,3-dichlorophenyl)-1,4-diazepan-1-yl)propyl)-1H-indazol-6-amine |
| 93 | 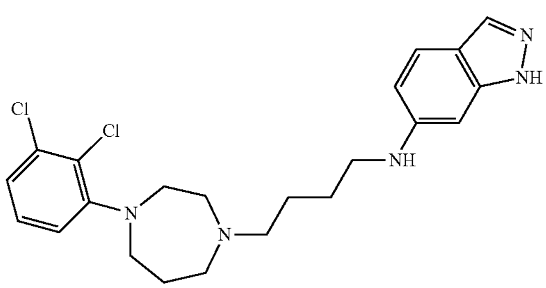 | N-(4-(4-(2,3-dichlorophenyl)-1,4-diazepan-1-yl)butyl)-1H-indazol-6-amine |
| 102 | 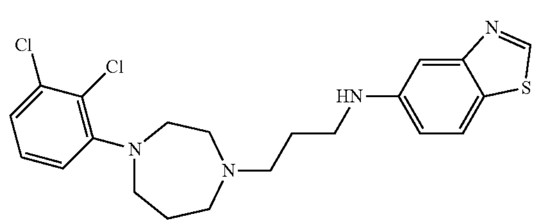 [SMILES: Clc1cccc(N2CCCN(CCCNc3ccc4scnc4c3)CC2)c1Cl] | N-(3-(4-(2,3-dichlorophenyl)-1,4-diazepan-1-yl)propyl)benzo[d]thiazol-5-amine |

TABLE 2-continued

| Compound Number | Structure | Name |
|---|---|---|
| 103 | 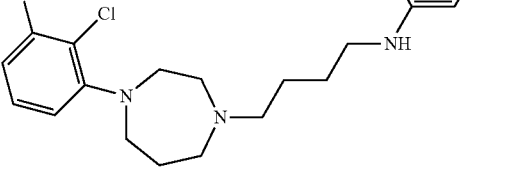 | N-(4-(4-(2,3-dichlorophenyl)-1,4-diazepan-1-yl)butyl)benzo[d]thiazol-5-amine |
| 116 | 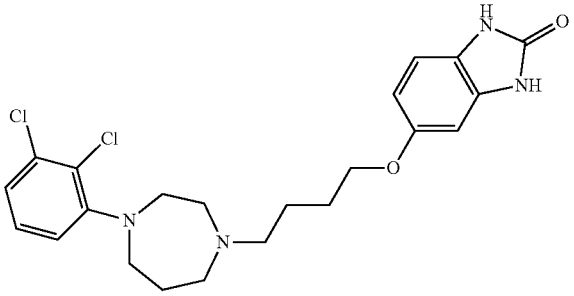 [SMILES: O=c1[nH]c2ccc(OCCCCN3CCCN(c4cccc(Cl)c4Cl)CC3)cc2[nH]1] | 5-(4-(4-(2,3-dichlorophenyl)-1,4-diazepan-1-yl)butoxy)-1H-benzo[d]imidazol-2(3H)-one |
| 117 | 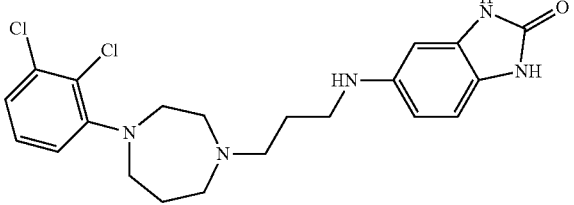 | 5-(3-(4-(2,3-dichlorophenyl)-1,4-diazepan-1-yl)propylamino)-1H-benzo[d]imidazol-2(3H)-one |
| 118 | 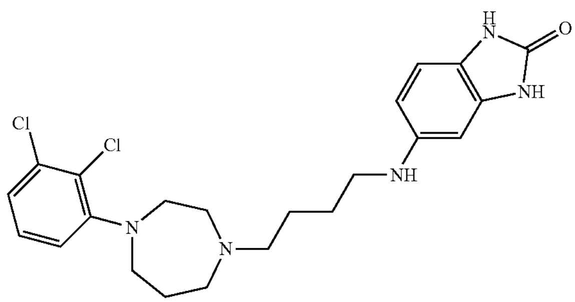 [SMILES: O=c1[nH]c2ccc(NCCCCN3CCCN(c4cccc(Cl)c4Cl)CC3)cc2[nH]1] | 5-(4-(4-(2,3-dichlorophenyl)-1,4-diazepan-1-yl)butylamino)-1H-benzo[d]imidazol-2(3H)-one |

In one embodiment, the compound of the invention has the structure of formula VI:

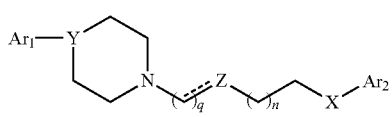

VI wherein n is 0, 1, or 2;
q is 1 or 2;
X is O, NH, or $CH_2$;
Y is N or CH;
Z is C, CH, $CH_2$, cycloalkyl, aryl, or heteroaryl;
----- is optionally a single, double, or triple bond as valencies permit; and
$Ar_1$ and $Ar_2$ are independently an unsubstituted or substituted monocyclic or bicyclic aryl or heteroaryl;

or a pharmaceutically acceptable salt, prodrug, or optical isomer thereof.

In one embodiment, $Ar_2$ is an unsubstituted or substituted bicyclic aryl or heteroaryl. In another embodiment, Z is C, CH, $CH_2$, cycloalkyl, monocyclic aryl, or monocyclic heteroaryl.

In one embodiment for the compound of formula VI, n is 0. In a different embodiment, n is 1. In another embodiment, X is O or NH.

In one embodiment for the compound of formula VI, $Ar_1$ is selected from the group consisting of substituted phenyl (e.g., dichlorophenyl, methoxyphenyl), 2H-benzo[b][1,4]oxazin-3(4H)-one, 2,3-dihydrobenzo[b][1,4]dioxinyl, and benzo[d]oxazol-2(3H)-one, or any subgroup selected from the list. In a further embodiment, $Ar_1$ is dichlorophenyl.

In another embodiment for the compound of formula VI, $Ar_2$ is selected from the group consisting of 1H-indazole, benzo[d]thiazole, imidazol-2(3H)-one, 3,4-dihydroisoquinolin-1(2H)-one, 3,4-dihydroquinolin-2(1H)-one, 1H-benzo[d]imidazol-2(3H)-one, 3,4-dihydro-1,8-naphthyridin-2(1H)-one, quinolin-2(1H)-one, 2-methylphenylacetamide, and benzo[d]oxazol-2(3H)-one, or any subgroup selected from the list. In a further embodiment, Ar$_2$ is selected from the group consisting of 1H-indazole, benzo[d]thiazole, and imidazol-2(3H)-one.

In another embodiment for the compound of formula VI, Ar$_1$ is dichlorophenyl or dihydrobenzodioxinyl and Ar$_2$ is dihydroquinolinone, benzothiazole, or indazole.

In another embodiment for the compound of formula V, Ar$_1$ is dichlorophenyl, methoxyphenyl, or dihydrobenzodioxinyl and Ar$_2$ is dihydroquinolinone, benzothiazole, indazole, benzoimidazolone, or quinolinone.

In another embodiment for the compound of formula VI, Y is N or CH, n is 0 or 1, X is O, Ar$_1$ is dichlorophenyl, and Ar$_2$ is selected from the group consisting of 1H-indazole, benzo[d]thiazole, and 1H-benzoimidazol-2(3H)-one.

In certain embodiments for the compound of formula VI, Ar$_2$ is not naphthyridinone, dihydronaphthyridinone, quinolinone, dihydroquinolinone, tetrahydropyridoazepinone, or isoindole.

In one embodiment, the compound of formula VI is selected from the group of compounds shown in Tables 3 and 4.

TABLE 3

20 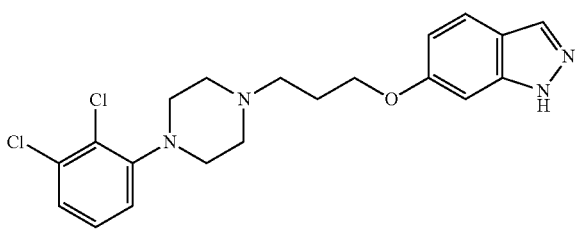 [SMILES: Clc1cccc(N2CCN(CCCOc3ccc4cn[nH]c4c3)CC2)c1Cl] 6-(3-(4-(2,3-dichlorophenyl)piperazin-1-yl)propoxy)-1H-indazole

21 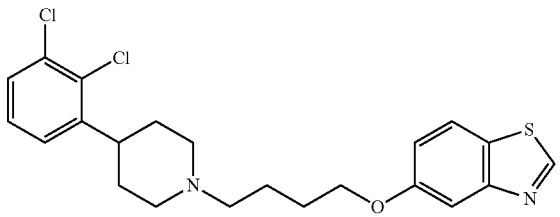 5-(4-(4-(2,3-dichlorophenyl)piperidin-1-yl)butoxy)benzo[d]thiazole 22 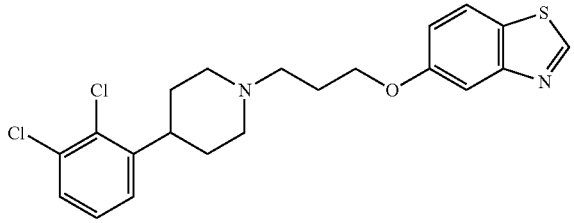 [SMILES: Clc1cccc(C2CCN(CCCOc3ccc4scnc4c3)CC2)c1Cl] 5-(3-(4-(2,3-dichlorophenyl)piperidin-1-yl)propoxy)benzo[d]thiazole 23 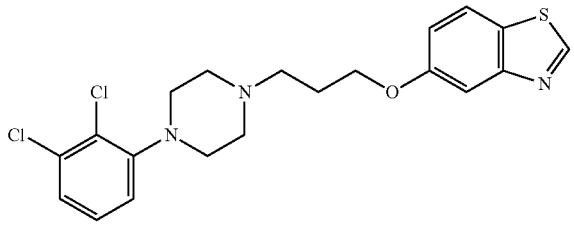 [SMILES: Clc1cccc(N2CCN(CCCOc3ccc4scnc4c3)CC2)c1Cl] 5-(3-(4-(2,3-dichlorophenyl)piperazin-1-yl)propoxy)benzo[d]thiazole 24 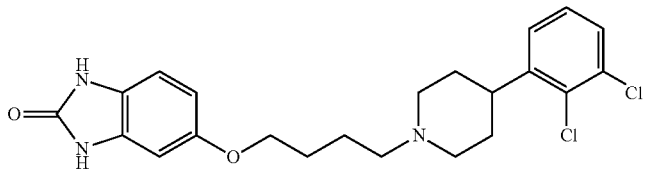 [SMILES: O=c1[nH]c2ccc(OCCCCN3CCC(c4cccc(Cl)c4Cl)CC3)cc2[nH]1] 5-(4-(4-(2,3-dichlorophenyl)piperidin-1-yl)butoxy)-1H-benzo[d]imidazol-2(3H)-one TABLE 3-continued

| 25 | 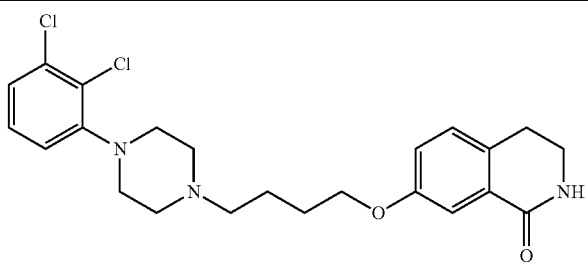 | 7-(4-(4-(2,3-dichlorophenyl)piperazin-1-yl)butoxy)-3,4-dihydroisoquinolin-1(2H)-one |
| 26 | 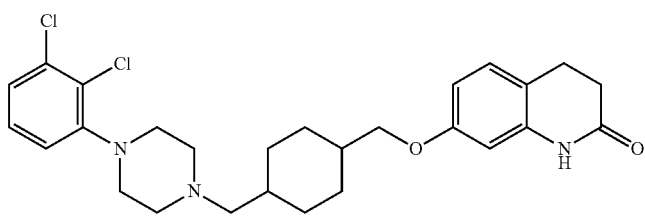 [SMILES: O=C1CCc2ccc(OCC3CCC(CN4CCN(c5cccc(Cl)c5Cl)CC4)CC3)cc2N1] | 7-((4-((4-(2,3-dichlorophenyl)piperazin-1-yl)methyl)cyclohexyl)methoxy)-3,4-dihydroquinolin-2(1H)-one |
| 27 | 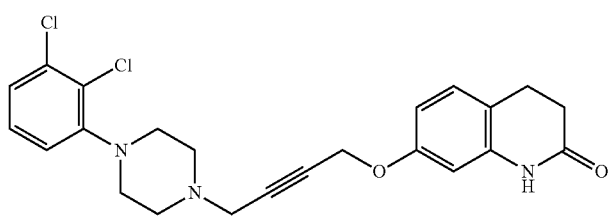 | 7-(4-(4-(2,3-dichlorophenyl)piperazin-1-yl)but-2-ynyloxy)-3,4-dihydroquinolin-2(1H)-one |
| 28 | 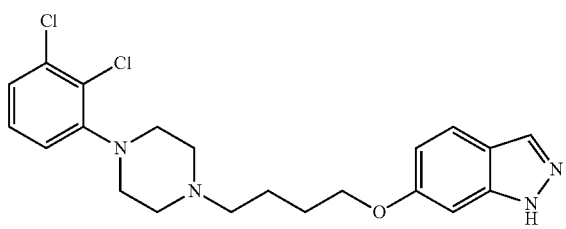 [SMILES: Clc1cccc(N2CCN(CCCCOc3ccc4cn[nH]c4c3)CC2)c1Cl] | 6-(4-(4-(2,3-dichlorophenyl)piperazin-1-yl)butoxy)-1H-indazole |
| 29 | 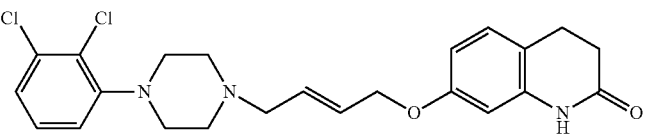 | (E)-7-(4-(4-(2,3-dichlorophenyl)piperazin-1-yl)but-2-enyloxy)-3,4-dihydroquinolin-2(1H)-one |
| 30 | 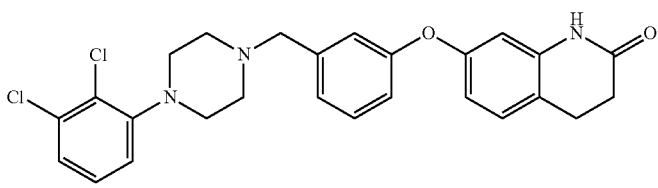 [SMILES: O=C1CCc2ccc(Oc3cccc(CN4CCN(c5cccc(Cl)c5Cl)CC4)c3)cc2N1] | 7-(3-((4-(2,3-dichlorophenyl)piperazin-1-yl)methyl)phenoxy)-3,4-dihydroquinolin-2(1H)-one |
| 31 | 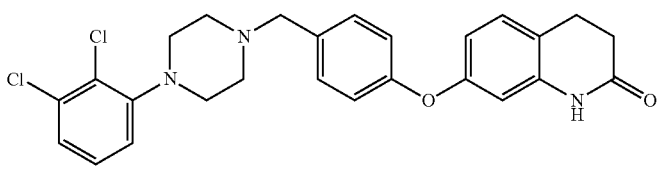 [SMILES: O=C1CCc2ccc(Oc3ccc(CN4CCN(c5cccc(Cl)c5Cl)CC4)cc3)cc2N1] | 7-(4-((4-(2,3-dichlorophenyl)piperazin-1-yl)methyl)phenoxy)-3,4-dihydroquinolin-2(1H)-one |

TABLE 3-continued

| 32 | 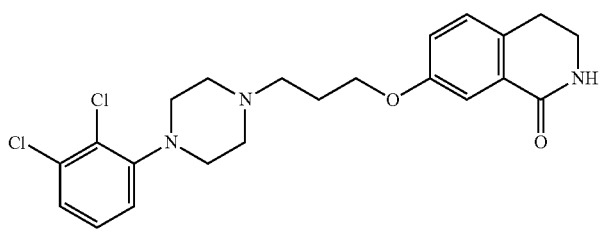 [SMILES: O=C1NCCc2ccc(OCCCN3CCN(c4cccc(Cl)c4Cl)CC3)cc21] | 7-(3-(4-(2,3-dichlorophenyl)piperazin-1-yl)propoxy)-3,4-dihydroisoquinolin-1(2H)-one |
| --- | --- | --- |
| 33 | 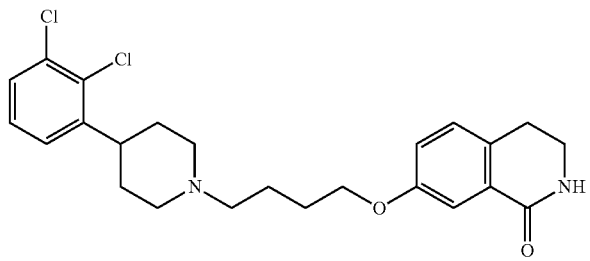 [SMILES: O=C1NCCc2ccc(OCCCCN3CCC(c4cccc(Cl)c4Cl)CC3)cc21] | 7-(4-(4-(2,3-dichlorophenyl)piperidin-1-yl)butoxy)-3,4-dihydroisoquinolin-1(2H)-one |
| 34 | 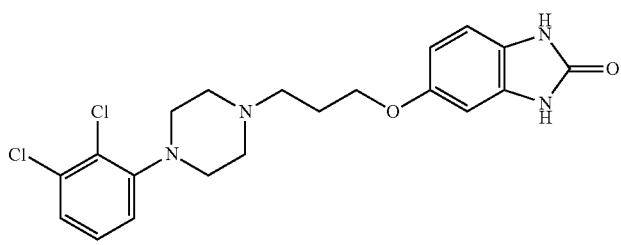 [SMILES: O=c1[nH]c2ccc(OCCCN3CCN(c4cccc(Cl)c4Cl)CC3)cc2[nH]1] | 5-(3-(4-(2,3-dichlorophenyl)piperazin-1-yl)propoxy)-1H-benzo[d]imidazol-2(3H)-one |
| 35 | 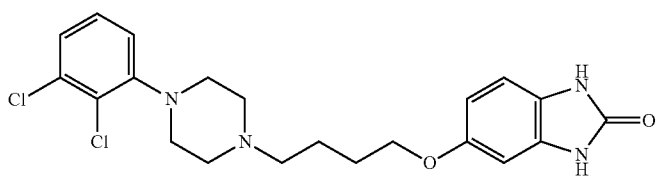 [SMILES: O=c1[nH]c2ccc(OCCCCN3CCN(c4cccc(Cl)c4Cl)CC3)cc2[nH]1] | 5-(4-(4-(2,3-dichlorophenyl)piperazin-1-yl)butoxy)-1H-benzo[d]imidazol-2(3H)-one |
| 36 | 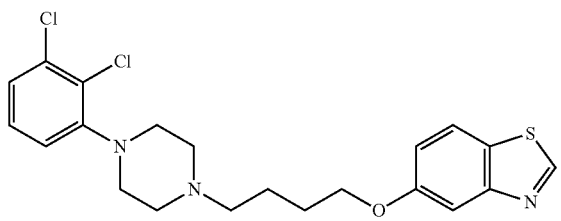 [SMILES: Clc1cccc(N2CCN(CCCCOc3ccc4scnc4c3)CC2)c1Cl] | 5-(4-(4-(2,3-dichlorophenyl)piperazin-1-yl)butoxy)benzo[d]thiazole |
| 37 | 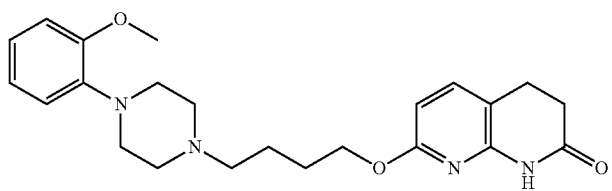 [SMILES: COc1ccccc1N1CCN(CCCCOc2ccc3c(n2)NC(=O)CC3)CC1] | 7-(4-(4-(2-methoxyphenyl)piperazin-1-yl)butoxy)-3,4-dihydro-1,8-naphthyridin-2(1H)-one |
| 38 | 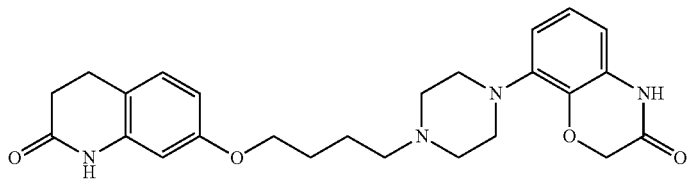 [SMILES: O=C1CCc2ccc(OCCCCN3CCN(c4cccc5c4OCC(=O)N5)CC3)cc2N1] | 8-(4-(4-(2-oxo-1,2,3,4-tetrahydroquinolin-7-yloxy)butyl)piperazin-1-yl)-2H-benzo[b][1,4]oxazin-3(4H)-one |

TABLE 3-continued

| | | |
|---|---|---|
| 39 | | 7-(4-(4-(2-methoxyphenyl)piperazin-1-yl)butoxy)-3,4-dihydroquinolin-2(1H)-one |
| 40 | | 7-(4-(4-(2,3-dihydrobenzo[b][1,4]dioxin-5-yl)piperazin-1-yl)butoxy)-3,4-dihydroquinolin-2(1H)-one |
| 41 | | 7-(4-(4-(2,3-dihydrobenzo[b][1,4]dioxin-5-yl)piperazin-1-yl)butoxy)-3,4-dihydro-1,8-naphthyridin-2(1H)-one |
| 42 | | 7-(4-(4-(2,3-dihydrobenzo[b][1,4]dioxin-5-yl)piperazin-1-yl)butoxy)quinolin-2(1H)-one |
| 43 | | N-(5-(4-(4-(2,3-dichlorophenyl)piperazin-1-yl)butoxy)-2-methylphenyl)acetamide |
| 44 | | 6-(3-(4-(2,3-dichlorophenyl)piperidin-1-yl)propoxy)-1H-indazole |
| 45 | | 6-(4-(4-(2,3-dichlorophenyl)piperidin-1-yl)butoxy)-1H-indazole |

TABLE 3-continued
| | | |
|---|---|---|
| 48 | 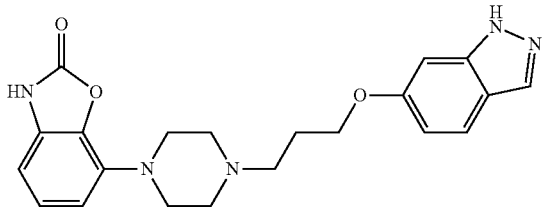 [SMILES: O=c1[nH]c2cccc(N3CCN(CCCOc4ccc5cn[nH]c5c4)CC3)c2o1] | 7-(4-(3-(1H-indazol-6-yloxy)propyl)piperazin-1-yl)benzo[d]oxazol-2(3H)-one |
| 49 | 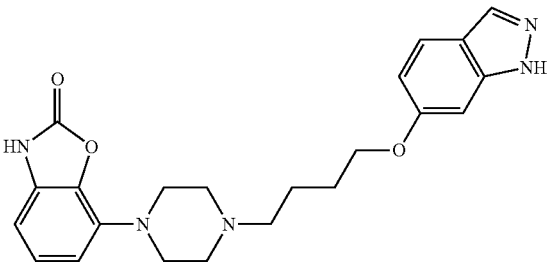 | 7-(4-(4-(1H-indazol-6-yloxy)butyl)piperazin-1-yl)benzo[d]oxazol-2(3H)-one |
| 50 | 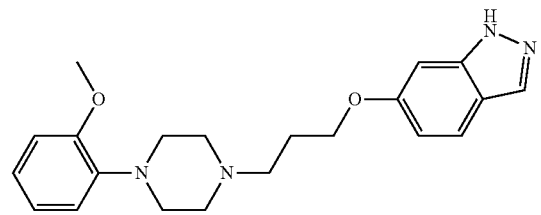 [SMILES: COc1ccccc1N1CCN(CCCOc2ccc3cn[nH]c3c2)CC1] | 6-(3-(4-(2-methoxyphenyl)piperazin-1-yl)propoxy)-1H-indazole |
| 51 | 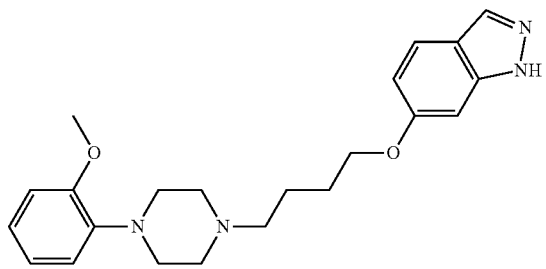 [SMILES: COc1ccccc1N1CCN(CCCCOc2ccc3cn[nH]c3c2)CC1] | 6-(4-(4-(2-methoxyphenyl)piperazin-1-yl)butoxy)-1H-indazole |
TABLE 4
| | | |
|---|---|---|
| 88 | 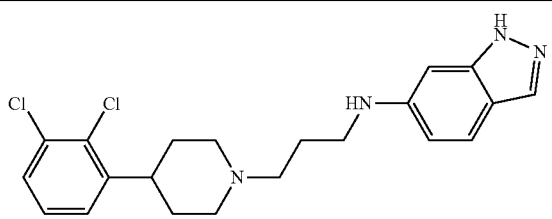 | N-(3-(4-(2,3-dichlorophenyl)piperidin-1-yl)propyl)-1H-indazol-6-amine |
| 89 | 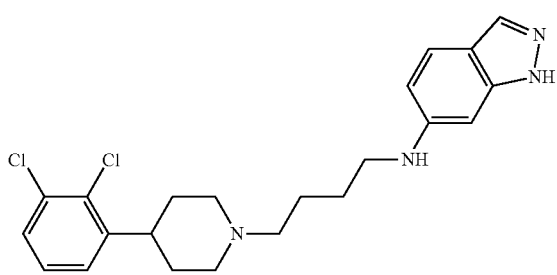 [SMILES: Clc1cccc(C2CCN(CCCCNc3ccc4cn[nH]c4c3)CC2)c1Cl] | N-(4-(4-(2,3-dichlorophenyl)piperidin-1-yl)butyl)-1H-indazol-6-amine |

TABLE 4-continued
| | | |
|---|---|---|
| 90 | 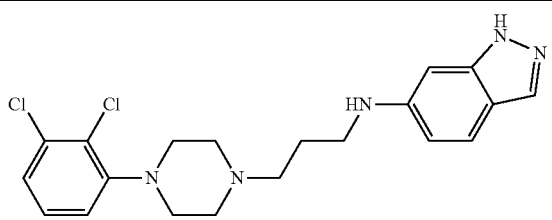 | N-(3-(4-(2,3-dichlorophenyl)piperazin-1-yl)propyl)-1H-indazol-6-amine |
| 91 | 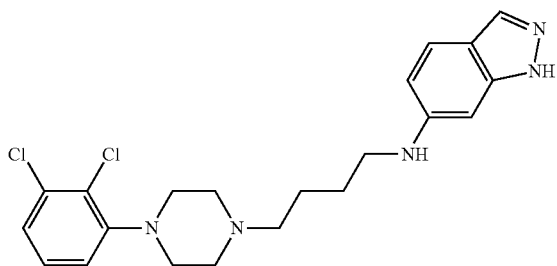 [SMILES: Clc1cccc(N2CCN(CCCCNc3ccc4cn[nH]c4c3)CC2)c1Cl] | N-(4-(4-(2,3-dichlorophenyl)piperazin-1-yl)butyl)-1H-indazol-6-amine |
| 94 | 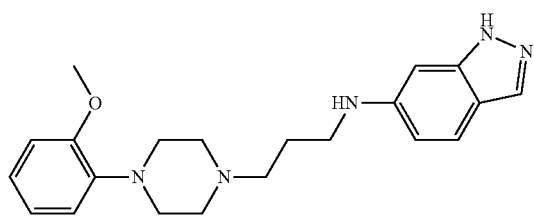 | N-(3-(4-(2-methoxyphenyl)piperazin-1-yl)propyl)-1H-indazol-6-amine |
| 95 | 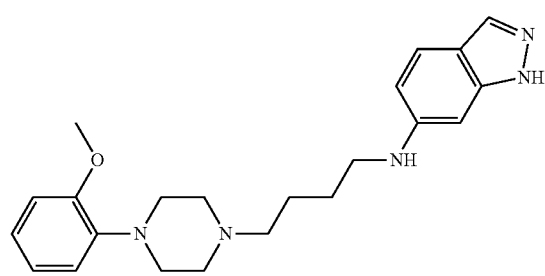 [SMILES: COc1ccccc1N1CCN(CCCCNc2ccc3cn[nH]c3c2)CC1] | N-(4-(4-(2-methoxyphenyl)piperazin-1-yl)butyl)-1H-indazol-6-amine |
| 96 | 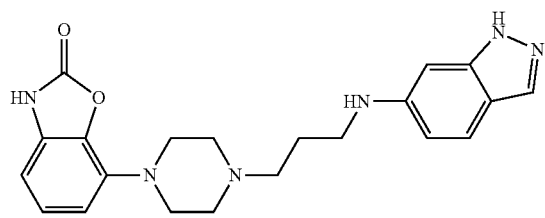 [SMILES: O=c1[nH]c2cccc(N3CCN(CCCNc4ccc5cn[nH]c5c4)CC3)c2o1] | 7-(4-(3-(1H-indazol-6-ylamino)propyl)piperazin-1-yl)benzo[d]oxazol-2(3H)-one |
| 97 | 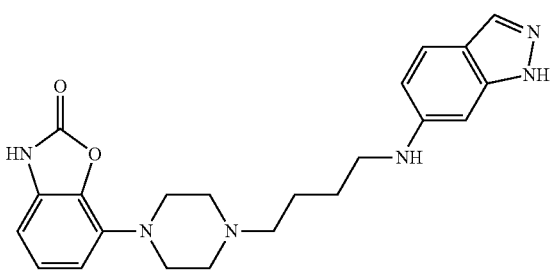 | 7-(4-(4-(1H-indazol-6-ylamino)butyl)piperazin-1-yl)benzo[d]oxazol-2(3H)-one |

TABLE 4-continued

| | | |
|---|---|---|
| 98 | 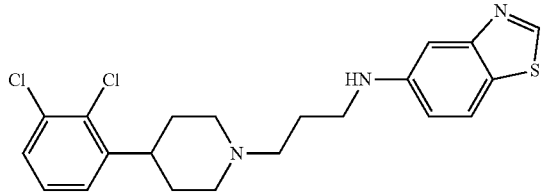 [SMILES: Clc1cccc(C2CCN(CCCNc3ccc4scnc4c3)CC2)c1Cl] | N-(3-(4-(2,3-dichlorophenyl)piperidin-1-yl)propyl)benzo[d]thiazol-5-amine |
| 99 | 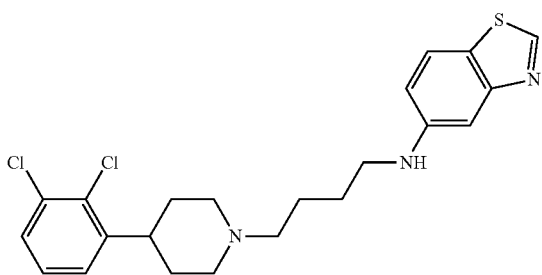 [SMILES: Clc1cccc(C2CCN(CCCCNc3ccc4scnc4c3)CC2)c1Cl] | N-(4-(4-(2,3-dichlorophenyl)piperidin-1-yl)butyl)benzo[d]thiazol-5-amine |
| 100 | 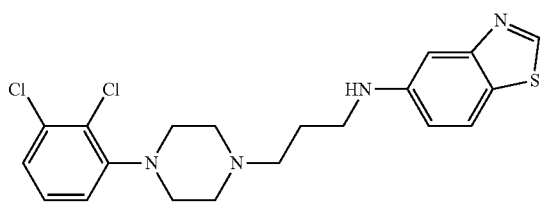 | N-(3-(4-(2,3-dichlorophenyl)piperazin-1-yl)propyl)benzo[d]thiazol-5-amine |
| 101 | 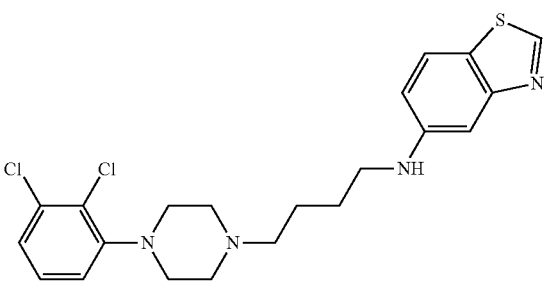 [SMILES: Clc1cccc(N2CCN(CCCCNc3ccc4scnc4c3)CC2)c1Cl] | N-(4-(4-(2,3-dichlorophenyl)piperazin-1-yl)butyl)benzo[d]thiazol-5-amine |
| 104 | 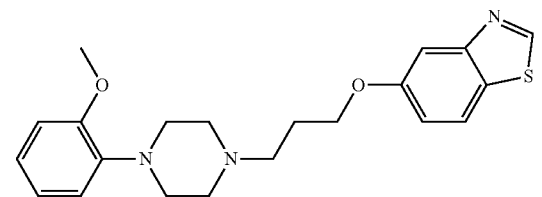 [SMILES: COc1ccccc1N1CCN(CCCOc2ccc3scnc3c2)CC1] | 5-(3-(4-(2-methoxyphenyl)piperazin-1-yl)propoxy)benzo[d]thiazole |
| 105 | 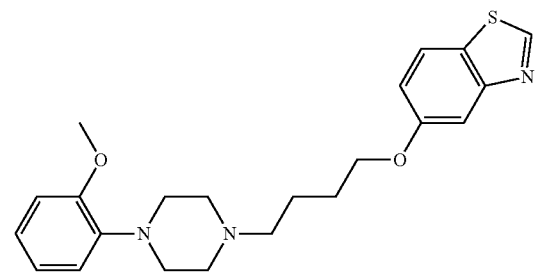 [SMILES: COc1ccccc1N1CCN(CCCCOc2ccc3scnc3c2)CC1] | 5-(4-(4-(2-methoxyphenyl)piperazin-1-yl)butoxy)benzo[d]thiazole |

TABLE 4-continued

| | | |
|---|---|---|
| 106 | 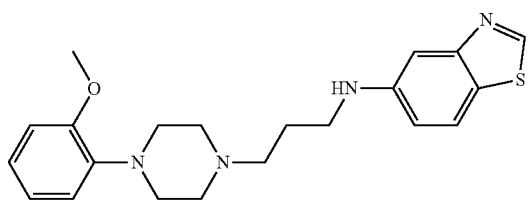 [SMILES: COc1ccccc1N1CCN(CCCNc2ccc3scnc3c2)CC1] | N-(3-(4-(2-methoxyphenyl)piperazin-1-yl)propyl)benzo[d]thiazol-5-amine |
| 107 | 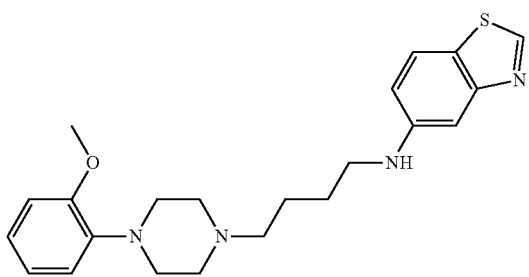 [SMILES: COc1ccccc1N1CCN(CCCCNc2ccc3scnc3c2)CC1] | N-(4-(4-(2-methoxyphenyl)piperazin-1-yl)butyl)benzo[d]thiazol-5-amine |
| 108 | 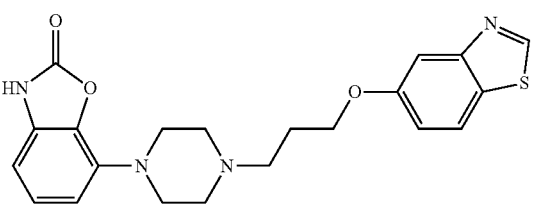 [SMILES: O=c1[nH]c2cccc(N3CCN(CCCOc4ccc5scnc5c4)CC3)c2o1] | 7-(4-(3-(benzo[d]thiazol-5-yloxy)propyl)piperazin-1-yl)benzo[d]oxazol-2(3H)-one |
| 109 | 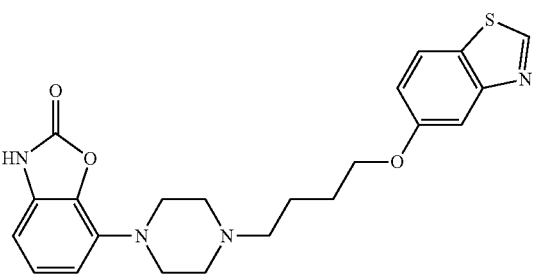 | 7-(4-(4-(benzo[d]thiazol-5-yloxy)butyl)piperazin-1-yl)benzo[d]oxazol-2(3H)-one |
| 110 | 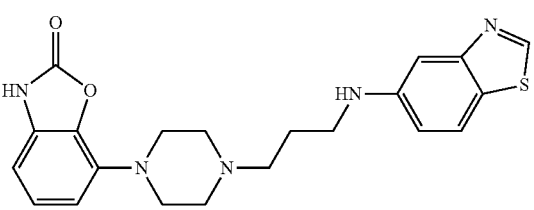 | 7-(4-(3-(benzo[d]thiazol-5-ylamino)propyl)piperazin-1-yl)benzo[d]oxazol-2(3H)-one |
| 111 | 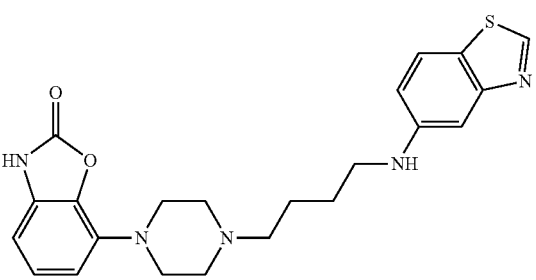 [SMILES: O=c1[nH]c2cccc(N3CCN(CCCCNc4ccc5scnc5c4)CC3)c2o1] | 7-(4-(4-(benzo[d]thiazol-5-ylamino)butyl)piperazin-1-yl)benzo[d]oxazol-2(3H)-one |

TABLE 4-continued

| # | Structure | Name |
|---|---|---|
| 112 | 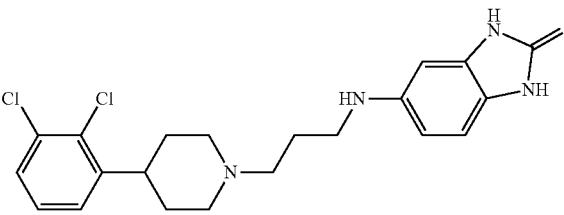 | 5-(3-(4-(2,3-dichlorophenyl)piperidin-1-yl)propylamino)-1H-benzo[d]imidazol-2(3H)-one |
| 113 | 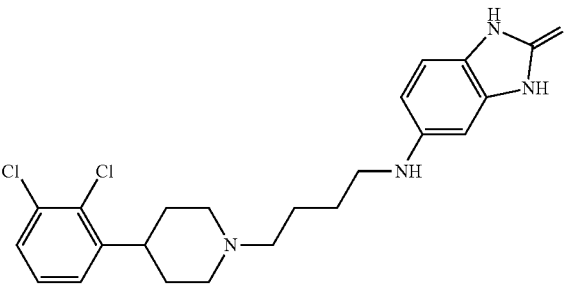 | 5-(4-(4-(2,3-dichlorophenyl)piperidin-1-yl)butylamino)-1H-benzo[d]imidazol-2(3H)-one |
| 114 | 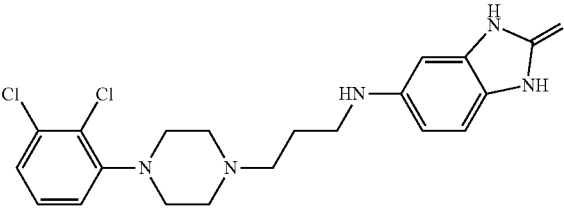 | 5-(3-(4-(2,3-dichlorophenyl)piperazin-1-yl)propylamino)-1H-benzo[d]imidazol-2(3H)-one |
| 115 | 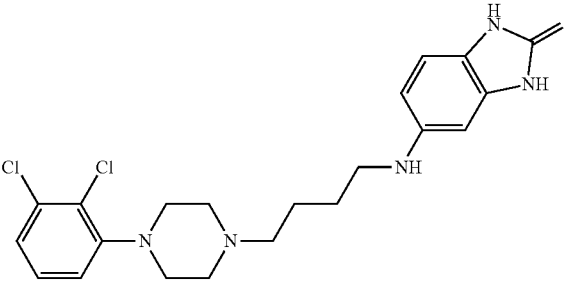 | 5-(4-(4-(2,3-dichlorophenyl)piperazin-1-yl)butylamino)-1H-benzo[d]imidazol-2(3H)-one |
| 119 | 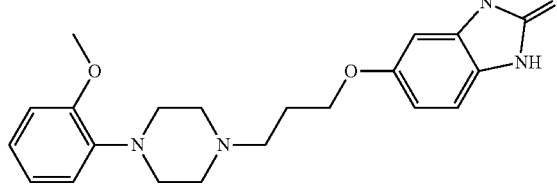 | 5-(3-(4-(2-methoxyphenyl)piperazin-1-yl)propoxy)-1H-benzo[d]imidazol-2(3H)-one |
| 120 | 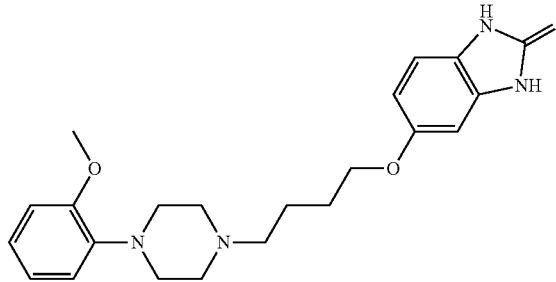 | 5-(4-(4-(2-methoxyphenyl)piperazin-1-yl)butoxy)-1H-benzo[d]imidazol-2(3H)-one |

TABLE 4-continued

| 121 | 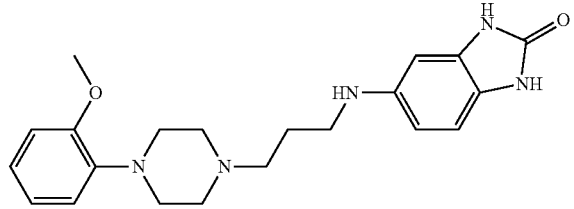 [SMILES: COc1ccccc1N1CCN(CCCNc2ccc3[nH]c(=O)[nH]c3c2)CC1] | 5-(3-(4-(2-methoxyphenyl)piperazin-1-yl)propylamino)-1H-benzo[d]imidazol-2(3H)-one |
| 122 | 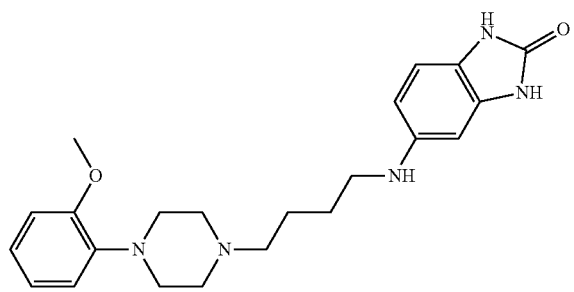 [SMILES: COc1ccccc1N1CCN(CCCCNc2ccc3[nH]c(=O)[nH]c3c2)CC1] | 5-(4-(4-(2-methoxyphenyl)piperazin-1-yl)butylamino)-1H-benzo[d]imidazol-2(3H)-one |
| 123 | 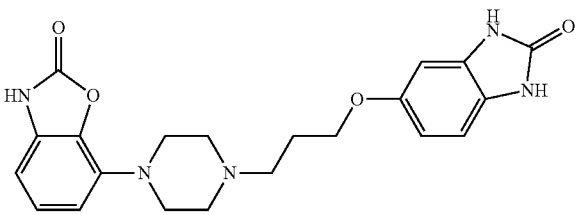 [SMILES: O=c1[nH]c2ccc(OCCCN3CCN(c4cccc5[nH]c(=O)oc45)CC3)cc2[nH]1] | 7-(4-(3-(2-oxo-2,3-dihydro-1H-benzo[d]imidazol-5-yloxy)propyl)piperazin-1-yl)benzo[d]oxazol-2(3H)-one |
| 124 | 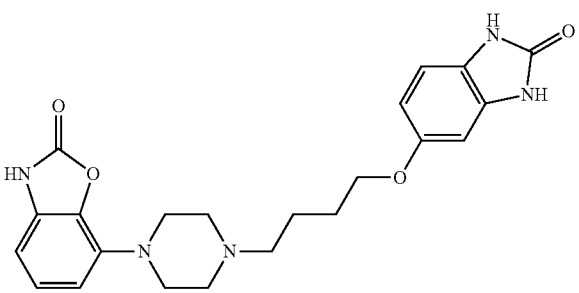 [SMILES: O=c1[nH]c2ccc(OCCCCN3CCN(c4cccc5[nH]c(=O)oc45)CC3)cc2[nH]1] | 7-(4-(4-(2-oxo-2,3-dihydro-1H-benzo[d]imidazol-5-yloxy)butyl)piperazin-1-yl)benzo[d]oxazol-2(3H)-one |
| 125 | 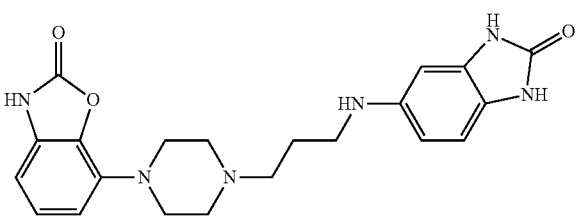 [SMILES: O=c1[nH]c2ccc(NCCCN3CCN(c4cccc5[nH]c(=O)oc45)CC3)cc2[nH]1] | 7-(4-(3-(2-oxo-2,3-dihydro-1H-benzo[d]imidazol-5-ylamino)propyl)piperazin-1-yl)benzo[d]oxazol-2(3H)-one |
| 126 | 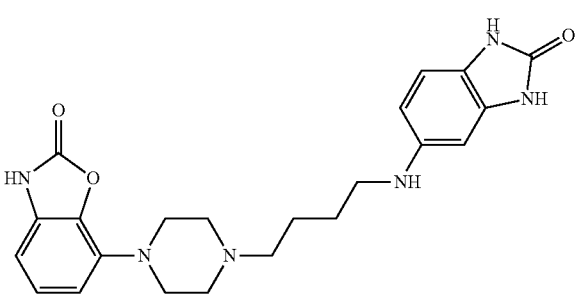 | 7-(4-(4-(2-oxo-2,3-dihydro-1H-benzo[d]imidazol-5-ylamino)butyl)piperazin-1-yl)benzo[d]oxazol-2(3H)-one |

The compounds of the invention can be synthesized in a similar way as Examples 1-51 below and/or according to Feenstra et al., *Bioorg. Med. Chem. Lett.* 11:2345 (2001) (incorporated herein by reference in its entirety).

The compounds of this invention include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4^+$ salts.

Compounds of the formulae herein include those having quaternization of any basic nitrogen-containing group therein.

The compounds of this invention include deuterium-substituted versions of the disclosed compounds, e.g., compounds comprising 1, 2, 3, 4, 5, 6, 7, 8, 9, or 10 or more deuterium atoms.

The discussion herein is, for simplicity, provided without reference to stereoisomerism. Those skilled in the art will appreciate that the compounds of the invention can contain one or more asymmetric centers and thus occur as racemates and racemic mixtures, single optical isomers, individual diastereomers, and diastereomeric mixtures. All such isomeric forms of these compounds are expressly included in the present invention.

Similarly, compounds of the invention containing a double bond can exist in the form of geometric isomers, which can be readily separated and recovered by conventional procedures. Such isomeric forms are included in the scope of this invention.

Further, the compounds of the invention include prodrugs of the compounds that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; a N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. No. 6,680,324 and U.S. Pat. No. 6,680,322.

The term "pharmaceutically acceptable prodrug" (and like terms) as used herein refers to those prodrugs of the compounds of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compounds of the invention.

Methods.

The compounds in Tables 1 and 3 were designed and synthesized as novel, functionally selective ligands of dopamine $D_2$ receptors to elucidate the key signal transduction pathways essential for antipsychotic efficacy and the undesired ones associated with side-effects. These novel compounds were evaluated in multiple $D_2$ binding and functional assays: $D_2$ radioligand binding, $D_2$ cAMP GloSensor, $D_2$ ERK phosphorylation (p-ERK), and/or $D_2$ β-arrestin 2 translocation (Tango). In the $D_2$ cAMP GloSensor assay, these compounds showed different activity profiles ranging from full agonists to antagonists to inverse agonists of the $G_i$-regulated cAMP pathway. In the $D_2$ β-arrestin recruitment (Tango) assay, these compounds showed activity profiles ranging from little agonist activity to full agonist activity of the β-arrestin pathway. In the $D_2$ ERK phosphorylation (p-ERK) assay, these compounds again showed different activity profiles ranging from antagonists to partial agonists that are more efficacious compared to aripiprazole with similar potency. Several β-arrestin biased, functionally selective $D_2$ ligands were efficacious in D-amphetamine-induced and phencyclidine (PCP)-induced hyperlocomotion mouse models and did not induce catalepsy in wild-type mice at pharmacologically active doses. Interestingly, these compounds showed significantly attenuated antipsychotic-like activity and increased catalepsy in β-arrestin-2 knockout mice. These novel, pharmacologically active compounds are useful agents for studying dopamine receptor function and signaling pathways, as well as for treating CNS disorders. Furthermore, the compounds may have advantageous pharmacokinetic characteristics for treating CNS disorders, including a longer half life in brain and higher brain: plasma ratio over 24 h compared to other antipsychotic compounds. Additionally, the receptor binding pattern of the compounds (e.g., relative low potency at histamine receptors) suggests that the compounds may exhibit a lower risk for side effects, such as sedation and/or cognitive impairment.

Thus, one aspect of the invention relates to a method of modulating the activity of a $D_2$ dopamine receptor comprising contacting the receptor with a compound of the invention. The $D_2$ dopamine receptor may be present in a cell, an isolated cell membrane or an artificial membrane. The cell may be a cultured cell, a cell isolated from a subject, or a cell in a subject (e.g., an animal model of disease or a patient). The receptor may be a wild-type or modified receptor and may be naturally-occurring or recombinantly expressed. The term "modulating" is intended to encompass any type of change in one or more activities of the receptor, including increasing or decreasing the activity of one or more receptor-linked signaling pathways.

Many of the compounds of the invention display potent antipsychotic activity in animal models in vivo and are thus predicted to possess antipsychotic actions in humans and other animals. The compounds would thus be effective for treating diseases including, but not limited to, a variety of psychiatric disorders including: schizophrenia, schizoaffective disorder, schizophreniform disorder, bipolar disorder, mania, manic psychosis, Tourette's syndrome and Tourette-like disorders, obsessive-compulsive disorder, depression with psychotic features, psychosis not otherwise specified (Psychosis NOS) and additional affective and non-affective psychiatric disorders. Additionally, the compounds would be effective against a number of neurological disorders including Huntington's Disease, Parkinsonian Psychosis, Alzheimer's Disease and associated psychosis and various organic brain syndromes. Further, the compounds would be effective at a variety of autism spectrum and autistic disorders. Given the $D_2$-receptor functional selectivity, the compounds would also be effective against pituitary diseases including pituitary adenomas and prolactinomas as well as endocrinological disorders including, but not limited to, galactorrhea.

The compounds have significant and unexpected advantages over conventional antipsychotic drugs in that they are predicted to effectively treat psychotic disorders without appreciable extra-pyramidal side effects (EPS), having minimal propensity for elevating serum prolactin and with a potentially lower risk of inducing tardive dyskinesia. Given the low affinities for $H_1$-histamine and partial agonism for $5\text{-HT}_{2C}$ serotonin receptors the compounds are expected to differ from approved atypical antipsychotic drugs by virtue of a lower propensity to induce weight gain and associated metabolic adverse consequences (diabetes, hyperlipidemia, hyperglycemia, hypercholesterolemia, hypertension and so on (Kroeze et al., *Neuropsychopharmacology* 28:519 (2003)). The compounds also lack agonist activity at $5\text{-HT}_{2B}$ serotonin receptors and hERG potassium channels and are thus predicted to have a low incidence of cardiovascular side-effects including prolongation of the Q-T interval and drug-induced valvular heart disease (Roth, N *Engl. J. Med.* 356:6 (2007)). Given the affinities of certain compounds for $5\text{-HT}_6$ and $5\text{-HT}_7$ receptors the compounds are expected to have potential cognition-enhancing and antidepressant actions (Abbas et al., *Psychopharmacology* (Berl) 205:119 (2009); Woolley et al., *Neuropharmacology* 41:210 (2001)). Thus, these compounds are likely to also be effective in treating bipolar depression, unipolar depression, and a variety of anxiety disorders as well as disorders such as Alzheimer's Disease, dementia, Niemann-Pick Disorder, and other late-life dementias.

Thus, one aspect of the invention relates to a method of treating a central nervous system disorder associated with $D_2$ dopamine receptors in a subject, comprising delivering to the subject a therapeutically effective amount of the compound of the invention. In certain embodiments, the disorder associated with $D_2$ dopamine receptors is a psychiatric, neurological, pituitary, or endocrine disorder.

In one embodiment of the invention, one or more of the compounds of the invention is administered to the subject as needed to treat a disorder. The compound can be administered continuously or intermittently. In one embodiment, the compound is administered to the subject more than once a day or once every 1, 2, 3, 4, 5, 6, or 7 days. In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules, e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject.

The compound of the invention can be delivered to the subject by any suitable route, e.g., oral, rectal, buccal (e.g., sub-lingual), vaginal, parenteral (e.g., subcutaneous, intramuscular, intradermal, or intravenous), topical (i.e., both skin and mucosal surfaces, including airway surfaces) and transdermal administration. The compound is delivered to the subject at a dose that is effective to treat the disorder. The effective dosage will depend on many factors including the gender, age, weight, and general physical condition of the subject, the severity of the disorder, the particular compound or composition being administered, the duration of the treatment, the nature of any concurrent treatment, the carrier used, and like factors within the knowledge and expertise of those skilled in the art. As appropriate, a treatment effective amount in any individual case can be determined by one of ordinary skill in the art by reference to the pertinent texts and literature and/or by using routine experimentation (see, e.g., Remington, The Science and Practice of Pharmacy ($21^{st}$ ed. 2005)). In one embodiment, the compound is administered at a dose of about 0.001 to about 10 mg/kg body weight, e.g., about 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, or 10 mg/kg. In some instances, the dose can be even lower, e.g., as low as 0.0005 or 0.0001 mg/kg or lower. In some instances, the dose can be even higher, e.g., as high as 20, 50, 100, 500, or 1000 mg/kg or higher. The present invention encompasses every sub-range within the cited ranges and amounts.

In one aspect of the invention, the compound of the invention is delivered to a subject concurrently with an additional therapeutic agent. The additional therapeutic agent can be delivered in the same composition as the compound or in a separate composition. The additional therapeutic agent can be delivered to the subject on a different schedule or by a different route as compared to the compound. The additional therapeutic agent can be any agent that provides a benefit to the subject. Further agents include, without limitation, anti-psychotics, anti-depressants, agents for neurological disorders, and chemotherapeutic agents.

Examples of anti-psychotic agents include, without limitation, for psychosis: prochloroperazine, chlorpromazine, droperidol, fluphenazine, periciazine, perphenazine, thiothixene, triflupromazine, haloperidol, molindone, pimozide, and thioridazine: and for schizophrenia: olanzapine, paliperidone, aripiprazole, quetiapine, risperidone, clozapine, flupenthixene, iloperidone, loxapine, mesoridazine, promazine, reserpine, thioridazine, zuclopenthixol, asenapine, levomepromazine, ziprasidone, molindone, pimozide, and thioridazine.

Examples of agents for depression and related disorders include, without limitation, for depression: modafinil, desvenlafaxine, nortriptyline, seleginline, amoxapine, citalopram, clomipramine, fluoxetine, isocarboxazid, mapriotiline, nefazodone, niacin, nortriptyline, phenelzine, protriptyline, tranylcypromine, trazodone, trimipramine, desipramine, imipramine, methylphenidate, buprorion, alprazolam, amitriptyline, chlordiazepoxide, perphenazine, doxepin, mirtazapine, 5-hydroxytryptophan, duloxetine, escitalopram, venlafaxine, desvenlafaxine, paroxetine, fluoxetine, olanzapine, 1-methylfolate, amitriptyline, sertraline, fluvoxamine, paliperidone, aripiprazole, quetiapine, risperidone, amisulpride; for anxiety: atomoxetine, aspirin, meprobamate, atenolol, buspirone, chlorodiazepoxide, chlorprothixene, clorazepate, diazepam, gabapentin, halazepam, hydroxyzine, lorazepam, meprobamate, nadolol, oxazepam, phenyloin, trifluoperazine, clonidine, clonazepam, oxcarbazepine, prochloroperazine, alprazolam, amitriptyline, chlordiazepoxide, perphenazine, doxepin, mirtazapine, 5-hydroxytryptophan, duloxetine, escitalopram, venlafaxine, desvenlafaxine, paroxetine, sertraline, fluvoxamine, amisulpride; and for bipolar disorder: clonidine, clonazapam, oxcarbazepine, carbamazepine, divalproex, lamotrigine, levetiracetam, lithium, topiramate, valproic acid, verapamil, buprorion, duloxetine, escitalopram, venlafaxine, 1-methylfolate, fluoxetine, olanzapine, sertraline, olanzapine, paliperidone, aripiprazole, quetiapine, risperidone, asenapine, levomepromazine, ziprasidone.

Examples of agents for neurological disorders include, without limitation, for Alzheimer's disease: caprylidene, donepezil, galantamine, tacrine, vitamin E, ergoloid mesylates, rivastigmine; for Parkinson's disease: nadolol, zonisamide, amantadine, apomorphine, belladonna, benztropine, biperiden, bromocriptine, carbidopa, entacapone, levodopa, pergolide mesylate, pramipexole, procyclidine, rasagiline, ropinirole, rotiotine, scopolamine, tolcapone, trihexylphenidyl, rivastigmine, seleginline; for Huntington's disease: baclofen, pregabalin, tetrabenazine, methylprednisolone, desvenlafaxine, nortriptyline; and for dementia: haloperidol and ergoloid mesylates.

Examples of chemotherapeutic agents include, without limitation, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacytidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II or rIL2), interferon alfa-2a, interferon alfa-2b, interferon alfa-n1, interferon alfa-n3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozotocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Examples of other chemotherapeutic agents include, but are not limited to, 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; prostatic carcinoma antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine;

edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; odansteron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has a CNS disorder associated with $D_2$ dopamine receptors. In other embodiments, the subject used in the methods of the invention is an animal model of a CNS disorder associated with $D_2$ dopamine receptors.

The subject can be a subject "in need of" the methods of the present invention, e.g., in need of the therapeutic effects of the inventive methods. For example, the subject can be a subject that is experiencing a CNS disorder associated with $D_2$ dopamine receptors and/or is anticipated to experience a CNS disorder associated with $D_2$ dopamine receptors, and the methods and compositions of the invention are used for therapeutic and/or prophylactic treatment.

The compounds of the invention described above can be formulated for administration in a pharmaceutical carrier in accordance with known techniques. See, e.g., Remington, *The Science And Practice of Pharmacy* ($21^{st}$ ed. 2005). In the manufacture of a pharmaceutical formulation according to the invention, the compound is typically admixed with, inter alia, an acceptable carrier. The carrier must, of course, be acceptable in the sense of being compatible with any other ingredients in the formulation and must not be deleterious to the patient. The carrier can be a solid or a liquid, or both, and can be formulated with the compound as a unit-dose formulation, for example, a tablet, which can contain from 0.01% or 0.5% to 95% or 99% by weight of the compound. One or more compounds can be incorporated in the formulations of the invention, which can be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the compound and a suitable carrier (which can contain one or more accessory ingredients as noted above). In general, the formulations of the invention are prepared by uniformly and intimately admixing the compound with a liquid or finely divided solid carrier, or both, and then, if necessary, shaping the resulting mixture. For example, a tablet can be prepared by compressing or molding a powder or granules containing the compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid binder.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the compound, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose (e.g., in a syringe or other injection device) or multi-dose containers, for example sealed ampoules and vials, and can be stored in a freeze-dried (lyophilized) condition requiring only the addition of the sterile liquid carrier, for example, saline or water-for-injection immediately prior to use. Extemporaneous injection solutions and suspensions can be prepared from sterile powders, granules and tablets of the kind previously described. For example, in one aspect of the present invention, there is provided an injectable, stable, sterile composition comprising one or more compounds, in a unit dosage form in a sealed container. The compound is provided in the form of a lyophilizate which is capable of being reconstituted with a suitable pharmaceutically acceptable carrier to form a liquid composition suitable for injection thereof into a subject. The unit dosage form typically comprises from about 0.001 mg to about 10 grams of the compound. When the compound is substantially water-insoluble (e.g., when conjugated to a lipid), a sufficient amount of emulsifying agent which is physiologically acceptable can be employed in sufficient quantity to emulsify the compound in an aqueous carrier. One such useful emulsifying agent is phosphatidyl choline.

Formulations suitable for rectal administration are preferably presented as unit dose suppositories. These can be prepared by admixing the compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharm. Res.* 3:318 (1986)) and typically take the form of an optionally buffered aqueous solution of the compound. Suitable formulations comprise citrate or bis\tris buffer (pH 6) or ethanol/water and contain from 0.1 to 0.2 M active ingredient.

Other pharmaceutical compositions can be prepared from the compounds disclosed herein, such as aqueous base emulsions. In such an instance, the composition will contain a sufficient amount of pharmaceutically acceptable emulsifying agent to emulsify the desired amount of the compound. Particularly useful emulsifying agents include phosphatidyl cholines and lecithin.

In addition to compound, the pharmaceutical compositions can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions can contain microbial preservatives. Useful microbial preservatives include methylparaben, propylparaben, and benzyl alcohol. The microbial preservative is typically employed when the formulation is placed in a vial designed for multidose use. Other additives that are well known in the art include, e.g., detackifiers, anti-foaming agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents (e.g., EDTA and/or EGTA), viscomodulators, tonicifiers (e.g., a sugar such as sucrose, lactose, and/or mannitol), flavorants, colorants, odorants, opacifiers, suspending agents, binders, fillers, plasticizers, lubricants, and mixtures thereof. The amounts of such additives can be readily determined by one skilled in the art, according to the particular properties desired.

The additive can also comprise a thickening agent. Suitable thickening agents can be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products. Such thickening agents as described above can be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

Further, the present invention provides liposomal formulations of the compounds disclosed herein. The technology for forming liposomal suspensions is well known in the art. When the compound is in the form of an aqueous-soluble material, using conventional liposome technology, the same can be incorporated into lipid vesicles. In such an instance, due to the water solubility of the compound, the compound will be substantially entrained within the hydrophilic center or core of the liposomes. The lipid layer employed can be of any conventional composition and can either contain cholesterol or can be cholesterol-free. When the compound of interest is water-insoluble, again employing conventional liposome formation technology, the compound can be substantially entrained within the hydrophobic lipid bilayer which forms the structure of the liposome. In either instance, the liposomes which are produced can be reduced in size, as through the use of standard sonication and homogenization techniques. The liposomal formulations containing the compound disclosed herein, can be lyophilized to produce a lyophilizate which can be reconstituted with a pharmaceutically acceptable carrier, such as water, to regenerate a liposomal suspension.

The present invention is explained in greater detail in the following non-limiting Examples.

EXAMPLE 1

Synthesis of Compounds

The compounds shown in Table 5 were synthesized as described below.

TABLE 5

| Compound Number | Structure | Name |
|---|---|---|
| 1 | 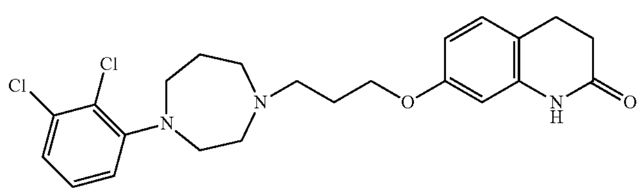 [SMILES: O=C1CCc2ccc(OCCCN3CCCN(c4cccc(Cl)c4Cl)CC3)cc2N1] | 7-(3-(4-(2,3-dichlorophenyl)-1,4-diazepan-1-yl)propoxy)-3,4-dihydroquinolin-2(1H)-one (UNC10000003A) |
| 2 | 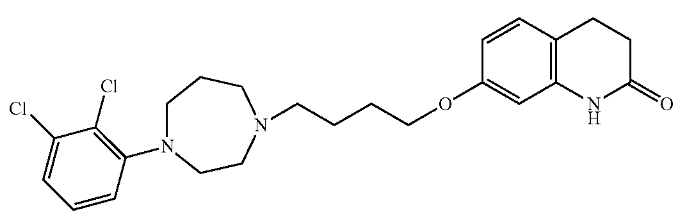 [SMILES: O=C1CCc2ccc(OCCCCN3CCCN(c4cccc(Cl)c4Cl)CC3)cc2N1] | 7-(4-(4-(2,3-dichlorophenyl)-1,4-diazepan-1-yl)butoxy)-3,4-dihydroquinolin-2(1H)-one (UNC10000006A, or UNC0006) |
| 3 | 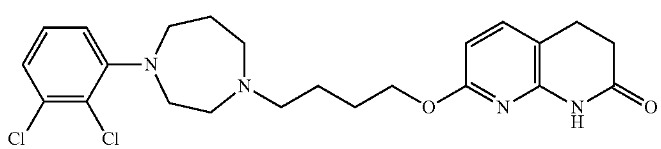 [SMILES: O=C1CCc2ccc(OCCCCN3CCCN(c4cccc(Cl)c4Cl)CC3)nc2N1] | 7-(4-(4-(2,3-dichlorophenyl)-1,4-diazepan-1-yl)butoxy)-3,4-dihydro-1,8-naphthyridin-2(1H)-one (UNC10099975A, or UNC9975) |
| 4 | 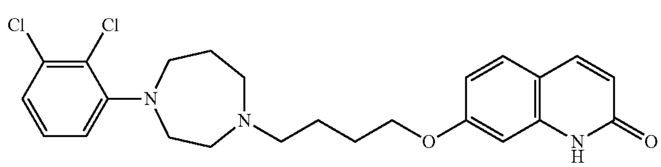 [SMILES: O=c1ccc2ccc(OCCCCN3CCCN(c4cccc(Cl)c4Cl)CC3)cc2[nH]1] | 7-(4-(4-(2,3-dichlorophenyl)-1,4-diazepan-1-yl)butoxy)quinolin-2(1H)-one (UNC10099978A) |
| 5 | 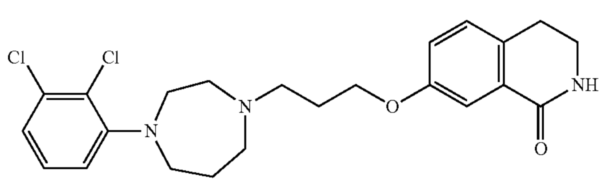 [SMILES: O=C1NCCc2ccc(OCCCN3CCCN(c4cccc(Cl)c4Cl)CC3)cc21] | 7-(3-(4-(2,3-dichlorophenyl)-1,4-diazepan-1-yl)propoxy)-3,4-dihydroisoquinolin-1(2H)-one (UNC10099983A) |

TABLE 5-continued

| Compound Number | Structure | Name |
| --- | --- | --- |
| 6 | 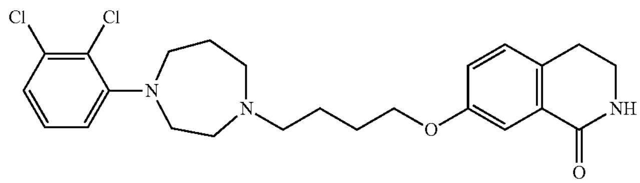 [SMILES: O=C1NCCc2ccc(OCCCCN3CCCN(c4cccc(Cl)c4Cl)CC3)cc21] | 7-(4-(4-(2,3-dichlorophenyl)-1,4-diazepan-1-yl)butoxy)-3,4-dihydroisoquinolin-1(2H)-one (UNC10099984A) |
| 7 | 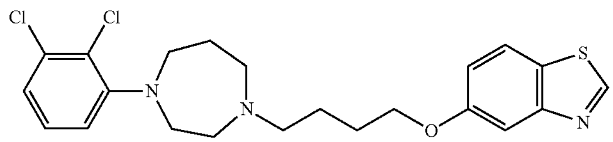 [SMILES: Clc1cccc(N2CCCN(CCCCOc3ccc4scnc4c3)CC2)c1Cl] | 5-(4-(4-(2,3-dichlorophenyl)-1,4-diazepan-1-yl)butoxy)benzo[d]thiazole (UNC10099992A) |
| 8 | 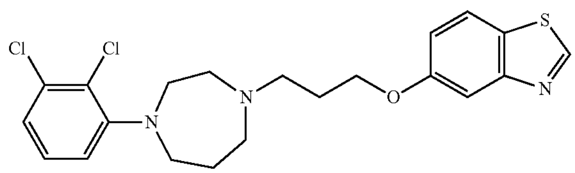 [SMILES: Clc1cccc(N2CCCN(CCCOc3ccc4scnc4c3)CC2)c1Cl] | 5-(3-(4-(2,3-dichlorophenyl)-1,4-diazepan-1-yl)propoxy)benzo[d]thiazole (UNC10099996A) |
| 9 | 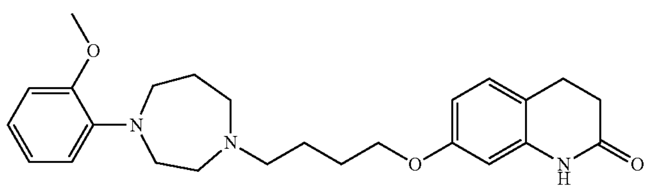 | 7-(4-(4-(2-methoxyphenyl)-1,4-diazepan-1-yl)butoxy)-3,4-dihydroquinolin-2(1H)-one (UNC10107953A) |
| 10 | 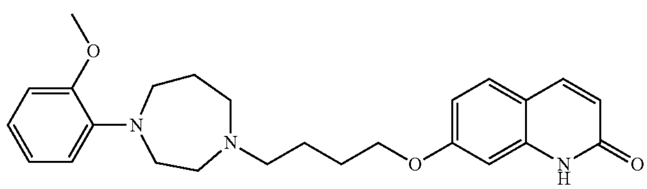 [SMILES: COc1ccccc1N1CCCN(CCCCOc2ccc3ccc(=O)[nH]c3c2)CC1] | 7-(4-(4-(2-methoxyphenyl)-1,4-diazepan-1-yl)butoxy)quinolin-2(1H)-one (UNC10107954A) |
| 11 | 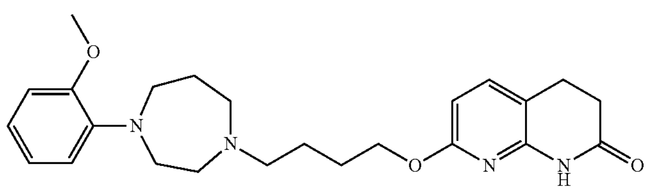 [SMILES: COc1ccccc1N1CCCN(CCCCOc2ccc3c(n2)NC(=O)CC3)CC1] | 7-(4-(4-(2-methoxyphenyl)-1,4-diazepan-1-yl)butoxy)-3,4-dihydro-1,8-naphthyridin-2(1H)-one (UNC10107955A) |
| 12 | 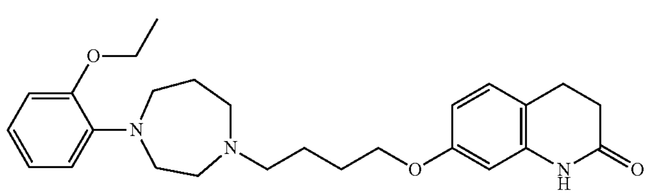 | 7-(4-(4-(2-ethoxyphenyl)-1,4-diazepan-1-yl)butoxy)-3,4-dihydroquinolin-2(1H)-one (UNC10107958A) |
| 13 | 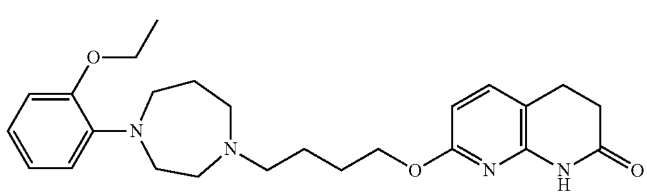 [SMILES: CCOc1ccccc1N1CCCN(CCCCOc2ccc3c(n2)NC(=O)CC3)CC1] | 7-(4-(4-(2-ethoxyphenyl)-1,4-diazepan-1-yl)butoxy)-3,4-dihydro-1,8-naphthyridin-2(1H)-one (UNC10107959A) |

TABLE 5-continued

| Compound Number | Structure | Name |
|---|---|---|
| 14 | 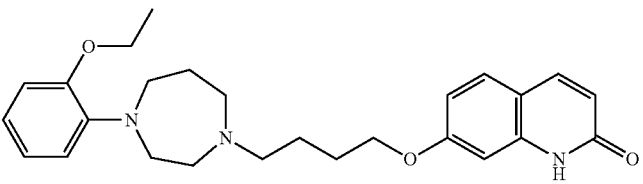 [SMILES: CCOc1ccccc1N1CCCN(CCCCOc2ccc3ccc(=O)[nH]c3c2)CC1] | 7-(4-(4-(2-ethoxyphenyl)-1,4-diazepan-1-yl)butoxy)quinolin-2(1H)-one (UNC10107962A) |
| 15 | 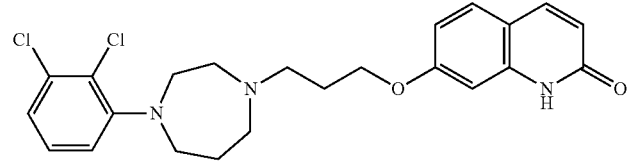 [SMILES: O=c1ccc2ccc(OCCCN3CCCN(c4cccc(Cl)c4Cl)CC3)cc2[nH]1] | 7-(3-(4-(2,3-dichlorophenyl)-1,4-diazepan-1-yl)propoxy)quinolin-2(1H)-one (UNC10107966A) |
| 16 | 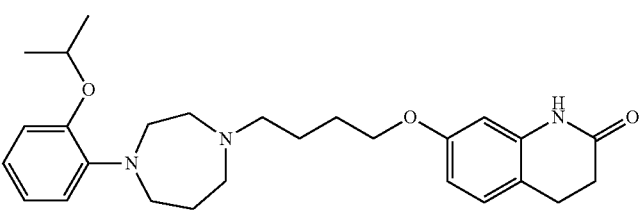 [SMILES: CC(C)Oc1ccccc1N1CCCN(CCCCOc2ccc3c(c2)NC(=O)CC3)CC1] | 7-(4-(4-(2-isopropoxyphenyl)-1,4-diazepan-1-yl)butoxy)-3,4-dihydroquinolin-2(1H)-one (UNC10107967A) |
| 17 | 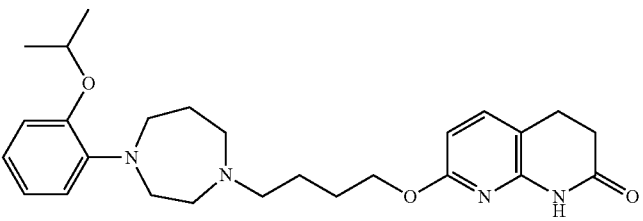 [SMILES: CC(C)Oc1ccccc1N1CCCN(CCCCOc2ccc3c(n2)NC(=O)CC3)CC1] | 7-(4-(4-(2-isopropoxyphenyl)-1,4-diazepan-1-yl)butoxy)-3,4-dihydro-1,8-naphthyridin-2(1H)-one (UNC10107968A) |
| 18 | 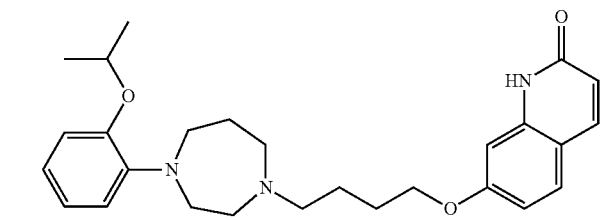 [SMILES: CC(C)Oc1ccccc1N1CCCN(CCCCOc2ccc3ccc(=O)[nH]c3c2)CC1] | 7-(4-(4-(2-isopropoxyphenyl)-1,4-diazepan-1-yl)butoxy)quinolin-2(1H)-one (UNC10107969A) |
| 19 | 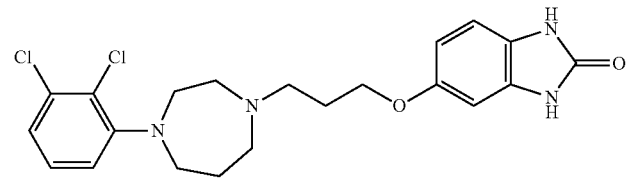 [SMILES: O=c1[nH]c2ccc(OCCCN3CCCN(c4cccc(Cl)c4Cl)CC3)cc2[nH]1] | 5-(3-(4-(2,3-dichlorophenyl)-1,4-diazepan-1-yl)propoxy)-1H-benzo[d]imidazol-2(3H)-one (UNC10108005A) |
| 20 | 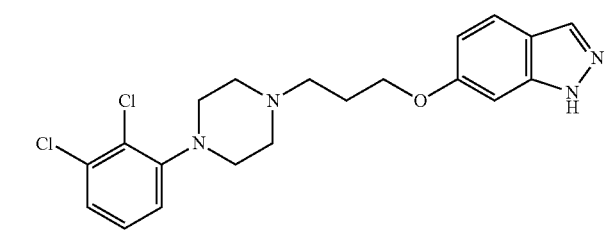 [SMILES: Clc1cccc(N2CCN(CCCOc3ccc4cn[nH]c4c3)CC2)c1Cl] | 6-(3-(4-(2,3-dichlorophenyl)piperazin-1-yl)propoxy)-1H-indazole (UNC10099976A) |

TABLE 5-continued

| Compound Number | Structure | Name |
|---|---|---|
| 21 | 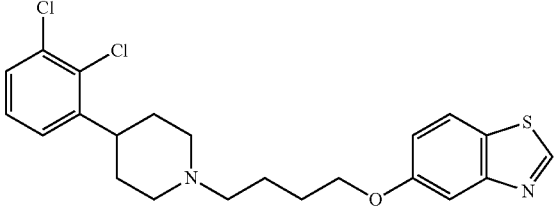 | 5-(4-(4-(2,3-dichlorophenyl)piperidin-1-yl)butoxy)benzo[d]thiazole (UNC10099993A) |
| 22 | 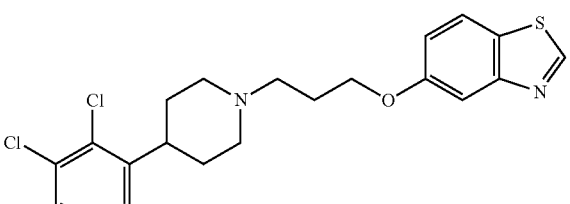 | 5-(3-(4-(2,3-dichlorophenyl)piperidin-1-yl)propoxy)benzo[d]thiazole (UNC10099994A) |
| 23 | 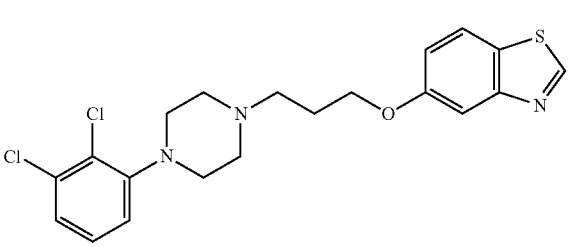 [SMILES: Clc1cccc(N2CCN(CCCOc3ccc4scnc4c3)CC2)c1Cl] | 5-(3-(4-(2,3-dichlorophenyl)piperazin-1-yl)propoxy)benzo[d]thiazole (UNC10099995A) |
| 24 | 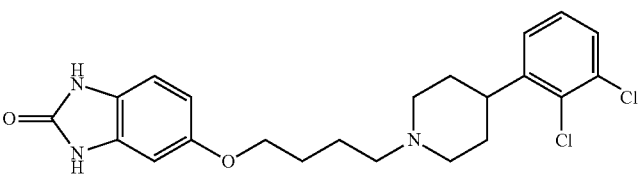 [SMILES: O=c1[nH]c2ccc(OCCCCN3CCC(c4cccc(Cl)c4Cl)CC3)cc2[nH]1] | 5-(4-(4-(2,3-dichlorophenyl)piperidin-1-yl)butoxy)-1H-benzo[d]imidazol-2(3H)-one (UNC10108006A) |
| 25 | 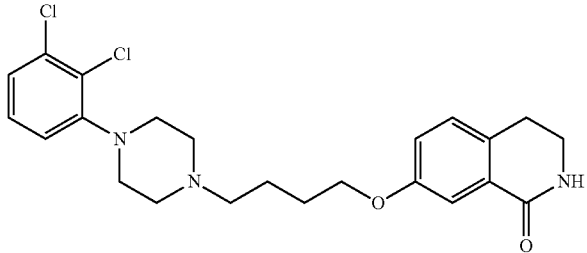 [SMILES: O=C1NCCc2ccc(OCCCCN3CCN(c4cccc(Cl)c4Cl)CC3)cc21] | 7-(4-(4-(2,3-dichlorophenyl)piperazin-1-yl)butoxy)-3,4-dihydroisoquinolin-1(2H)-one (UNC10000004A) |
| 26 | 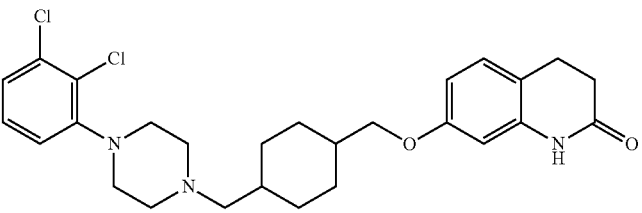 [SMILES: O=C1CCc2ccc(OCC3CCC(CN4CCN(c5cccc(Cl)c5Cl)CC4)CC3)cc2N1] | 7-((4-((4-(2,3-dichlorophenyl)piperazin-1-yl)methyl)cyclohexyl)methoxy)-3,4-dihydroquinolin-2(1H)-one (UNC10000007A) |
| 27 | 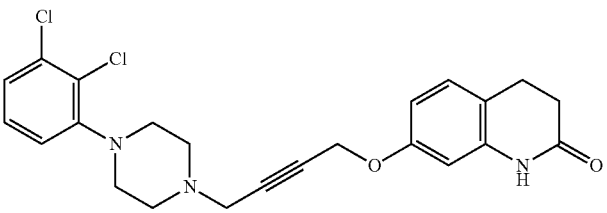 [SMILES: O=C1CCc2ccc(OCC#CCN3CCN(c4cccc(Cl)c4Cl)CC3)cc2N1] | 7-(4-(4-(2,3-dichlorophenyl)piperazin-1-yl)but-2-ynyloxy)-3,4-dihydroquinolin-2(1H)-one (UNC10000009A) |

TABLE 5-continued

| Compound Number | Structure | Name |
|---|---|---|
| 28 | 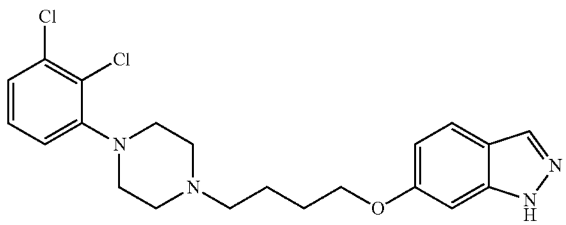 [SMILES: Clc1cccc(N2CCN(CCCCOc3ccc4cn[nH]c4c3)CC2)c1Cl] | 6-(4-(4-(2,3-dichlorophenyl)piperazin-1-yl)butoxy)-1H-indazole (UNC10000010A) |
| 29 | 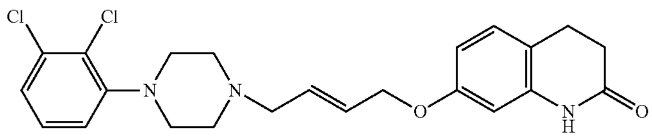 [SMILES: O=C1CCc2ccc(OC/C=C/CN3CCN(c4cccc(Cl)c4Cl)CC3)cc2N1] | (E)-7-(4-(4-(2,3-dichlorophenyl)piperazin-1-yl)but-2-enyloxy)-3,4-dihydroquinolin-2(1H)-one (UNC10000011A) |
| 30 | 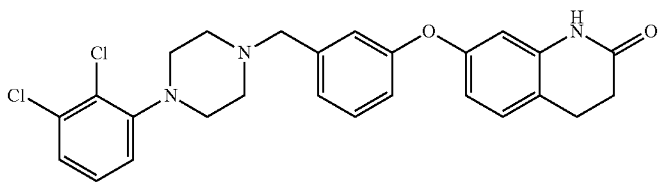 [SMILES: O=C1CCc2ccc(Oc3cccc(CN4CCN(c5cccc(Cl)c5Cl)CC4)c3)cc2N1] | 7-(3-((4-(2,3-dichlorophenyl)piperazin-1-yl)methyl)phenoxy)-3,4-dihydroquinolin-2(1H)-one (UNC10099972A) |
| 31 | 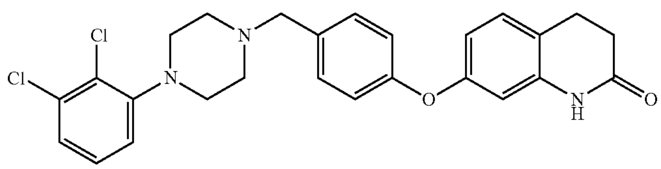 [SMILES: O=C1CCc2ccc(Oc3ccc(CN4CCN(c5cccc(Cl)c5Cl)CC4)cc3)cc2N1] | 7-(4-((4-(2,3-dichlorophenyl)piperazin-1-yl)methyl)phenoxy)-3,4-dihydroquinolin-2(1H)-one (UNC10099973A) |
| 32 | 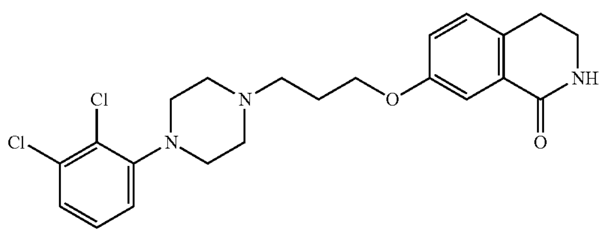 [SMILES: O=C1NCCc2ccc(OCCCN3CCN(c4cccc(Cl)c4Cl)CC3)cc21] | 7-(3-(4-(2,3-dichlorophenyl)piperazin-1-yl)propoxy)-3,4-dihydroisoquinolin-1(2H)-one (UNC10099981A) |
| 33 | 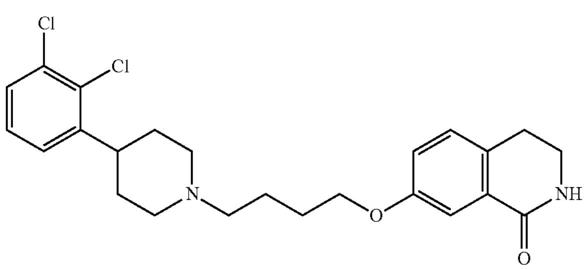 [SMILES: O=C1NCCc2ccc(OCCCCN3CCC(c4cccc(Cl)c4Cl)CC3)cc21] | 7-(4-(4-(2,3-dichlorophenyl)piperidin-1-yl)butoxy)-3,4-dihydroisoquinolin-1(2H)-one (UNC10099985A) |
| 34 | 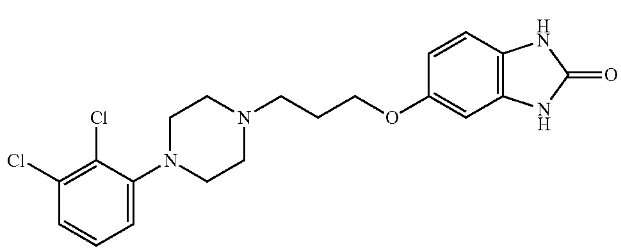 [SMILES: O=c1[nH]c2ccc(OCCCN3CCN(c4cccc(Cl)c4Cl)CC3)cc2[nH]1] | 5-(3-(4-(2,3-dichlorophenyl)piperazin-1-yl)propoxy)-1H-benzo[d]imidazol-2(3H)-one (UNC10099988A) |

TABLE 5-continued

| Compound Number | Structure | Name |
|---|---|---|
| 35 | 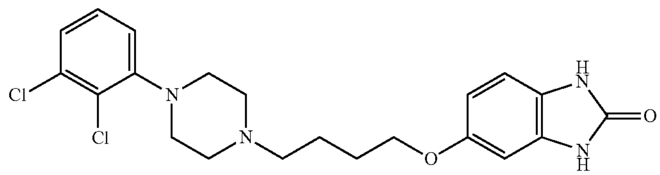 [SMILES: O=c1[nH]c2ccc(OCCCCN3CCN(c4cccc(Cl)c4Cl)CC3)cc2[nH]1] | 5-(4-(4-(2,3-dichlorophenyl)piperazin-1-yl)butoxy)-1H-benzo[d]imidazol-2(3H)-one (UNC10099990A) |
| 36 | 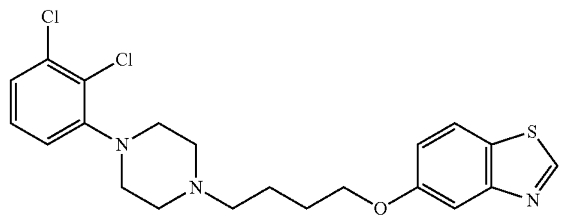 [SMILES: Clc1cccc(N2CCN(CCCCOc3ccc4scnc4c3)CC2)c1Cl] | 5-(4-(4-(2,3-dichlorophenyl)piperazin-1-yl)butoxy)benzo[d]thiazole (UNC10099991A) |
| 37 | 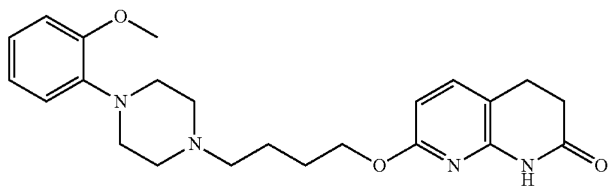 [SMILES: COc1ccccc1N1CCN(CCCCOc2ccc3c(n2)NC(=O)CC3)CC1] | 7-(4-(4-(2-methoxyphenyl)piperazin-1-yl)butoxy)-3,4-dihydro-1,8-naphthyridin-2(1H)-one (UNC10107957A) |
| 38 | 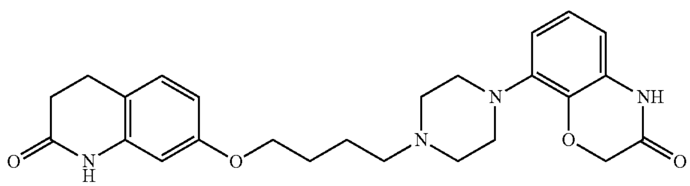 [SMILES: O=C1CCc2ccc(OCCCCN3CCN(c4cccc5c4OCC(=O)N5)CC3)cc2N1] | 8-(4-(4-(2-oxo-1,2,3,4-tetrahydroquinolin-7-yloxy)butyl)piperazin-1-yl)-2H-benzo[b][1,4]oxazin-3(4H)-one (UNC10108010A) |
| 39 | 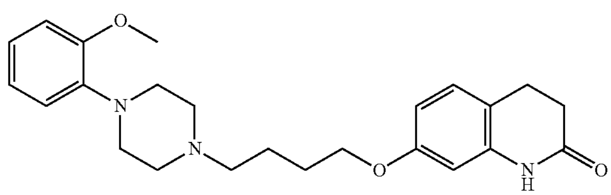 [SMILES: COc1ccccc1N1CCN(CCCCOc2ccc3c(c2)NC(=O)CC3)CC1] | 7-(4-(4-(2-methoxyphenyl)piperazin-1-yl)butoxy)-3,4-dihydroquinolin-2(1H)-one (UNC10108016A) |
| 40 | 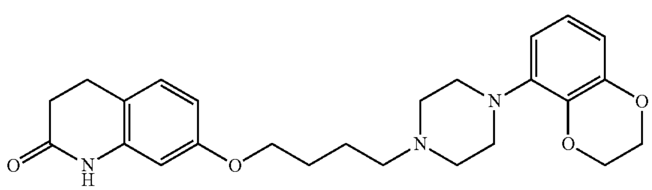 [SMILES: O=C1CCc2ccc(OCCCCN3CCN(c4cccc5c4OCCO5)CC3)cc2N1] | 7-(4-(4-(2,3-dihydrobenzo[b][1,4]dioxin-5-yl)piperazin-1-yl)butoxy)-3,4-dihydroquinolin-2(1H)-one (UNC10108017A) |
| 41 | 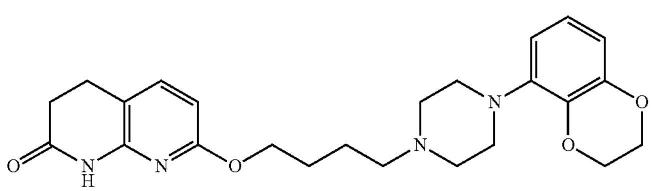 [SMILES: O=C1CCc2ccc(OCCCCN3CCN(c4cccc5c4OCCO5)CC3)nc2N1] | 7-(4-(4-(2,3-dihydrobenzo[b][1,4]dioxin-5-yl)piperazin-1-yl)butoxy)-3,4-dihydro-1,8-naphthyridin-2(1H)-one (UNC10108018A) |
| 42 | 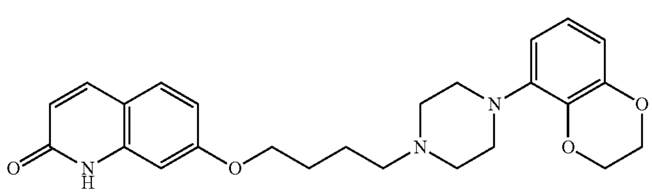 [SMILES: O=c1ccc2ccc(OCCCCN3CCN(c4cccc5c4OCCO5)CC3)cc2[nH]1] | 7-(4-(4-(2,3-dihydrobenzo[b][1,4]dioxin-5-yl)piperazin-1-yl)butoxy)quinolin-2(1H)-one (UNC10108019A) |

TABLE 5-continued

| Compound Number | Structure | Name |
|---|---|---|
| 43 | 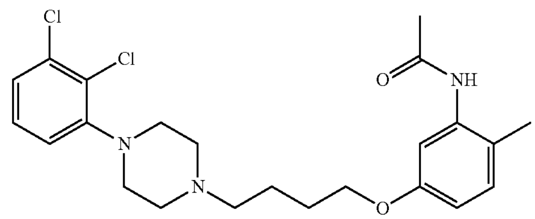 [SMILES: CC(=O)Nc1cc(OCCCCN2CCN(c3cccc(Cl)c3Cl)CC2)ccc1C] | N-(5-(4-(4-(2,3-dichlorophenyl)piperazin-1-yl)butoxy)-2-methylphenyl)acetamide (UNC10108049A) |
| 44 | 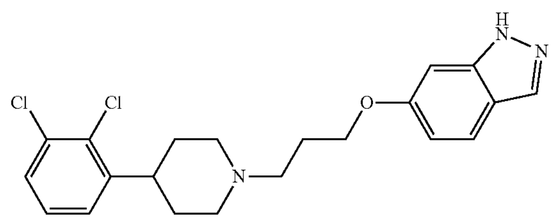 [SMILES: Clc1cccc(C2CCN(CCCOc3ccc4cn[nH]c4c3)CC2)c1Cl] | 6-(3-(4-(2,3-dichlorophenyl)piperidin-1-yl)propoxy)-1H-indazole |
| 45 | 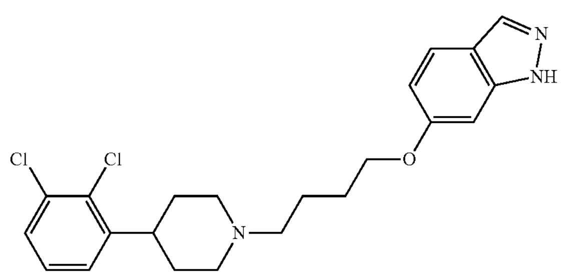 [SMILES: Clc1cccc(C2CCN(CCCCOc3ccc4cn[nH]c4c3)CC2)c1Cl] | 6-(4-(4-(2,3-dichlorophenyl)piperidin-1-yl)butoxy)-1H-indazole |
| 46 | 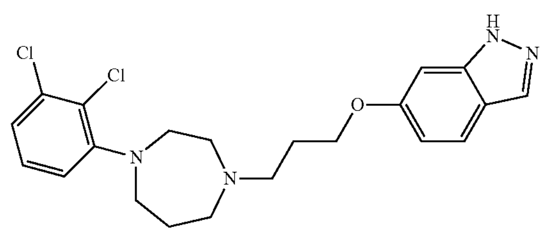 [SMILES: Clc1cccc(N2CCCN(CCCOc3ccc4cn[nH]c4c3)CC2)c1Cl] | 6-(3-(4-(2,3-dichlorophenyl)-1,4-diazepan-1-yl)propoxy)-1H-indazole |
| 47 | 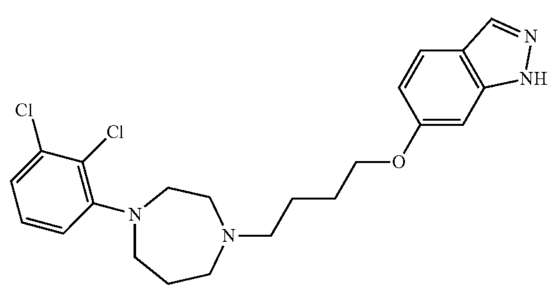 [SMILES: Clc1cccc(N2CCCN(CCCCOc3ccc4cn[nH]c4c3)CC2)c1Cl] | 6-(4-(4-(2,3-dichlorophenyl)-1,4-diazepan-1-yl)butoxy)-1H-indazole |
| 48 | 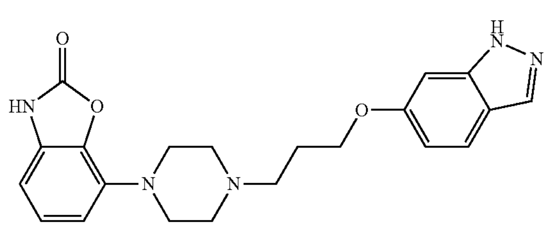 [SMILES: O=c1[nH]c2cccc(N3CCN(CCCOc4ccc5cn[nH]c5c4)CC3)c2o1] | 7-(4-(3-(1H-indazol-6-yloxy)propyl)piperazin-1-yl)benzo[d]oxazol-2(3H)-one |

TABLE 5-continued

| Compound Number | Structure | Name |
|---|---|---|
| 49 | 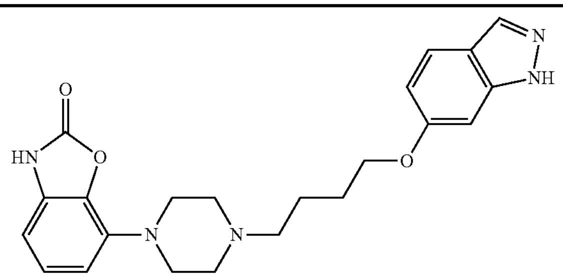 | 7-(4-(4-(1H-indazol-6-yloxy)butyl)piperazin-1-yl)benzo[d]oxazol-2(3H)-one |
| 50 | 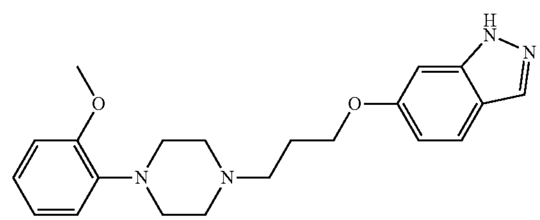 [SMILES: COc1ccccc1N1CCN(CCCOc2ccc3cn[nH]c3c2)CC1] | 6-(3-(4-(2-methoxyphenyl)piperazin-1-yl)propoxy)-1H-indazole |
| 51 | 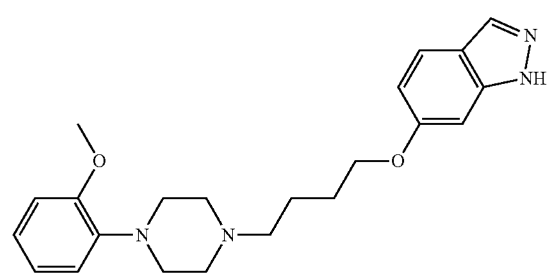 [SMILES: COc1ccccc1N1CCN(CCCCOc2ccc3cn[nH]c3c2)CC1] | 6-(4-(4-(2-methoxyphenyl)piperazin-1-yl)butoxy)-1H-indazole |

General Procedures.

Unless stated to the contrary, where applicable, the following conditions apply: all commercial grade reagents were used without further purification. MeCN and $CH_2Cl_2$ were distilled from $CaH_2$ under a $N_2$ atmosphere prior to use; THF was distilled from Na/benzophenone under $N_2$. All other dry solvents were of anhydrous quality purchased from Sigma-Aldrich. Brine (NaCl), $NaHCO_3$, and $NH_4Cl$ refer to saturated aqueous solutions. Melting points were uncorrected. Mass spectra (MS) and HPLC (UV 254 nM or ELSD) data for all compounds were recorded on an 1100 LC/MS system (Agilent Technology Corporation) using a 4.6×50 mm column (CenturySIL C-18 AQ⁺, 5μ) with a linear gradient 30-90% (v/v) acetonitrile-water with 0.035% trifluoroacetic acid over 5 min with a flow rate of 3.5 mL/min. Analytical TLC was performed using 2.5×5 cm plates coated with 0.25 mm of silica gel $GF_{254}$. Column chromatography was performed on silica gel G (200-300 mesh) with reagent grade solvents. $^1H$ NMR spectra (300 MHz) are reported as follows: chemical shifts in ppm (δ scale) downfield from TMS as the internal standard with either $CDCl_3$ or DMSO-$d_6$ as the solvent. Multiplicities are indicated as the following: bs=broad singlet, s=singlet, d=doublet, t=triplet, q=quartet, m=multiplet.

Synthesis of Compound 1

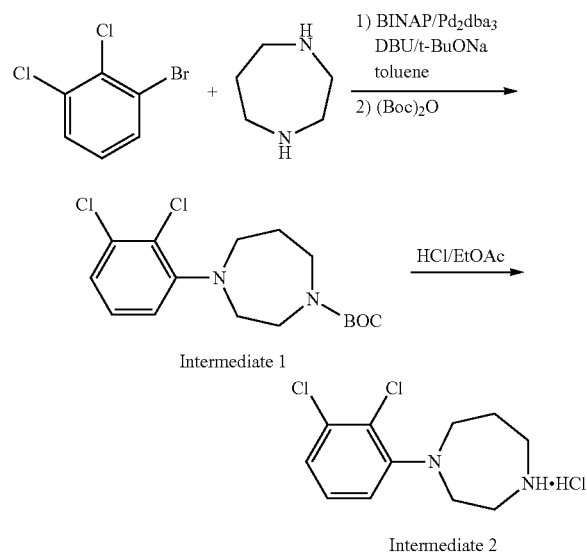

Scheme 1. Synthesis of intermediate 2

Scheme 2. Synthesis of intermediate 3

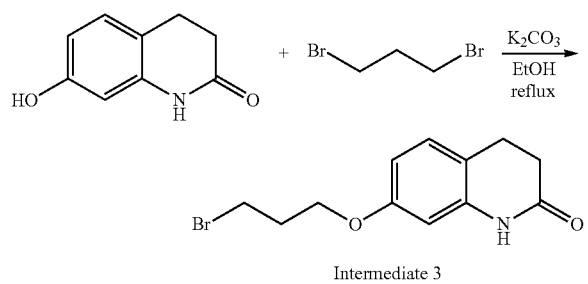

Scheme 3. Synthesis of compound 1

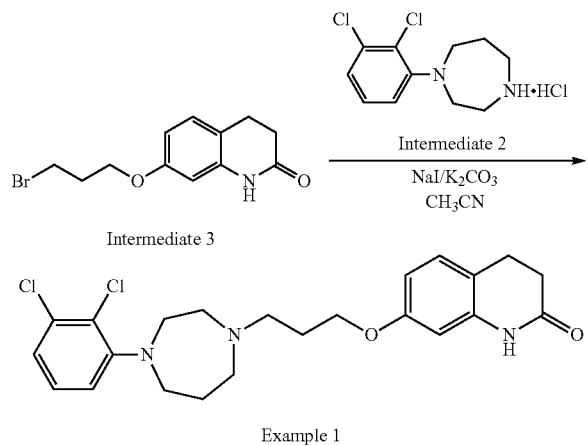

Intermediate 1:

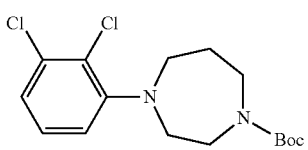

A well-dried flask was first charged with 1-bromo-2,3-dichlorobenzene (4 g, 17.7 mmol) and 1,4-diazepane (2.1 g, 20.9 mmol), which was evacuated and backfilled with $N_2$ through a balloon under gentle warming (40° C.). Toluene was charged and the mixture was bubbled with $N_2$ for 10 min, then BINAP (318 mg, 0.51 mmol) and $Pd_2 dba_3$ (156 mg, 0.17 mmol) was added to the mixture, followed by DBU (3.4 mL). The resulting mixture was warmed at 60-70° C. while fine powder of tBuONa was added in one portion to start the amination. After the reaction mixture cooled to rt, $(Boc)_2O$ (11 g, 51 mmol) solution in DCM was added dropwise to the reaction mixture, then stirred for 3 h at rt. The reaction mixture was diluted with water and extracted with EtOAc. The combined EtOAc layers were washed with brine, dried over anhydrous $Na_2SO_4$, concentrated in vacuo and purified by flash chromatography on silica gel column (elution with PE/EtOAc=10:1) to give tert-butyl 4-(2,3-dichlorophenyl)-1,4-diazepane-1-carboxylate (intermediate 1) (4.1 g, 70%) as a yellow oil.

Intermediate 2:

Excess HCl in EtOAc was added dropwise to a solution of intermediate 1 (4.0 g, 11.6 mmol) in EtOAc and the reaction mixture was stirred at rt for 1.5 h. The reaction mixture was filtered to give 1-(2,3-dichlorophenyl)-1,4-diazepane hydrochloride salt (intermediate 2) (3.0 g, 90%) as a white solid. HPLC: 99%, RT 2.108 min. MS (ESI) m/z 245.0 $[M+H]^+$. mp: 186-187° C.

Intermediate 3:

7-hydroxy-3,4-dihydroquinolin-2(1H)-one (195 mg, 1.2 mmol), 1,3-dibromopropane (960 mg, 4.8 mmol) and anhydrous $K_2CO_3$ (166 mg, 1.2 mmol) were dissolved in EtOH and the solution was heated to reflux overnight. The solution was diluted with water and extracted with EtOAc. The combined organic layers were washed with saturated aq $NaHCO_3$, brine, dried over anhydrous $Na_2SO_4$, concentrated in vacuo and purified by flash chromatography on silica gel column (elution with PE/EtOAc=2:1) to give 7-(3-bromopropoxy)-3,4-dihydroquinolin-2(1H)-one (intermediate 3) (300 mg, 88%) as a white solid. HPLC: 99%, RT 2.775 min. MS (ESI) m/z 284.0 $[M+H]^+$.

Compound 1:

A mixture of intermediate 3 (142 mg, 0.5 mmol) and NaI (150 mg, 1.0 mmol) in $CH_3CN$ was heated to reflux for 30 min and then cooled to rt. Intermediate 2 (196 mg, 0.7 mmol) and anhydrous $K_2CO_3$ (173 mg, 1.25 mmol) were added to the mixture. The resulting mixture was heated to reflux for 4 h. Precipitated crystals were filtered off and the filtrate was evaporated under reduced pressure. The residue was extracted with EtOAc. The combined EtOAc layers were washed with brine, dried over anhydrous $Na_2SO_4$, concentrated in vacuo and purified by flash chromatography on silica gel column (elution with DCM/MeOH=30:1) to give 7-(3-(4-(2,3-dichlorophenyl)-1,4-diazepan-1-yl)propoxy)-3,4-dihydroquinolin-2(1H)-one (compound 1) (140 mg, 63%). $^1H$ NMR (300 MHz, $CDCl_3$): δ 8.16 (s, 1H), 7.10-6.98 (m, 4H), 6.53 (dd, J=8.1 Hz, 2.4 Hz, 1H), 6.34 (d, J=2.1 Hz, 1H), 4.01 (t, J=6.6 Hz, 2H), 3.32-3.28 (m, 4H), 2.92-2.87 (m, 6H), 2.76 (t, J=6.6 Hz, 2H), 2.62 (t, J=6.6 Hz, 2H), 2.04-1.97 (m, 4H). HPLC: 99%, RT 2.421 min. MS (ESI) m/z 448.1 $[M+H]^+$. mp: 130-131° C.

Synthesis of Compound 2

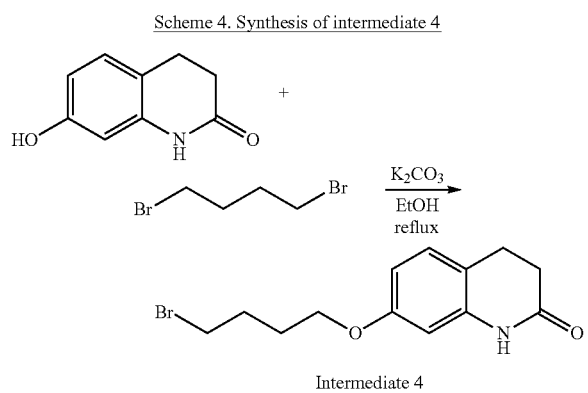

Scheme 4. Synthesis of intermediate 4

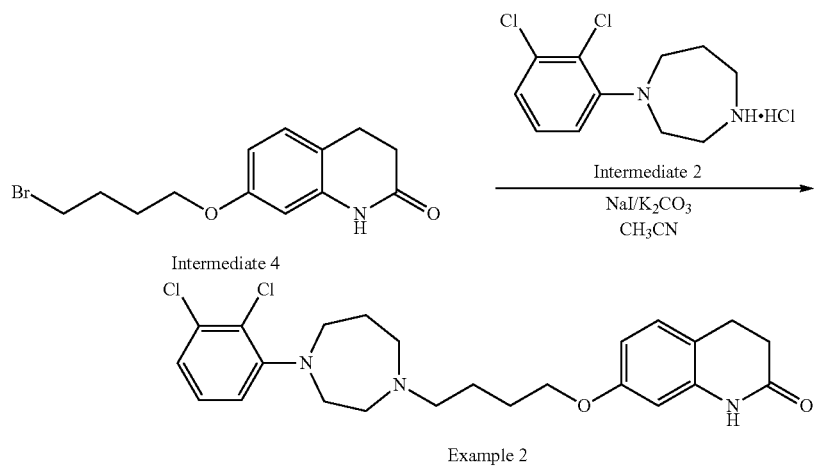

Scheme 5. Synthesis of compound 2

Intermediate 4:

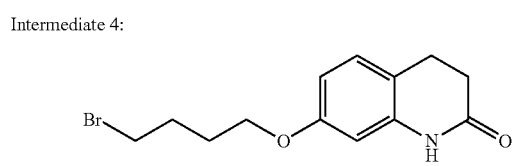 [SMILES: O=C1CCc2ccc(OCCCCBr)cc2N1]

7-hydroxy-3,4-dihydroquinolin-2(1H)-one (163 mg, 1.0 mmol), 1,4-dibromobutane (0.36 mL, 3.0 mmol) and anhydrous $K_2CO_3$ (138 mg, 1.0 mmol) were dissolved in EtOH and the solution was heated to reflux overnight. The solution was diluted with water and extracted with EtOAc. The combined organic layers were washed with saturated $NaHCO_3$, brine, dried over anhydrous $Na_2SO_4$, concentrated in vacuo and purified by flash chromatography on silica gel column (elution with PE/EtOAc=2:1) to give 7-(4-bromobutoxy)-3,4-dihydroquinolin-2(1H)-one (intermediate 4) (220 mg, 74%) as a white solid. mp: 106-109° C.

Compound 2:

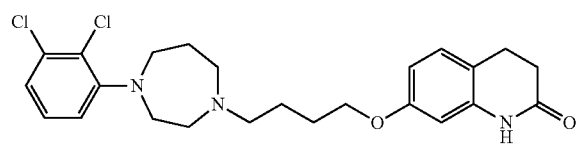

A mixture of intermediate 4 (156 mg, 0.52 mmol) and NaI (120 mg, 0.8 mmol) in $CH_3CN$ was heated to reflux for 30 min and then cooled to rt. Intermediate 2 (119 mg, 0.4 mmol) and anhydrous $K_2CO_3$ (189 mg, 1.37 mmol) were then added to the mixture. The resulting mixture was heated to reflux for 4 h. Precipitated crystals were filtered off and the filtrate was evaporated under reduced pressure. The residue was extracted with EtOAc. The combined EtOAc layers were washed with brine, dried over anhydrous $Na_2SO_4$, concentrated in vacuo and purified by flash chromatography on silica gel column (elution with DCM/MeOH=30:1) to give 7-(4-(4-(2,3-dichlorophenyl)-1,4-diazepan-1-yl)butoxy)-3,4-dihydroquinolin-2(1H)-one (compound 2) (75 mg, 41%). $^1$H NMR (300 MHz, $CDCl_3$): δ 8.08 (s, 1H), 7.10-6.99 (m, 4H), 6.52 (dd, J=6.6 Hz, 2.1 Hz, 1H), 6.33 (s, 1H), 3.96 (t, J=6.0 Hz, 2H), 3.31-3.27 (m, 4H), 2.92-2.84 (m, 6H), 2.64-2.60 (m, 4H), 2.02-1.98 (m, 2H), 1.84-1.70 (m, 4H). HPLC: 99%, RT 2.435 min. MS (ESI) m/z 462.2 $[M+H]^+$. mp: 88-89° C.

Synthesis of Compound 3

Scheme 6. Synthesis of intermediate 12

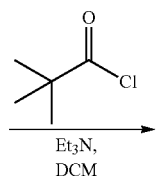

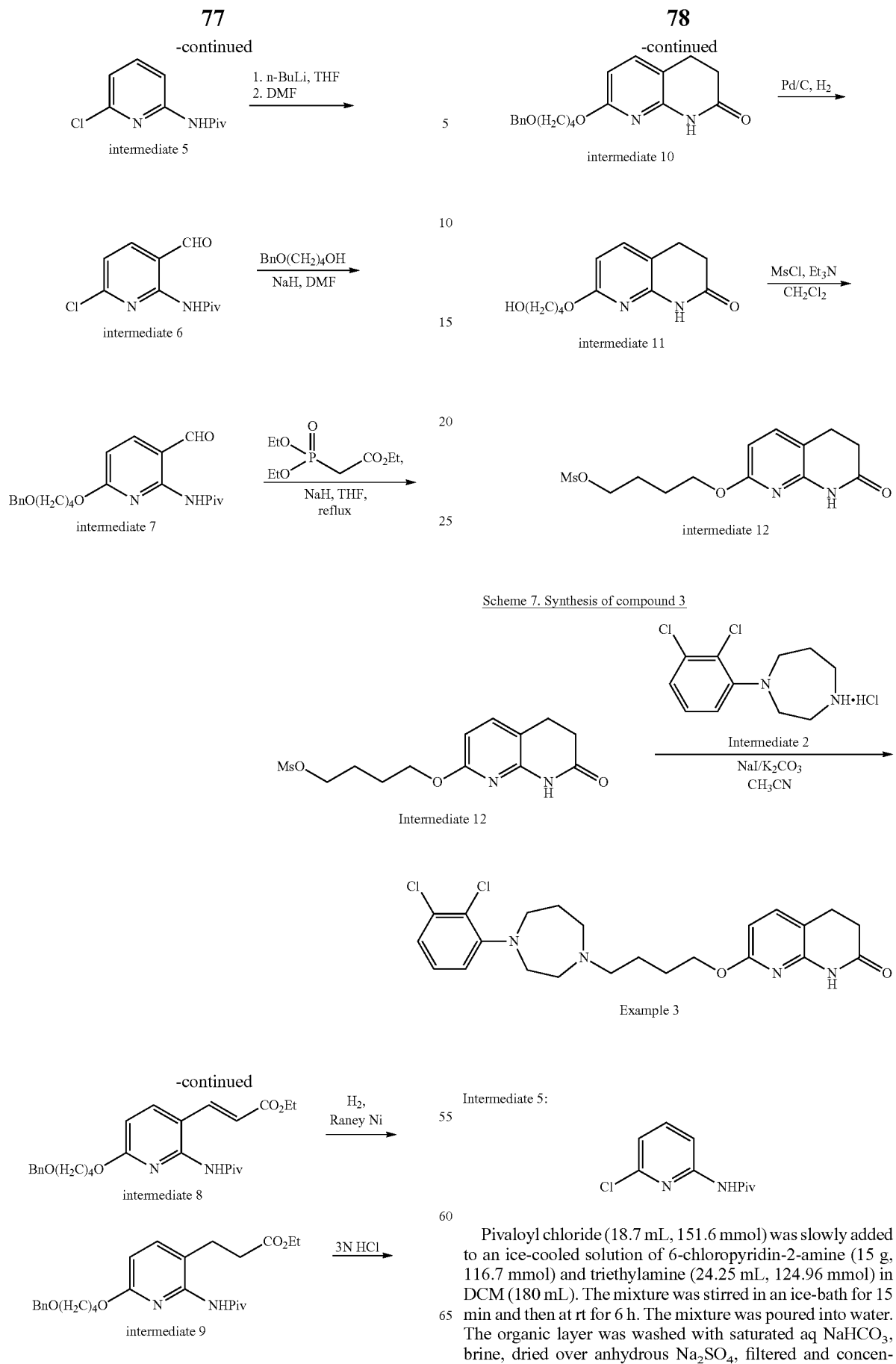
Pivaloyl chloride (18.7 mL, 151.6 mmol) was slowly added to an ice-cooled solution of 6-chloropyridin-2-amine (15 g, 116.7 mmol) and triethylamine (24.25 mL, 124.96 mmol) in DCM (180 mL). The mixture was stirred in an ice-bath for 15 min and then at rt for 6 h. The mixture was poured into water. The organic layer was washed with saturated aq NaHCO₃, brine, dried over anhydrous Na₂SO₄, filtered and concentrated in vacuo to give N-(6-chloropyridin-2-yl)pivalamide (intermediate 5) (20.01 g, 81%) as a yellow solid.

Intermediate 6:

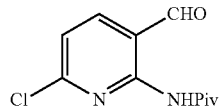

A solution of intermediate 5 (19.28 g, 90.6 mmol) in THF (181 mL) was treated with n-BuLi (108.8 mL, 272 mmol) and the resulting mixture was stirred at −20° C. for 3 h. After addition of DMF (20.81 mL, 271.86 mmol), the reaction was allowed to warm to rt. The reaction was poured into cold 6N HCl and stirred for 15 min. The mixture was then neutralized with anhydrous $K_2CO_3$ to pH=7 and extracted with $Et_2O$. The combined organic layers were washed with water, brine, dried over anhydrous $Na_2SO_4$, concentrated in vacuo and purified by recrystallization from EtOAc and hexanes to afford N-(6-chloro-3-formylpyridin-2-yl)pivalamide (intermediate 6) (12.84 g, 59%).

Intermediate 7:

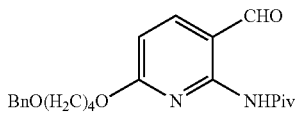

To a solution of 4-(benzyloxy)butan-1-ol (15.42 g, 85.6 mmol) in DMF (120 mL) was added sodium hydride (4.11 g, 171 mmol) at 0° C. The mixture was stirred for 20 min, then intermediate 6 (10.28 g, 42.7 mmol) was added portion-wise and the resulting mixture was stirred overnight. The mixture was quenched with saturated aq $NH_4Cl$ and extracted with EtOAc. The combined organic layers were washed with water, brine, dried over anhydrous $Na_2SO_4$ and concentrated in vacuo. The residue was purified by flash chromatography on silica gel column (elution with PE/EtOAc=8:1-4:1) to give N-(6-(4-(benzyloxy)butoxy)-3-formylpyridin-2-yl)pivalamide (intermediate 7) (5.04 g, 31%).

Intermediate 8:

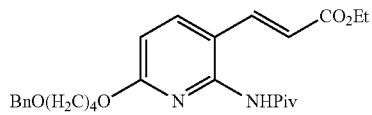

Under $N_2$, an ice-cooled flask containing THF (100 mL) was charged with sodium hydride (5.7 g, 142.5 mmol) to which ethyl 2-(diethoxyphosphoryl)acetate (32 g, 142 mmol) was added. The ice bath was removed and a solution of intermediate 7 (21.8 g, 56.7 mmol) in THF (120 mL) was slowly added to the preformed anion. The reaction was heated to reflux overnight. The reaction mixture was cooled to rt and partitioned between EtOAc and water. The organic layer was separated and the aqueous layer was extracted with EtOAc. The combined organic layers were washed with brine, dried over anhydrous $Na_2SO_4$ and concentrated in vacuo to give ethyl 3-(6-(4-(benzyloxy)butoxy)-2-pivalamidopyridin-3-yl) acrylate (intermediate 8) (13.3 g, 52%) as a white solid. mp: 75-76° C.

Intermediate 9:

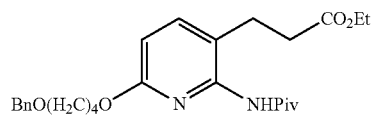

Intermediate 8 (2.46 g, 5.4 mmol) was hydrogenated under an atmosphere of $H_2$ (40 psi) using Raney Ni (1.59 g, 27.1 mmol) in THF (120 mL). The reaction was filtered to remove the Raney Ni and the filtrate was concentrated to afford ethyl 3-(6-(4-(benzyloxy)butoxy)-2-pivalamidopyridin-3-yl)propanoate (intermediate 9) (1.76 g, 71.5% crude) as an oil.

Intermediate 10:

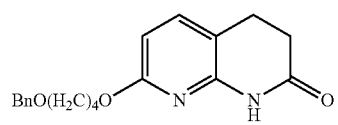

To a solution of intermediate 9 (1.76 g, 3.9 mmol) in 1,4-dioxane (14 mL) was added 3N HCl (7.1 mL) and the mixture was then heated to reflux for 3 h. The mixture was cooled to rt and then anhydrous $K_2CO_3$ was slowly added to neutralize the reaction mixture to pH=8, then extracted with EtOAc. The combined organic layers were washed with water, brine, dried over anhydrous $Na_2SO_4$ and concentrated in vacuo. The crude product was purified by flash chromatography on silica gel column (elution with PE/EtOAc=4:1-1:1) to give 7-(4-(benzyloxy)butoxy)-3,4-dihydro-1,8-naphthyridin-2(1H)-one (intermediate 10) (671 mg, 54%) as an oil.

Intermediate 11:

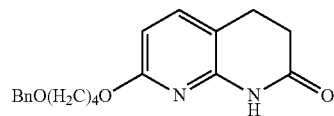

To the solution of intermediate 10 (900 mg, 2.8 mmol) in EtOH (25 mL) was added 10% Pd/C (400 mg) under an atmosphere of $H_2$ overnight. The reaction was filtered to remove the Pd/C and the filtrate was concentrated and washed with $Et_2O$ to give 7-(4-hydroxybutoxy)-3,4-dihydro-1,8-naphthyridin-2(1H)-one (intermediate 11) (360 mg, 55%) as a white solid.

Intermediate 12:

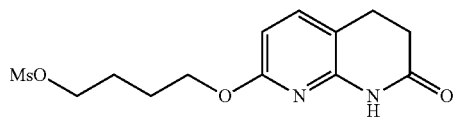

A mixture of intermediate 11 (140 mg, 0.593 mmol), $Et_3N$ (240 mg, 2.37 mmol) and methylsulfonyl chloride (102 mg, 0.89 mmol) was dissolved in DCM and the solution was stirred for 6 h at rt. The solution was then washed with water, brine, and dried over anhydrous $Na_2SO_4$. After filtration, the solvent was evaporated in vacuo to give 4-(7-oxo-5,6,7,8- tetrahydro-1,8-naphthyridin-2-yloxy)butyl methanesulfonate (intermediate 12) (180 mg, 96%) as a yellow solid.

Compound 3:

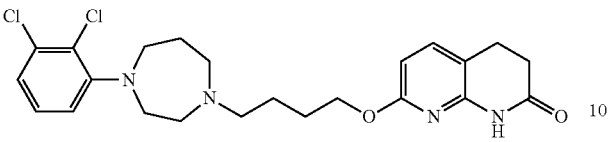

Intermediate 12 (85 mg, 0.27 mmol) was dissolved in CH$_3$CN then NaI (55 mg, 0.37 mmol), Et$_3$N (91 mg, 0.9 mmol), and intermediate 2 (102 mg, 0.36 mmol) were added. The resulting mixture was stirred at 70° C. overnight. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=30:1) to give 7-(4-(4-(2,3-dichlorophenyl)-1,4-diazepan-1-yl)butoxy)-3,4-dihydro-1,8-naphthyridin-2(1H)-one (compound 3) (78 mg, 63%). $^1$H NMR (300 MHz, CDCl$_3$): δ 7.64 (s, 1H), 7.38 (d, J=8.1 Hz, 1H), 7.27-7.15 (m, 2H), 7.06 (d, J=8.1 Hz, 1H), 6.37 (d, J=8.1 Hz, 1H), 4.36 (t, J=6.0 Hz, 2H), 3.61-3.49 (m, 7H), 3.32-3.20 (m, 5H), 2.90-2.85 (m, 2H), 2.67-2.62 (m, 2H), 2.21-2.16 (m, 2H), 1.90-1.85 (m, 2H). HPLC: 99%, RT 2.682 min. MS (ESI) m/z 463.1 [M+H]$^+$. mp: 110-111° C.

Synthesis of Compound 4

Scheme 8. Synthesis of compound 4

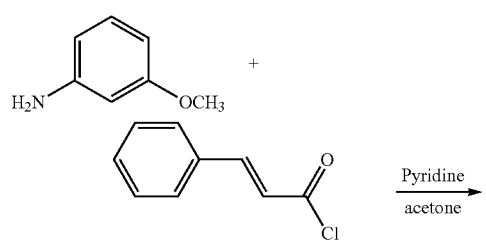

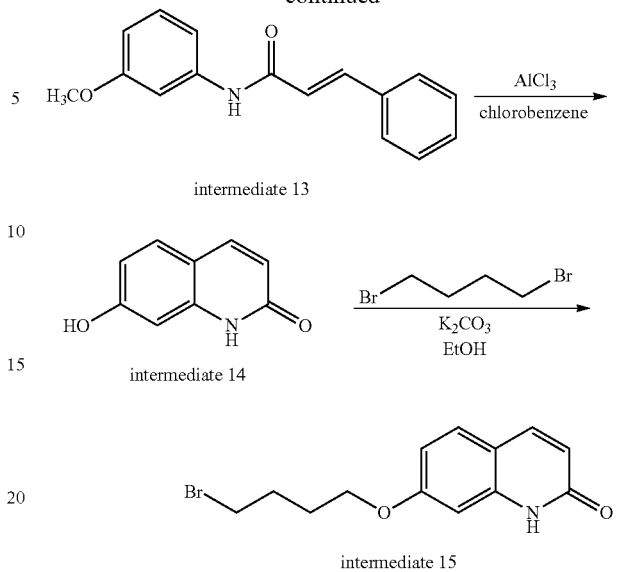

Scheme 9. Synthesis of compound 4

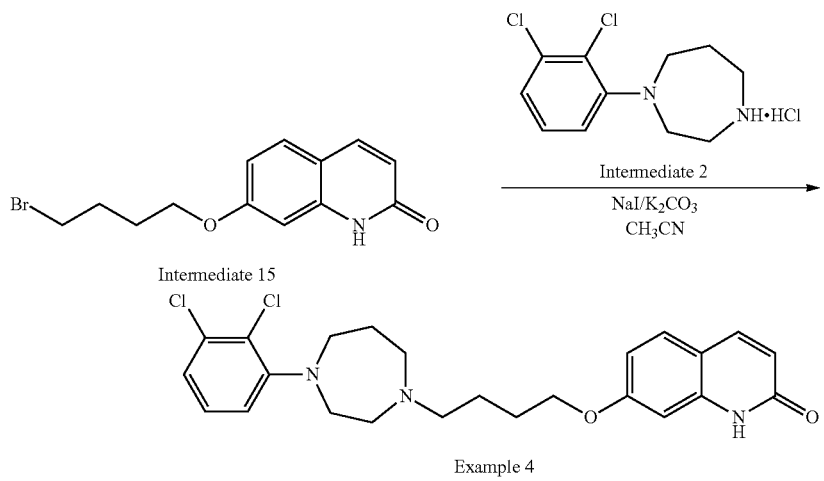

Intermediate 13:

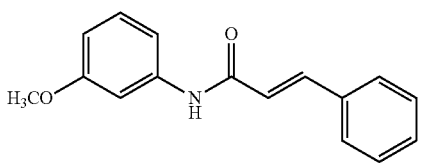

A solution of cinnamoyl chloride (4.25 g, 25.6 mmol) in acetone (25 mL) was added to a solution of 3-methoxyaniline (2.74 mL, 24.4 mmol) and anhydrous K$_2$CO$_3$ (3.7 g, 26.8 mmol) in acetone-ice (28 mL-28 g) and the resulting reaction mixture was stirred at rt for 3 h. The reaction mixture was then poured into ice water, filtered, and washed with water. Recrystallization from EtOH gave N-(3-methoxyphenyl)cinnamamide (intermediate 13) (4.56 g, 74%) as a white solid.

83

Intermediate 14:

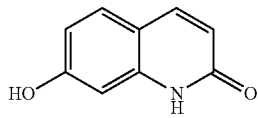

AlCl₃ (11.5 g, 86.3 mmol) was added portion-wise to a suspension of intermediate 13 (4.2 g, 16.6 mmol) in chlorobenzene (90 mL) at 0° C. The reaction mixture was gradually warmed to 120° C. and stirred for 3 h. The mixture was poured into ice water and the resulting precipitate was collected by filtration, washed with water, and purified by flash chromatography on silica gel column (elution with DCM/MeOH=60:1) to give 7-hydroxyquinolin-2(1H)-one (intermediate 14) (1.41 g, 53%) as a white solid.

Intermediate 15:

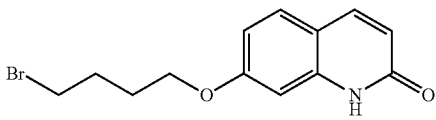

A mixture of intermediate 14 (193 mg, 1.2 mmol), 1,4-dibromobutane (0.43 mL, 3.6 mmol) and anhydrous K₂CO₃ (166 mg, 1.2 mmol) was dissolved in EtOH and the solution was heated to reflux overnight. The solution was diluted with water and extracted with EtOAc. The combined organic layers was washed with saturated aq NaHCO₃, brine, dried over anhydrous Na₂SO₄, concentrated in vacuo and purified by flash chromatography on silica gel column (elution with PE/EtOAc=2:1) to give 7-(4-bromobutoxy)quinolin-2(1H)-one (intermediate 15) (147 mg, 41%) as a yellow solid.

84

Compound 4:

A mixture of intermediate 15 (120 mg, 0.41 mmol) and NaI (123 mg, 0.82 mmol) in CH₃CN was heated to reflux for 30 min and then cooled to rt. Intermediate 2 (175 mg, 0.62 mmol) and anhydrous K₂CO₃ (226 mg, 1.64 mmol) were added to the mixture. The resulting mixture was heated to reflux overnight. The mixture was evaporated under reduced pressure and the residue was extracted with EtOAc. The combined EtOAc layers were washed with brine, dried over anhydrous Na₂SO₄, concentrated in vacuo and purified by flash chromatography on silica gel column (elution with DCM/MeOH=30:1) to give 7-(4-(4-(2,3-dichlorophenyl)-1,4-diazepan-1-yl)butoxy)quinolin-2(1H)-one (compound 4) (50 mg, 26%). ¹H NMR (300 MHz, CDCl₃) δ 11.54 (br., 1H), 7.71 (d, J=6.9 Hz, 1H) 7.44 (d, J=8.1 Hz, 1H), 7.09-7.07 (m, 2H), 7.01-6.97 (m, 1H), 6.82-6.78 (m, 2H), 6.53 (d, J=9.3 Hz, 1H), 4.10 (t, J=6.6 Hz, 2H), 3.30 (d, J=5.1 Hz, 4H), 2.87-2.81 (m, 4H), 2.62 (t, J=7.5 Hz, 2H), 2.01-1.99 (m, 2H), 1.92-1.82 (m, 2H), 1.76-1.68 (m, 2H). HPLC: 99%, RT 2.461 min. MS (ESI) m/z 460.2 [M+H]⁺. mp: 55-57° C.

Synthesis of Compound 5

Scheme 10. Synthesis of intermediate 20

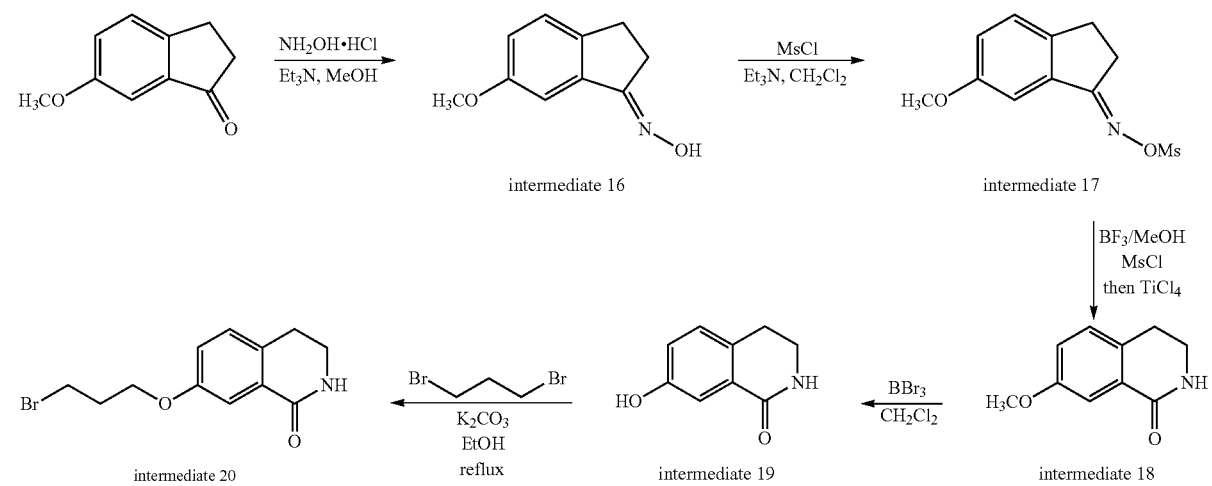

Scheme 11. Synthesis of compound 5

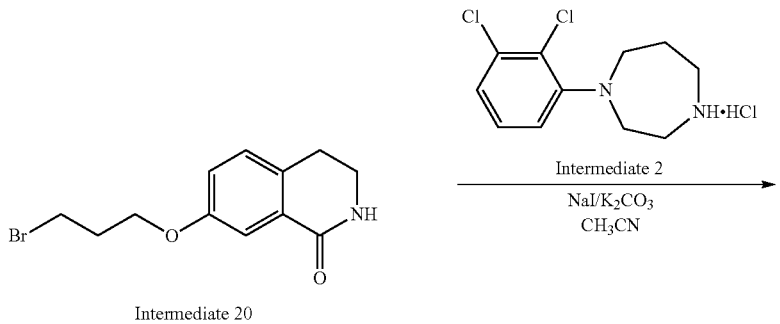

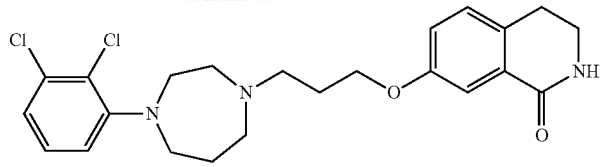

Example 5

Intermediate 16:

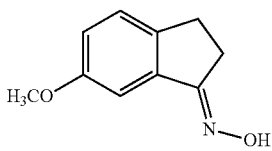

To the solution of 6-methoxy-2,3-dihydro-1H-inden-1-one (6.5 g, 40 mmol) in 100 mL of MeOH was added Et$_3$N (11.1 mL, 80 mmol) and hydroxylamine hydrochloride (3.9 g, 56 mmol). The mixture was stirred at rt for 2 h. The mixture was evaporated and redissolved in EtOAc, the organic phase was washed with water, brine, dried over anhydrous Na$_2$SO$_4$, filtered and concentrated to give (E)-6-methoxy-2,3-dihydro-1H-inden-1-one oxime (intermediate 16) (6.6 g, 93%).

Intermediate 17:

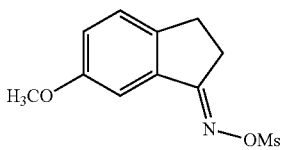

To the solution of intermediate 16 (6.6 g, 37.2 mmol) in CH$_2$Cl$_2$ (120 mL) was added Et$_3$N (20.6 mL, 149 mmol), DMAP (455 mg, 3.73 mmol) and MsCl (4.35 mL, 55.87 mmol). The mixture was stirred at rt overnight. The reaction mixture was washed successively with water, saturated aq NH$_4$Cl, brine, dried over anhydrous MgSO$_4$, filtered and concentrated. The crude product was purified by flash chromatography on silica gel column (elution with PE/CH$_2$Cl$_2$=1:1) to give (E)-6-methoxy-2,3-dihydro-1H-inden-1-one O-methylsulfonyl oxime (intermediate 17) (736 g, 82%) as a white solid.

Intermediate 18:

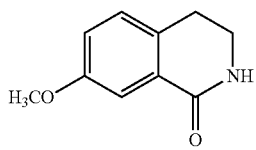

To the solution of intermediate 17 (7.76 g, 30.4 mmol) in 1,2-dichloroethane (150 mL) was added BF$_3$ (5.52 mL, 48.7 mmol, in MeOH), MsCl (3.8 mL, 48.7 mmol) and TiCl$_4$ (5.35 mL, 48.7 mmol). The mixture was stirred at rt for 5 h. CH$_2$Cl$_2$ (150 mL) was then added to the reaction mixture. The solution was washed with water and brine. The water layer was neutralized by aqueous Na$_2$CO$_3$ to pH=7 and was extracted with CH$_2$Cl$_2$. The combined organic layers were dried over anhydrous MgSO$_4$, filtered and concentrated. The crude product was purified by flash chromatography on silica gel column (elution with PE/EtOAc=4:1) to give 7-methoxy-3,4-dihydroisoquinolin-1(2H)-one (intermediate 18) (5.1 g, 95%) as a white solid.

Intermediate 19:

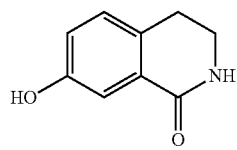

BBr$_3$ (4.75 mL, 47.5 mmol, in CH$_2$Cl$_2$) was added to a cold solution (ice-bath) of intermediate 18 (3.36 g, 18.98 mmol) in CH$_2$Cl$_2$ (100 mL). The mixture was then warmed to rt and stirred overnight. Water was carefully added dropwise to quench the reaction. EtOAc was added and the mixture was washed with water, brine, dried over anhydrous MgSO$_4$, filtered and concentrated to afford 7-hydroxy-3,4-dihydroisoquinolin-1(2H)-one (intermediate 19) (2.46 g, 80%) as a white solid. mp: 201-203° C.

Intermediate 20:

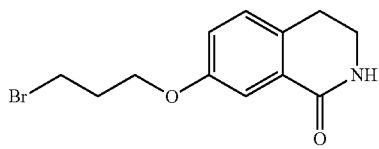

A mixture of intermediate 19 (326 mg, 2 mmol), 1,3-dibromopropane (0.62 mL, 6 mmol) and anhydrous K$_2$CO$_3$ (276 mg, 2 mmol) was dissolved in 4 mL of EtOH and the solution was heated to reflux and stirred overnight. The mixture was diluted with water and extracted with EtOAc. The combined EtOAc layers were washed with water, brine, dried over anhydrous Na$_2$SO$_4$, concentrated in vacuo and purified by flash chromatography on silica gel column (elution with PE/EtOAc=5:1) to give 7-(3-bromopropoxy)-3,4-dihydroisoquinolin-1(2H)-one (intermediate 20) (360 mg, 63%) as a white solid.

Compound 5:

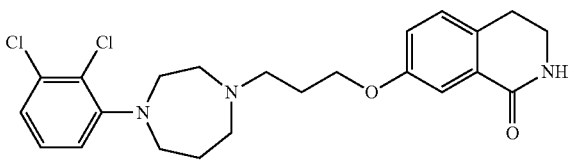

A mixture of intermediate 20 (110 mg, 0.39 mmol) and NaI (117 mg, 0.78 mmol) in CH₃CN was heated to reflux for 30 min and then cooled to rt. Intermediate 2 (165 mg, 0.58 mmol) and anhydrous K₂CO₃ (216 mg, 1.56 mmol) were added to the mixture. The resulting mixture was heated to reflux and stirred overnight. The reaction solution was diluted with water and extracted with EtOAc. The combined EtOAc layers were washed with brine, dried over anhydrous Na₂SO₄, concentrated in vacuo and purified by flash chromatography on silica gel column (elution with DCM/MeOH=30: 1) to give 7-(3-(4-(2,3-dichlorophenyl)-1,4-diazepan-1-yl) propoxy)-3,4-dihydroisoquinolin-1(2H)-one (compound 5) (125 mg, 71%). ¹H NMR (300 MHz, CDCl₃) δ 7.60 (d, J=2.1 Hz, 1H), 7.14-7.08 (m, 3H), 7.02-7.00 (m, 2H), 6.02 (br., 1H), 4.10 (t, J=6.3 Hz, 2H), 3.56-3.53 (m, 2H), 3.31-3.27 (m, 4H), 2.96-2.88 (m, 6H), 2.77-2.72 (m, 2H), 2.01 (m, 4H). HPLC: 99%, RT 2.578 min. MS (ESI) m/z 448.1 [M+H]⁺. mp: 116-117° C.

Synthesis of Compound 6

Scheme 12. Synthesis of intermediate 21

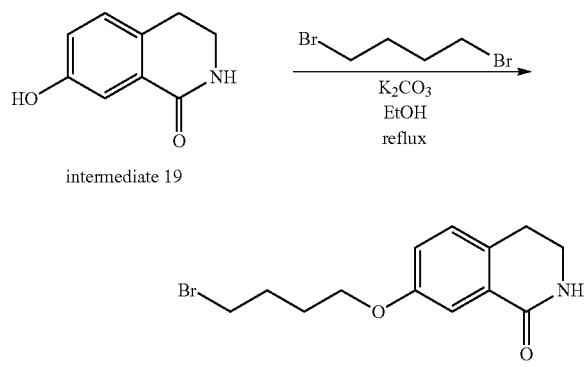

intermediate 19 intermediate 21

Intermediate 21:

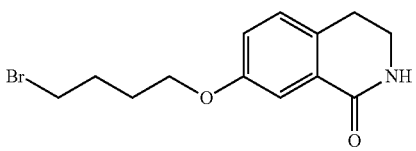

A mixture of intermediate 19 (196 mg, 1.2 mmol), 1,4-dibromobutane (0.43 mL, 3.6 mmol) and anhydrous K₂CO₃ (166 mg, 1.22 mmol) was dissolved in EtOH (4 mL) and the solution was heated to reflux and stirred overnight. The mixture was diluted with water and extracted with EtOAc. The combined EtOAc layers were washed with water, brine, dried over anhydrous Na₂SO₄, concentrated in vacuo and purified by flash chromatography on silica gel column (elution with PE/EtOAc=3:1) to give 7-(4-bromobutoxy)-3,4-dihydroisoquinolin-1(2H)-one (intermediate 21) (230 mg, 63%) as a white solid.

Compound 6:

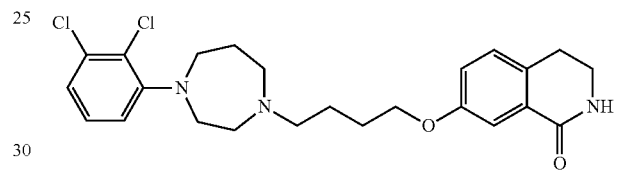

A mixture of intermediate 21 (100 mg, 0.34 mmol) and NaI (102 mg, 0.68 mmol) in CH₃CN was heated to reflux for 30 min and then cooled to rt. Intermediate 2 (144 mg, 0.51 mmol) and anhydrous K₂CO₃ (188 mg, 1.36 mmol) were added to the mixture. The resulting mixture was heated to reflux and stirred overnight. The reaction solution was diluted with water and extracted with EtOAc. The combined EtOAc layers were washed with brine, dried over anhydrous Na₂SO₄, concentrated in vacuo and purified by flash chromatography on silica gel column (elution with DCM/MeOH=30:

Scheme 13. Synthesis of compound 6

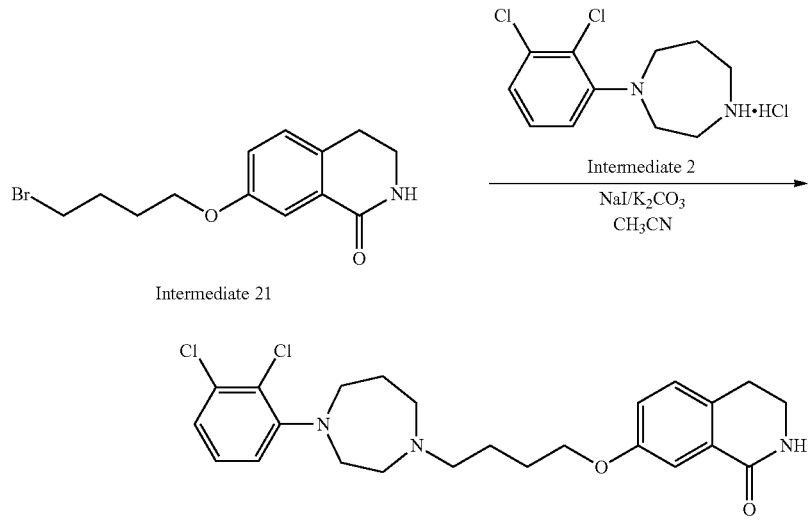

Example 6

1) to give 7-(4-(4-(2,3-dichlorophenyl)-1,4-diazepan-1-yl) butoxy)-3,4-dihydroisoquinolin-1(2H)-one (compound 6) (107 mg, 68%). $^1$H NMR (300 MHz, CDCl$_3$) δ 7.58 (s, 1H), 7.20-7.09 (m, 3H), 7.02-6.98 (m, 2H), 6.04 (br., 1H), 4.05 (t, J=6.6 Hz, 2H), 3.54-3.52 (m, 2H), 3.32-3.28 (m, 4H), 2.95-2.91 (m, 6H), 2.70-2.68 (m, 2H), 2.06-2.04 (m, 2H), 1.84-1.77 (m, 4H). HPLC: 99%, RT 2.676 min. MS (ESI) m/z 462.4 [M+H]$^+$. mp: 86-88° C.

Synthesis of Compound 7 ing a temperature no greater than 5° C. The resulting solution was added dropwise with vigorous stirring to a solution of crystalline cobalt chloride (42 g, 176 mmol) and potassium thiocyanate (25.6 g, 264 mmol) in water (100 mL), after which the mixture was stirred at 0-10° C. for 3 h and allowed to stand overnight. It was then stirred at 50° C. for 16 h until nitrogen evolution had ceased. The precipitate was removed by filtration, washed with water, and dried at 80° C. to give 4-methoxy-2-nitro-1-thiocyanatobenzene (intermediate 22) (9.82 g, 58%). mp: 127-128° C.

Scheme 14. Synthesis of intermediate 26

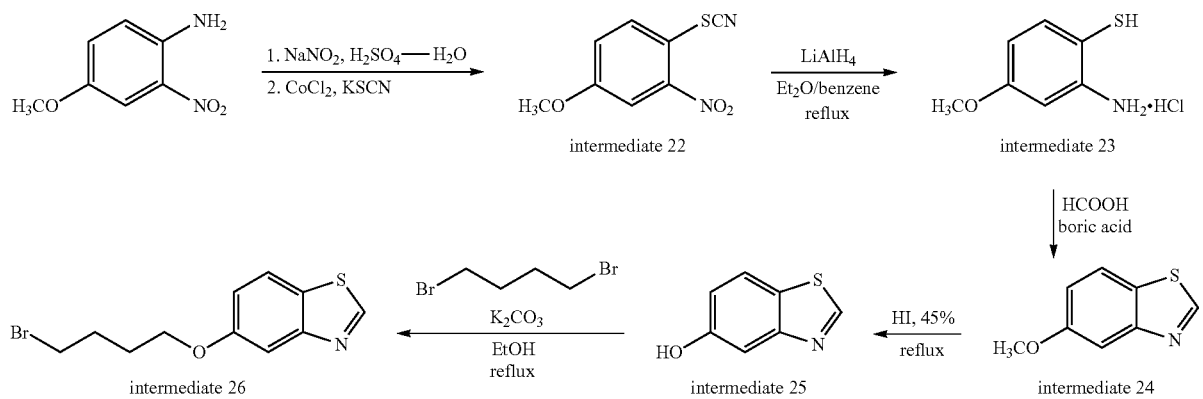

Scheme 15. Synthesis of compound 7

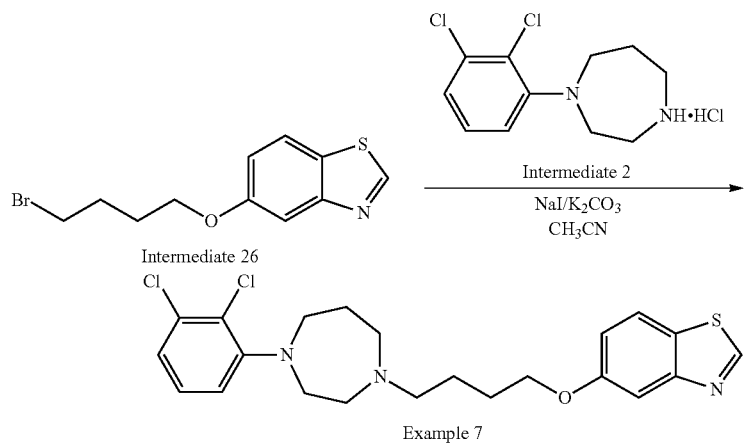

Intermediate 22:

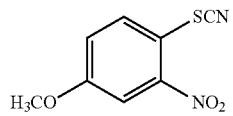

A sample of 3-nitro-4-aminoanisole (13.5 g, 80 mmol) was dissolved in water (100 mL) and concentrated H$_2$SO$_4$ (44 mL), cooled to 0° C., and diazotized with a solution of sodium nitrite (14.3 g, 207.2 mmol) in water (25 mL) while maintain- Intermediate 23:

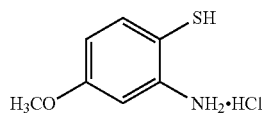

A solution of intermediate 22 (4 g, 19 mmol) in benzene was added dropwise with stirring and cooling to a suspension of technical-grade lithium aluminum hydride (9.4 g, 247 mmol) in absolute ether (90 mL), after which the mixture was heated to reflux and stirred under a stream of dry nitrogen for 8 h. The excess lithium aluminum hydride was quenched by ice water. Water (25 mL) was then added, the mixture acidified to pH=6 with dilute HCl, and then extracted with benzene. The extract was dried with MgSO₄, evaporated, and purified by flash column chromatography to afford 2-amino-4-methoxybenzenethiol hydrochloride (intermediate 23) (1.43 g, 49%) as a light yellow solid.

Intermediate 24:

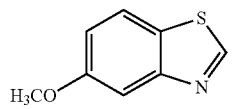

A mixture of intermediate 23 (1.33 g, 6.9 mmol), boric acid (2.3 g, 37.2 mmol) and formic acid (17 mL) was heated to reflux and stirred for 6 h. The reaction mixture was cooled to rt and diluted with water. The solution was made alkaline and extracted with ethyl acetate. Further purification by column chromatography (elution with PE/EtOAc=3:1) gave 5-methoxybenzo[d]thiazole (intermediate 24) (290 mg, 15%). HPLC: 99%, RI 2.646 min. MS (ESI) m/z 166.0 [M+H]⁺.

Intermediate 25:

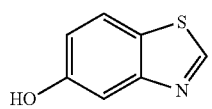

A mixture of intermediate 24 (272 mg, 1.65 mmol) and hydroiodic acid (45%, 2 mL) was heated to reflux for 5 h. The mixture was diluted with water and filtered. The filtrate was neutralized and the solids were filtered, washed with water, and combined to give benzo[d]thiazol-5-ol (intermediate 25) (206 mg, 83%). HPLC: 99%, RT 2.038 min. MS (ESI) m/z 152.1 [M+H]⁺.

Intermediate 26:

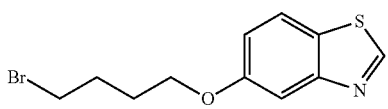

A mixture of intermediate 25 (206 mg, 1.4 mmol), 1,4-dibromobutane (0.5 mL, 4.2 mmol) and anhydrous K₂CO₃ (193 mg, 1.4 mmol) in EtOH (20 mL) was heated to reflux and stirred overnight. The yellow solid was filtered and purified by column chromatography (elution with PE/EtOAc=4:1) to afford 5-(4-bromobutoxy)benzo[d]thiazole (intermediate 26) (108 mg, 39%) as a yellow oil. HPLC: 99%, RT 3.426 min. MS (ESI) m/z 288.0 [M+H]⁺.

Compound 7:

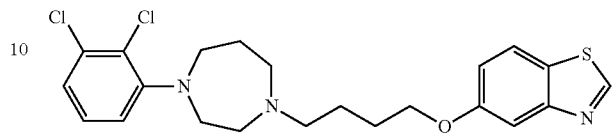

A mixture of intermediate 26 (47 mg, 0.16 mmol) and NaI (48 mg, 0.32 mmol) in CH₃CN was heated to reflux for 30 min and then cooled to rt. Intermediate 2 (70 mg, 0.25 mmol) and anhydrous K₂CO₃ (88 mg, 0.64 mmol) were added to the mixture. The resulting mixture was heated to reflux and stirred overnight. The reaction solution was diluted with water and extracted with EtOAc. The combined EtOAc layers were washed with brine, dried over anhydrous Na₂SO₄, concentrated in vacuo and purified by flash chromatography on silica gel column (elution with DCM/MeOH=30:1) to give 5-(4-(4-(2,3-dichlorophenyl)-1,4-diazepan-1-yl)butoxy)benzo[d]thiazole (compound 7) (31 mg, 42%). ¹H NMR (300 MHz, CDCl₃) δ 8.97 (s, 1H), 7.80 (d, J=8.7 Hz, 1H), 7.60 (d, J=3.0 Hz, 1H), 7.11-7.07 (m, 3H), 7.01-6.98 (m, 1H), 4.10 (t, J=5.7 Hz, 2H),), 3.33-3.27 (m, 4H), 2.96-2.95 (m, 4H), 2.73-2.71 (m, 2H), 2.06-2.04 (m, 2H), 1.92-1.80 (m, 4H), HPLC: 99%, RT 2.702 min. MS (ESI) m/z 450.1 [M+H]⁺. mp: 82-84° C.

Synthesis of Compound 8

Scheme 16. Synthesis of intermediate 27

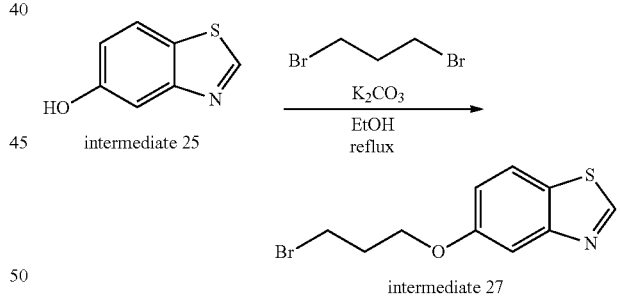

Scheme 17. Synthesis of compound 8

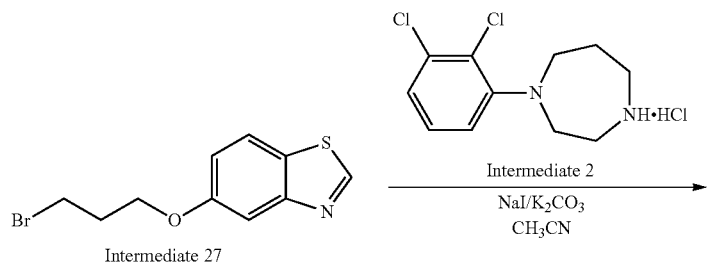

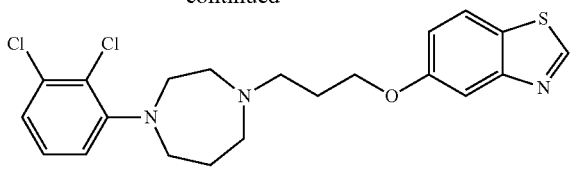

Example 8

Intermediate 27:

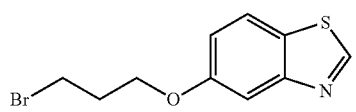

A mixture of intermediate 25 (1 g, 6.6 mmol), 1,3-dibromopropane (1.83 mL, 18 mmol), anhydrous K$_2$CO$_3$ (828 mg, 6.0 mmol) and EtOH (20 mL) was heated to reflux and stirred overnight. The yellow solid was filtered and purified by column chromatography (elution with PE/EtOAc=3:1) to afford 5-(3-bromopropoxy)benzo[d]thiazole (intermediate 27) (543 mg, 33%) as a yellow oil.

Compound 8:

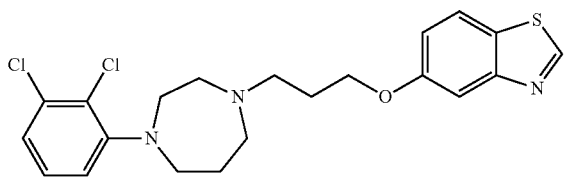

A mixture of intermediate 27 (106 mg, 0.39 mmol) and NaI (140 mg, 0.78 mmol) in CH$_3$CN was heated to reflux for 30 min and then cooled to rt. Intermediate 2 (165 mg, 0.59 mmol) and anhydrous K$_2$CO$_3$ (215 mg, 1.56 mmol) were added to the mixture. The resulting mixture was heated to reflux and stirred overnight. The reaction solution was diluted with water and extracted with EtOAc. The combined EtOAc layers were washed with brine, dried over anhydrous Na$_2$SO$_4$, concentrated in vacuo and purified by flash chromatography on silica gel column (elution with DCM/MeOH=30:1) to give 5-(3-(4-(2,3-dichlorophenyl)-1,4-diazepan-1-yl) propoxy)benzo[d]thiazole (compound 8) (98 mg, 60%) as a yellow solid. $^1$H NMR (300 MHz, DMSO-d6) δ 9.37 (s, 1H), 8.05 (d, J=10.5 Hz, 1H), 7.66 (d, J=4.8 Hz, 1H), 7.32-7.30 (m, 2H), 7.25-7.23 (m, 1H), 7.14 (dd, J=9.0 Hz, 2.4 Hz, 1H), 4.19 (t, J=6.0 Hz, 2H), 3.61-3.29 (m, 10H), 2.31-2.26 (m, 4H). HPLC: 99%, RT 2.601 min. MS (ESI) m/z 436.3 [M+H]$^+$. mp: 93-94° C.

Synthesis of Compound 9

Scheme 18. Synthesis of intermediate 29

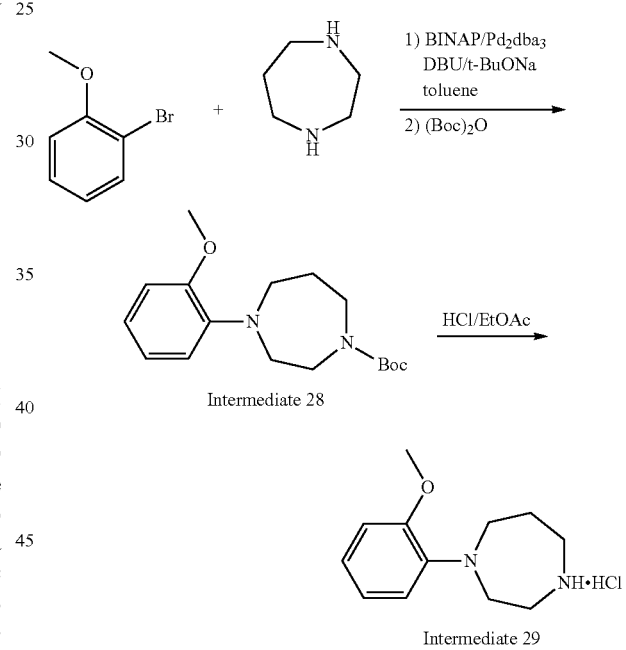

Scheme 19. Synthesis of compound 9

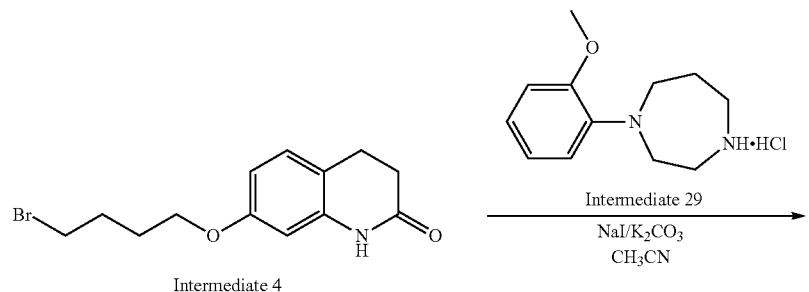

-continued

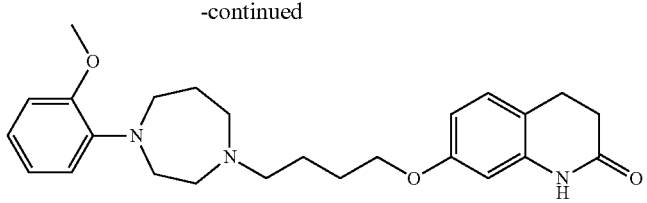

Example 9

Compound 28:

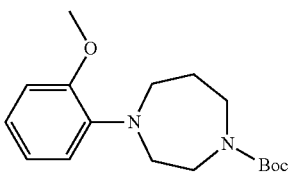

A well-dried flask was first charged with 1-bromo-2-methoxybenzene (2.5 g, 13.4 mmol) and 1,4-diazepane (1.6 g, 16.1 mmol), which was then evacuated and backfilled with N₂ through a balloon under gentle warming (40° C.). Toluene was added and the mixture was bubbled with N₂ for 10 min, then BINAP (250 mg, 0.4 mmol) and Pd₂ dba₃ (156 mg, 0.17 mmol) was added to the mixture. After the addition of DBU (2.4 mL), the solution was warmed at 60-70° C. while tBuONa (2.25 g, 20.1 mmol) was added in one portion to start the amination. After the reaction mixture cooled to rt, (Boc)₂O (7.3 g, 33.5 mmol) was dissolved in DCM and added dropwise to the reaction mixture and stirred for 3 h at rt. The reaction mixture was diluted with water and extracted with EtOAc. The combined EtOAc layers were washed with brine, dried over anhydrous Na₂SO₄, concentrated in vacuo and purified by flash chromatography on silica gel column (elution with PE/EtOAc=30:1) to give tert-butyl 4-(2-methoxyphenyl)-1,4-diazepane-1-carboxylate (intermediate 28) (396 mg, 10%) as a yellow oil.

Intermediate 29:

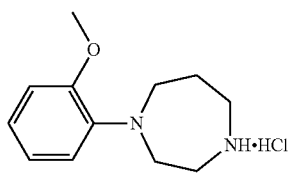

Excess HCl in EtOAc was added dropwise to a solution of intermediate 28 (396 mg, 1.29 mmol) in EtOAc and the reaction mixture was stirred at rt for 1.5 h. Filtration gave 1-(2-methoxyphenyl)-1,4-diazepane hydrochloride (intermediate 29) (200 mg, 64%) as a white solid.

Compound 9:

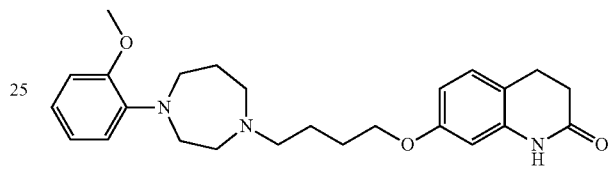

A mixture of intermediate 4 (150 mg, 0.51 mmol) and NaI (150 mg, 1.02 mmol) in CH₃CN was heated to reflux for 30 min and then cooled to rt. Intermediate 29 (121 mg, 0.5 mmol) and anhydrous K₂CO₃ (276 mg, 2.0 mmol) were added to the mixture. The resulting mixture was heated to reflux and stirred overnight. The reaction solution was diluted with water and extracted with EtOAc. The combined EtOAc layers were washed with brine, dried over anhydrous Na₂SO₄, concentrated in vacuo and purified by flash chromatography on silica gel column (elution with DCM/MeOH=30:1) to give 7-(4-(4-(2-methoxyphenyl)-1,4-diazepan-1-yl)butoxy)-3,4-dihydroquinolin-2(1H)-one (compound 9) (25 mg, 11%). HPLC: 95%, RT 2.314 min. MS (ESI) m/z 424.2 [M+H]⁺.

Synthesis of Compound 10

Scheme 20. Synthesis of compound 10

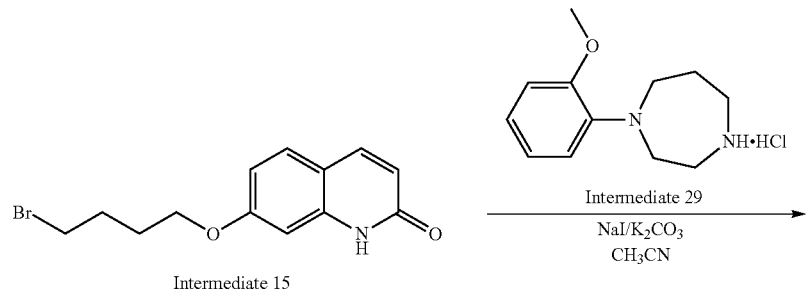

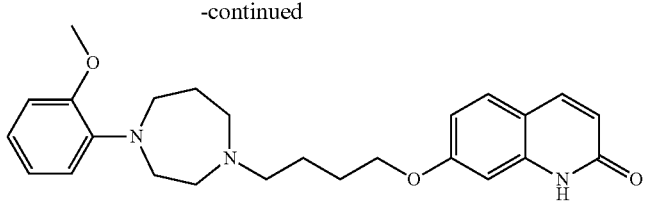

Example 10

Compound 10:

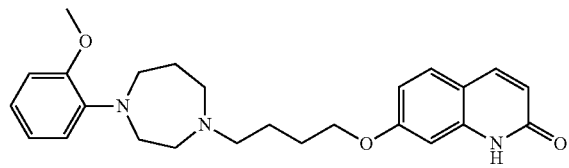

A mixture of intermediate 15 (150 mg, 0.51 mmol) and NaI (150 mg, 1.02 mmol) in CH$_3$CN was heated to reflux for 30 min and then cooled to rt. Intermediate 29 (124 mg, 0.51 mmol) and anhydrous K$_2$CO$_3$ (282 mg, 2.04 mmol) were added to the mixture. The resulting mixture was heated to reflux and stirred overnight. The reaction solution was diluted with water and extracted with EtOAc. The combined EtOAc layers were washed with brine, dried over anhydrous Na$_2$SO$_4$, concentrated in vacuo and purified by flash chromatography on silica gel column (elution with DCM/MeOH=30:1) to give 7-(4-(4-(2-methoxyphenyl)-1,4-diazepan-1-yl)butoxy)quinolin-2(1H)-one (compound 10) (61 mg, 26%). $^1$H NMR (300 MHz, CDCl$_3$) δ 7.69 (d, J=9.6 Hz, 1H), 7.43 (d, J=8.7 Hz, 1H), 6.91-6.85 (m, 5H), 6.79 (d, J=9.0 Hz, 1H), 6.65 (s, 1H) 6.49 (d, J=9.3 Hz, 1H), 4.07 (t, J=6.0 Hz, 2H), 3.83 (s, 3H), 3.34-3.29 (m, 4H), 2.93-2.86 (m, 4H), 2.69-2.65 (m, 2H), 2.06-2.02 (m, 2H), 1.86-1.84 (m, 2H), 1.77-1.73 (m, 2H). HPLC: 95%, RT 1.902 min. MS (ESI) m/z 422.3 [M+H]$^+$.

Synthesis of Compound 11

Scheme 21. Synthesis of compound 11

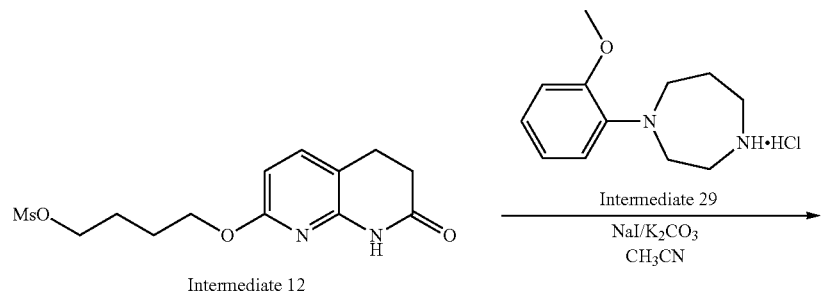

Intermediate 12

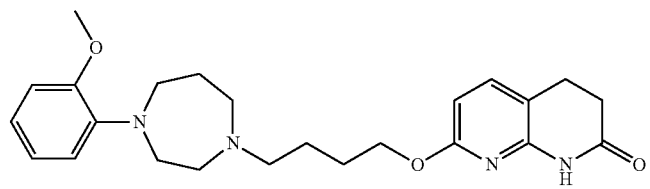

Example 11

Synthesis of Compound 12

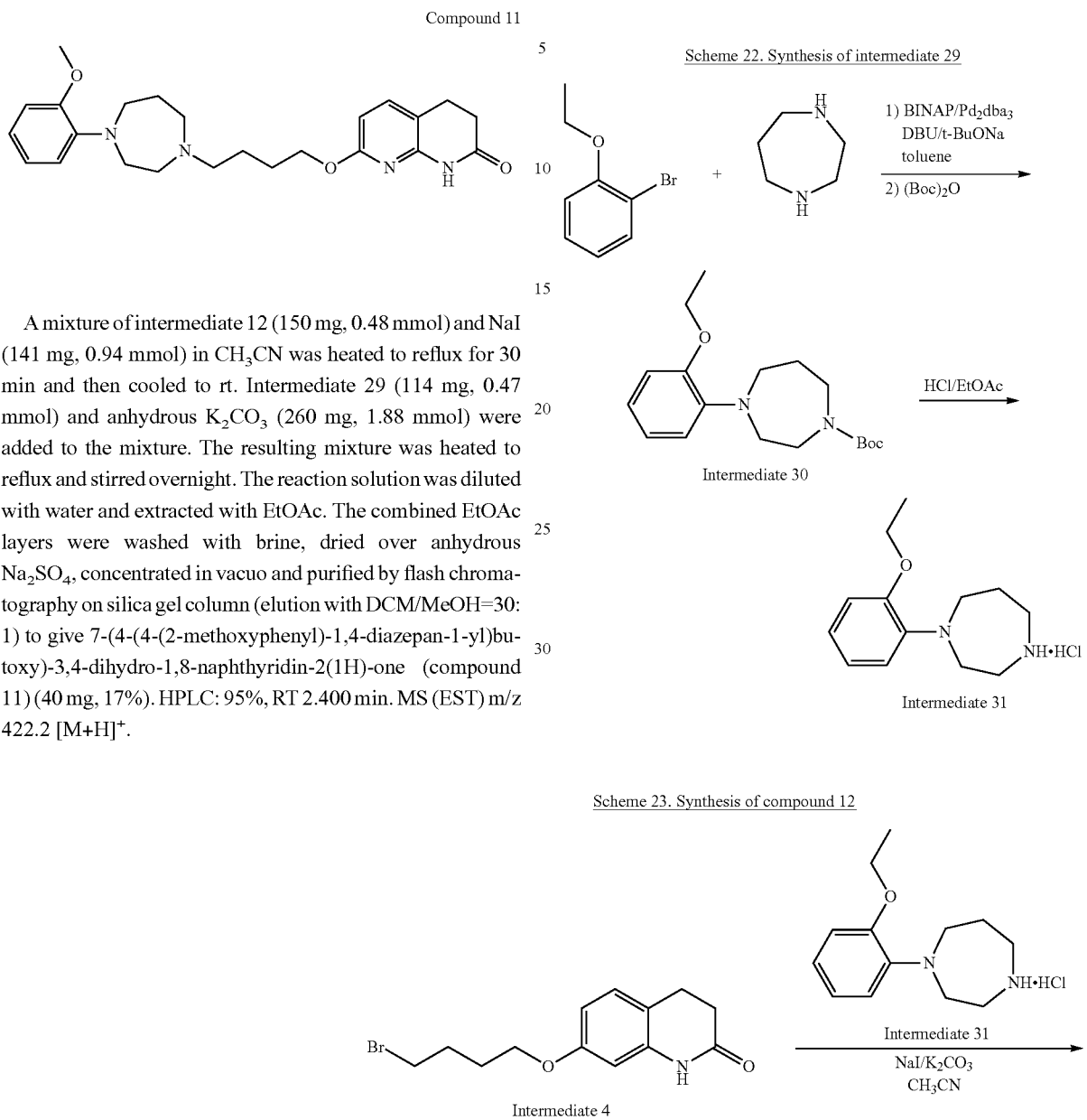

Compound 11

A mixture of intermediate 12 (150 mg, 0.48 mmol) and NaI (141 mg, 0.94 mmol) in CH$_3$CN was heated to reflux for 30 min and then cooled to rt. Intermediate 29 (114 mg, 0.47 mmol) and anhydrous K$_2$CO$_3$ (260 mg, 1.88 mmol) were added to the mixture. The resulting mixture was heated to reflux and stirred overnight. The reaction solution was diluted with water and extracted with EtOAc. The combined EtOAc layers were washed with brine, dried over anhydrous Na$_2$SO$_4$, concentrated in vacuo and purified by flash chromatography on silica gel column (elution with DCM/MeOH=30:1) to give 7-(4-(4-(2-methoxyphenyl)-1,4-diazepan-1-yl)butoxy)-3,4-dihydro-1,8-naphthyridin-2(1H)-one (compound 11) (40 mg, 17%). HPLC: 95%, RT 2.400 min. MS (EST) m/z 422.2 [M+H]$^+$.

Compound 30:

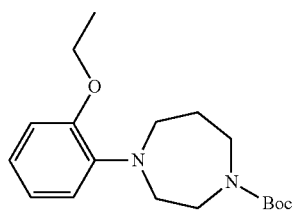

A well-dried flask was first charged with 1-bromo-2-ethoxybenzene (2.5 g, 12.4 mmol) and 1,4-diazepane (1.5 g, 15.0 mmol), which was evacuated and backfilled with $N_2$ through a balloon under gentle warming (40° C.). Toluene was charged and the mixture was bubbled with $N_2$ for 10 min, then BINAP (234 mg, 0.38 mmol) and $Pd_2\,dba_3$ (119 mg, 0.13 mmol) was added to the mixture. After the addition of DBU (2.25 mL), the solution was warmed at 60-70° C. while a fine powder of tBuONa (2.1 g, 18.75 mmol) was added in one portion to start the amination. After the reaction mixture cooled to rt, $(Boc)_2O$ (6.9 g, 31.25 mmol) was dissolved in DCM and added dropwise to the reaction mixture, then stirred for 3 h at rt. The reaction mixture was diluted with water and extracted with EtOAc. The combined EtOAc layers were washed with brine, dried over anhydrous $Na_2SO_4$, concentrated in vacuo and purified by flash chromatography on silica gel column (elution with PE/EtOAc=30:1) to give tert-butyl 4-(2-ethoxyphenyl)-1,4-diazepane-1-carboxylate (intermediate 30) (800 mg, 20%). HPLC: 99%, RT 2.485 min. MS (ESI) m/z 321.0 $[M+H]^+$.

Intermediate 31:

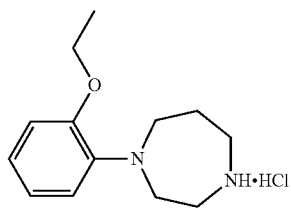

Excess HCl in EtOAc was added dropwise to a solution of intermediate 30 (800 mg, 2.5 mmol) in EtOAc and the reaction mixture was stirred at rt for 1.5 h. Filtration gave 1-(2-ethoxyphenyl)-1,4-diazepane hydrochloride (intermediate 31) (382 mg, 59%) as a white solid.

Compound 12:

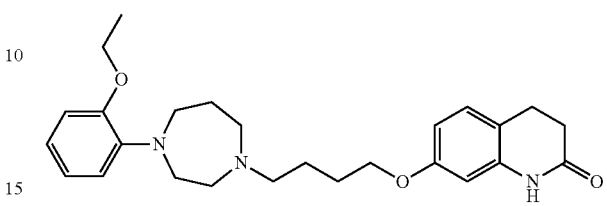

A mixture of intermediate 4 (150 mg, 0.5 mmol) and NaI (150 mg, 1.0 mmol) in $CH_3CN$ was heated to reflux for 30 min and then cooled to rt. Intermediate 31 (129 mg, 0.5 mmol) and anhydrous $K_2CO_3$ (276 mg, 2.0 mmol) were then added to the mixture. The resulting mixture was heated to reflux and stirred overnight. The reaction solution was diluted with water and extracted with EtOAc. The combined EtOAc layers were washed with brine, dried over anhydrous $Na_2SO_4$, concentrated in vacuo and purified by flash chromatography on silica gel column (elution with DCM/MeOH=50:1) to give 7-(4-(4-(2-ethoxyphenyl)-1,4-diazepan-1-yl)butoxy)-3,4-dihydroquinolin-2(1H)-one (compound 12) (95 mg, 44%). $^1$H NMR (300 MHz, $CDCl_3$) δ 7.75 (bs, 1H), 7.04 (d, J=8.1 Hz, 1H), 6.92-6.83 (m, 4H), 6.52 (dd, J=8.4 Hz, 2.1 Hz, 1H), 6.30 (d, J=2.7 Hz, 1H), 4.04 (q, J=6.9 Hz, 2H), 3.96-3.94 (m, 2H), 3.38-3.29 (m, 4H), 3.02-2.93 (m, 4H), 2.89 (t, J=6.9 Hz, 2H), 2.74-2.70 (m, 2H), 2.61 (t, J=8.1 Hz, 2H), 2.14-2.10 (m, 2H), 1.83-1.79 (m, 4H), 1.45 (t, J=6.9 Hz, 3H). HPLC: 99%, RT 2.438 min. MS (ESI) m/z 438.2 $[M+H]^+$.

Synthesis of Compound 13

Scheme 24. Synthesis of compound 13

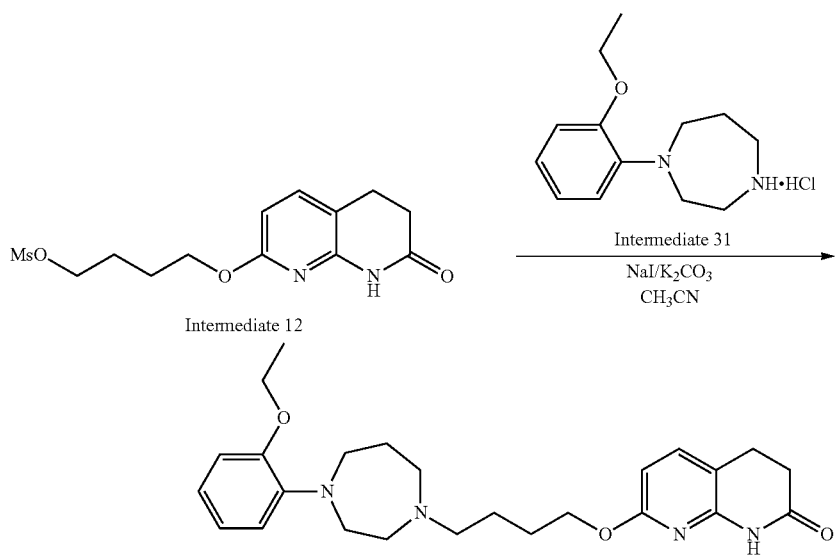

Example 13

Compound 13:

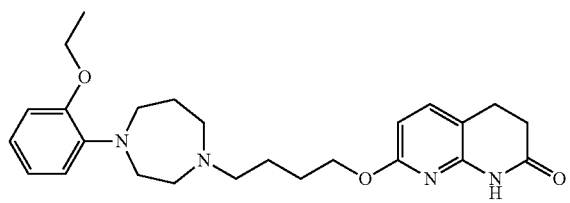

Compound 14:

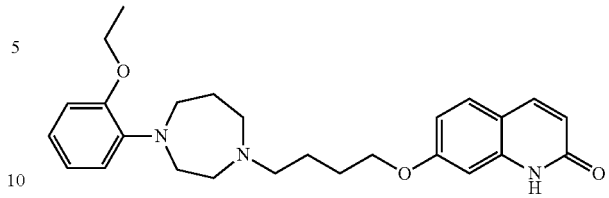

A mixture of intermediate 12 (150 mg, 0.48 mmol) and NaI (150 mg, 1.0 mmol) in CH$_3$CN was heated to reflux for 30 min and then cooled to rt. Intermediate 31 (124 mg, 0.48 mmol) and anhydrous K$_2$CO$_3$ (265 mg, 1.92 mmol) were added to the mixture. The resulting mixture was heated to reflux and stirred overnight. The reaction solution was diluted with water and extracted with EtOAc. The combined EtOAc layers were washed with brine, dried over anhydrous Na$_2$SO$_4$, concentrated in vacuo and purified by flash chromatography on silica gel column (elution with DCM/MeOH=50:1) to give 7-(4-(4-(2-ethoxyphenyl)-1,4-diazepan-1-yl)butoxy)-3,4-dihydro-1,8-naphthyridin-2(1H)-one (compound 13) (50 mg, 24%). $^1$H NMR (300 MHz, CDCl$_3$) δ 7.55 (bs, 1H), 7.35 (d, J=8.1 Hz, 1H), 6.89-6.85 (m, 4H), 6.34 (d, J=8.1 Hz, 1H), 4.24-4.20 (m, 2H), 4.04 (q, J=6.9 Hz, 2H), 3.41-3.37 (m, 2H), 3.31 (t, J=5.7 Hz, 2H), 3.15-2.95 (m, 4H), 2.86 (t, J=6.9 Hz, 2H), 2.79-2.69 (m, 2H), 2.64 (t, J=7.5 Hz, 2H), 2.20-2.12 (s, 2H), 1.82-1.76 (m, 4H), 1.45 (t, J=6.9 Hz, 3H). HPLC: 99%, RT 2.393 min. MS (ESI) m/z 439.2 [M+H]$^+$.

Synthesis of Compound 14

A mixture of intermediate 15 (150 mg, 0.51 mmol) and NaI (150 mg, 1.0 mmol) in CH$_3$CN was heated to reflux for 30 min and then cooled to rt. Intermediate 31 (130 mg, 0.51 mmol) and anhydrous K$_2$CO$_3$ (282 mg, 2.04 mmol) were added to the mixture. The resulting mixture was heated to reflux and stirred overnight. The reaction solution was diluted with water and extracted with EtOAc. The combined EtOAc layers were washed with brine, dried over anhydrous Na$_2$SO$_4$, concentrated in vacuo and purified by flash chromatography on silica gel column (elution with DCM/MeOH=50:1) to give 7-(4-(4-(2-ethoxyphenyl)-1,4-diazepan-1-yl)butoxy)quinolin-2(1H)-one (compound 14) (50 mg, 24%). $^1$H NMR (300 MHz, CDCl$_3$) δ 10.89 (bs, 1H), 7.69 (d, J=9.6 Hz, 1H), 7.44 (d, J=9.0 Hz, 1H), 6.92-6.78 (m, 5H), 6.71 (d, J=2.7 Hz, 1H), 6.51 (d, J=9.6 Hz, 1H), 4.10-4.01 (m, 4H), 3.36-3.30 (m, 4H), 2.89-2.79 (m, 4H), 2.62-2.59 (m, 4H), 2.02-2.01 (m, Scheme 25. Synthesis of compound 14

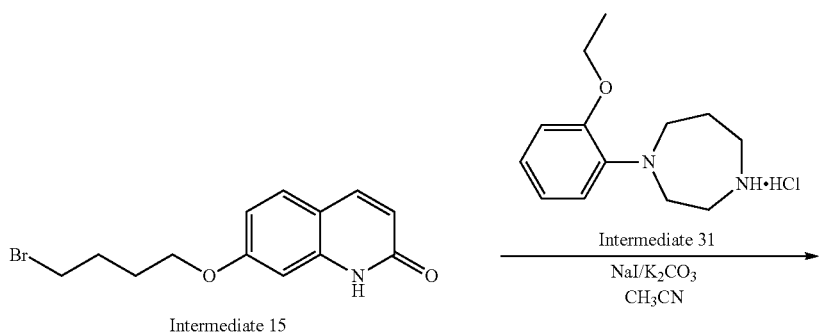

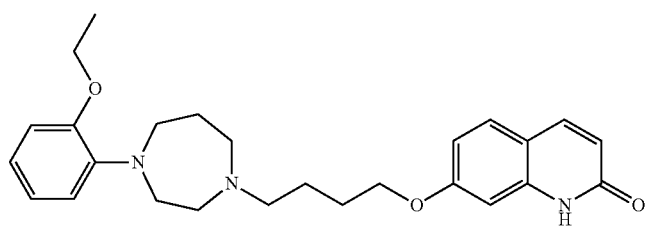

Example 14

2H), 1.89-1.82 (m, 2H), 1.45 (t, J=6.9 Hz, 3H). HPLC: 99%, RT 2.375 min. MS (ESI) m/z 436.2 [M+H]+.

Synthesis of Compound 15

Scheme 26. Synthesis of intermediate 32

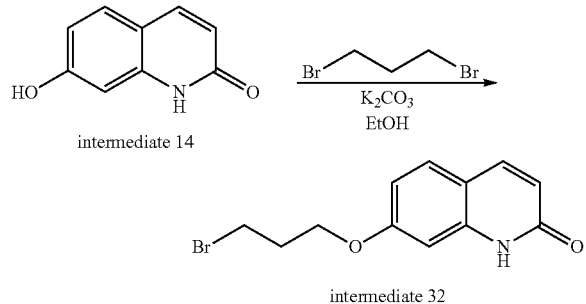

Compound 15:

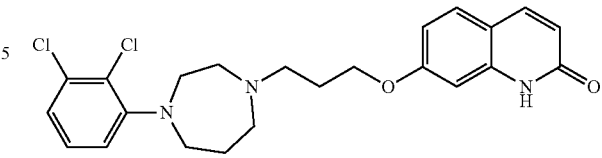

A mixture of intermediate 32 (217 mg, 0.77 mmol) and NaI (231 mg, 1.54 mmol) in CH$_3$CN was heated to reflux for 30 min and then cooled to rt. Intermediate 2 (217 mg, 0.77 mmol) and anhydrous K$_2$CO$_3$ (425 mg, 3.08 mmol) were added to the mixture. The resulting mixture was heated to reflux and stirred overnight. The reaction solution was diluted with water and extracted with EtOAc. The combined EtOAc layers were washed with brine, dried over anhydrous Na$_2$SO$_4$, concentrated in vacuo and purified by flash chromatography on silica gel column (elution with DCM/MeOH=30:1) to give 7-(3-(4-(2,3-dichlorophenyl)-1,4-diazepan-1-yl)propoxy)quinolin-2(1H)-one (compound 15) (135 mg, 39%).

Scheme 27. Synthesis of compound 15

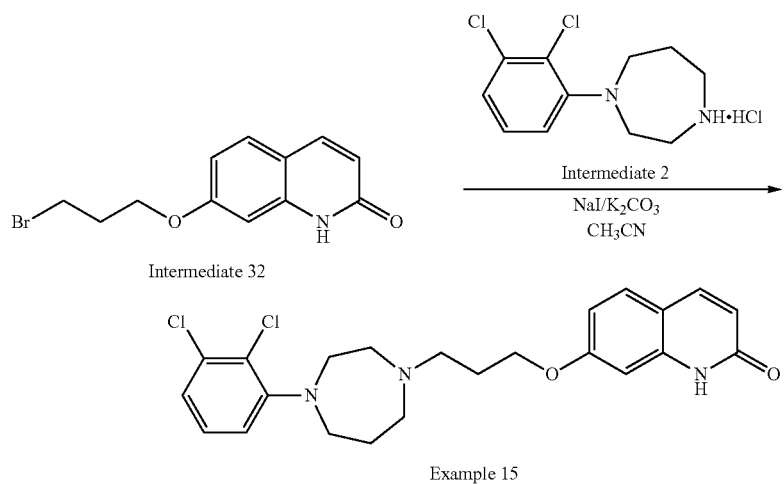

Intermediate 32:

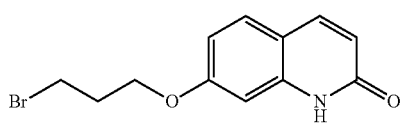

A mixture of intermediate 14 (193 mg, 1.2 mmol), 1,3-dibromopropane (0.37 mL, 3.6 mmol) and anhydrous K$_2$CO$_3$ (166 mg, 1.2 mmol) was dissolved in EtOH and the solution was heated to reflux overnight. The solution was diluted with water and extracted with EtOAc. The combined organic layers were washed with saturated aq NaHCO$_3$, brine, dried over anhydrous Na$_2$SO$_4$, concentrated in vacuo and purified by flash chromatography on silica gel column (elution with PE/EtOAc=2:1) to give 7-(3-bromopropoxy)quinolin-2(1H)-one (intermediate 32) (185 mg, 55%) as a white solid.

$^1$H NMR (300 MHz, CDCl$_3$) δ 11.96 (bs., 1H), 7.72 (d, J=9.3 Hz, 1H) 7.45 (d, J=8.7 Hz, 1H), 7.09-7.07 (m, 2H), 7.01-6.99 (m, 1H), 6.83-6.81 (m, 2H), 6.54 (d, J=9.0 Hz, 1H), 4.15 (t, J=5.7 Hz, 2H), 3.31 (d, J=5.1 Hz, 4H), 2.92-2.96 (m, 4H), 2.76 (t, J=6.6 Hz, 2H), 2.03-1.01 (m, 4H). HPLC: 99%, RT 2.348 min. MS (ESI) m/z 446.1 [M+H]+. mp: 117-118° C.

Synthesis of Compound 16

Scheme 28. Synthesis of intermediate 34

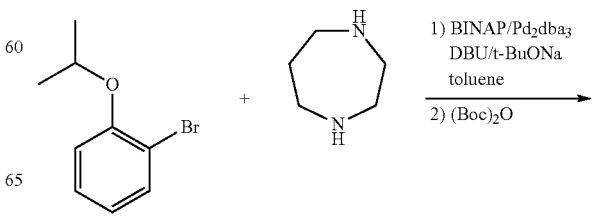

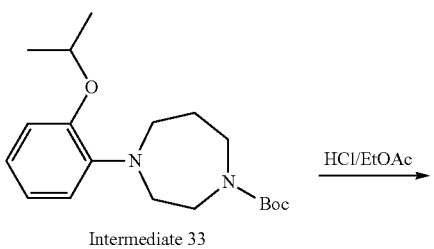

Intermediate 33

→ HCl/EtOAc

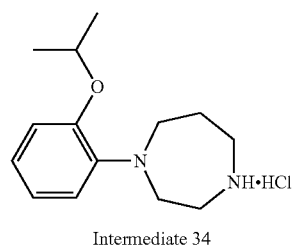

Intermediate 34 with N$_2$ through a balloon under gentle warming (40° C.). Toluene was charged and the mixture was bubbled with N$_2$ for 10 min, then BINAP (44 mg, 0.07 mmol) and Pd$_2$ dba$_3$ (14 mg, 0.02 mmol) were added to the mixture. After the addition of DBU (0.5 mL), the solution was warmed at 60-70° C. while a fine powder of tBuONa (334 mg, 3.48 mmol) was added in one portion to start the amination. After the reaction mixture cooled to rt, (Boc)$_2$O (1.265 g, 5.8 mmol) was dissolved in DCM and added dropwise to the reaction mixture then stirred for 3 h at rt. The reaction mixture was diluted with water and extracted with EtOAc. The combined EtOAc layers were washed with brine, dried over anhydrous Na$_2$SO$_4$, concentrated in vacuo and purified by flash chromatography on silica gel column (elution with PE/EtOAc=30:1) to give tert-butyl 4-(2-isopropoxyphenyl)-1,4-diazepane-1-carboxylate (intermediate 33) (172 mg, 22%).

Scheme 29. Synthesis of compound 16

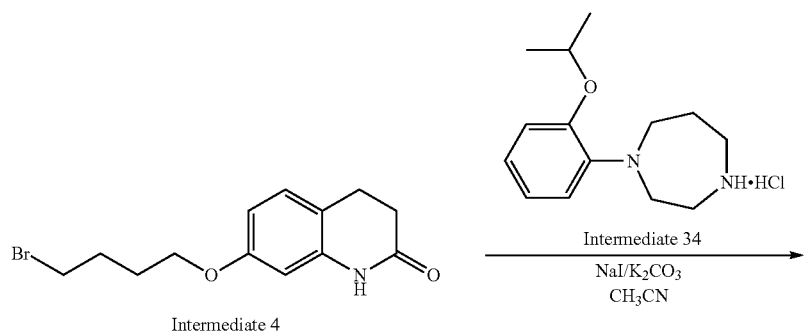

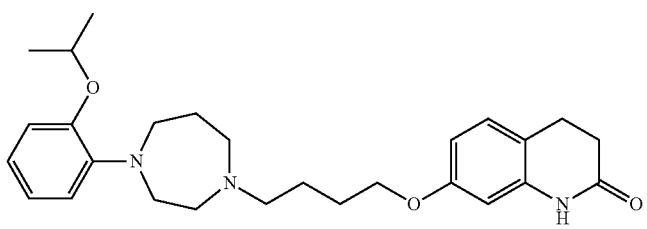

Example 16

Intermediate 33:

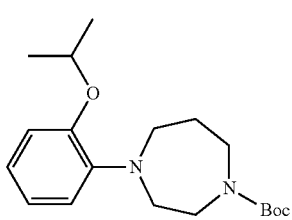

Intermediate 34:

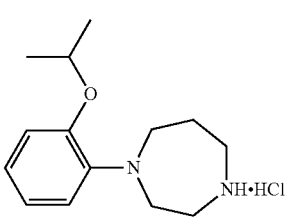

A well-dried flask was first charged with 1-bromo-2-isopropoxybenzene (500 mg, 2.32 mmol) and 1,4-diazepane (348 mg, 3.48 mmol), which was evacuated and backfilled Excess HCl in EtOAc was added dropwise to a solution of intermediate 33 (172 mg, 0.51 mmol) in EtOAc and the reaction mixture was stirred at rt for 1.5 h. Filtration gave 1-(2-isopropoxyphenyl)-1,4-diazepane hydrochloride (intermediate 34) (175 mg, 100%) as a white solid.

Compound 16:

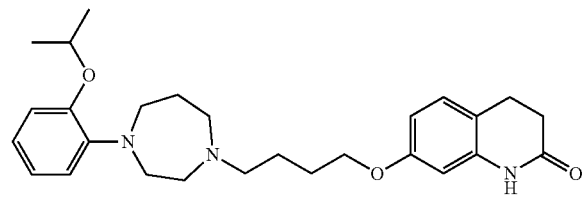

A mixture of intermediate 4 (75 mg, 0.25 mmol) and NaI (75 mg, 0.5 mmol) in CH$_3$CN was heated to reflux for 30 min and then cooled to rt. Intermediate 34 (100 mg, 0.37 mmol) and anhydrous K$_2$CO$_3$ (138 mg, 1.0 mmol) were added to the mixture. The resulting mixture was heated to reflux and stirred overnight. The reaction solution was diluted with water and extracted with EtOAc. The combined EtOAc layers were washed with brine, dried over anhydrous Na$_2$SO$_4$, concentrated in vacuo and purified by flash chromatography on silica gel column (elution with DCM/MeOH=50:1) to give 7-(4-(4-(2-isopropoxyphenyl)-1,4-diazepan-1-yl)butoxy)-3,4-dihydroquinolin-2(1H)-one (compound 16) (81 mg, 72%). $^1$H NMR (300 MHz, CDCl$_3$) δ 7.72 (bs, 1H), 7.03 (d, J=8.1 Hz, 1H), 6.89-6.85 (m, 4H), 6.51 (d, J=8.1 Hz, 1H), 6.30 (s, 1H), 4.62-4.57 (m, 1H), 4.02-3.92 (m, 2H), 3.42-3.36 (m, 2H), 3.32-3.28 (m, 2H), 3.07-3.00 (m, 4H), 2.89 (t, J=7.2 Hz, 2H), 2.80-2.74 (m, 2H), 2.61 (t, J=6.9 Hz, 2H), 2.20-2.10 (m, 2H), 1.90-1.76 (m, 4H), 1.35 (d, J=6.0 Hz, 6H). HPLC: 99%, RT 2.506 min. MS (ESI) m/z 452.4 [M+H]$^+$.

Synthesis of Compound 17

Compound 17:

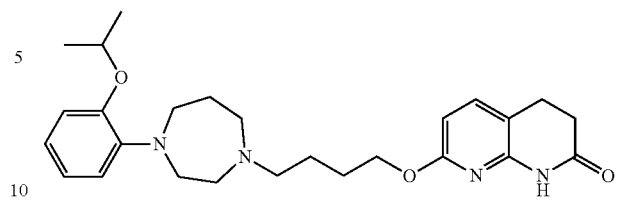

A mixture of intermediate 12 (114 mg, 0.36 mmol) and NaI (109 mg, 0.73 mmol) in CH$_3$CN was heated to reflux for 30 min and then cooled to rt. Intermediate 34 (98 mg, 0.36 mmol) and anhydrous K$_2$CO$_3$ (200 mg, 1.45 mmol) were added to the mixture. The resulting mixture was heated to reflux and stirred overnight. The reaction solution was diluted with water and extracted with EtOAc. The combined EtOAc layers were washed with brine, dried over anhydrous Na$_2$SO$_4$, concentrated in vacuo and purified by flash chromatography on silica gel column (elution with DCM/MeOH=50:1) to give 7-(4-(4-(2-isopropoxyphenyl)-1,4-diazepan-1-yl)butoxy)-3,4-dihydro-1,8-naphthyridin-2(1H)-one (compound 17) (52 mg, 32%). $^1$H NMR (300 MHz, CDCl$_3$) δ 7.58 (bs., 1H), 7.35 (d, J=8.1 Hz, 1H), 6.89-6.86 (m, 4H), 6.34 (d, J=8.1 Hz, 1H), 4.62-4.57 (m, 1H), 4.22 (m, 2H), 3.42-3.36 (m, 2H), 3.30 (t, J=6.3 Hz, 2H), 3.08-3.01 (m, 4H), 2.89-2.77 (m, 4H), 2.64 (t, J=7.2 Hz, 2H), 2.21-2.11 (m, 2H), 1.90-1.72 (m., 4H), 1.35 (d, J=6.0 Hz, 6H). HPLC: 99%, RT 2.463 min. MS (ESI) m/z 453.3 [M+H]$^+$.

Scheme 30. Synthesis of compound 17

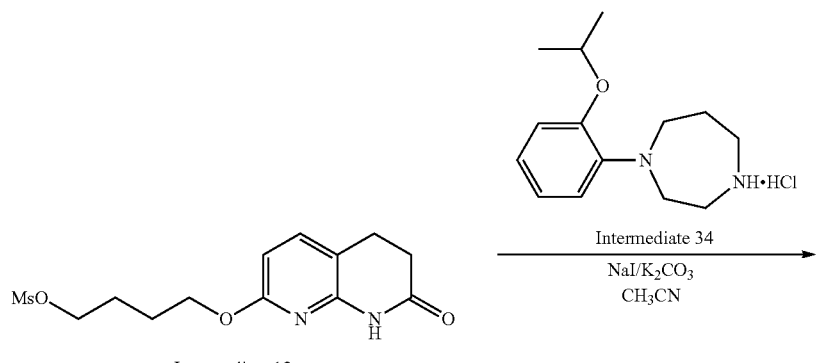

Intermediate 12

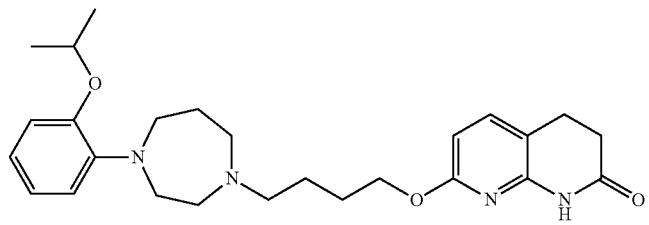

Example 17

Synthesis of Compound 18

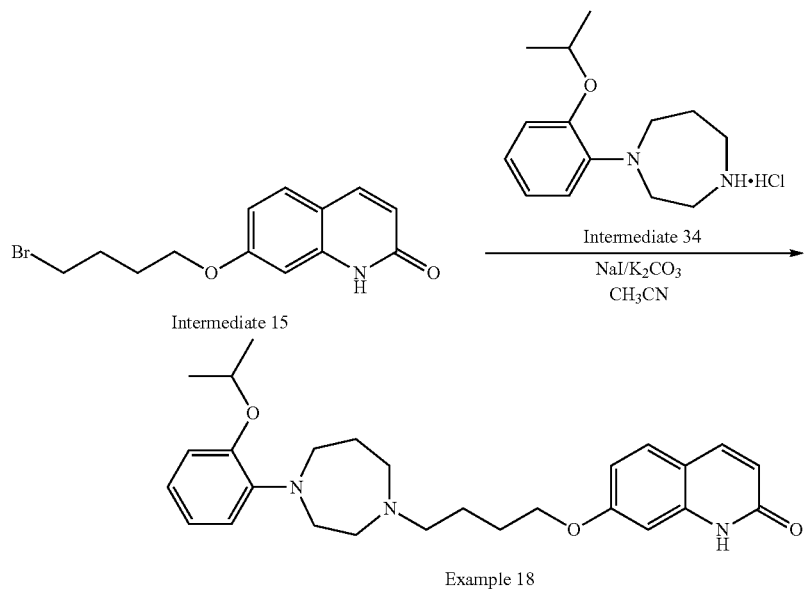

Compound 18:

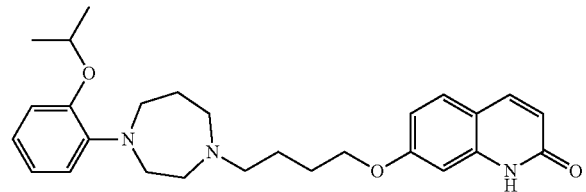

A mixture of intermediate 15 (120 mg, 0.41 mmol) and NaI (123 mg, 0.82 mmol) in CH₃CN was heated to reflux for 30 min and then cooled to rt. Intermediate 34 (111 mg, 0.41 mmol) and anhydrous $K_2CO_3$ (226 mg, 1.64 mmol) were added to the mixture. The resulting mixture was heated to reflux and stirred overnight. The reaction solution was diluted with water and extracted with EtOAc. The combined EtOAc layers were washed with brine, dried over anhydrous $Na_2SO_4$, concentrated in vacuo and purified by flash chromatography on silica gel column (elution with DCM/MeOH=50:1) to give 7-(4-(4-(2-isopropoxyphenyl)-1,4-diazepan-1-yl)butoxy)quinolin-2(1H)-one (compound 18) (115 mg, 62%). $^1$H NMR (300 MHz, CDCl₃) δ 11.68 (bs., 1H), 7.71 (d, J=9.3 Hz, 1H), 7.44 (d, J=9.3 Hz, 1H), 6.89-6.79 (m, 6H), 6.53 (d, J=9.6 Hz, 1H), 4.62-4.54 (m, 1H), 4.11-4.07 (m, 2H), 3.34-3.29 (m, 4H), 2.94-2.86 (m, 4H), 2.72-2.62 (m, 2H), 2.12-1.96 (m, 2H), 1.87-1.76 (m, 4H), 1.35 (d, J=6.0 Hz, 6H). HPLC: 99%, RT 2.434 min. MS (ESI) m/z 450.3 [M+H]⁺.

Synthesis of Compound 19

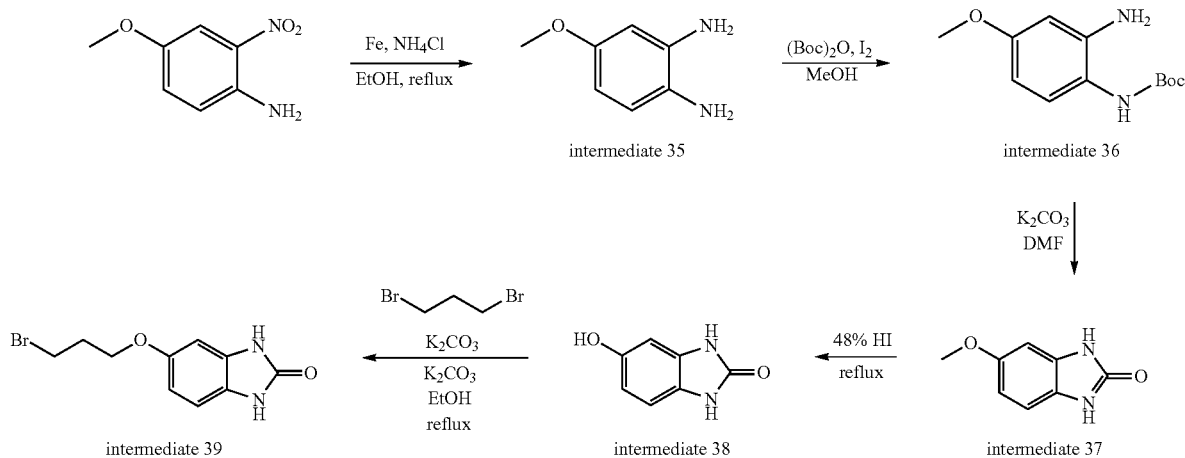

Scheme 33. Synthesis of compound 19

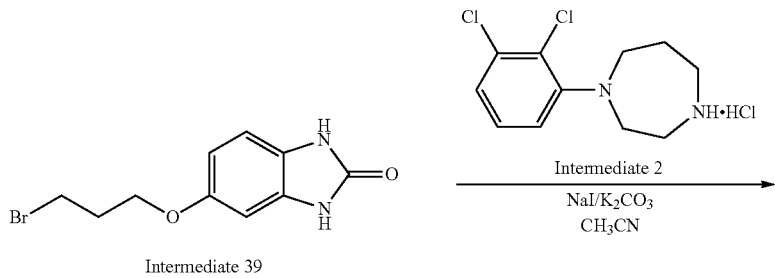

Intermediate 39

$\xrightarrow{\text{Intermediate 2}}_{\substack{\text{NaI/K}_2\text{CO}_3 \\ \text{CH}_3\text{CN}}}$

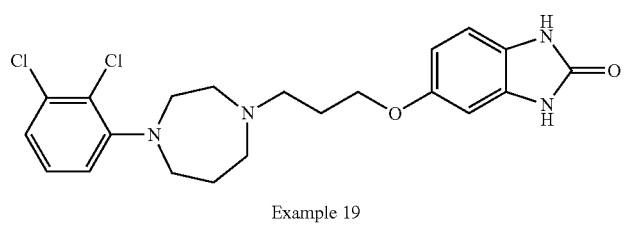

Example 19

Intermediate 35:

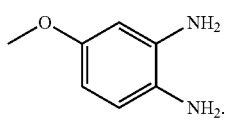

To a solution of 4-methoxy-2-nitroaniline (10 g, 59.4 mmol) in EtOH (200 mL) and water (80 mL) was added iron (12 g, 210 mmol) and ammonium chloride (9.63 g, 180 mmol). The mixture was then heated to reflux and stirred overnight. The mixture was filtered and the filtrate was evaporated to remove the EtOH and the residue was purified by flash chromatography on silica gel column (elution with DCM/MeOH=80:1) to give 4-methoxybenzene-1,2-diamine (intermediate 35) (5.65 g, 69%) as a yellow solid.

Intermediate 36:

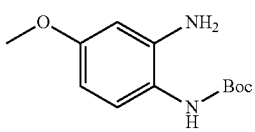

Intermediate 35 (5.6 g, 40.5 mmol) was dissolved in MeOH (10 mL). To this solution was added (Boc)₂O (8.86 g, 40.6 mmol) followed by iodine (515 mg, 4.06 mmol), which was then stirred at rt for 1 h. The solvent was evaporated, and the residue was dissolved in EtOAc and washed with 5% aq Na₂S₂O₃ and saturated aq NaHCO₃. The organic layer was dried over anhydrous Na₂SO₄, concentrated in vacuo and purified by flash chromatography on silica gel column (elution with DCM/MeOH=100:1) to give tert-butyl 2-amino-4-methoxyphenylcarbamate (intermediate 36) (7.4 g, 69%) as a brown solid. mp: 108-110° C.

Intermediate 37:

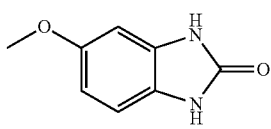

Intermediate 36 (7.3 g, 30.6 mmol) was dissolved in DMF (70 mL). To this solution was added anhydrous K₂CO₃ (4.7 g, 33.7 mmol) and the mixture was heated to reflux (130° C.) for 5 h. The solvent was removed under pressure, the residue was poured into ice water, and the aq phase was extracted with EtOAc. The combined organic layers were dried over anhydrous Na₂SO₄, concentrated under vacuum, and the resulting yellow solid was recrystallized from EtOH to give 5-methoxy-1H-benzo[d]imidazol-2(3H)-one (intermediate 37) (3.6 g, 72%) as a yellow solid. mp: 249-251° C.

Intermediate 38:

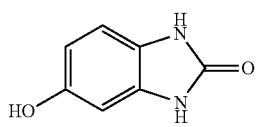

A mixture of intermediate 37 (3.6 g, 22 mmol) and 48% hydrogen iodide (30 mL) was heated to reflux (130° C.) and stirred for 12 h. The reaction mixture was neutralized to pH=8 with aq NaOH and then extracted with EtOAc. The combined organic layers were dried over anhydrous Na₂SO₄, concentrated under vacuum and purified by flash chromatography on silica gel column (elution with DCM/MeOH=80:1) to give 5-hydroxy-1H-benzo[d]imidazol-2(3H)-one (intermediate 38) (16.9 g, 80%). HPLC: 99%, RT 1.377 min. MS (ESI) m/z 151.0 [M+H]⁺. mp: 186-187° C.

Intermediate 39:

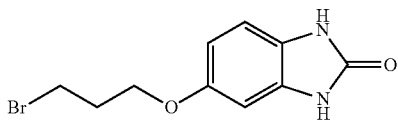

A solution of intermediate 38 (5 g, 33.3 mmol), 1,3-dibromopropane (4 mL, 33.3 mmol) and anhydrous K$_2$CO$_3$ (4.6 g, 33.3 mmol) in EtOH (25 mL) was heated to reflux and stirred overnight. The solvent was removed under vacuum. The residue was diluted with water and extracted with EtOAc. The combined EtOAc layers were washed with water, brine, dried over anhydrous Na$_2$SO$_4$, concentrated in vacuo and purified by flash chromatography on silica gel column (elution with DCM/MeOH=100:1) to give 5-(3-bromopropoxy)-1H-benzo[d]imidazol-2(3H)-one (intermediate 39) (240 mg, 12%) as a yellow solid.

Compound 19:

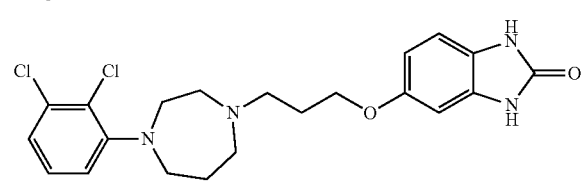

Intermediate 39 (80 mg, 0.29 mmol) was dissolved in CH$_3$CN (9 mL), then NaI (89 mg, 0.59 mmol) was added and the mixture was heated to reflux for 30 min, then cooled to rt. Intermediate 2 (43 mg, 0.15 mmol) and anhydrous K$_2$CO$_3$ (163 mg, 1.19 mmol) were added. The resulting mixture was heated to reflux and stirred for 6 h. The reaction solution was diluted with water and extracted with EtOAc. The combined EtOAc layers were washed with brine, dried over anhydrous Na$_2$SO$_4$, concentrated in vacuo and purified by flash chromatography on silica gel column (elution with DCM/MeOH=5:1) to give 5-(3-(4-(2,3-dichlorophenyl)-1,4-diazepan-1-yl)propoxy)-1H-benzo[c]imidazol-2(3H)-one (compound 19) (41 mg, 32%). $^1$H NMR (300 MHz, CDCl$_3$): δ 9.37 (bs, 1H), 9.05 (bs., 1H), 7.09-7.07 (m, 2H), 7.00-6.97 (m, 1H), 6.91-6.88 (m, 1H), 6.66-6.60 (m, 2H), 4.10-3.90 (m, 2H), 3.31-3.29 (m, 4H), 2.95-2.80 (m, 4H), 2.76-2.71 (m, 2H), 2.04-1.92 (m, 4H). HPLC: 99%, RT 2.241 min. MS (ESI) m/z 436.9 [M+H]$^+$. mp: 148-150° C.

Synthesis of Compound 20

Scheme 34. Synthesis of intermediate 41

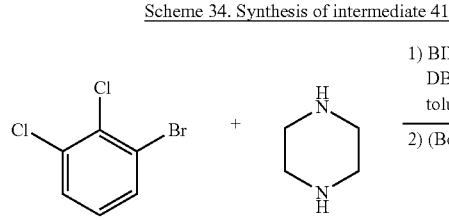

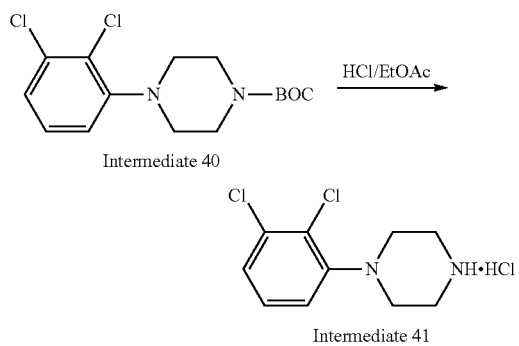

Scheme 35. Synthesis of intermediate 44

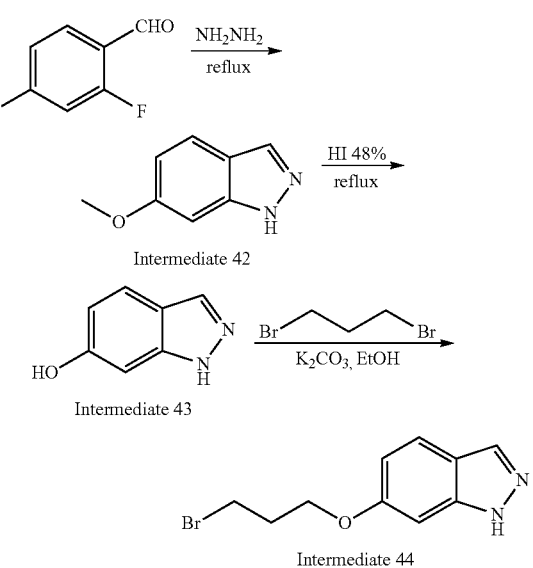

Scheme 36. Synthesis of compound 20

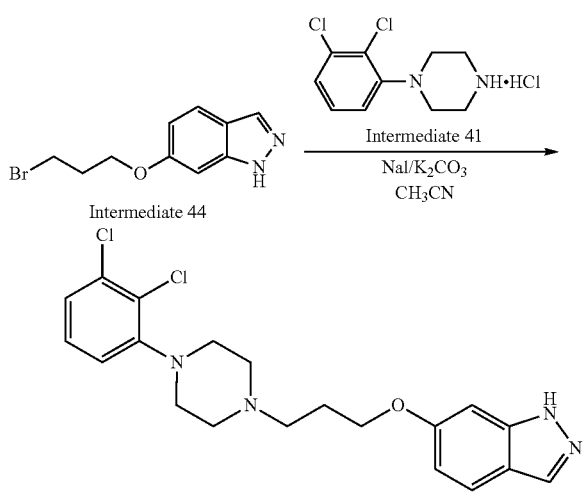

Intermediate 40:

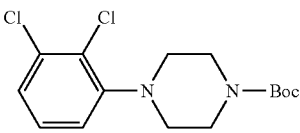

A well-dried flask was first charged with 1-bromo-2,3-dichlorobenzene (10 g, 44 mmol) and piperazine (4.55 g, 53 mmol), which was evacuated and backfilled with $N_2$ through a balloon under gentle warming (40° C.). Toluene was charged and the mixture was bubbled with $N_2$ for 10 min, then BINAP (822 mg, 1.32 mmol) and $Pd_2 dba_3$ (403 mg, 0.44 mmol) were added to the mixture. After the addition of DBU (8.0 mL), the solution was warmed at 60-70° C. while a fine powder of tBuONa (7.39 g, 66 mmol) was added in one portion to start the amination. After the reaction mixture cooled to rt, $(Boc)_2O$ (24 g, 110 mmol) was dissolved in DCM and added dropwise to the reaction mixture, then stirred at rt for 3 h. The reaction mixture was diluted with water and extracted with EtOAc. The combined EtOAc layers were washed with brine, dried over anhydrous $Na_2SO_4$, concentrated in vacuo and purified by flash chromatography on silica gel column (elution with PE/EtOAc=10:1) to give tert-butyl 4-(2,3-dichlorophenyl)piperazine-1-carboxylate (intermediate 40) (11.1 g, 76%) as a white solid.

Intermediate 41:

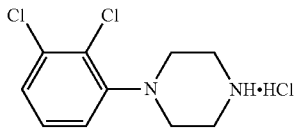

Excess HCl in EtOAc was added dropwise to a solution of intermediate 40 (11.1 g, 33.5 mmol) in EtOAc and the reaction mixture was stirred at rt for 1.5 h. Filtration gave 1-(2,3-dichlorophenyl)piperazine hydrochloride salt (intermediate 41) (7.5 g, 78%) as a white solid. HPLC: 99%, RT 2.052 min. MS (ESI) m/z 231.0[M+H]$^+$.

Intermediate 42:

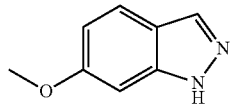

A mixture of 2-fluoro-4-methoxybenzaldehyde (1 g, 6.5 mmol) and hydrazine (7 mL) was heated to reflux for 4 h. The mixture was extracted with $CH_2Cl_2$. The combined organic layers were washed with water, brine, concentrated in vacuo, and purified by column chromatography (elution with PE/EtOAc=5:1) to afford 6-methoxy-1H-indazole (intermediate 42) (568 mg, 59%) as a yellow solid. HPLC: 99%, RT 2.159 min. MS (ESI) m/z 149.1[M+H]$^+$.

Intermediate 43:

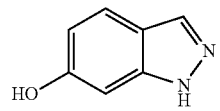

A mixture of 6-methoxy-1H-indazole (560 mg, 3.8 mmol) and HI (2.4 mL 48%) was heated to reflux for 4 h. The mixture was extracted with $CH_2Cl_2$. The combined organic layers were washed with water, brine, concentrated in vacuo, and purified by column chromatography ($CH_2Cl_2$/MeOH=60/1) to give 1H-indazol-6-ol (intermediate 43) (436 mg, 86%).

Intermediate 44:

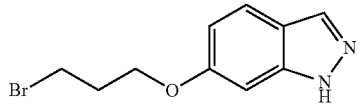

A mixture of 1H-indazol-6-ol (600 mg, 4.5 mmol), 1,3-dibromopropane (1.4 mL, 13.4 mmol) and anhydrous $K_2CO_3$ (618 mg, 4.5 mmol) in EtOH (20 mL) was heated to reflux and stirred overnight. Filtration gave a yellow solid which was purified by column chromatography (elution with PE/EtOAc=3:1) to afford 6-(3-bromopropoxy)-1H-indazole (intermediate 44) (84 mg, 7%) as a yellow oil.

Compound 20:

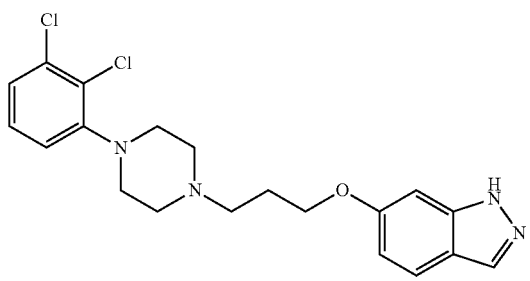

A mixture of intermediate 44 (84 mg, 0.31 mmol) and NaI (94 mg, 0.63 mmol) in $CH_3CN$ was heated to reflux for 30 min and then cooled to rt. Intermediate 41 (125 mg, 0.47 mmol) and anhydrous $K_2CO_3$ (172 mg, 1.25 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous $Na_2SO_4$, concentrated in vacuo and purified by flash chromatography on silica gel column (elution with DCM/MeOH=40:1) to give 6-(3-(4-(2,3-dichlorophenyl)piperazin-1-yl)propoxy)-1H-indazole (compound 20) (90 mg, 71%). $^1$H NMR (300 MHz, CDCl$_3$): δ 7.97 (s, 1H), 7.61 (d, J=8.7 Hz, 1H), 7.16-7.14 (m, 2H), 6.98-6.95 (m, 1H), 6.87-6.82 (m, 2H), 4.10 (t, J=6.6 Hz, 2H), 3.10 (m, 4H), 2.71-2.63 (m, 6H), 2.10-2.04 (m, 2H). HPLC: 99%, RT 2.462 min. MS (ESI) m/z 405.2 [M+H]$^+$. mp: 159-161° C.

Synthesis of Compound 21

Scheme 37. Synthesis of intermediate 47

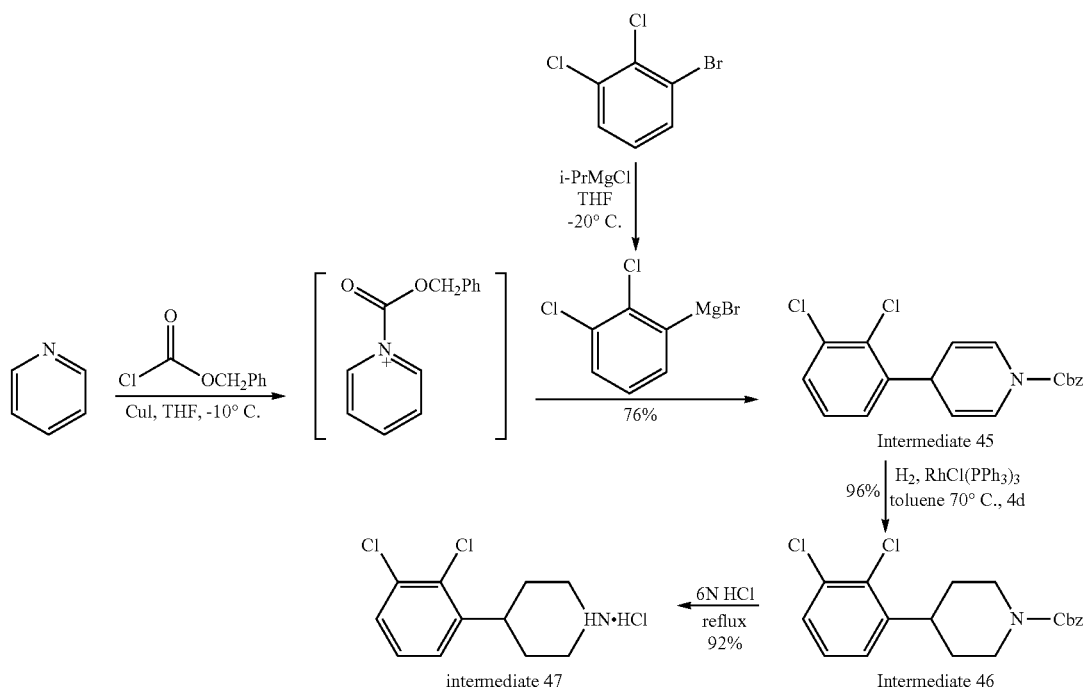

To a −30° C. solution of 1-bromo-2,3-dichlorobenzene (10 g, 44 mmol) in THF (120 mL) was added i-PrMgCl (2.0 M in THF, 35 mL, 70 mmol) at a rate such that the temperature <−20° C. Meanwhile, to a −10° C. solution of CuI (420 mg, 2.2 mmol) in THF (120 mL) was added pyridine (7.1 mL, 88 mmol) and then benzyl carbonochloridate (9.7 mL, 68 mmol) such that the temperature <0° C. To this heterogeneous mixture was added the initially formed Grignard at a rate such that the temperature <0° C. The resulting solution was stirred at 0° C. for 30 min and then allowed to warm to rt. The reaction was then quenched with 10% aq $NH_4Cl$. EtOAc was added and the blue aq layer was removed. The organic layer was washed with 10% aq $NH_4Cl$, 1 N HCl, and a 20% aq NaCl solution. The organic layer was then concentrated and the residue was dissolved and crystallized from MeOH. The slurry was filtered and the filtercake washed with MeOH to give benzyl 4-(2,3-dichlorophenyl)pyridine-1(4H)-carboxylate (intermediate 45) (12 g, 76%) as an off-white solid. HPLC: 99%, RT 4.118 min. MS (ESI) m/z 382.0 $[M+Na]^+$. mp: 69-70° C.

Intermediate 46:

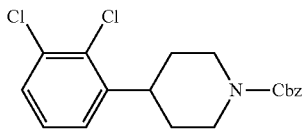

To a solution of intermediate 45 (7.0 g, 19.5 mmol) in toluene (150 mL) was added RhCl $(PPh_3)_3$ (2.1 g, 2.0 mmol) as a slurry in toluene (50 mL). The reaction was subjected to an atmosphere of $H_2$ at 40 psi and heated to 70° C. After 6 h, the reaction was filtered through silica gel and the silica gel Scheme 38. Synthesis of compound 21

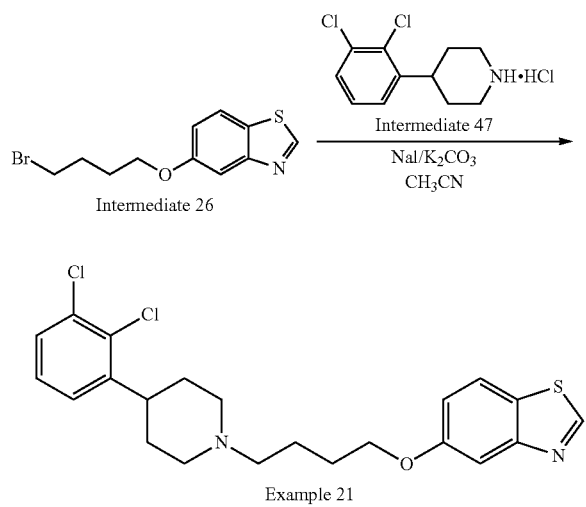

Intermediate 45:

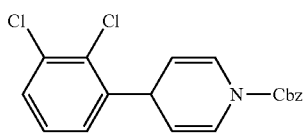

was washed with 1:9 EtOAc/toluene. The filtrate was dissolved in toluene, concentrated in vacuo, and purified by flash chromatography on silica gel column (elution with PE/EtOAc=50:1) to give benzyl 4-(2,3-dichlorophenyl)piperidine-1-carboxylate (intermediate 46) (6.8 g, 96%) as an oil. HPLC: 99%, RT 30843 min. MS (ESI) m/z 386.1 [M+NA]⁺.

Intermediate 47:

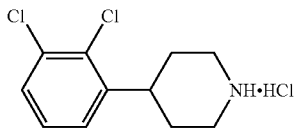

To 6 N HCl (30 mL) was added a solution of intermediate 46 (5.2 g, 14 mmol) in THF (10 mL). The mixture was heated to reflux for 3 h and then concentrated in vacuo. The residue was washed with Et$_2$O to give 4-(2,3-dichlorophenyl)piperidine (intermediate 47) (3.5 g, 92%) as a white solid. HPLC: 99%, RT 2.149 min. MS (ESI) m/z 230.1 [M+H]⁺

Compound 21:

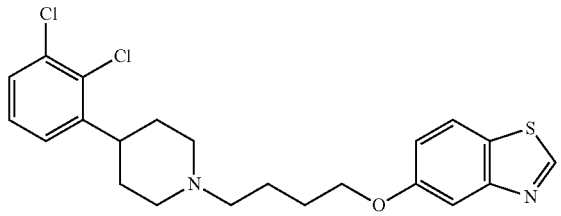

A mixture of intermediate 26 (114 mg, 0.4 mmol) and NaI (120 mg, 0.8 mmol) in CH$_3$CN was heated to reflux for 30 min and then cooled to rt. Intermediate 47 (160 mg, 0.6 mmol) and anhydrous K$_2$CO$_3$ (221 mg, 1.6 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=30:1) to give 5-(4-(4-(2,3-dichlorophenyl)piperidin-1-yl)butoxy)benzo[d]thiazole (compound 21) (144 mg, 66%). ¹H NMR (300 MHz, CDCl$_3$): δ 8.97 (s, 1H), 7.80 (d, J=8.7 Hz, 1H), 7.61 (d, J=2.1 Hz, 1H), 7.33-7.29 (m, 1H), 7.26-7.16 (m, 1H), 7.09 (dd, J=2.1 Hz, 8.7 Hz, 3H), 4.10 (t, J=6.6 Hz, 2H), 3.13-3.09 (m, 2H), 2.50 (t, J=7.5 Hz, 2H), 2.14-2.10 (m, 2H), 1.91-1.74 (m, 10H). HPLC: 99%, RT 2.689 min. MS (ESI) m/z 435.3 [M+H]⁺. mp: 79-81° C.

Synthesis of Compound 22

Scheme 39. Synthesis of compound 22

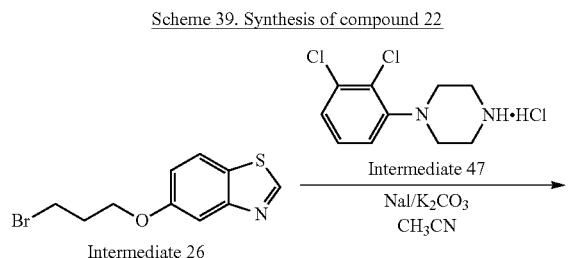

Intermediate 26

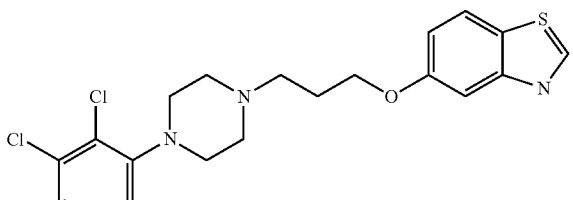

Example 22

Compound 22:

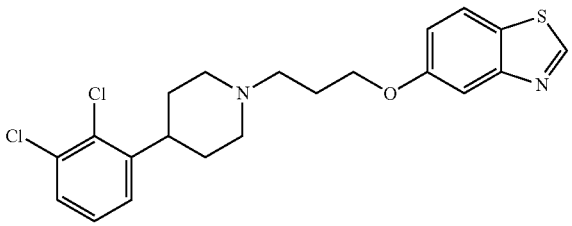

A mixture of intermediate 26 (218 mg, 0.8 mmol) and NaI (240 mg, 1.6 mmol) in CH$_3$CN was heated to reflux for 30 min and then cooled to rt. Intermediate 47 (320 mg, 1.2 mmol) and anhydrous K$_2$CO$_3$ (442 mg, 3.8 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=30:1) to give 5-(3-(4-(2,3-dichlorophenyl)piperidin-1-yl)propoxy)benzo[d]thiazole (compound 22) (211 mg, 56%). ¹H NMR (300 MHz, CDCl$_3$): δ 8.98 (s, 1H), 7.80 (d, J=8.7 Hz, 1H), 7.62 (d, J=3.0 Hz, 1H), 7.34-7.31 (m, 1H), 7.24-7.18 (m, 3H), 7.15-7.09 (m, 1H), 4.15 (t, J=5.7 Hz, 2H), 3.18-3.12 (m, 3H), 2.70-2.66 (m, 2H), 2.27-2.19 (m, 2H), 2.17-2.10 (m, 2H), 1.92-1.81 (m, 4H). HPLC: 99%, RT 2.622 min. MS (ESI) m/z 421.1 [M+H]⁺. mp: 114-116° C.

Synthesis of Compound 23

Scheme 40. Synthesis of compound 23

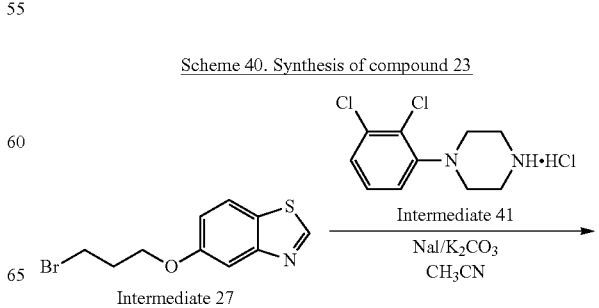

Intermediate 27

-continued

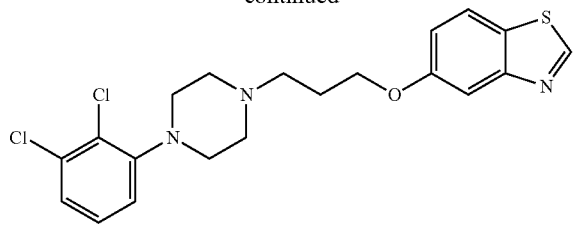

Example 23

Compound 23:

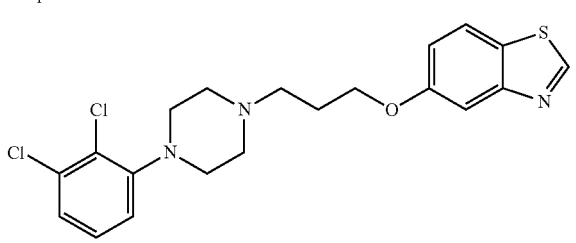

A mixture of intermediate 27 (218 mg, 0.8 mmol) and NaI (240 mg, 1.6 mmol) in CH$_3$CN was heated to reflux for 30 min and then cooled to rt. Intermediate 41 (320 mg, 1.2 mmol) and anhydrous K$_2$CO$_3$ (442 mg, 3.2 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=30:1) to give 5-(3-(4-(2,3-dichlorophenyl)piperazin-1-yl)propoxy)benzo[d]thiazole (compound 23) (209 mg, 62%). $^1$H NMR (300 MHz, CDCl$_3$): δ 8.97 (s, 1H), 7.80 (d, J=8.7 Hz, 1H), 7.63 (d, J=2.1 Hz, 1H), 7.16-7.09 (m, 3H), 6.94 (dd, J=3.6 Hz, 6.0 Hz, 1H), J=5.7 Hz, 2H), 3.09 (m, 4H), 2.68-2.63 (m, 6H), 2.10-2.05 (m, 2H). HPLC: 99%, RT 2.607 min. MS (ESI) m/z 422.0 [M+H]$^+$. mp: 127-129° C.

Synthesis of Compound 24

Scheme 41. Synthesis of intermediate 48

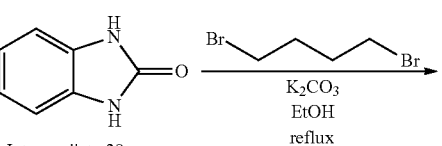

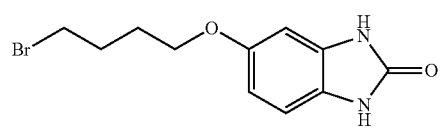

Intermediate 48

Scheme 42. Synthesis of compound 24

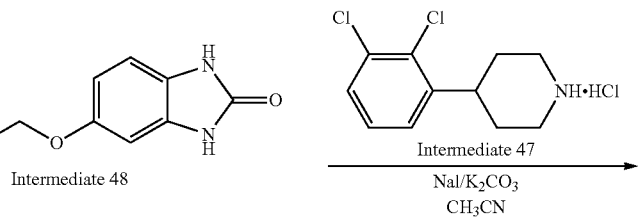

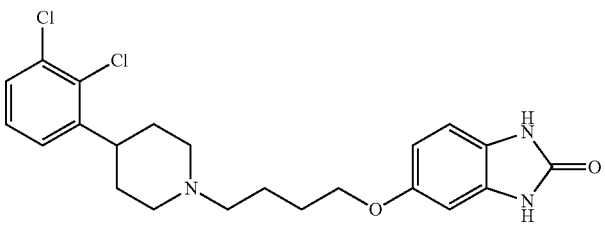

Example 24

Intermediate 48:

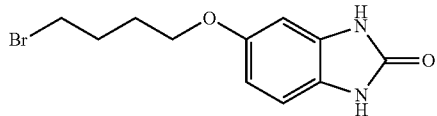

A mixture of intermediate 38 (253 mg, 1.68 mmol), 1,4-dibromobutane (0.6 mL, 5.04 mmol) and anhydrous K$_2$CO$_3$ (232 mg, 1.68 mmol) was dissolved in EtOH and the solution was heated to reflux overnight. The solution was diluted with water and extracted with EtOAc. The combined organic layers were washed with saturated NaHCO$_3$, brine, dried over anhydrous Na$_2$SO$_4$, concentrated in vacuo and purified by flash chromatography on silica gel column (elution with PE/EtOAc=4:1) to give 7-(4-bromobutoxy)quinolin-2(1H)-one (intermediate 48) (120 mg, 25%) as a yellow solid.

Compound 24:

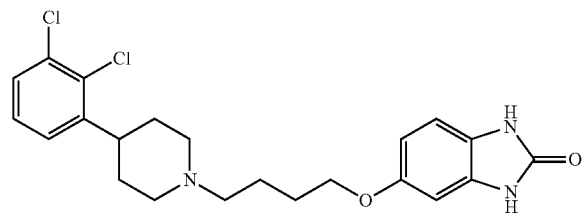

A mixture of intermediate 48 (200 mg, 0.7 mmol) and NaI (210 mg, 1.4 mmol) in CH$_3$CN was heated to reflux for 30 min and then cooled to rt. Intermediate 47 (167 mg, 0.63 mmol) and anhydrous K$_2$CO$_3$ (386 mg, 2.8 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=5:1) to give 5-(4-(4-(2,3-dichlorophenyl)piperidin-1-yl)butoxy)-1H-benzo[d]imidazol-2(3H)-one (compound 24) (61 mg, 20%). $^1$H NMR (300 MHz, CDCl$_3$): δ 9.59 (brs, 1H), 9.29 (brs, 1H), 7.33-7.30 (m, 2H), 7.20-7.13 (m, 1H), 6.92 (d, J=8.7 Hz, 1H), 6.65-6.59 (m, 2H), 3.94-3.91 (m, 2H), 3.15-3.04 (m, 3H), 2.51-2.49 (m, 2H), 2.15 (t, J=11.1 Hz, 2H), 1.90-1.74 (m, 8H). HPLC: 99%, RT 2.332 min. MS (ESI) m/z 434.0 [M+H]$^+$. mp: 180-182° C.

Synthesis of Compound 25

Compound 25:

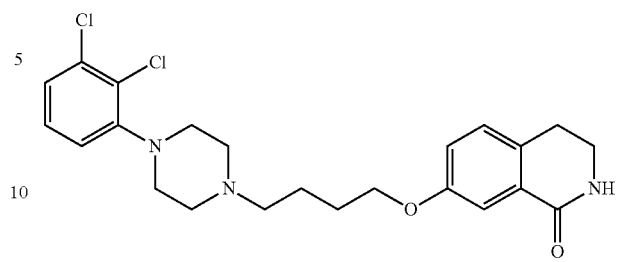

A mixture of intermediate 21 (220 mg, 0.74 mmol) and NaI (222 mg, 1.48 mmol) in CH$_3$CN was heated to reflux for 30 min and then cooled to rt. Intermediate 41 (278 mg, 1.04 mmol) and anhydrous K$_2$CO$_3$ (1409 mg, 2.96 mmol) were added to the mixture. The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=50:1) to give 7-(4-(4-(2,3-dichlorophenyl)piperazin-1-yl)butoxy)-3,4-dihydroisoquinolin-1(2H)-one (compound 25) (215 mg, 65%). $^1$H NMR (300 MHz, CDCl$_3$): δ 7.58 (d, J=2.7 Hz, 1H), 7.14-7.11 (m, 3H), 7.01-6.94 (m, 2H), 6.18 (brs, 1H), 4.05 (t, J=6.3 Hz, 2H), 3.56-3.51 (m, 2H), 3.07 (m, 4H), 2.90 (t, J=8.1 Hz, 2H), 2.66 (m, 4H), 2.49-2.46 (m, 2H), 1.86-1.68 (m, 4H). HPLC: 99%, RT 2.374 min. MS (ESI) m/z 448.3 [M+H]$^+$.

Scheme 43. Synthesis of compound 25

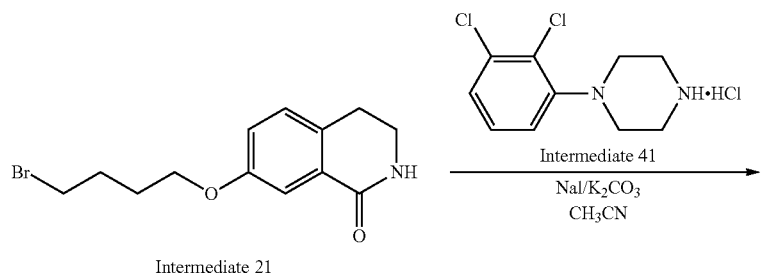

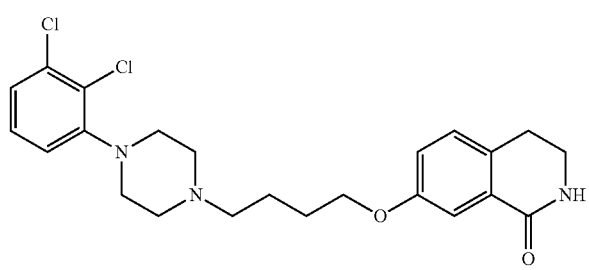

Example 25

Synthesis of Compound 26

Scheme 44. Synthesis of intermediate 49

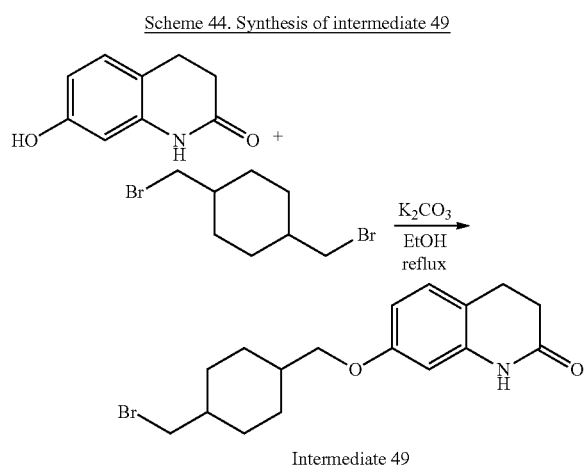

Intermediate 49

Compound 26:

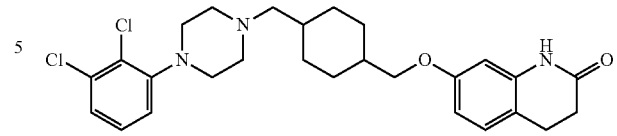

A mixture of intermediate 49 (70 mg, 0.2 mmol) and NaI (60 mg, 0.4 mmol) in $CH_3CN$ was heated to reflux for 30 min and then cooled to rt. Intermediate 41 (81 mg, 0.3 mmol) and anhydrous $K_2CO_3$ (110 mg, 0.8 mmol) were added to the mixture. The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous $Na_2SO_4$, concentrated in vacuo and purified by flash chromatography on silica gel column (elution with DCM/MeOH=50:1) to give 7-((4-((4-(2,3-dichlorophenyl)piperazin-1-yl)methyl)cyclohexyl)methoxy)-3,4-dihydroquinolin-2(1H)-one (compound 26) (63 mg, 63%). $^1$H NMR (300 MHz, $CDCl_3$): δ 8.06 (s, 1H),

Scheme 45. Synthesis of compound 26

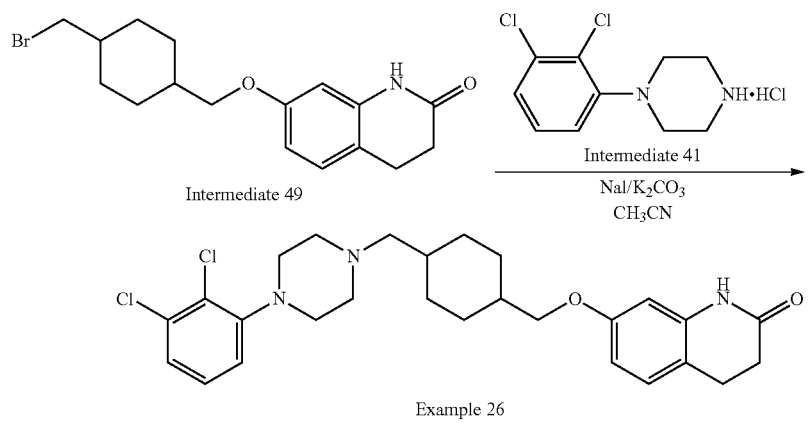

Example 26

Intermediate 49:

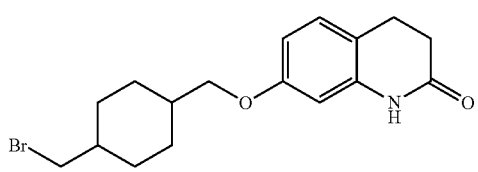

A mixture of 7-hydroxy-3,4-dihydroquinolin-2(1H)-one (196 mg, 1.2 mmol), 1,4-bis(bromomethyl)cyclohexane (972 mg, 3.6 mmol) and anhydrous $K_2CO_3$ (166 mg, 1.2 mmol) was dissolved in EtOH and the solution was heated to reflux overnight. The solution was diluted with water and extracted with EtOAc. The combined organic layers were washed with saturated aq $NaHCO_3$, brine, dried over anhydrous $Na_2SO_4$, concentrated in vacuo and purified by flash chromatography on silica gel column to give 7-((4-(bromomethyl)cyclohexyl)methoxy)-3,4-dihydroquinolin-2(1H)-one (intermediate 49) (130 mg, 30%) as a white solid.

7.13-7.15 (m, 2H), 7.04 (d, J=8.4 Hz, 1H), 6.94-6.97 (m, 1H), 6.52 (dd, J=2.4 Hz, 8.4 Hz, 1H), 6.32 (d, J=2.1 Hz, 1H), 3.71-3.74 (m, 2H), 3.05-3.07 (m, 4H), 2.87-2.92 (m, 2H), 2.59-2.64 (m, 6H), 2.24 (d, J=6.9 Hz, 2H), 3.83 (d, J=9.9 Hz, 2H), 1.53-1.69 (m, 6H), 0.94-1.10 (m, 4H). HPLC: 99%, RT 2.652 min. MS (ESI) m/z 502.2 $[M+H]^+$.

Synthesis of Compound 27

Scheme 46. Synthesis of intermediate 50

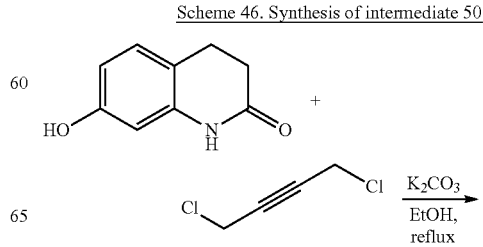

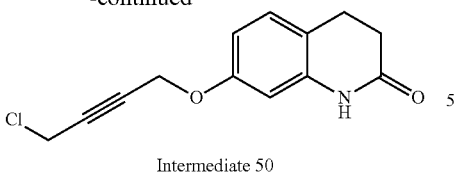

Intermediate 50 min and then cooled to rt. Intermediate 41 (320 mg, 1.2 mmol) and anhydrous K$_2$CO$_3$ (442 mg, 3.2 mmol) were added to the mixture. The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=50:

Scheme 47. Synthesis of compound 27

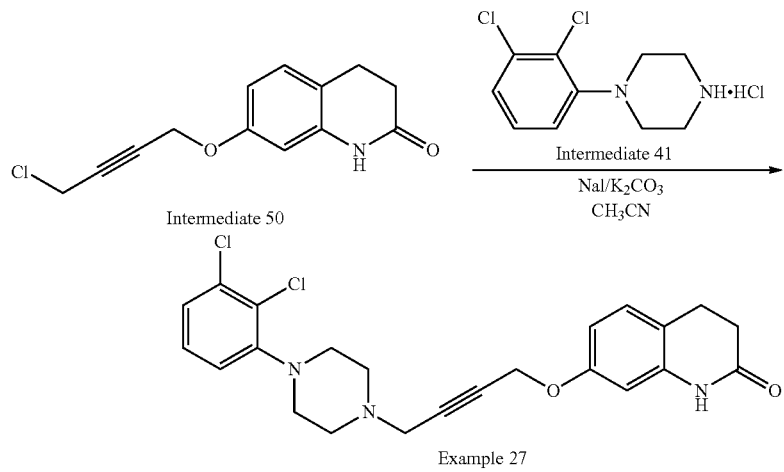

Example 27

Intermediate 50:

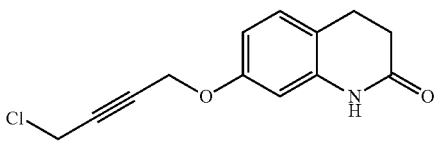

A mixture of 7-hydroxy-3,4-dihydroquinolin-2(1H)-one (930 mg, 6 mmol), 1,4-dichlorobut-2-yne (326 mg, 2 mmol) and anhydrous K$_2$CO$_3$ (276 mg, 2 mmol) was dissolved in EtOH and the solution was heated to reflux overnight. The solution was diluted with water and extracted with EtOAc. The combined organic layers were washed with saturated aq NaHCO$_3$, brine, dried over anhydrous Na$_2$SO$_4$, concentrated in vacuo and purified by flash chromatography on silica gel column to give 7-(4-chlorobut-2-ynyloxy)-3,4-dihydroquinolin-2(1H)-one (intermediate 50) (330 mg, 66%) as a yellow solid.

Compound 27:

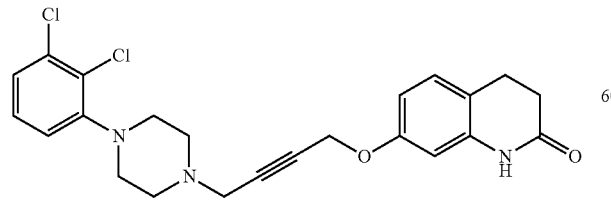

A mixture of intermediate 50 (200 mg, 0.8 mmol) and NaI (240 mg, 1.6 mmol) in CH$_3$CN was heated to reflux for 30

1) to give 7-(4-(4-(2,3-dichlorophenyl)piperazin-1-yl)but-2-ynyloxy)-3,4-dihydroquinolin-2(1H)-one (compound 27) (280 mg, 79%). $^1$H NMR (300 MHz, CDCl$_3$): δ 7.85 (s, 1H), 7.20-7.13 (m, 2H), 7.08 (d, J=8.4 Hz, 1H), 6.97 (dd, J=3.0 Hz, 6.6 Hz, 1H), 4.73 (s, 2H), 3.42 (s, 2H), 3.10 (s, 4H), 2.93-2.88 (m, 2H), 2.75 (s, 4H), 2.64-2.59 (m, 2H), 2.06 (s, 1H), 1.70 (s, 2H), 1.29-1.24 (m, 1H). HPLC: 99%, RT 2.403 min. MS (ESI) m/z 444.1 [M+H]$^+$.

Synthesis of Compound 28

Scheme 48. Synthesis of intermediate 51

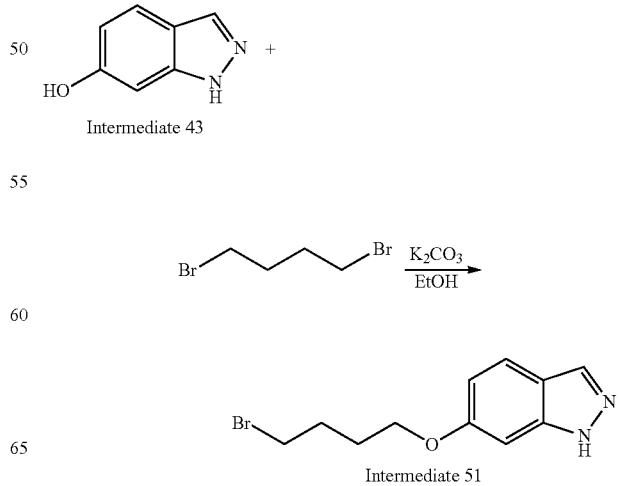

Intermediate 51

Scheme 49. Synthesis of compound 28

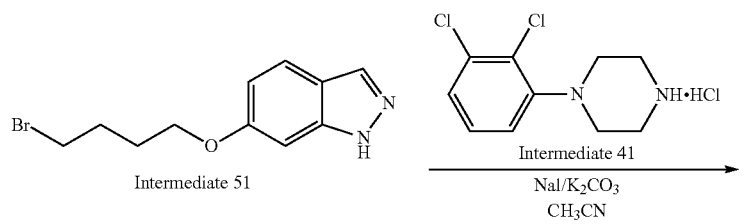

Intermediate 51

Example 28

Intermediate 51:

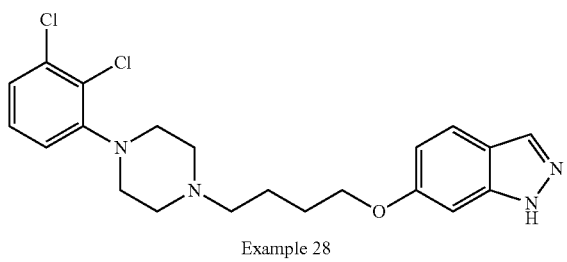

A mixture of 1H-indazol-6-ol (intermediate 43) (320 g, 2.39 mmol), 1,4-dibromobutane (0.9 mL, 7.2 mmol), anhydrous K₂CO₃ (55 mg, 2.39 mmol) and EtOH (5 mL) was heated to reflux and stirred overnight. A yellow solid was filtered and purified by column chromatography (elution with PE/EtOAc=3:1) to afford 5-(3-bromopropoxy)benzo[d]thiazole (intermediate 51) (70 mg, 17%) as a yellow oil.

Compound 28:

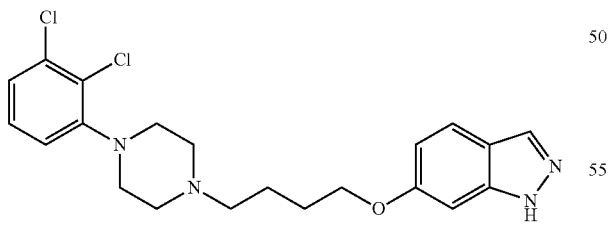

A mixture of intermediate 51 (65 mg, 0.24 mmol) and NaI (72 mg, 0.48 mmol) in CH₃CN was heated to reflux for 30 min and then cooled to rt. Intermediate 41 (97 mg, 0.36 mmol) and anhydrous K₂CO₃ (132 mg, 0.96 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous Na₂SO₄, concentrated in vacuo and purified by flash chromatography on silica gel column (elution with DCM/MeOH 30:1) to give 6-(4-(4-(2,3-dichlorophenyl)piperazin-1-yl)butoxy)-1H-indazole (compound 28) (35 mg, 35%). $^1$H NMR (300 MHz, CDCl₃): δ 7.97 (s, 1H), 7.61 (d, J=8.7 Hz 1H), 7.17-7.15 (m, 2H), 6.96 (dd, J=3.0 Hz, 6.6 Hz, 1H), 6.86-6.81 (m, 2H), 4.05 (t, J=5.4 Hz, 2H), 3.16 (s, 4H), 2.79 (s, 4H), 2.64-2.60 (m, 2H), 1.89-1.83 (m, 4H). HPLC: 99%, RT 2.491 min. MS (ESI) m/z 419.2 [M+H]⁺. mp: 101-103° C.

Synthesis of Compound 29

Scheme 50. Synthesis of intermediate 52

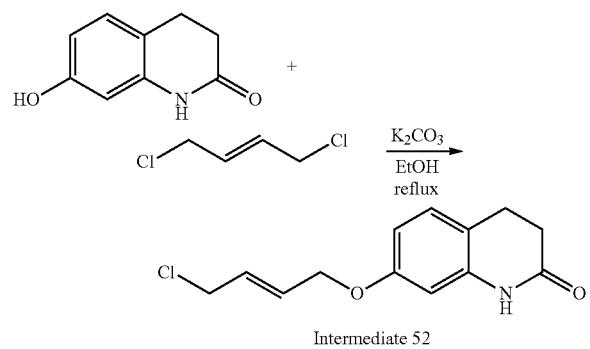

Intermediate 52

Scheme 51. Synthesis of compound 29

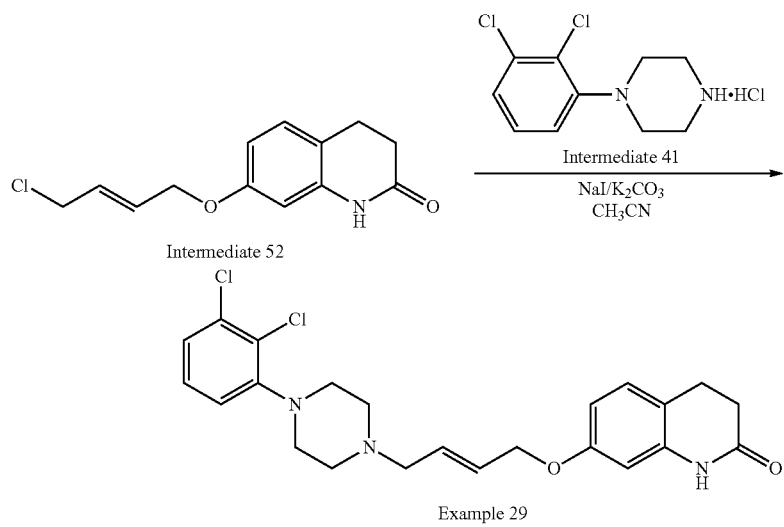

Intermediate 52:

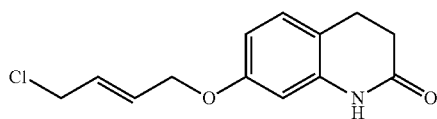

A mixture of 7-hydroxy-3,4-dihydroquinolin-2(1H)-one (196 mg, 1.2 mmol), (E)-1,4-dichlorobut-2-ene (450 mg, 3.6 mmol) and anhydrous $K_2CO_3$ (166 mg, 1.2 mmol) was dissolved in EtOH and the solution was heated to reflux and stirred overnight. The solution was diluted with water and extracted with EtOAc. The combined organic layers were washed with saturated aq $NaHCO_3$, brine, dried over anhydrous $Na_2SO_4$, concentrated in vacuo and purified by flash chromatography on silica gel column to give (E)-7-(4-chlorobut-2-enyloxy)-3,4-dihydroquinolin-2(1H)-one (intermediate 52) (102 mg, 34%) as a white solid.

Compound 29:

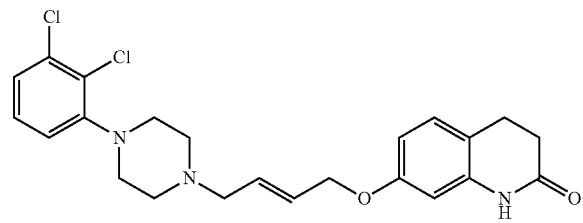

A mixture of intermediate 52 (75 mg, 0.25 mmol) and NaI (75 mg, 0.5 mmol) in $CH_3CN$ was heated to reflux for 30 min and then cooled to rt. Intermediate 41 (102 mg, 0.38 mmol) and anhydrous $K_2CO_3$ (138 mg, 1 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous $Na_2SO_4$, concentrated in vacuo and purified by flash chromatography on silica gel column (elution with DCM/MeOH=50:1) to give (E)-7-(4-(4-(2,3-dichlorophenyl)piperazin-1-yl)but-2-enyloxy)-3,4-dihydroquinolin-2(1H)-one (compound 29) (79 mg, 71%). $^1$H NMR (300 MHz, $CDCl_3$): δ 7.77 (s, 1H), 7.16-7.14 (m, 2H), 7.05 (d, J=8.1 Hz, 1H), 6.98-6.94 (m, 1H), 6.53 (d, J=8.1 Hz, 1H), 6.33 (s, 1H), 5.94-5.89 (m, 2H), 4.51 (d, J=4.2 Hz, 2H), 3.19-3.08 (m, 6H), 2.90 (t, J=6.9 Hz, 2H), 2.67-2.59 (m, 6H). HPLC: 99%, RT 2.468 min. MS (ESI) m/z 446.1 $[M+H]^+$. mp: 151-152° C.

Synthesis of Compound 30

Scheme 52. Synthesis of intermediate 53

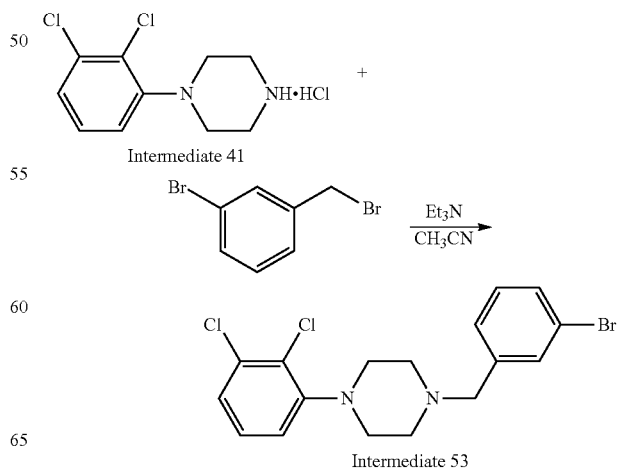

Scheme 53. Synthesis of compound 30

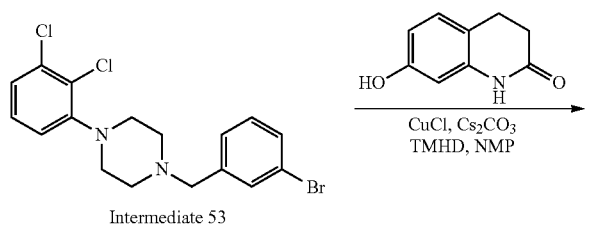

Intermediate 53

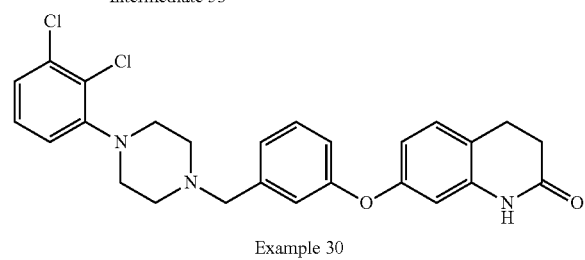

Example 30

Intermediate 53:

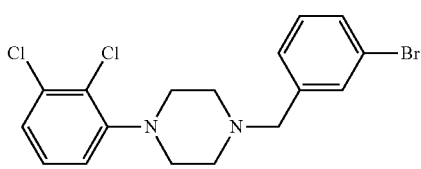

A mixture of 1-(2,3-dichlorophenyl)piperazine hydrochloride (intermediate 41) (294 mg, 1.1 mmol), 1-bromo-3-(bromomethyl)benzene (250 mg, 1 mmol) and anhydrous triethylamine (253 mg, 2.5 mmol) was dissolved in CH₃CN and the solution was heated to reflux for 4 h. The solution was diluted with water and extracted with EtOAc. The combined organic layers were washed with saturated aq NaHCO₃, brine, dried over anhydrous Na₂SO₄, concentrated in vacuo and purified by flash chromatography on silica gel column (elution with PE/EtOAc=8:1) to give 1-(3-bromobenzyl)-4-(2,3-dichlorophenyl)piperazine (intermediate 53) (220 mg, 74%) as a white solid.

Compound 30:

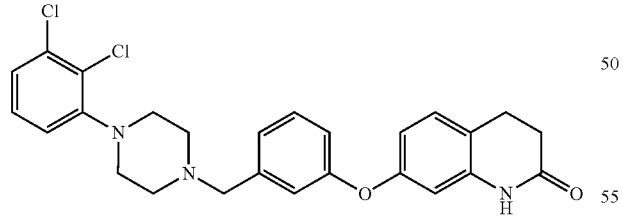

To a solution of 7-hydroxy-3,4-dihydroquinolin-2(1H)-one (196 mg, 1.2 mmol in NMP was added Cs₂CO₃ (391 mg, 1.2 mmol). The slurry was degassed by evacuating and filling the reaction flask with N₂ three times. Intermediate 53 (240 mg, 0.6 mmol) and TMHD (11 mg, 0.06 mmol) were added followed by the addition of CuCl (60 mg, 0.6 mmol). The reaction mixture was degassed by evacuating and filling the reaction flask with N₂ three times, and then warmed to 120° C. under N₂ for 7.5 h. The reaction mixture was cooled to rt and diluted with Et₂O. The slurry was filtered and the filtercake was washed with Et₂O. Combined filtrates were washed with 2 N HCl, 0.6 N HCl, 2 M NaOH, and 10% aq NaCl. The resulting organic layer was dried, concentrated, and purified by flash chromatography on a silica gel column (elution with PE/EtOAc=1:1) to give 7-(3-((4-(2,3-dichlorophenyl)piperazin-1-yl)methyl)phenoxy)-3,4-dihydro quinolin-2(1H)-one (compound 30) (110 mg, 38%). ¹H NMR (300 MHz, CDCl₃): δ 7.62 (s, 1H), 7.31 (d, J=7.2 Hz, 2H), 7.15-7.05 (m, 4H), 6.96-6.89 (m, 2H), 6.62 (dd, J=2.1 Hz, 8.1 Hz, 1H), 6.41 (d, J=2.1 Hz, 1H), 3.57 (s, 2H), 3.06 (m, 4H), 2.94 (t, J=7.5 Hz, 2H), 2.66-2.61 (m, 5H). HPLC: 99%, RT 2.637 min. MS (ESI) m/z 482.1 [M+H]⁺. mp: 182-183° C.

Synthesis of Compound 31

Scheme 54. Synthesis of intermediate 54

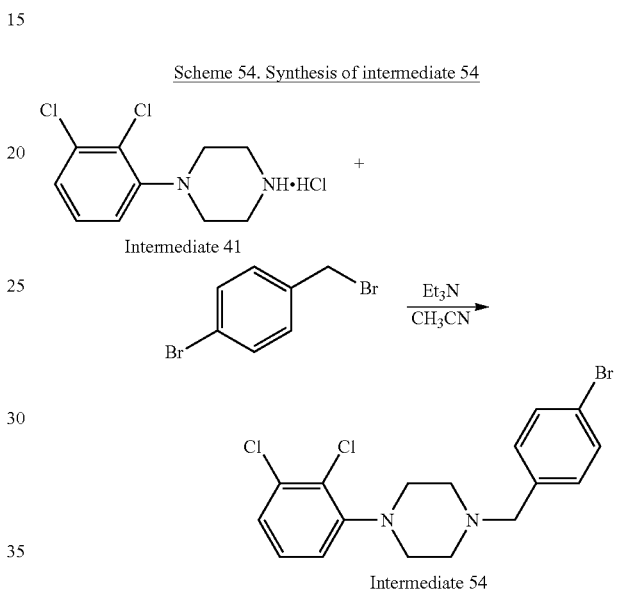

Intermediate 54

Scheme 55. Synthesis of compound 31

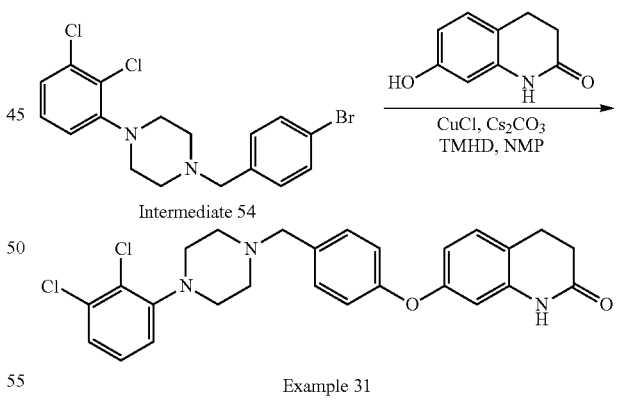

Example 31

Intermediate 54:

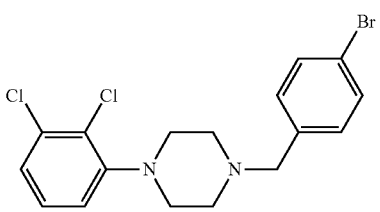

A mixture of intermediate 41 (294 mg, 1.1 mmol), 1-bromo-4-(bromomethyl)benzene (250 mg, 1.0 mmol) and anhydrous triethylamine (253 mg, 2.5 mmol) was dissolved in CH₃CN and the solution was heated to reflux for 4 h. The solution was diluted with water and extracted with EtOAc. The combined organic layers were washed with saturated aq NaHCO₃, brine, dried over anhydrous Na₂SO₄, concentrated in vacuo and purified by flash chromatography on silica gel column (elution with PE/EtOAc=8:1) to give 1-(4-bromobenzyl)-4-(2,3-dichlorophenyl)piperazine (intermediate 54) (220 mg, 74%) as a white solid.

Compound 31:

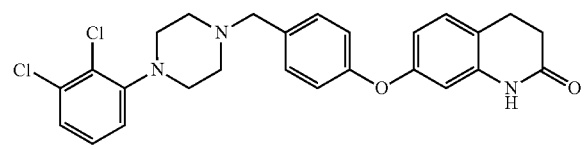

To a solution of 7-hydroxy-3,4-dihydroquinolin-2(1H)-one (228 mg, 1.4 mmol) in NMP was added Cs₂CO₃ (456 mg, 1.4 mmol). The slurry was degassed by evacuating and filling the reaction flask with N₂ three times. Intermediate 54 (280 mg, 0.7 mmol) and TMHD (13 mg, 0.07 mmol) were added followed by the addition of CuCl (70 mg, 0.7 mmol). The reaction mixture was degassed by evacuating and filling the reaction flask with N₂ three times, and then warmed to 120° C. under N₂ for 7.5 h. The reaction mixture was cooled to rt and diluted with Et₂O. The slurry was filtered and the filtercake was washed with Et₂O. Combined filtrates were washed with 2 N HCl, 0.6 N HCl, 2 M NaOH, and 10% aq NaCl. The resulting organic layer was dried, concentrated, and purified by flash chromatography on a silica gel column (elution with PE/EtOAc=1:1) to give 7-(4-((4-(2,3-dichlorophenyl)piperazin-1-yl)methyl)phenoxy)-3,4-dihydro quinolin-2(1H)-one (compound 31) (120 mg, 35%). ¹H NMR (300 MHz, CDCl₃): δ 7.67 (s, 1H), 7.32 (d, J=8.7 Hz, 2H), 7.16-7.09 (m, 3H), 6.98-6.94 (m, 3H), 6.64-6.61 (m, 1H), 6.41 (d, J=3.0 Hz, 1H), 3.56 (s, 2H), 3.07 (m, 4H), 2.94 (t, J=6.6 Hz, 2H), 2.66-2.61 (m, 6H). HPLC: 99%, RT 2.626 min. MS (ESI) m/z 482.1 [M+H]⁺. mp: 185-186° C.

Synthesis of Compound 32

Scheme 56. Synthesis of compound 32

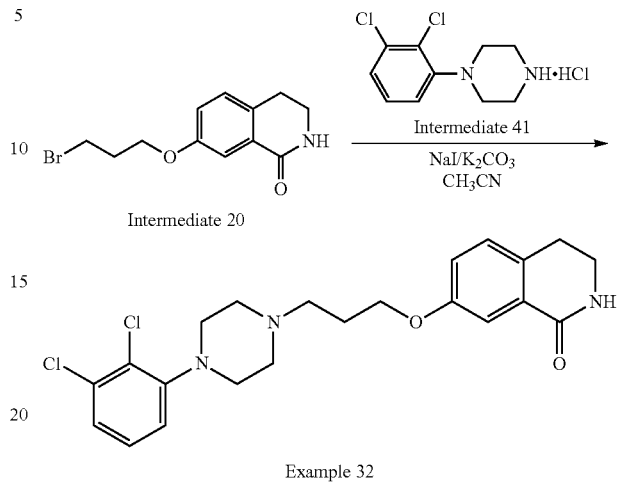

Example 32

Compound 32:

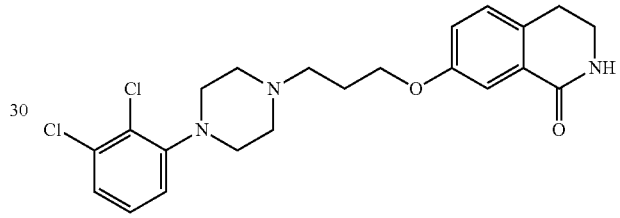

A mixture of intermediate 20 (110 mg, 0.39 mmol) and NaI (117 mg, 0.78 mmol) in CH₃CN was heated to reflux for 30 min and then cooled to rt. Intermediate 41 (157 mg, 0.59 mmol) and anhydrous K₂CO₃ (216 mg, 1.56 mmol) were added to the mixture. The resulting mixture was heated to reflux and stirred for 6 h. Precipitated crystals were filtered off and the filtrate was evaporated under reduced pressure. The residue was extracted with EtOAc. The combined EtOAc layers were washed with brine, dried over anhydrous Na₂SO₄, concentrated in vacuo and purified by flash chromatography on silica gel column (elution with DCM/MeOH=30: 1) to give 7-(3-(4-(2,3-dichlorophenyl)piperazin-1-yl)propoxy)-3,4-dihydroisoquinolin-1(2H)-one (compound 32) (88 mg, 52%). ¹H NMR (300 MHz, CDCl₃): δ 7.61 (s, 1H), 7.14-7.11 (m, 3H), 7.03-6.98 (m, 2H), 5.93 (brs, 1H), 4.11 (m, 2H), 3.55 (m, 2H), 3.09-2.94 (m, 6H), 2.65-2.61 (m, 6H), 2.02 (s, 2H). HPLC: 99%, RT 2.612 min. MS (ESI) m/z 434.1 [M+H]⁺. mp: 162-164° C.

Synthesis of Compound 33

Scheme 57. Synthesis of compound 33

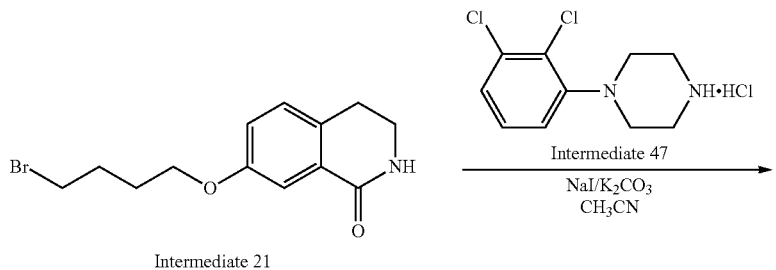

Intermediate 21

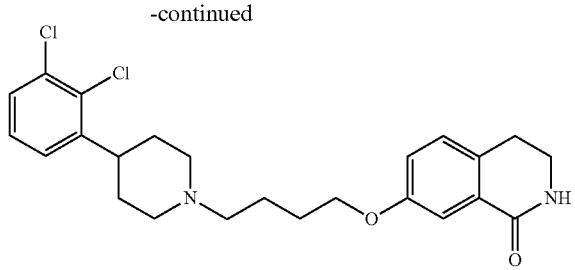

Example 33

Compound 33:

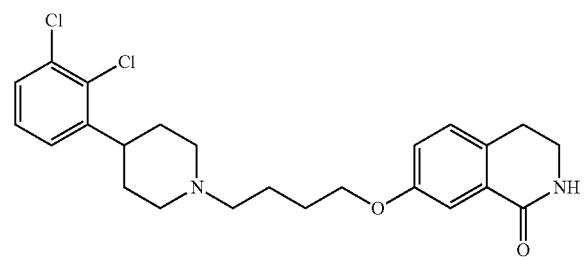

A mixture of intermediate 21 (103 mg, 0.35 mmol) and NaI (105 mg, 0.7 mmol) in CH$_3$CN was heated to reflux for 30 min and then cooled to rt. Intermediate 47 (142 mg, 0.53 mmol) and anhydrous K$_2$CO$_3$ (194 mg, 1.4 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH 30:1) to give 7-(4-(4-(2,3-dichlorophenyl)piperidin-1-yl)butoxy)-3,4-dihydroisoquinolin-1(2H)-one (compound 33) (108 mg, 69%). $^1$H NMR (300 MHz, CDCl$_3$): δ 7.58 (d, J=2.1 Hz, 1H), 7.23-7.11 (m, 5H), 7.02-6.99 (m, 1H), 6.05 (s, 1H), 4.05 (t, J=6.0 Hz, 2H), 3.56-3.53 (m, 2H), 3.15-3.06 (m, 3H), 2.93 (t, J=6.6 Hz, 2H), 2.51 (m, 2H), 2.18 (m, 2H), 1.82 (m, 8H). HPLC: 99%, RT 2.746 min. MS (ESI) ink 447.2 [M+H]$^+$. mp: 113-114° C.

Synthesis of Compound 34

Scheme 58. Synthesis of compound 34

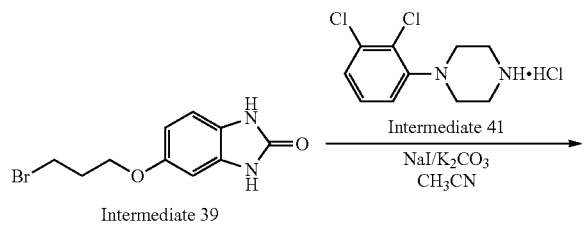

Example 34

Compound 34:

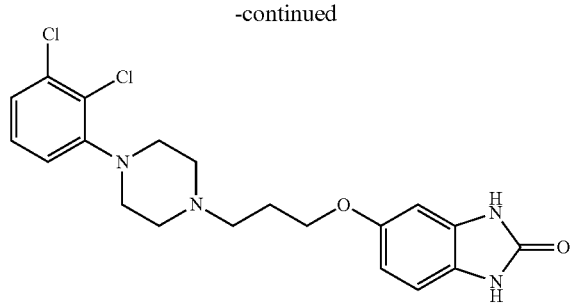

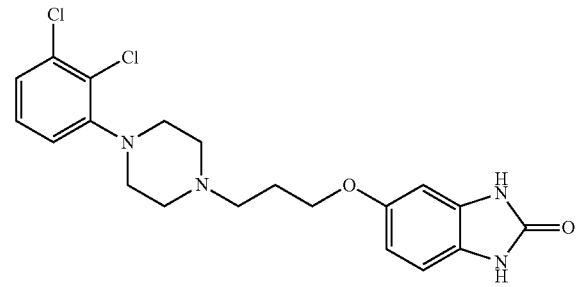

A mixture of intermediate 39 (126 mg, 0.47 mmol) and NaI (140 mg, 0.93 mmol) in CH$_3$CN was heated to reflux for 30 min and then cooled to rt. Intermediate 41 (188 mg, 0.71 mmol) and anhydrous K$_2$CO$_3$ (259 mg, 1.88 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=15:1) to give 5-(3-(4-(2,3-dichlorophenyl)piperazin-1-yl)propoxy)-1H-benzo[d]imidazol-2(3H)-one (compound 34) (54 mg, 27%). $^1$H NMR (300 MHz, DMSO): δ 10.60 (s, 1H), 10.36 (s, 1H), 7.32 (d, J=5.1 Hz, 2H), 7.16-7.18 (m, 1H), 6.80 (d, J=9.6 Hz, 1H), 6.51-6.53 (d, J=6.6 Hz, 2H), 3.99-3.95 (m, 2H), 2.81-3.26 (s, 5H), 2.80-2.60 (m, 5H), 1.80-2.01 (m, 2H). HPLC: 99%, RT 2.228 min. MS (ESI) m/z 421.1 [M+H]$^+$.

Synthesis of Compound 35

Scheme 59. Synthesis of compound 35

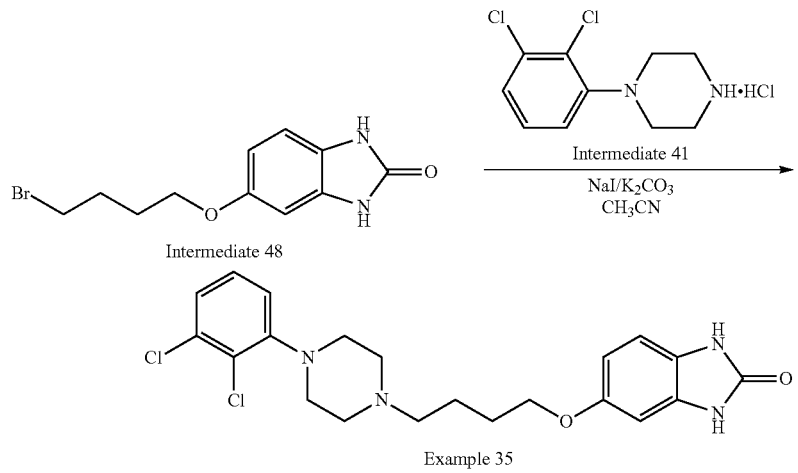

Intermediate 48

Intermediate 41

NaI/K₂CO₃
CH₃CN

Example 35

Compound 35:

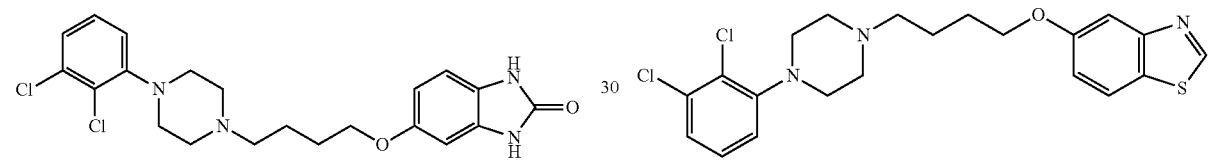

A mixture of intermediate 48 (110 mg, 0.39 mmol) and NaI (117 mg, 0.78 mmol) in CH$_3$CN was heated to reflux for 30 min and then cooled to rt. Intermediate 41 (156 mg, 0.59 mmol) and anhydrous K$_2$CO$_3$ (215 mg, 1.56 mmol) were added to the mixture. The resulting mixture was heated to reflux and stirred overnight. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=15: 1) to give 5-(3-(4-(2,3-dichlorophenyl)piperazin-1-yl)propoxy)-1H-benzo[d]imidazol-2(3H)-one (compound 35) (54 mg, 32%). $^1$H NMR (300 MHz, CDCl$_3$): δ 9.53 (s, 1H), 9.24 (s, 1H), 7.17-7.13 (m, 2H), 6.97-6.91 (m, 2H), 6.66-6.60 (m, 2H), 3.95 (t, J=5.7 Hz, 2H), 3.20-3.01 (m, 4H), 2.80-2.61 (m, 4H), 2.52 (t, J=7.5 Hz, 2H), 1.82-1.73 (m, 4H). HPLC: 99%, RT 2.325 min. MS (ESI) m/z 435.1 [M+H]$^+$.

Synthesis of Compound 36

Scheme 60. Synthesis of compound 36

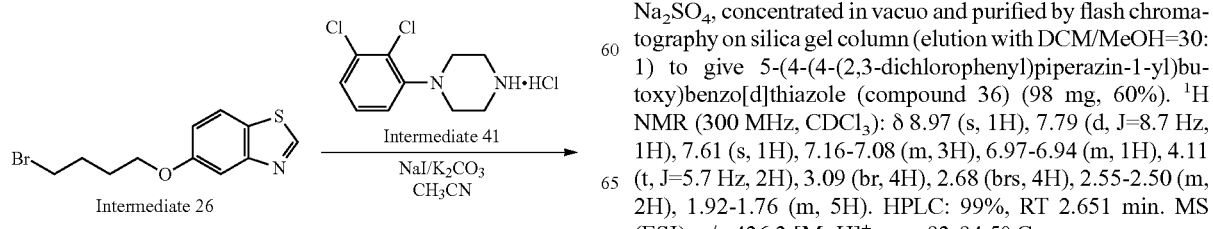

Example 36

Compound 36:

A mixture of intermediate 26 (108 mg, 0.38 mmol) and NaI (114 mg, 0.76 mmol) in CH$_3$CN was heated to reflux for 30 min and then cooled to rt. Intermediate 41 (152 mg, 0.57 mmol) and anhydrous K$_2$CO$_3$ (210 mg, 1.52 mmol) were added to the mixture. The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=30: 1) to give 5-(4-(4-(2,3-dichlorophenyl)piperazin-1-yl)butoxy)benzo[d]thiazole (compound 36) (98 mg, 60%). $^1$H NMR (300 MHz, CDCl$_3$): δ 8.97 (s, 1H), 7.79 (d, J=8.7 Hz, 1H), 7.61 (s, 1H), 7.16-7.08 (m, 3H), 6.97-6.94 (m, 1H), 4.11 (t, J=5.7 Hz, 2H), 3.09 (br, 4H), 2.68 (brs, 4H), 2.55-2.50 (m, 2H), 1.92-1.76 (m, 5H). HPLC: 99%, RT 2.651 min. MS (ESI) m/z 436.3 [M+H]$^+$. mp: 93-94.5° C.

Synthesis of Compound 37

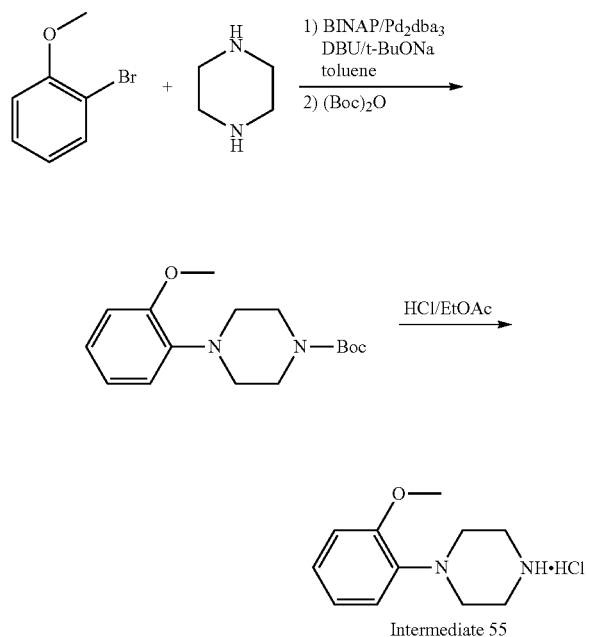

Scheme 61. Synthesis of intermediate 55

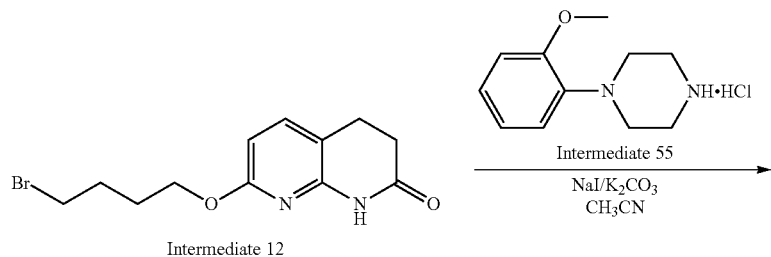

Scheme 62. Synthesis of compound 37

Intermediate 55:

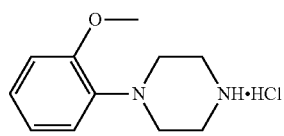

A well-dried flask was first charged with 1-bromo-2-methoxybenzene (4.0 g, 21.3 mmol) and piperazine (2.2 g, 25.6 mmol), which was evacuated and backfilled with $N_2$ through a balloon under gentle warming (40° C.). Toluene was charged and the mixture was bubbled with $N_2$ for 10 min, then BINAP (398 mg, 0.64 mmol) and $Pd_2$ $dba_3$ (195 mg, 0.21 mmol) was added to the mixture. After the addition of DBU (3.8 mL), the solution was warmed at 60-70° C. while a fine powder of tBuONa (3.5 g, 31.9 mmol) was added in one portion to start the amination. After the reaction mixture cooled to rt, $(Boc)_2O$ (11.6 g, 53.2 mmol) was dissolved in DCM and added dropwise to the reaction mixture, then stirred at rt for 3 h. The reaction mixture was diluted with water and extracted with EtOAc. The combined EtOAc layers were washed with brine, dried over anhydrous $Na_2SO_4$, concentrated in vacuo and purified by flash chromatography on silica gel column (elution with PE/EtOAc=10:1) to give tert-butyl 4-(2-methoxyphenyl)piperazine-1-carboxylate as a white solid. Excess HCl in EtOAc was added dropwise to a solution of tert-butyl 4-(2-methoxyphenyl)piperazine-1-carboxylate in EtOAc and the reaction mixture was stirred at rt for 1.5 h. Filtration gave 1-(2-methoxyphenyl)piperazine hydrochloride salt (intermediate 55) (2.6 g, 42%) as a white solid. HPLC: 99%, RT 1.586 min. MS (ESI) m/z 193.1 $[M+H]^+$.

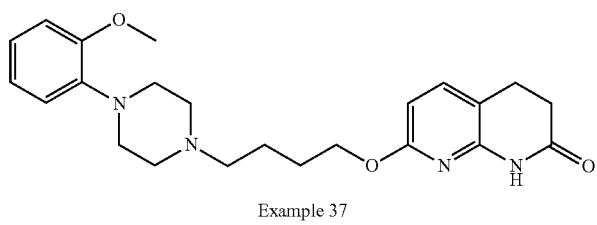

Example 37

Compound 37:

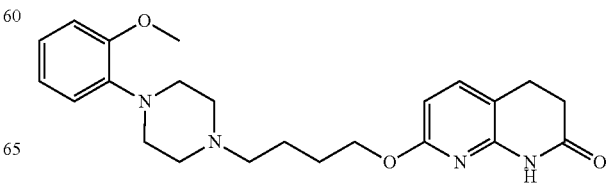

A mixture of intermediate 12 (314 mg, 0.48 mmol) and NaI (150 mg, 0.96 mmol) in CH₃CN was heated to reflux for 30 min and then cooled to rt. Intermediate 55 (228 mg, 0.48 mmol) and anhydrous K₂CO₃ (138 mg, 1.92 mmol) were added to the mixture. The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na₂SO₄, concentrated in vacuo and purified by flash chromatography on silica gel column (elution with DCM/MeOH=30:1) to give 7-(4-(4-(2-methoxyphenyl)piperazin-1-yl)butoxy)-3,4-dihydroquinolin-2(1H)-one (compound 37) (98 mg, 60%). ¹H NMR (300 MHz, CDCl₃): δ 7.55 (s, 1H), 7.35 (d, J=8.1 Hz, 1H), 7.02-6.85 (m, 3H), 6.37-6.34 (m, 1H), 4.29-4.20 (m, 2H), 3.86 (s, 3H), 3.11 (brs, 4H), 2.86 (t, J=6.9 Hz, 2H), 2.67-2.61 (m, 5H), 2.48 (t, J=7.2 Hz, 1H), 1.82-1.62 (m, 6H). HPLC: 99%, RT 2.109 min. MS (ESI) m/z 411.2 [M+H]⁺.

Synthesis of Compound 38

Scheme 63. Synthesis of intermediate 59

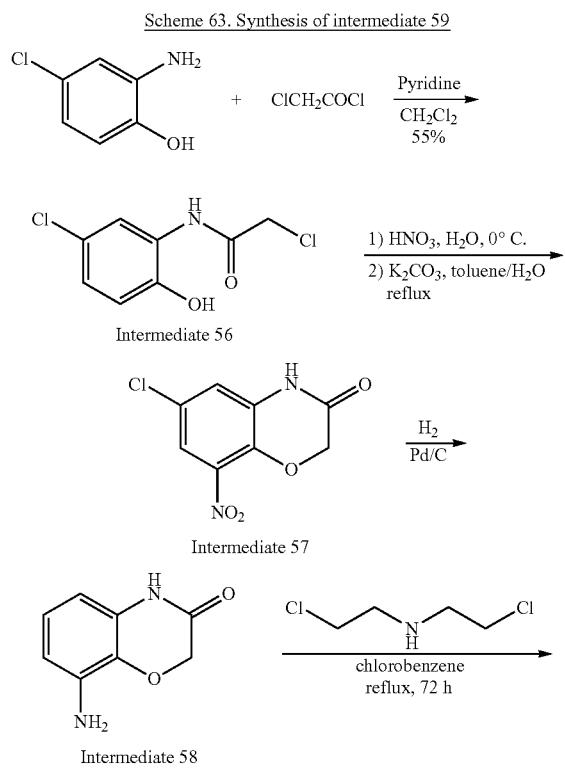

Scheme 64. Synthesis of compound 38

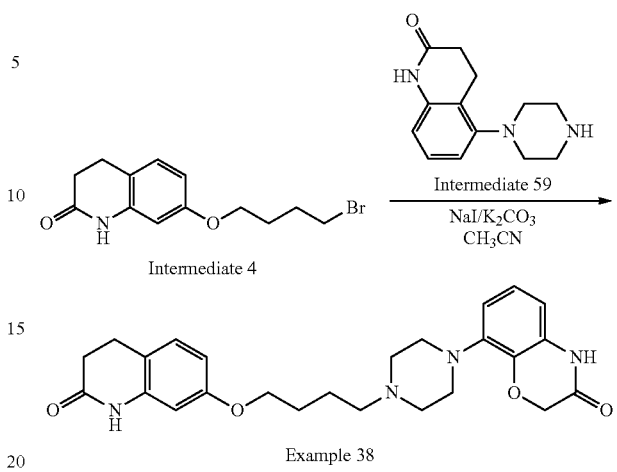

Intermediate 56:

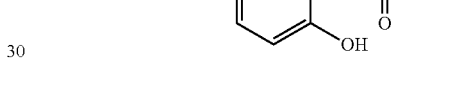

To a cooled (0° C.) solution of 2-amino-4-chlorophenol (30 g, 209 mmol) in DCM (200 mL) and pyridine (17 mL) was added a solution of chloroacetyl chloride in DCM (23.6 g, 230 mmol in 75 mL). The mixture was allowed to reach rt slowly and was subsequently stirred for 18 h. The precipitate was filtered, washed with DCM, and dried overnight at 50° C. to give crude 2-chloro-N-(5-chloro-2-hydroxyphenyl)acetamide (intermediate 56) (26 g, 55%), as a brown solid which was used in the next step without any further purification.

Intermediate 57:

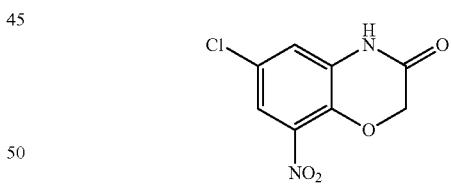

Intermediate 56 (26 g, 118 mmol) was suspended in water at 0° C. To the suspension was added HNO₃ (1.5 equiv, 15 mL, 174 mmol) over a period of 0.75 h. The resulting red solution was allowed to reach rt after 1 h, then water was added to give a dark brown solid which was isolated by filtration. The resulting filtrate was washed with cold water (3×100 mL) and dried to give a yellow solid. Ring closure to intermediate 57 was established by heating the yellow solid with K₂CO₃ in toluene/water (50/1, v/v) for 2 h. The reaction mixture was cooled to rt and the resulting brown precipitate was filtered and purified by silica gel chromatography (EtOAc/PA, 1/1, v/v to 1/0, v/v) to give 6-chloro-8-nitro-2H-benzo[b][1,4]oxazin-3(4H)-one (intermediate 57) (21 g, 78%) as a brown solid.

Intermediate 58:

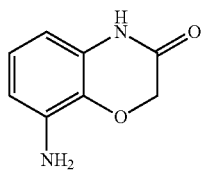

Intermediate 57 (326 mg, 1.4 mmol) was dissolved in EtOH, then Pd/C (0.03 g) was added. The mixture was hydrogenated under $H_2$ for 4 h at 50° C. The reaction mixture was filtered over Hyflo and the filtrate was concentrated in vacuo to give 8-amino-2H-benzo[b][1,4]oxazin-3(4H)-one (intermediate 58) (83%) as a brown solid, which was used in the next step without any further purification.

Intermediate 59:

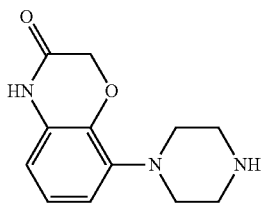

Compound 38:

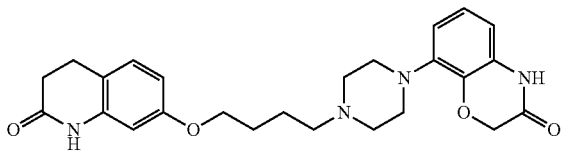

A mixture of intermediate 4 (110 mg, 0.37 mmol) and NaI (110 mg, 0.74 mmol) in $CH_3CN$ was heated to reflux for 30 min and then cooled to rt. Intermediate 59 (118 mg, 0.5 mmol) and anhydrous $K_2CO_3$ (138 mg, 1.92 mmol) were added to the mixture. The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous $Na_2SO_4$, concentrated in vacuo and purified by flash chromatography on silica gel column (elution with DCM/MeOH=30:1) to give 8-(4-(4-(2-oxo-1,2,3,4-tetrahydroquinolin-7-yloxy)butyl)piperazin-1-yl)-2H-benzo[b][1,4]oxazin-3 (4H)-one (compound 38) (55 mg, 34%). $^1H$ NMR (300 MHz, $CDCl_3$): δ 10.56 (s, 1H), 9.96 (s, 1H), 7.04 (d, J=8.4 Hz, 1H), 6.85 (t, 1H), 6.57-6.43 (m, 4H), 4.53 (s, 2H), 3.92 (t, J=5.7 Hz, 2H), 2.97 (br, 4H), 2.78 (t, J=6.9 Hz, 2H), 2.43-2.38 (m, 4H), 1.72-1.58 (m, 4H). HPLC: 99%, RT 1.970 min. MS (ESI) m/z 451.0 $[M+H]^+$.

Synthesis of Compound 39

Scheme 65. Synthesis of compound 39

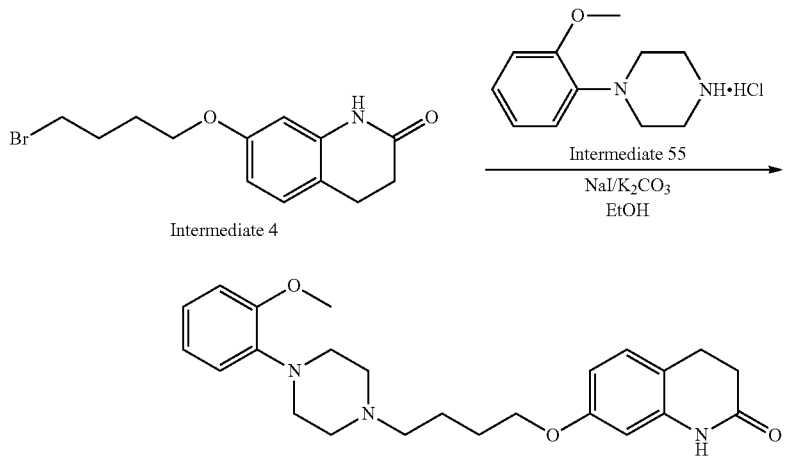

To a solution of intermediate 58 (164 mg, 1.0 mmol) in chlorobenzene (5 mL) was added bis(2-chloroethyl)amine hydrochloric acid (285 mg, 1.6 mmol) and the mixture was heated to reflux for 100 h. The reaction mixture was concentrated in vacuo and the residue was stirred in EtOAc for 2 h. The resulting brown solid was filtered and purified by silica gel chromatography to give 8-(piperazin-1-yl)-2H-benzo[b][1,4]oxazin-3(4H)-one (intermediate 59) (150 mg, 64%). HPLC: 99%, RT 1.344 min. MS (ESI) m/z 234.1$[M+H]^+$.

Compound 39:

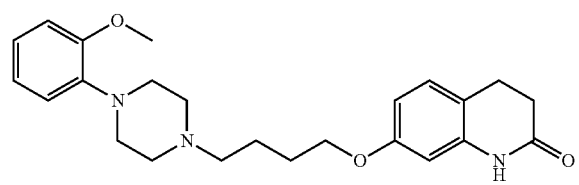

A mixture of intermediate 4 (110 mg, 0.34 mmol) and NaI (102 mg, 1.36 mmol) in CH$_3$CN was heated to reflux for 30 min and then cooled to rt. Intermediate 55 (117 mg, 0.51 mmol) and anhydrous K$_2$CO$_3$ (188 mg, 1.36 mmol) were added to the mixture. The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by flash chromatography on silica gel column (elution with DCM/MeOH=30:1) to give 7-(5-(4-(2-methoxyphenyl)piperazin-1-yl)pentyloxy)-3,4-dihydroquinolin-2(1H)-one (compound 39) (112 mg, 81%). $^1$H NMR (300 MHz, CDCl$_3$): δ 7.92 (brs, 1H), 7.06-6.85 (m, 5H), 6.52 (d, J=6.6 Hz, 1H), 6.31 (s, 1H), 3.98-3.94 (m, 2H), 3.86 (s, 3H), 3.12 (br, 4H), 2.92-2.87 (m, 2H), 2.69-2.59 (m, 6H), 2.52-2.47 (m, 2H), 1.82-1.72 (m, 4H). HPLC: 99%, RT 2.100 min. MS (ESI) m/z 410.2 [M+H]$^+$.

Synthesis of Compound 40

Scheme 66. Synthesis of intermediate 61

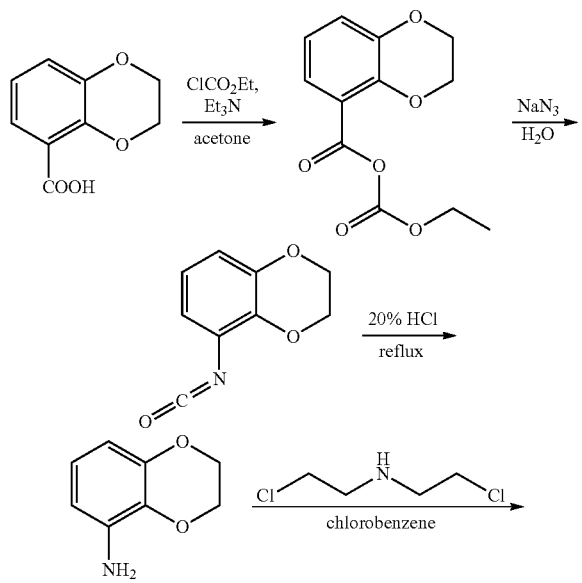

Scheme 67. Synthesis of compound 40

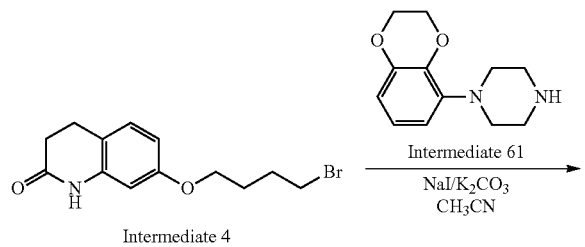

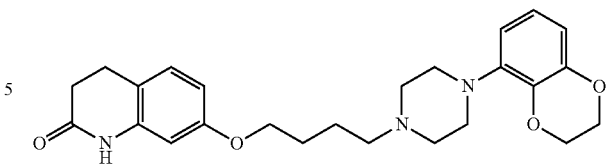

Example 40

Intermediate 60:

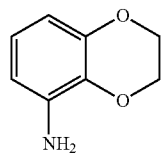

Triethylamine in acetone was added dropwise to the solution of 2,3-dihydrobenzo[b][1,4]dioxine-5-carboxylic acid (360 mg, 2 mmol) in water and acetone at 0° C. To the mixture was added ethyl carbonochloridate in acetone slowly. The mixture was stirred for 4 h then a solution of NaN$_3$ (196 mg, 3.02 mmol) in water was added dropwise. The reaction mixture was stirred for 1 h then it was poured into ice water and extracted with Et$_2$O. The combined organic extracts were washed with brine, dried with MgSO$_4$, and concentrated in vacuo. The residue was dissolved in anhydrous toluene and the mixture was heated on a steam bath until nitrogen evolution had ceased. The toluene was then removed in vacuo and 20% aq HCl (4 mL) was added and the solution was heated to reflux and stirred overnight. The reaction was concentrated under reduced pressure. The residue was dissolved in water, made strongly alkaline by the addition of 40% aq NaOH, then extracted with Et$_2$O. The combined organic extracts were washed with brine, dried by MgSO$_4$, and purified by flash chromatography on silica gel column (PE:EtOAc=5:1) to give 2,3-dihydrobenzo[b][1,4]dioxin-5-amine (intermediate 60) (270 mg, 70%). HPLC: 99%, RT 1.214 min. MS (ESI) m/z 152.1 [M+H]$^+$.

Intermediate 61:

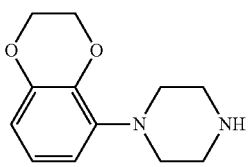

Bis(2-chloroethyl)amine hydrochloride salt (452 mg, 2.54 mmol) was added to a solution of intermediate 60 (320 mg, 2.12 mmol) in chlorobenzene (4 mL) and the mixture was heated to reflux and stirred overnight. The solvent was removed under reduced pressure and the residue was purified by flash chromatography on silica gel column (DCM:MeOH=30:1-20:1), followed by a wash with EtOAc, to give 1-(2,3-dihydrobenzo[b][1,4]dioxin-5-yl)piperazine (intermediate 61) (236 mg, 51%). HPLC: 99%, RT 1.673 min. MS (ESI) m/z 221.1 [M+H]$^+$.

Compound 40:

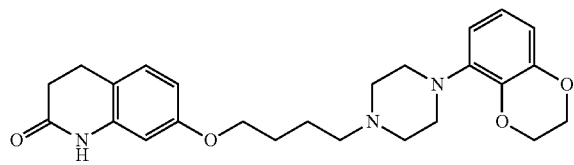

A mixture of intermediate 4 (100 mg, 0.34 mmol) and NaI (102 mg, 0.68 mmol) in $CH_3CN$ was heated to reflux for 30 min and then cooled to rt. Intermediate 61 (112 mg, 0.51 mmol) and anhydrous $K_2CO_3$ (188 mg, 1.36 mmol) were added to the mixture. The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous $Na_2SO_4$, concentrated in vacuo and purified by flash chromatography on silica gel column (elution with DCM/MeOH 30:1) to give 7-(4-(4-(2,3-dihydrobenzo[b][1,4]dioxin-5-yl)piperazin-1-yl)butoxy)-3,4-dihydroquinolin-2(1H)-one (compound 40) (125 mg, 83%). $^1$H NMR (300 MHz, $CDCl_3$): δ 7.88 (s, 1H), 7.04 (d, J=8.1 Hz, 1H), 6.80-6.77 (m, 1H), 6.61-6.51 (m, 3H), 6.31 (d, J=1.8 Hz, 1H), 4.33-4.24 (m, 4H), 3.96 (m, 2H), 3.10 (m, 4H), 2.89 (t, J=7.5 Hz, 2H), 2.66-2.59 (m, 6H), 2.50-2.46 (m, 2H), 1.81-1.71 (m, 6H). HPLC: 99%, RT 2.468 min. MS (ESI) m/z 438.2 $[M+H]^+$.

Synthesis of Compound 41

Scheme 68. Synthesis of compound 41

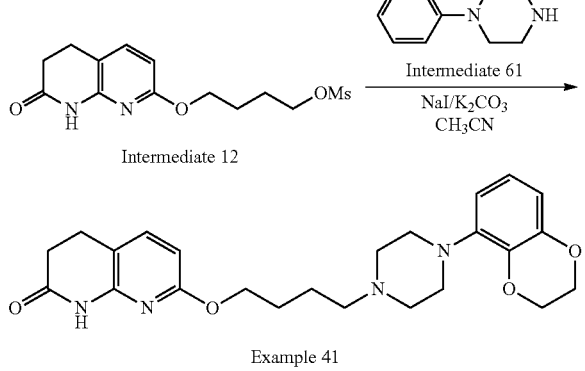

Compound 41:

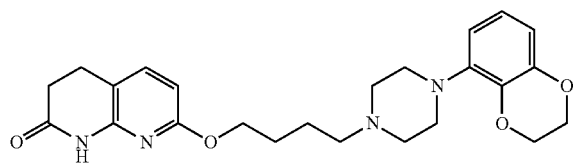

A mixture of intermediate 12 (100 mg, 0.32 mmol) and NaI (95 mg, 0.64 mmol) in $CH_3CN$ was heated to reflux for 30 min and then cooled to rt. Intermediate 61 (105 mg, 0.48 mmol) and anhydrous $K_2CO_3$ (176 mg, 1.27 mmol) were added to the mixture. The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous $Na_2SO_4$, concentrated in vacuo and purified by flash chromatography on silica gel column (elution with DCM/MeOH=30: 1) to give 7-(4-(4-(2,3-dihydrobenzo[b][1,4]dioxin-5-yl)piperazin-1-yl)butoxy)-3,4-dihydro-1,8-naphthyridin-2(1H)-one (compound 41) (115 mg, 83%). $^1$H NMR (300 MHz, $CDCl_3$): δ 7.60 (s, 1H), 7.36 (d, J=8.1 Hz, 1H), 7.27 (s, 1H), 6.78 (t, J=8.1 Hz, 1H), 6.61-6.53 (m, 2H), 6.35 (d, J=8.1 Hz, 1H), 4.33-4.20 (m, 6H), 3.10 (s, 4H), 2.86 (dd, J=7.5 Hz, 2H), 2.67-2.62 (m, 6H), 2.51-2.46 (m, 2H), 1.82-1.69 (m, 6H). HPLC: 99%, RT 2.084 min. MS (ESI) m/z 439.2 $[M+H]^+$.

Synthesis of Compound 42

Scheme 69. Synthesis of compound 42

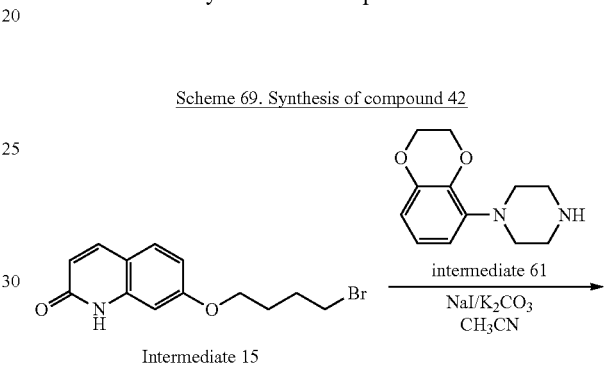

Compound 42:

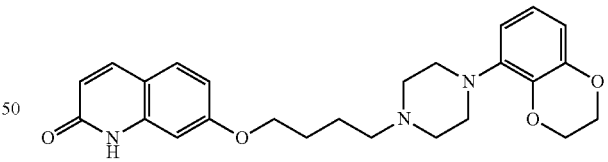

A mixture of intermediate 15 (70 mg, 0.24 mmol) and NaI (70 mg, 0.48 mmol) in $CH_3CN$ was heated to reflux for 30 min and then cooled to rt. Intermediate 61 (78 mg, 0.36 mmol) and anhydrous $K_2CO_3$ (162 mg, 0.96 mmol) were added to the mixture. The resulting mixture was heated to reflux and stirred for 4 h. Precipitated crystals were filtered off and the filtrate was evaporated under reduced pressure. The residue was extracted with EtOA. The combined EtOAc layers were washed with brine, dried over anhydrous $Na_2SO_4$, concentrated in vacuo and purified by flash chromatography on silica gel column (elution with DCM/MeOH=30:1) to give 7-(4-(4-(2,3-dihydrobenzo[b][1,4]dioxin-5-yl)piperazin-1-yl)butoxy)quinolin-2(1H)-one (compound 42) (52 mg, 50%). $^1$H NMR (300 MHz, $CDCl_3$): δ 11.65 (brs, 1H), 7.72 (d, J=9.6

Hz, 1H), 7.45 (d, J=8.4 Hz, 1H), 6.82-6.75 (m, 3H), 6.61-6.52 (m, 3H), 4.33-4.26 (m, 4H), 4.12-4.08 (m, 2H), 3.12 (br, 4H), 2.70 (br, 4H), 2.52 (br, 2H), 2.04-1.68 (m, 6H). HPLC: 99%, RT 2.167 min. MS (ESI) m/z 436.0 [M+H]$^+$.

Synthesis of Compound 43

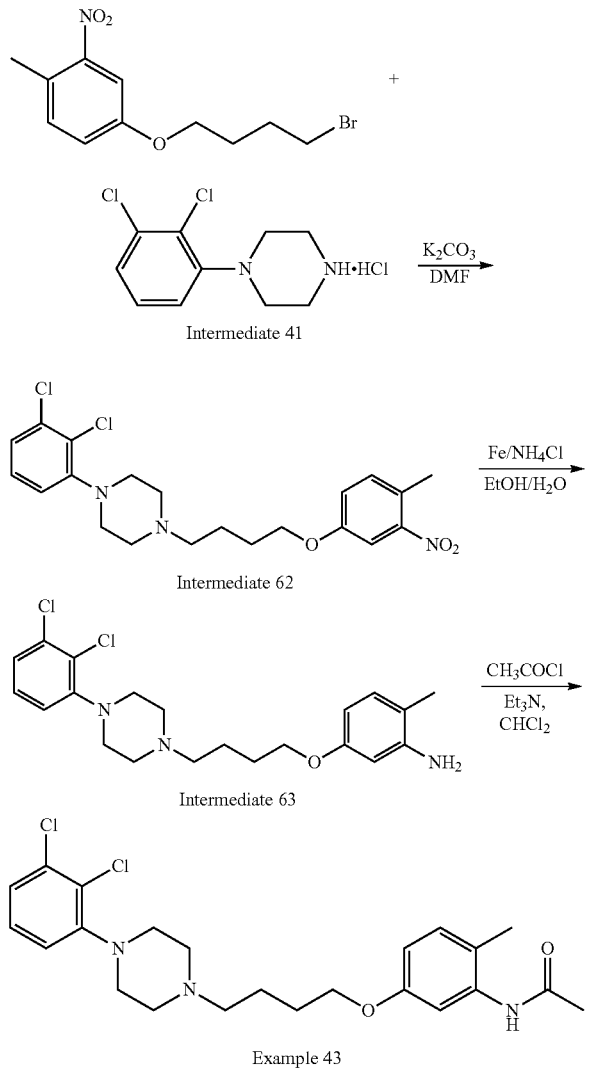

Intermediate 62:

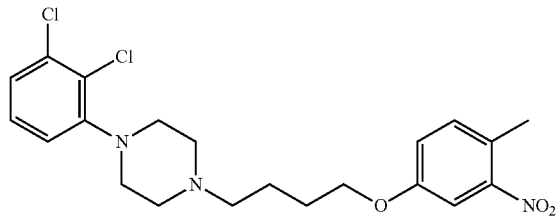

A mixture of 4-(4-bromobutoxy)-1-methyl-2-nitrobenzene (200 mg, 0.7 mmol), intermediate 41 (186 mg, 0.7 mmol) and anhydrous $K_2CO_3$ (195 mg, 1.4 mmol) was dissolved in $CH_3CN$ and the solution was heated to reflux and stirred overnight. The solution was concentrated in vacuo and purified by flash chromatography on silica gel column (elution with DCM/MeOH=50:1) to give 1-(2,3-dichlorophenyl)-4-(4-(4-methyl-3-nitrophenoxy)butyl)piperazine (intermediate 62) (180 mg, 59%) as a yellow solid.

Intermediate 63:

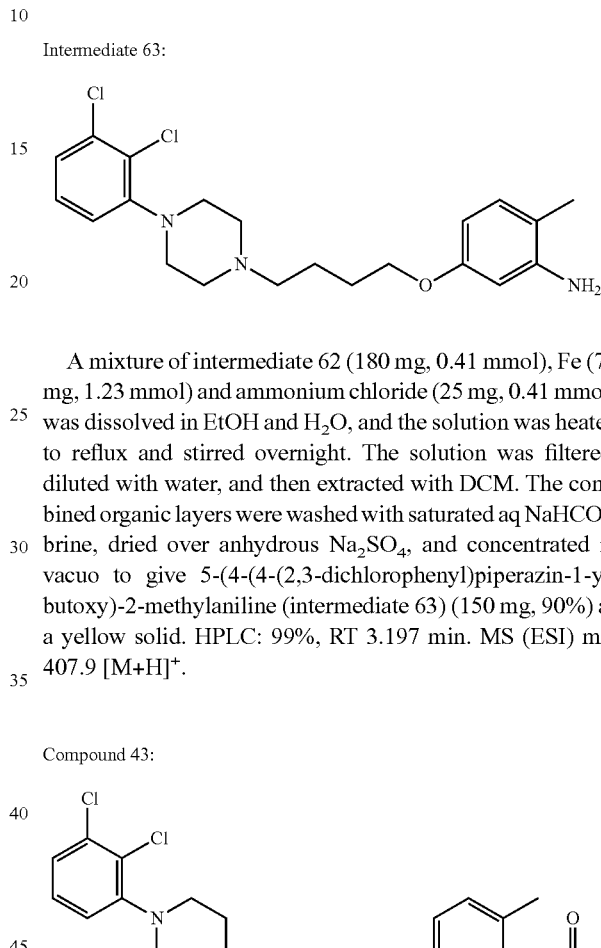

A mixture of intermediate 62 (180 mg, 0.41 mmol), Fe (70 mg, 1.23 mmol) and ammonium chloride (25 mg, 0.41 mmol) was dissolved in EtOH and $H_2O$, and the solution was heated to reflux and stirred overnight. The solution was filtered, diluted with water, and then extracted with DCM. The combined organic layers were washed with saturated aq $NaHCO_3$, brine, dried over anhydrous $Na_2SO_4$, and concentrated in vacuo to give 5-(4-(4-(2,3-dichlorophenyl)piperazin-1-yl)butoxy)-2-methylaniline (intermediate 63) (150 mg, 90%) as a yellow solid. HPLC: 99%, RT 3.197 min. MS (ESI) m/z 407.9 [M+H]$^+$.

Compound 43:

A mixture of intermediate 63 (120 mg, 0.29 mmol), acetyl chloride (35 mg, 0.44 mmol) and $Et_3N$ (54 mg, 0.54 mmol) was dissolved in DCM and the solution was stirred at rt. The solution was diluted with water and extracted with DCM. The combined organic layers were washed with saturated aq $NaHCO_3$, brine, dried over anhydrous $Na_2SO_4$, concentrated in vacuo and purified by flash chromatography on silica gel column (elution with DCM/MeOH=100:1-30:1) to give N-(5-(4-(4-(2,3-dichlorophenyl)piperazin-1-yl)butoxy)-2-methylphenyl)acetamide (compound 43) (45 mg, 35%) as a yellow solid. $^1$H NMR (300 MHz, CDCl$_3$): δ 7.56 (s, 1H), 7.18-7.13 (m, 2H), 7.07-6.88 (m, 3H), 6.62 (d, J=8.1 Hz, 1H), 3.99 (br, 2H), 3.26 (br, 4H), 2.92-2.75 (br, 6H), 2.21 (s, 3H), 2.19 (s, 3H), 1.86 (br, 6H). HPLC: 99%, RT 2.464 min. MS (ESI) m/z 449.8 [M+H]$^+$.

Synthesis of Compound 44

Scheme 71. Synthesis of compound 44

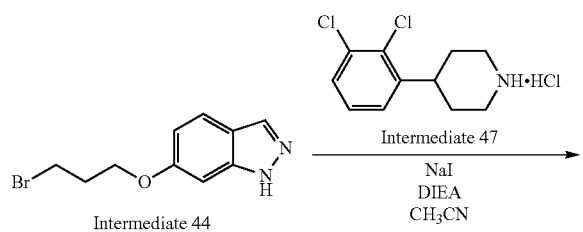

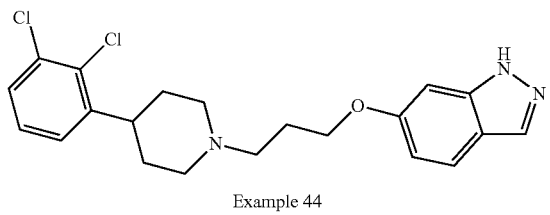

Example 44

Compound 44:

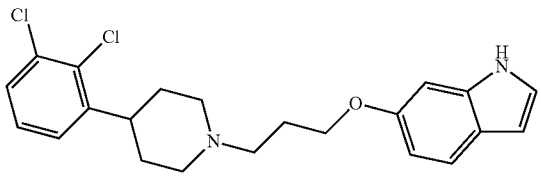

A mixture of intermediate 44 (41 mg, 0.16 mmol) and NaI (48.1 mg, 0.32 mmol) in CH$_3$CN (3 mL) was heated to reflux for 30 min and then cooled to rt. To this mixture was added intermediate 47 (64.3 mg, 0.24 mmol), followed then by DIEA (0.062 mL, 0.35 mmol). The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by ISCO to give 6-(3-(4-(2,3-dichlorophenyl)piperidin-1-yl)propoxy)-1H-indazole (compound 44) (42.1 mg, 65%). $^1$H NMR (400 MHz, CDCl$_3$): δ 7.92 (d, J=0.8 Hz, 1H), 7.57 (d, J=8.8 Hz, 1H), 7.33 (dd, J=7.8, 1.6 Hz, 1H), 7.28-7.24 (dd, J=7.8, 1 Hz, 1H), 7.18 (t, J=7.8 Hz, 1H), 6.98 (s, 1H), 6.77 (dd, J=8.8, 2.1 Hz, 1H), 4.10 (t, J=6.0 Hz, 2H), 3.56-3.40 (m, 2H), 3.39-3.26 (m, 1H), 3.11-2.97 (m, 2H), 2.73 (s, 2H), 2.39-2.15 (m, 4H), 2.04-1.94 (dd, J=16.8, 9.4 Hz, 2H). HPLC: 99%, RT 4.397 min. MS (ESI) m/z 404.15 [M+H]$^+$.

Synthesis of Compound 45

Scheme 72. Synthesis of compound 45

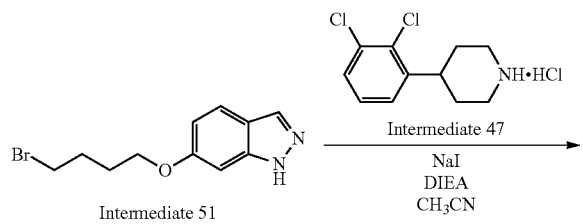

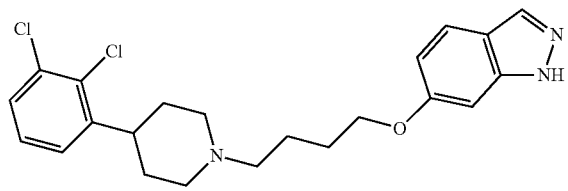

Example 45

Compound 45:

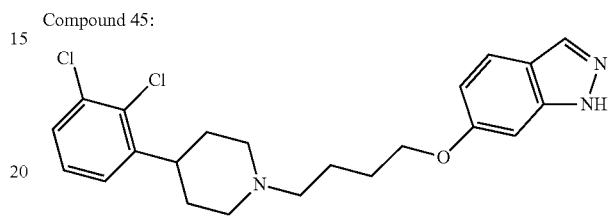

A mixture of intermediate 51 (40.6 mg, 0.15 mmol) and NaI (45.2 mg, 0.30 mmol) in CH$_3$CN (3 mL) was heated to reflux for 30 min and then cooled to rt. To this mixture was added intermediate 47 (60.3 mg, 0.23 mmol), followed then by DIEA (0.058 mL, 0.33 mmol). The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by ISCO to give 6-(4-(4-(2,3-dichlorophenyl)piperidin-1-yl)butoxy)-1H-indazole (compound 45) (37.6 mg, 60%). $^1$H NMR (400 MHz, CDCl$_3$): δ 7.93 (s, 1H), 7.54 (d, J=8.8 Hz, 1H), 7.33 (dd, J=7.9, 1.2 Hz, 1H), 7.25-7.20 (m, 1H), 7.15 (t, J=7.9 Hz, 1H), 6.93 (s, 1H), 6.74 (dd, J=8.8, 1.9 Hz, 1H), 3.94 (t, J=6.0 Hz, 2H), 3.75-3.67 (m, 2H), 3.46-3.36 (m, 1H), 3.15-3.08 (m, 2H), 3.03-2.91 (m, 2H), 2.59-2.43 (m, 2H), 2.18-2.06 (m, 2H), 2.06-1.96 (m, 2H), 1.88-1.75 (m, 2H). HPLC: 99%, RT 4.447 min. MS (ESI) m/z 418.10 [M+H]$^+$.

Synthesis of Compound 46

Scheme 73. Synthesis of compound 46

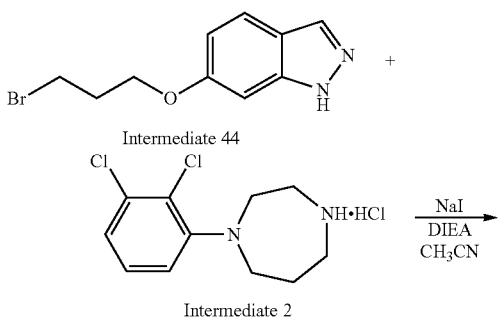

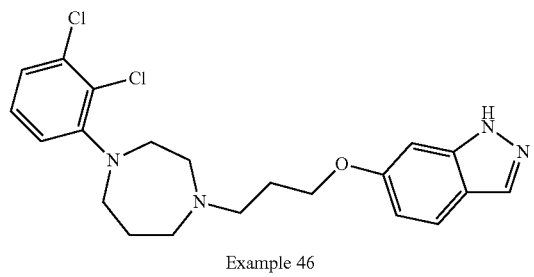

Example 46

Compound 46:

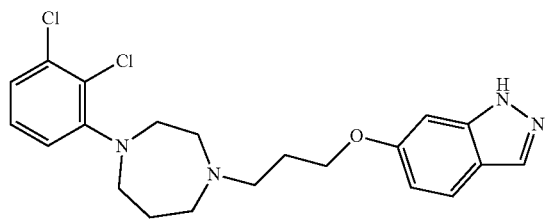

A mixture of intermediate 44 (43.7 mg, 0.17 mmol) and NaI (51.3 mg, 0.34 mmol) in CH$_3$CN (3 mL) was heated to reflux for 30 min and then cooled to rt. To this mixture was added intermediate 2 (57.9 mg, 0.21 mmol), followed then by DIEA (0.066 mL, 0.38 mmol). The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by ISCO to give 6-(3-(4-(2,3-dichlorophenyl)-1,4-diazepan-1-yl)propoxy)-1H-indazole (compound 46) (43.6 mg, 61%). $^1$H NMR (400 MHz, CDCl$_3$): δ 7.96 (d, J=0.8 Hz, 1H), 7.59 (d, J=8.8 Hz, 1H), 7.15-7.07 (m, 2H), 7.00 (dd, J=7.4, 2.3 Hz, 1H), 6.88 (s, 1H), 6.80 (dd, J=8.8, 2.1 Hz, 1H), 4.09 (t, J=6.1 Hz, 2H), 3.43-3.37 (m, 2H), 3.29 (t, J=6.1 Hz, 2H), 3.14-3.05 (m, 4H), 3.00-2.92 (m, 2H), 2.22-2.10 (m, 4H). HPLC: 99%, RT 4.201 min. MS (ESI) m/z 419.10 [M+H]$^+$.

Synthesis of Compound 47

Scheme 74. Synthesis of compound 47

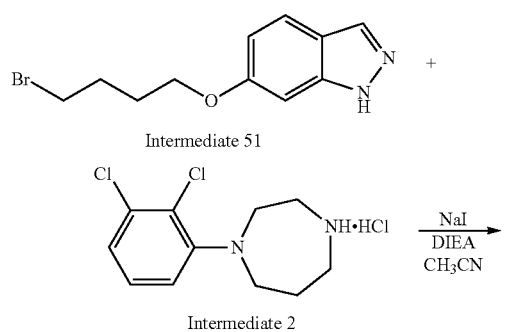

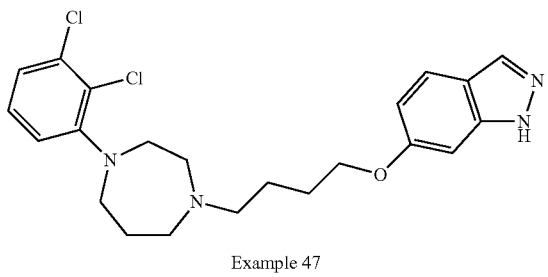

Example 47

Compound 47:

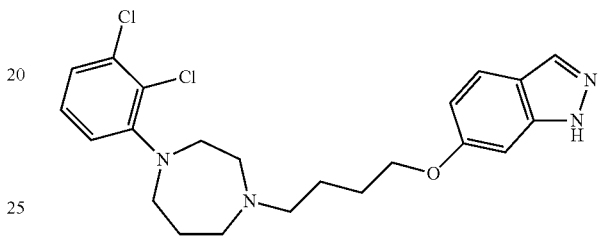

A mixture of intermediate 51 (54.2 mg, 0.20 mmol) and NaI (60.3 mg, 0.40 mmol) in CH$_3$CN (3 mL) was heated to reflux for 30 min and then cooled to rt. To this mixture was added intermediate 2 (62.4 mg, 0.22 mmol), followed then by DIEA (0.077 mL, 0.44 mmol). The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by ISCO to give 6-(4-(4-(2,3-dichlorophenyl)-1,4-diazepan-1-yl)butoxy)-1H-indazole (compound 47) (50.8 mg, 59%). HPLC: 99%, RT 4.526 min. MS (ESI) m/z 433.20 [M+H]$^+$.

Synthesis of Compound 48

Scheme 75. Synthesis of compound 48

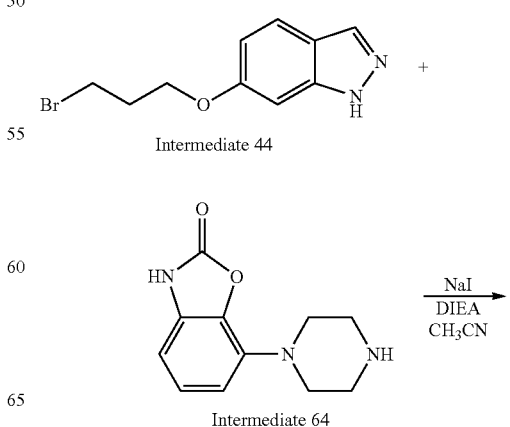

Example 48

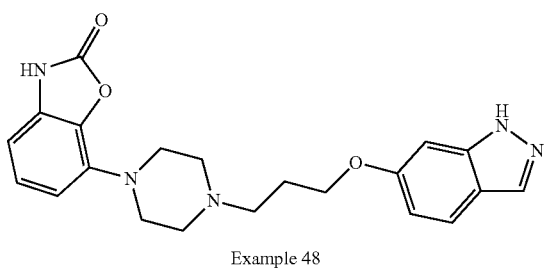

Example 49

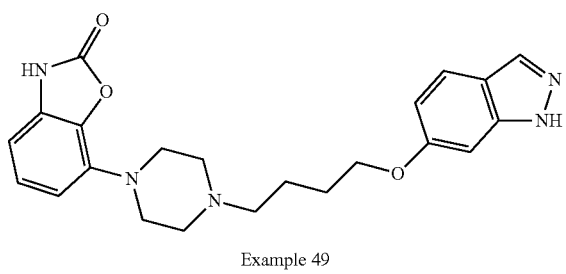

Compound 48:

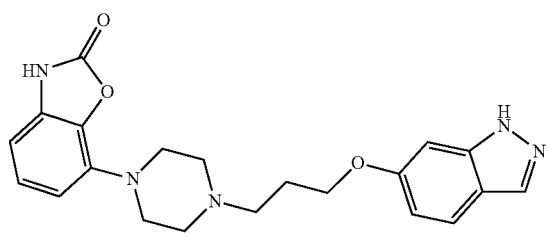

Compound 49:

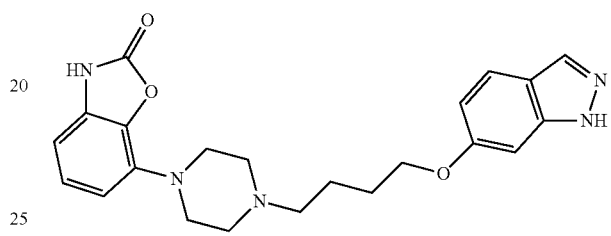

A mixture of intermediate 44 (43.6 mg, 0.17 mmol) and NaI (51.2 mg, 0.34 mmol) in CH$_3$CN (3 mL) was heated to reflux for 30 min and then cooled to rt. To this mixture was added intermediate 64 (45.0 mg, 0.21 mmol, prepared following the procedure in US Publication No. 2010/0119622) followed by DIEA (0.066 mL, 0.38 mmol). The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by ISCO to give 7-(4-(3-(1H-indazol-6-yloxy)propyl)piperazin-1-yl)benzo[d]oxazol-2(3H)-one (compound 48) (43.7 mg, 65%). HPLC: 99%, RT 3.551 min. MS (ESI) m/z 394.20 [M+H]$^+$.

Synthesis of Compound 49

A mixture of intermediate 51 (47.3 mg, 0.18 mmol) and NaI (52.6 mg, 0.35 mmol) in CH$_3$CN (3 mL) was heated to reflux for 30 min and then cooled to rt. To this mixture was added intermediate 64 (42.4 mg, 0.19 mmol), followed then by DIEA (0.067 mL, 0.39 mmol). The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by ISCO to give 7-(4-(4-(1H-indazol-6-yloxy)butyl)piperazin-1-yl)benzo[d]oxazol-2(3H)-one (compound 49) (43.5 mg, 61%). HPLC: 99%, RT 3.680 min. MS (ESI) m/z 408.20 [M+H]$^+$.

Synthesis of Compound 50

Scheme 76. Synthesis of compound 49

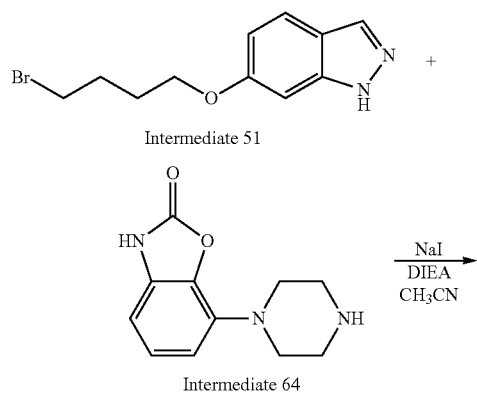

Scheme 77. Synthesis of intermediate 65

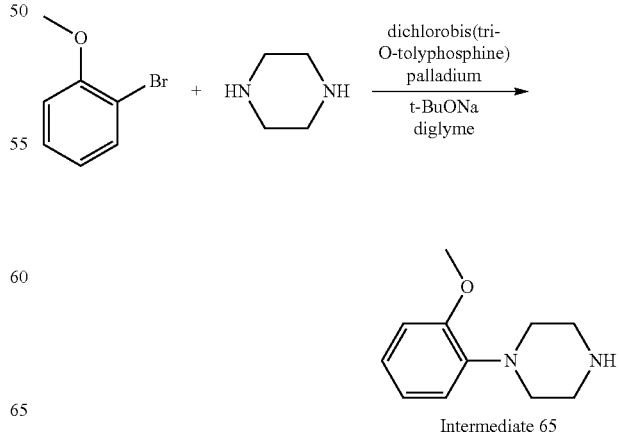

Scheme 78. Synthesis of compound 50

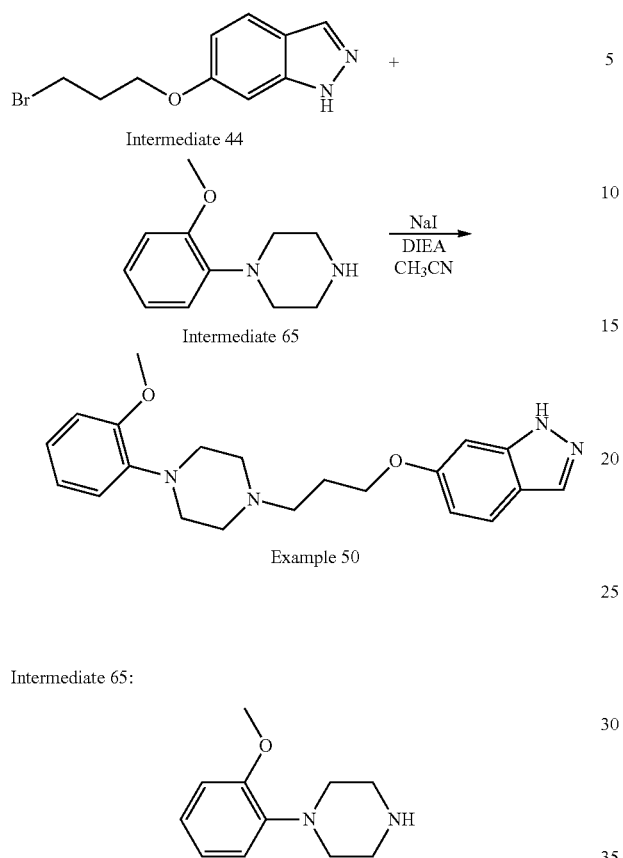

Example 50

Intermediate 65:

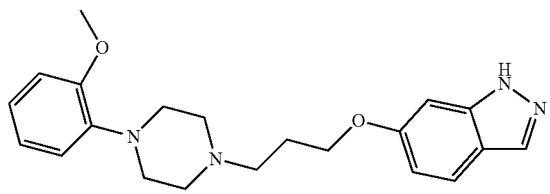

To a solution of 1-bromo-2-methoxybenzene (0.623 mL, 5.0 mmol) and piperazine (1722.8 mg, 20.0 mmol) in diglyme (5 mL) was added t-BuONa. The resulting mixture was stirred at rt for a few minutes before the addition of dichlorobis(tri-β-tolyphosphine)palladium (235.8 mg, 0.3 mmol). The resulting mixture was then stirred at 170° C. under microwave irradiation for 30 min. Water was added and the mixture was extracted with EtOAc. The combined organic layers were dried, concentrated, and purified by ISCO to give 1-(2-methoxyphenyl)piperazine (intermediate 65) (758 mg, 79%) as an off-white solid. HPLC: 95%, RT 2.641 min. MS (ESI) m/z 193.10 [M+H]$^+$.

Compound 50:

A mixture of intermediate 44 (42.2 mg, 0.17 mmol) and NaI (49.5 mg, 0.33 mmol) in CH$_3$CN (3 mL) was heated to reflux for 30 min and then cooled to rt. To this mixture was added intermediate 65 (35.0 mg, 0.18 mmol), followed then by DIEA (0.063 mL, 0.36 mmol). The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by ISCO to give 6-(3-(4-(2-methoxyphenyl)piperazin-1-yl)propoxy)-1H-indazole (compound 50) (36.6 mg, 60%). HPLC: 99%, RT 3.907 min. MS (ESI) m/z 367.20 [M+H]$^+$.

Synthesis of Compound 51

Scheme 79. Synthesis of compound 51

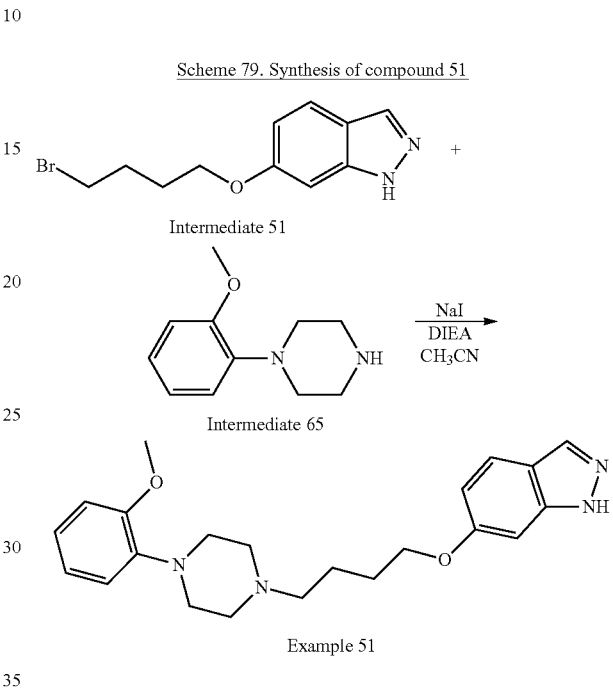

Example 51

Compound 51:

A mixture of intermediate 51 (41.6 mg, 0.15 mmol) and NaI (46.3 mg, 0.31 mmol) in CH$_3$CN (3 mL) was heated to reflux for 30 min and then cooled to rt. To this mixture was added intermediate 65 (32.7 mg, 0.17 mmol), followed then by DIEA (0.059 mL, 0.34 mmol). The resulting mixture was heated to reflux and stirred for 4 h. Precipitated crystals were filtered off and the filtrate was evaporated under reduced pressure. The residue was extracted with EtOAc. The combined EtOAc layers were washed with brine, dried over anhydrous Na$_2$SO$_4$, concentrated in vacuo and purified by ISCO to give 6-(4-(4-(2-methoxyphenyl)piperazin-1-yl)butoxy)-1H-indazole (compound 51) (35.6 mg, 62%). HPLC: 99%, RT 4.000 min. MS (ESI) m/z 381.20 [M+H]$^+$.

EXAMPLE 2

In Vitro Studies

Each of the synthesized compounds were tested in a variety of in vitro assays for D$_2$ receptor activity. Results are summarized in Table 6.

CHO-D$_2$ Membrane Preparation for GTP-Radioligand Binding Assays

Cells stably expressing D$_2$ receptors (CHO-D$_2$) were plated in 15-cm dishes (in DMEM containing 10% fetal bovine serum and grown to 90% confluence. Then, cells were washed with PBS, pH 7.4, and harvested by scraping into PBS, pH 7.4. Harvested cells were centrifuged at 1,000×g for 10 min, then hypotonically lysed by resuspension in ice-cold 50 mM HEPES, 1% BSA, pH 7.4. Membranes were isolated by centrifugation at 21,000×g for 20 min. The supernatant was removed and the membrane pellets were assayed for D2 ligand-stimulated GTP-gamma-S binding or stored at −80° C. until used for radioligand binding assays.

CHO-D$_2$ Radioligand Binding Assay

Membranes prepared as above were resuspended to 1 µg protein/µl (measured by Bradford assay using BSA as standard), and 50 µl were added to each well of a polypropylene 96-well plate containing (per well): 50 µl of buffer (20 mM HEPES, 10 mM MgCl$_2$, 1 mM EDTA, 1 mM EGTA, 100 mM N-methyl-D-gluconate, pH 7.4), 50 µl of 1.5 nM [$^3$H]N-methylspiperone (final concentration 0.3 nM) and reference or D2 test ligand at various concentrations ranging from 50 µM to 50 µM (final concentrations ranging from 10 µM to 10 µM, triplicate determinations for each concentration of D$_2$ test ligand). After a 1.5-hr incubation in the dark at room temperature, the reactions were harvested onto 0.3% PEI-soaked Filtermax GF/A filters (Wallac) and washed three times with ice-cold 50 mM Tris, pH 7.4 using a Perkin-Elmer Filtermate 96-well harvester. The filters were subsequently dried, placed on a hot plate (100° C.), and Melitilex-A (Wallac) scintillant was applied. The filters were then removed from the hot plate and allowed to cool. The filters were counted on a Wallac TriLux microbeta counter (3 min per well). Residual [$^3$H]N-methylspiperone binding to filtered membranes was plotted as a function of log [reference] or log [D$_2$ test ligand] and the data were regressed using the one-site competition model built into Prism 4.0 (GraphPad software).

D$_2$ Mediated cAMP GloSensor Assay

HEK293T cells co-expressing the cAMP biosensor GloSensor-22F (Promega) and hD$_2$ receptors were seeded (10,000 cells/20 µl/well) into white, clear-bottom, tissue culture plates in HBSS, 10% FBS, 20 mM HEPES, pH 7.4. After a one- to two-hour recovery, cells were treated with 10 µl of 3× test or reference drug prepared in HBSS, 10% FBS, 20 mM HEPES, pH 7.4. After 30 minutes, cells were challenged with 10 µl of 1,200 nM (4×) isoproterenol in 8% (4×) GloSensor reagent. Luminescence per well per second was read on a Wallac TriLux microbeta plate counter. Data were normalized to the isoproterenol response (100%) and the maximal quinpirole-induced inhibition thereof (0%) and regressed using the sigmoidal dose-response function built into GraphPad Prism 4.0. Notably, HEK293T cells expressing the GloSensor-22F alone (no hD$_2$) were assayed in parallel and displayed no inhibition of isoproterenol-stimulated cAMP, either by quinpirole or by the test compounds, suggesting that the effect observed in hD$_2$-expressing cells was due to compound acting via the recombinant receptor.

D$_2$ β-Arrestin Recruitment (Tango) Assay

Recruitment of β-arrestin to agonist-stimulated D$_2$ receptors was performed using a previously described "Tango"-type assay (Barnea et al., *Proc. Natl. Acad. Sci. USA* 105:64 (2008)). Briefly, HTLA cells stably expressing β-arrestin-TEV protease and a tetracycline transactivator-driven luciferase were plated in 15-cm dishes in DMEM containing 10% fetal bovine serum and transfected (via calcium phosphate) with 20 µg of a D$_2$V$_2$-TCS-tTA construct (Barnea et al., *Proc. Natl. Acad. Sci. USA* 105:64 (2008)). The next day, cells were plated in white, clear-bottom, 384-well plates (Greiner, 10,000 cells/well, 50 µl/well) in DMEM containing 1% dialyzed fetal bovine serum. The following day, the cells were challenged with 10 µl/well of reference agonist (6 µM) or D$_2$ test ligand (6 µM)±reference agonist prepared in HBS, 20 mM HEPES, pH 7.4, 18% DMSO (final ligand concentrations were 1 µM, final DMSO concentration was 3%). After 18 hours, the medium was removed and replaced with 1× BriteGlo reagent (Promega), and luminescence/well was read using a TriLux plate reader (1 sec/well). Data were normalized to vehicle (0%) and quinpirole (100%) controls and regressed using the sigmoidal dose-response function built into GraphPad Prism 4.0.

pERK High-Content Assay

Cell Culture: Chinese Hamster Ovary (CHO) cells stably expressing the hD$_{2L}$ dopamine receptor (Urban et al., Neuropsychopharmacology 32:67 (2007)) were maintained in Ham's F12 medium supplemented with 10% fetal bovine serum, 100 U/mL penicillin, 100 µg/mL streptomycin, and 0.5 µg/ml G418. On day 1 of the assay, cells were seeded onto black clear-bottom tissue culture-treated 96-well plates (Greiner, BioOne). On day 2 of the assay, cells were washed with serum-free medium (Ham's F-12, penicillin and streptomycin) and incubated in 100 µL serum-free medium overnight.

Immunofluorescence: Automatic multichannel pipetters were used for liquid handling and multichannel vacuum manifolds for aspirations. Each tested concentration was typically measured in triplicate or quadruplicate. For concentration curves, half-log-dilutions were used. Drug dilutions were prepared in stimulation medium (serum-free medium, 100 mg/L ascorbic acid). 100 µM dopamine and 1 µM PMA (phorbol 12-myristate 13-acetate) were used as positive controls. Medium only was used as a negative control. Specificity of the response was confirmed by pretreatment for 5 min with 10 µM of the antagonist spiperone and in experiments using wild type CHO cells.

Cells were stimulated on day 3 by fast addition of 50 µL equilibrated 3× drug dilutions in a tissue culture incubator for 5 min. Plates were placed on ice, the medium was aspirated, and 100 µL/well of freshly prepared ice-cold fixing buffer (4% formaldehyde and 0.5 mM CaCl$_2$ in PBS) solution was added. After 30 min fixing at room temperature, the plates were washed with 350 µL/well PBS/Ca (0.5 mM CaCl$_2$ in PBS) and permeabilized for 20 min in 100 µL/well 0.3% Triton X-100 in PBS/Ca. Plates were incubated in 100 µL/well blocking buffer (PBS/Ca, 5% goat serum, 0.1% Triton X-100) for 1 h at room temperature and then in blocking buffer containing rabbit phospho-Thr202/p-Tyr204-ERK antibody (Cell Signaling 9101) at 1:1000 at 4° C. overnight. Cells were washed 3× for 5-10 min with 250 µL/well wash buffer (PBS/Ca, 0.03% Triton X-100). Plates were incubated with 50 µL/well Alexa-594 coupled goat anti-rabbit IgG (Invitrogen) at 1:250, 5 µg/mL Hoechst 33342 nuclear stain, and 25 µg/mL concanavaline-Alexa488 conjugate (ConA, Invitrogen) in blocking buffer for 2 h at room temperature. Plates were washed three times with 250 µL/well washing buffer, post-fixed for 10 min in fixing buffer, washed with 250 µl PBS/Ca, filled with 200 µL/well PBS/Ca, sealed with transparent adhesive plate seals, and stored at 4° C.

Microscopy and Image Analysis: Plates were scanned with a high-content automated microscopic system (BD Pathway 855) using a 20× objective and a 2×2 image montage setting. The Alexa594 light path was used for the target signal, Alexa488 for whole cell staining, and Hoechst for the nuclear staining. Images were analyzed using the CellProfiler software. Well-averaged individual cell-based measurements were exported to Excel and cell-free background intensity was subtracted from the whole cell intensity. Concentration curves were analyzed in GraphPad Prism by fitting against a sigmoidal dose-response model and normalization to the dopamine curve.

The results in Table 6 show that, of the 43 compounds tested, 33 are partial agonists ($E_{max}$ of 10%-80%) of the β-arrestin pathway and another 8 compounds are full agonists ($E_{max}$>80%) of the β-arrestin pathway. The compounds are also exceedingly potent, with 39 having an $EC_{50}$ less than 100 nM and 23 having an $EC_{50}$ less than 10 nM.

The cAMP (Glo-Sensor) assay shows that the majority of the tested compounds are not agonists for the $G_i$-coupled signaling pathway and that 14 of the 43 compounds function as inverse agonists for the $G_i$-coupled signaling pathway (i.e., have a negative $E_{max}$). The p-ERK assay confirms that the majority of compounds lack agonism via canonical G-protein-dependent pathways.

Compounds 2 and 3 were tested for receptor binding specificity. Consistent with their high potency in $D_2$ functional assays, 2 and 3 displayed high affinities ($K_i$'s<10 nM) in the $D_2$ radioligand competition binding assay (Table 7). Although 2 and 3 also had high affinity for $D_3$-dopamine receptor, they displayed low affinities for other dopamine receptors (i.e., $D_1$, $D_4$, and $D_5$). At serotonin receptors, 2 and 3 had moderate to high binding affinity ($K_i$'s: 0.6-250 nM) at $5HT_{2A}$, $5HT_{2B}$, $5HT_{2C}$, and $5HT_{1A}$, but were significantly less potent in functional assays ($Ca^{2+}$ mobilization fluorometric imaging plate reader (FLIPR) or cAMP biosensor). 2 and 3 were antagonists at $5HT_{2A}$, $5HT_{2B}$, and $5HT_{2C}$ and weak agonists ($EC_{50}$'s>1 μM) at $5HT_{1A}$. In addition, 2 and 3 had moderate affinities to $H_1$-histamine receptor ($K_i$'s<10 nM) but were less potent in $H_1$ functional assays. In general, 2 and 3 display a similar G protein-coupled receptor selectivity profile as aripiprazole (Table 7).

TABLE 6

| Example Number | UNC # | $D_2$ Binding $K_i$ ± SEM (nM) | cAMP (GloSensor)[a] $EC_{50}$ (nM) | $E_{max}$ (%) | β-arrestin (Tango) $EC_{50}$ (nM) | $E_{max}$ (%) | p-ERK[b] % activ at 1 μM | $EC_{50}$ (nM) | $E_{max}$ (%) |
|---|---|---|---|---|---|---|---|---|---|
| 1 | UNC10000003A | 8.3 ± 1 | 6.1 | 39 | 3.1 | 77 | 51 | 6 | 43 |
| 2 | UNC10000006A | 3.6 ± 0.5 | 126 | −63 | 3.3 | 48 | 11 | NA | 11 |
| 3 | UNC10099975A | 1.2 ± 0.1 | 13 | −94 | 3.3 | 44 | 11 | NA | <5 |
| 4 | UNC10099978A | 3.4 ± 0.4 | neutral | | 2.8 | 49 | 18 | 1 | 26 |
| 5 | UNC10099983A | 5.7 ± 0.8 | 5.6 | −16 | 8.0 | 47 | 13 | | |
| 6 | UNC10099984A | 4.6 ± 0.6 | 9870 | −76 | 6.2 | 32 | 7 | NA | <5 |
| 7 | UNC10099992A | 18 ± 2 | neutral | | 23 | 38 | 4 | | |
| 8 | UNC10099996A | 20 ± 2 | 348 | −26 | 63 | 73 | 12 | | |
| 9 | UNC10107953A | 4 ± 0.2 | 163 | −63 | 4.6 | 26 | | | |
| 10 | UNC10107954A | 2.1 ± 0.1 | 306 | −98 | 2.5 | 16 | | | |
| 11 | UNC10107955A | 5.7 ± 0.3 | 222 | −118 | 6.1 | 21 | | | |
| 12 | UNC10107958A | 4.1 ± 0.2 | neutral | | 4.3 | 41 | | | |
| 13 | UNC10107959A | 4.4 ± 0.3 | neutral | | 4.0 | 43 | | | |
| 14 | UNC10107962A | 3.6 ± 0.2 | 27 | 16 | 4.8 | 58 | | | |
| 15 | UNC10107966A | 3.4 ± 0.2 | 13 | 64 | 2.2 | 84 | | | |
| 16 | UNC10107967A | 0.87 ± 0.04 | neutral | | 4.2 | 53 | | | |
| 17 | UNC10107968A | 1.29 ± 0.03 | 0.2 | 18 | 4.6 | 56 | | | |
| 18 | UNC10107969A | 0.93 ± 0.03 | 0.1 | 32 | 4.2 | 58 | | | |
| 19 | UNC10108005A | 4.5 ± 0.2 | neutral | | 8.5 | 48 | | | |
| 20 | UNC10099976A | 104 ± 13 | 9.7 | −22 | 59 | 90 | 45 | | |
| 21 | UNC10099993A | 42 ± 4 | 21 | −27 | 82 | 81 | 26 | | |
| 22 | UNC10099994A | 75 ± 12 | neutral | 51 | 100 | 59 | 58 | 50 | |
| 23 | UNC10099995A | 30 ± 5 | 9.8 | −16 | 107 | 91 | 48 | | |
| 24 | UNC10108006A | 10.9 ± 0.3 | neutral | | 25 | 81 | | | |
| 25 | UNC10000004A | 18 ± 3 | 3700 | | −74 | 18 | 55 | 12 | NA |
| 26 | UNC10000007A | 145 ± 22 | 46000 | −25 | 2100 | 51 | 6 | | |
| 27 | UNC10000009A | 1004 ± 136 | 1000 | −55 | 610 | 57 | 9 | | |
| 28 | UNC10000010A | 66 ± 10 | 5.7 | | −29 | 92 | 65 | 18 | |
| 29 | UNC10000011A | 15 ± 2 | neutral | | 26 | 68 | 21 | | |
| 30 | UNC10099972A | 113 ± 18 | neutral | 297 | 58 | 9 | | | |
| 31 | UNC10099973A | 108 ± 18 | 5.7 | −47 | 399 | 49 | 16 | | |
| 32 | UNC10099981A | 18 ± 2 | neutral | | 30 | 83 | 44 | | |
| 33 | UNC10099985A | 20 ± 3 | neutral | 24 | 64 | 26 | | | |
| 34 | UNC10099988A | 25 ± 3 | 512 | | 25 | 52 | 78 | 36 | |
| 35 | UNC10099990A | 15 ± 3 | neutral | 16 | 65 | 19 | | | |
| 36 | UNC10099991A | 17 ± 3 | neutral | 59 | 64 | 13 | | | |
| 37 | UNC10107957A | 1.7 ± 0.1 | 11 | | 17 | 1.0 | 67 | | |
| 38 | UNC10108010A | 0.47 ± 0.03 | 1.8 | 28 | 0.4 | 74 | | | |
| 39 | UNC10108016A | 0.32 ± 0.02 | neutral | | 0.5 | 50 | | | |
| 40 | UNC10108017A | 0.30 ± 0.02 | neutral | | 1.5 | 33 | | | |
| 41 | UNC10108018A | 0.45 ± 0.02 | 0.4 | −19 | 0.6 | 31 | | | |
| 42 | UNC10108019A | 0.40 ± 0.02 | neutral | | 0.9 | 31 | | | |
| 43 | UNC10108049A | 72 ± 4 | neutral | | 9.2 | 59 | | | |

[a]Neutral ligands are either antagonists or are inactive;
[b]NA: not applicable.

TABLE 7

| Receptor/Assay | Binding affinity or potency (nM)* | | |
|---|---|---|---|
| | Aripiprazole | UNC9975 | UNC0006 |
| $D_2$/binding ($K_i$) | 8.0 | 2.6 | 5.0 |
| $D_1$/binding ($K_i$) | 895 | 1040 | 825 |

TABLE 7-continued

| Receptor/Assay | Binding affinity or potency (nM)* | | |
|---|---|---|---|
| | Aripiprazole | UNC9975 | UNC0006 |
| $D_3$/binding ($K_i$) | 19 | 11 | 16 |
| $D_4$/binding ($K_i$) | 251 | 178 | 200 |
| $D_5$/binding ($K_i$) | 1051 | 513 | 615 |
| $5HT_{2A}$/binding ($K_i$) | 40 | 7.4 | 16 |
| $5HT_{2A}$/FLIPR ($IC_{50}$) | 3400 | 660 | 1400 |
| $5HT_{2B}$/binding ($K_i$) | 1.4 | 1.1 | 0.6 |
| $5HT_{2B}$/FLIPR ($IC_{50}$) | 98 | 76 | 115 |
| $5HT_{2C}$/binding ($K_i$) | 250 | 99 | 115 |
| $5HT_{2C}$/FLIPR ($IC_{50}$) | 7200 | 2200 | 3600 |
| $5HT_{1A}$/binding ($K_i$) | 18 | 29 | 60 |
| $5HT_{1A}$/cAMP ($EC_{50}$) | 450 | 1800 | 2500 |
| $H_1$/binding ($K_i$) | 6.0 | 6.1 | 4.5 |
| $H_1$/FLIPR ($pA_2$) | 34 | 46 | 29 |

*$K_i$, $IC_{50}$, $pA_2$, or $EC_{50}$ values are the average of at least two duplicate experiments with standard deviation (SD) values that are 3-fold less than the average.

In mouse pharmacokinetic (PK) studies, both 3 and aripiprazole displayed high exposure levels in brain and excellent CNS penetration (Table 8). Although the brain exposure level of 3 was about 3-fold lower, 3 had a longer half life in brain and higher brain plasma ratio over 24 h compared to aripiprazole.

TABLE 8

| Analyte | Time (h) | Brain Conc. (ng/g) | Plasma Conc. (ng/mL) | Brain/Plasma Ratio (mL/g) | SD | Matrix | $T_{max}$ (h) | $C_{max}$ (ng/mL) | $AUC_{last}$ (h · ng/mL) | $AUC_{INF}$ (h · ng/mL) | $T_{1/2}$ (h) |
|---|---|---|---|---|---|---|---|---|---|---|---|
| Aripiprazole | 0.08 | 88.8 | 53.3 | 1.76 | 1.49 | Plasma | 0.25 | 75.6 | 431 | 445 | 5.15 |
| | 0.25 | 143.0 | 75.6 | 1.87 | 0.17 | | | | | | |
| | 0.5 | 166.3 | 70.1 | 2.39 | 0.13 | | | | | | |
| | 1 | 134.0 | 68.0 | 1.98 | 0.22 | | | | | | |
| | 2 | 115.1 | 49.8 | 2.33 | 0.65 | Brain | 0.50 | 166 | 1096 | 1178 | 6.59 |
| | 4 | 75.8 | 31.8 | 2.37 | 0.25 | | | | | | |
| | 8 | 42.2 | 14.5 | 2.94 | 0.26 | | | | | | |
| | 24 | 8.8 | 2.0 | 5.03 | 1.47 | | | | | | |
| UNC9975 | 0.08 | 37.8 | 70.6 | 0.57 | 0.15 | Plasma | 0.08 | 70.6 | 59.9 | 61.5 | 0.81 |
| | 0.25 | 49.8 | 61.4 | 0.80 | 0.13 | | | | | | |
| | 0.5 | 27.2 | 23.7 | 1.12 | 0.19 | | | | | | |
| | 1 | 31.2 | 24.6 | 1.29 | 0.18 | | | | | | |
| | 2 | 23.0 | 6.3 | 3.67 | 0.67 | Brain | 0.25 | 49.8 | 267 | 329 | 10.6 |
| | 4 | 16.9 | 1.4 | 12.26 | 2.26 | | | | | | |
| | 8 | 9.9 | 0.0 | n/a | n/a | | | | | | |
| | 24 | 4.2 | 0.0 | n/a | n/a | | | | | | |

EXAMPLE 3

In Vivo Studies

Compounds 2 (UNC10000006A, or UNC0006) and 3 (UNC10099975A, or UNC9975) were evaluated in D-amphetamine-induced hyperlocomotion, phencyclidine (PCP)-induced hyperlocomotion, and/or catalepsy mouse models.

Mice. All experiments were approved by the Institutional Animal Care and Use Committees at the University of North Carolina, Chapel Hill and Duke University. C57BL/6J and β-arrestin-2 knockout (Bohn et al., Science 286:2495 (1999)) mice were housed under standard conditions—12 hour light/dark cycle and food and water provided ad libitum. Adult, age-matched male and female C57BL/6J and β-arrestin-2 knockout drug naive mice were used for all behavioral testing.

Locomotor activity. Mouse locomotor activity was assessed in photocell-based activity chambers under standardized environmental conditions, using an AccuScan activity monitor (AccuScan Instruments, Columbus, Ohio) with a 25.8×25.8 cm Plexiglas chamber and a beam spacing of 1.52 cm as described (Abbas et al., J. Neurosci. 29:7124 (2009)). Mice were injected (i.p.) with vehicle (0.9% saline/0.2% acetic acid), aripiprazole (0.10, 0.25, 0.50 or 2.0 mg/kg), or UNC9975 (0.25, 0.5 and 2.0 mg/kg) and placed into the open field. Thirty min later D-amphetamine (3 mg/kg) or phencyclidine (6.0 mg/kg) was administered and they were immediately returned to the open field for 80 min. Activity was monitored throughout this entire period. Horizontal activity was measured as the total distance traveled in centimeters. The means±SEMs of the locomotor responses of animals were analyzed using Graphpad Prism 5.0. To estimate the half-maximal inhibitory concentration ($ED_{50}$), dose responses of total locomotor activity during the 90 minutes after D-amphetamine or phencyclidine administration were plotted and best-fit decay curves were determined using a nonlinear regression one-phase decay equation. Cumulative locomotor responses were analyzed using a one-way ANOVA followed by Newman-Keuls multiple comparison test using Graphpad Prism 5.0. Statistical significance was set at p<0.05.

Catalepsy testing. In this testing paradigm, mice were initially injected (i.p.) with vehicle (0.9% saline/0.2% acetic acid), aripiprazole, UNC0006 (5 mg/kg), UNC9975 (5 mg/kg) or haloperidol (2 mg/kg) and returned to their home cage. The latency of movement was assessed 30, 60, 90 and 120 min after drug injection; the maximal latency to move in the mice was observed 60 min after drug treatments. Mice were placed upright on a screen placed at a 45 degree angle. The time required for the animal to move all four paws was scored in seconds (maximum of 5 minutes) and is reported as the latency to movement. An extended delay to voluntarily move on the inclined screen test is indicative of drug-induced catalepsy. The data are displayed as mean±SEM. Catalepsy data were analyzed for statistical significance using a one-way ANOVA followed by Newman-Keuls multiple comparison test using Graphpad Prism 5.0. Differences were considered significant at p<0.05.

UNC9975 exhibited potent antipsychotic-like activity in mouse hyperlocomotion studies which is attenuated in β-arrestin-2 knockout mice. In FIG. 1A, locomotion responses in inbred C57BL/6 mice are shown as 5 minute binned intervals to different doses (i.p.) of UNC9975 or vehicle followed 30 min later by 3 mg/kg D-Amphetamine (AMPH, i.p.). In FIG. 1B, total distance traveled after D-Amphetamine administration (30-70 min time interval) is shown. C57BL/6 mice were given vehicle or different doses of UNC9975 or aripiprazole 30 min prior to AMPH treatment. n=8 animals/group. *, p<0.05 versus vehicle+3 mg/kg D-Amphetamine group.

In FIGS. 1C and 1D, locomotor activities are shown as 5 min binned intervals of wild-type (WT) or β-arrestin-2 knockout (β-ARR2 KO) littermate mice given vehicle or different doses of UNC9975 followed 30 min later with 6 mg/kg phencyclidine (PCP, i.p.). FIG. 1E shows the total distance traveled by WT and β-ARR2 KO mice after PCP administration (30 to 70 min time interval), shown in FIGS. 1C and 1D—different doses of UNC9975 were given to mice 30 min before PCP treatment. n=14 WT and β-ARR2 KO pairs/group. *p<0.05, versus vehicle+6 mg/kg PCP group. FIG. 1F shows the total distance traveled by WT and β-ARR2 KO mice after aripiprazole followed by PCP treatments (30 to 70 min time interval). n=8 littermate WT and β-ARR2 KO pairs/group. *p<0.05, versus vehicle+6 mg/kg PCP group.

Figure 2:
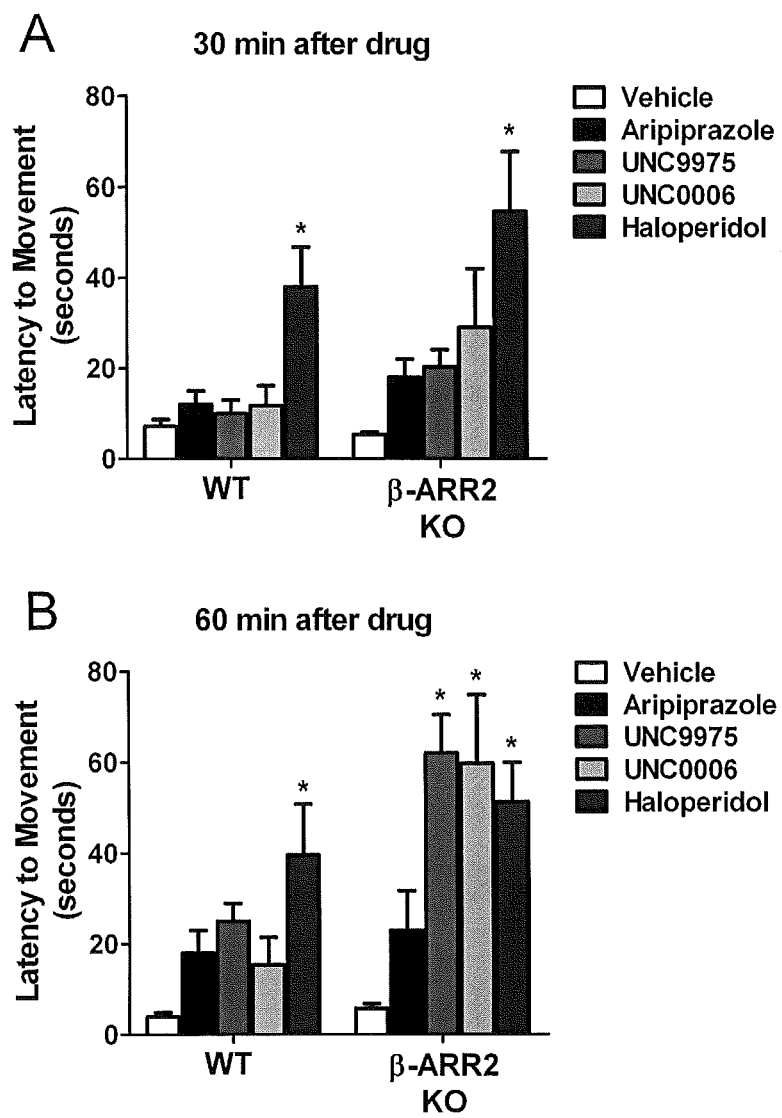
FIGS. 2A-2B show that UNC9975 and UNC0006 induce catalepsy in βarrestin-2 knockout mice but not in wild-type littermates.

UNC9975 and UNC0006 induced catalepsy in β-arrestin-2 knockout mice but not in wild-type littermates. In FIGS. 2A and 2B, wild-type and β-Arrestin-2 knockout littermate mice were administered (i.p.) vehicle, 5.0 mg/kg UNC9975, 5.0 mg/kg UNC0006, 5.0 mg/kg aripiprazole, or 2.0 mg/kg haloperidol. Following 30 and 60 min after drug injection, catalepsy was assessed using the inclined screen test where latency to move was scored. n=8 littermate wild-type and knockout animal pairs/group. *p<0.05 versus vehicle controls.

Through a combined medicinal chemistry and comprehensive in vitro and in vivo pharmacological profiling approach, novel $D_2$ β-arrestin-biased agonists were designed, synthesized and characterized, and demonstrated to have unique atypical antipsychotic drug-like activities in vivo. These novel compounds represent the first functionally selective β-arrestin-biased dopamine $D_2$ receptor ligands to exhibit antipsychotic activity in vivo. These findings show that based on the arrestin-bias of these compounds, β-arrestin may be an important contributor to both antipsychotic drug efficacy and antipsychotic side effects.

The disclosed compounds were discovered as unique, β-arrestin-biased functionally selective $D_2$ ligands. In addition to possessing high affinity for $D_2$ receptors, both UNC0006 and UNC9975 are potent partial agonists which induce $D_2$ receptors-mediated β-arrestin recruitment and signaling, and simultaneously are potent inverse agonists at $G_i$-dependent signaling. More significantly, the in vivo atypical antipsychotic drug-like activity of UNC9975 indicated a strict requirement for β-arrestin-2 for both full antipsychotic activity and protection against motoric side-effects. Similar to aripiprazole, this β-arrestin-biased ligand shows a potent ability to suppress both D-amphetamine and phencyclidine-induced hyperlocomotion in mice, indicating that the compound possesses antipsychotic drug-like activities in vivo. Significantly, the antipsychotic drug-like activity of UNC9975 was attenuated in β-arrestin-2 knockout mice, indicating β-arrestin-2 is required in vivo for full activity.

With the exception of aripiprazole, all FDA approved typical and atypical antipsychotic medications (e.g., haloperidol, chlorpromazine, clozapine, risperidone) share the common property of antagonizing $D_2$-mediated G protein-dependent and independent signaling (Masri et al., *Proc. Natl. Acad. Sci. USA* 105:13656 (2008)). Indeed, typical and atypical antipsychotic drugs, with the exception of aripiprazole, are inverse agonists at $G_i$-mediated signaling and antagonists at arrestin-ergic pathways. This combination of inverse agonism and antagonism is thought to underlie both the therapeutic benefit to prevent psychotic symptoms but can also cause serious extrapyramidal side-effects including catalepsy and other motor diskenesias (Roth et al., *Nat. Rev. Drug Discov.* 3:353 (2004)). Although aripiprazole, UNC0006 and UNC9975 do not induce catalepsy in wild-type mice at doses at which antipsychotic drug-like therapeutic activities are measured, UNC0006 and UNC9975 resemble haloperidol in inducing catalepsy in β-arrestin-2 knockout mice. This propensity to cause catalepsy in the absence of β-arrestin-2 suggests that UNC0006 and UNC9975 signal through β-arrestin-2 in vivo and that this signaling may protect against motoric side-effects due to inverse agonism at $D_2$ receptor $G_i$ pathways.

These findings have obvious implications for the development of novel therapeutic approaches for treating schizophrenia and related disorders. Atypical antipsychotic drugs, which differ from older medications (e.g., haloperidol and chlorpromazine) by virtue of their reduced propensity to induce motoric side-effects, are among the most widely prescribed medications. Many pharmacologic strategies which aim to target a multiplicity of non-$D_2$ receptor molecular targets (e.g., 5-$HT_{2A}$ inverse agonists, 5-$HT_{2C}$ agonists, mGluR$_{2/3}$ agonists, NK-3 antagonists, sigma antagonists, $D_1$- or $D_4$-selective antagonists and so forth) have led to a growing number of unsuccessful attempts to create safer and more effective atypical antipsychotic drugs (Roth et al., *Nat. Rev. Drug Discov.* 3:353 (2004); Conn et al., *Neuropsychopharmacology* 33:2048 (2008); Gray et al., *Mol. Psychiatry.* 12:904 (2007)). The present results suggest that novel atypical antipsychotic drugs with a unique mechanism of action may arise from the disclosed β-arrestin-biased $D_2$ ligands. These compounds may demonstrate special efficacies in psychotic disorders with a mood dysfunction given the prominent role of arrestin-ergic signaling in the action of lithium and related compounds.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

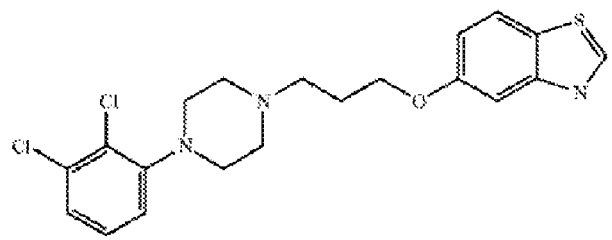

to read as:
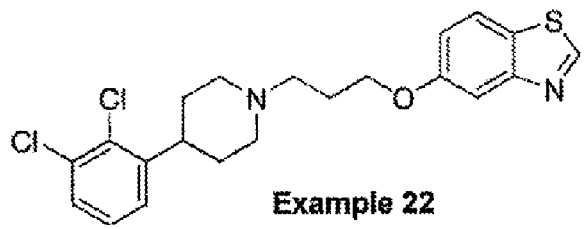
Example 22
Column 124, Line 4: Please correct "1H), J=5.7 Hz, 2H)," to read -- 1H), 4.15(t, J=5.7 Hz, 2H), --
Column 139, Line 49: Please correct "(ESI) ink 447.2" to read -- (ESI) m/z 447.2 --
Column 144, Line 4: Please correct "Pd$_2$ dba$_3$" to read -- Pd$_2$dba$_3$ --
Column 163, Line 23: Please correct "μM" to read -- pM --
Column 163, Line 23: Please correct "10 μM to 10" to read -- 10 pM to 10 --
In the Claims:
Column 173, Claim 4, Lines 30-39: Please correct the compound below:
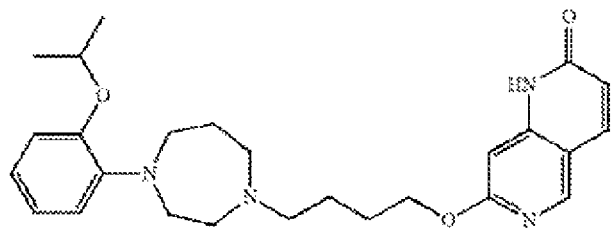
to read as:
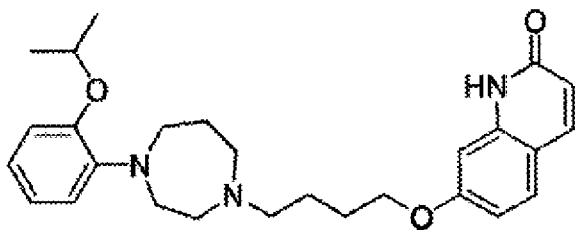

The invention claimed is:
1. A compound of formula I:

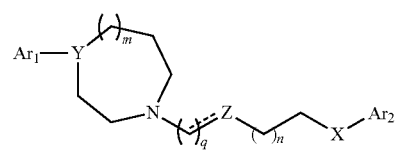

wherein m is 1;
n is 0, 1, or 2;
q is 1 or 2;
X is O, NH, or $CH_2$;
Y is N;
Z is C, CH, $CH_2$, cycloalkyl, aryl, or heteroaryl;
===== is a single, double, or triple bond as valencies permit;
$Ar_1$ is a substituted monocyclic or an unsubstituted or substituted bicyclic aryl or an unsubstituted or substituted monocyclic or bicyclic heteroaryl; and
$Ar_2$ is 3,4-dihydroquinolin-2(1H)-one, 3,4-dihydro-1,8-naphthyridin-2(1H)-one, quinolin-2(1H)-one, 3,4-dihydroisoquinolin-1(2H)-one, benzo[d]thiazole, 1H-benzo[d]imidazol-2(3H)-one, 1H-indazole, or benzo[d]oxazol-2(3H)-one;

or a pharmaceutically acceptable salt or optical isomer thereof.

2. The compound of claim 1, having the structure of formula III:

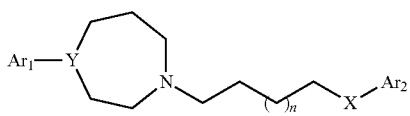

III wherein n is 0, 1, or 2;
X is O, NH, or CH$_2$;
Y is N;
Ar$_1$ is a substituted monocyclic or an unsubstituted or substituted bicyclic aryl or an unsubstituted or substituted heteroaryl; and
Ar$_2$ is 3,4-dihydroquinolin-2(1H)-one, 3,4-dihydro-1,8-naphthyridin-2(1H)-one, quinolin-2(1H)-one, 3,4-dihydroisoquinolin-1(2H)-one, benzo[d]thiazole, 1H-benzo[d]imidazol-2(3H)-one, 1H-indazole, or benzo[d]oxazol-2(3H)-one;

or a pharmaceutically acceptable salt or optical isomer thereof.

3. The compound of claim 1, having the structure of formula V:

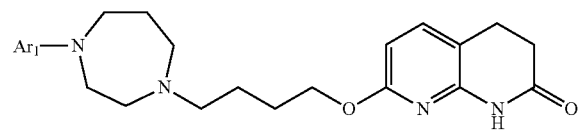

V or a pharmaceutically acceptable salt or optical isomer thereof.

4. The compound of claim 1, selected from the group consisting of:

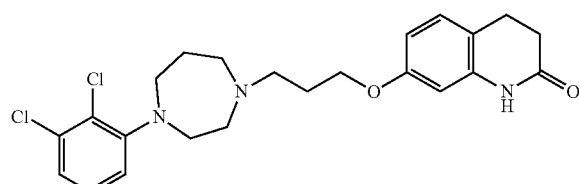

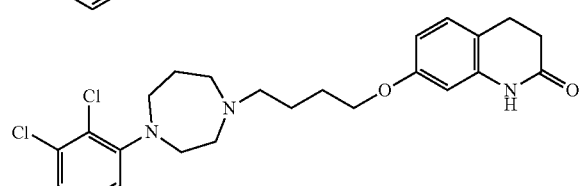

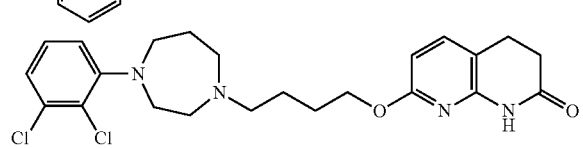

-continued

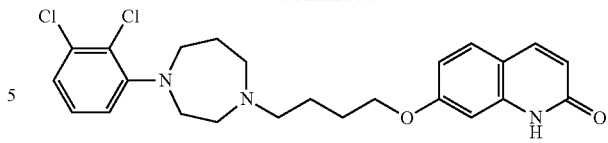

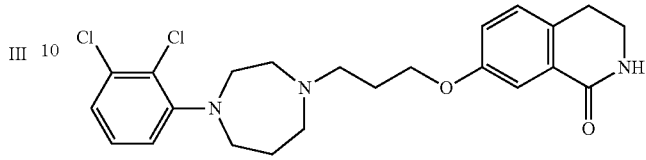

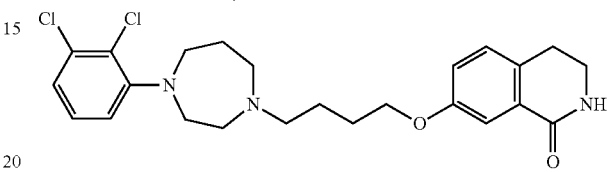

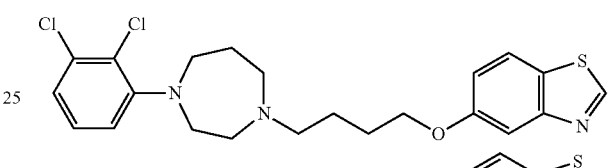

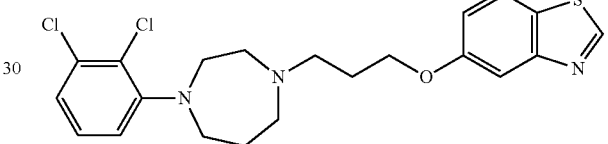

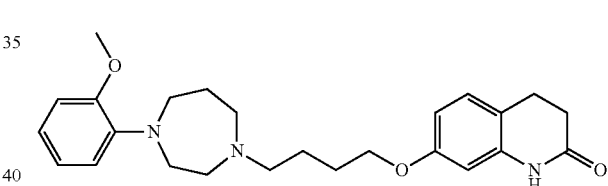

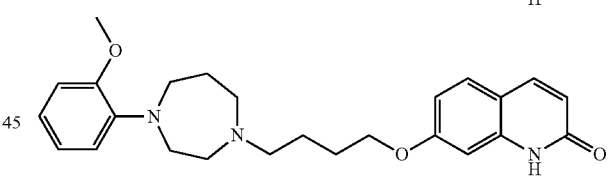

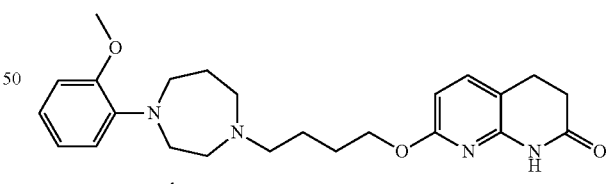

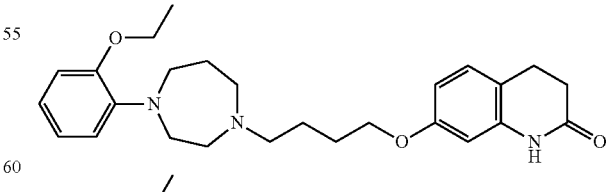

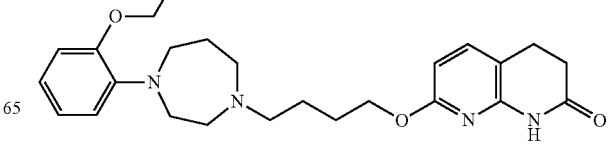

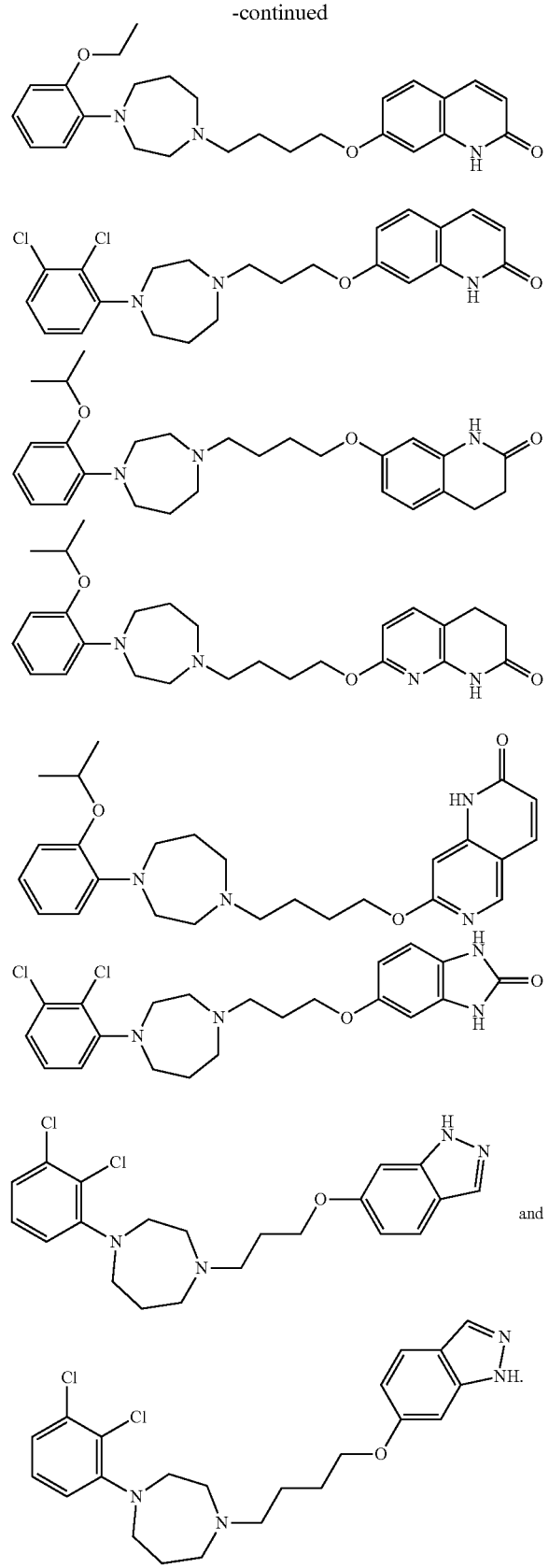
5. The compound of claim 1, selected from the group consisting of:
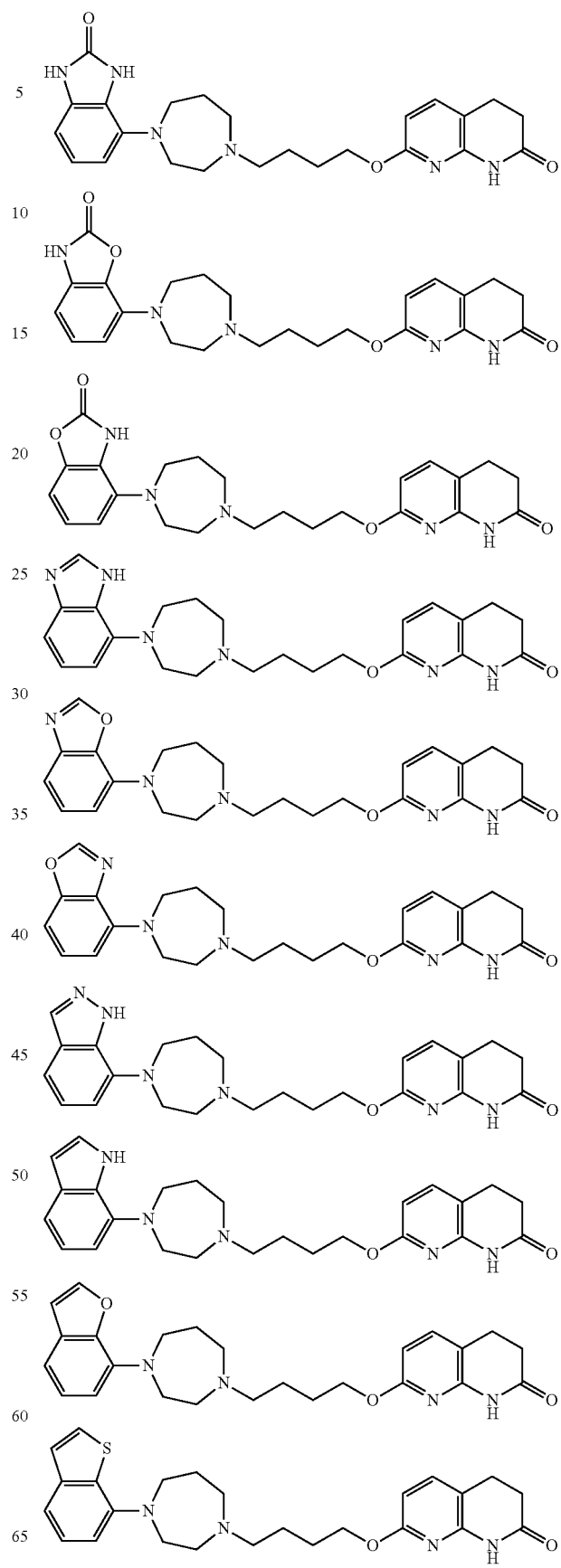

175
-continued
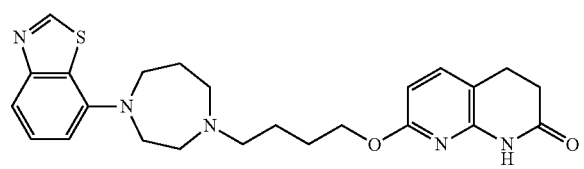
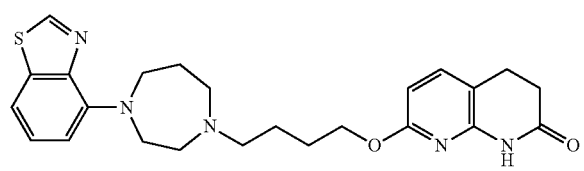
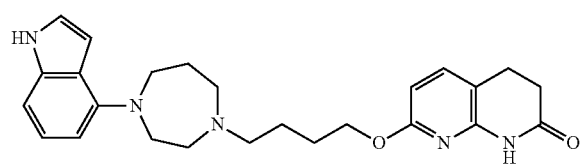
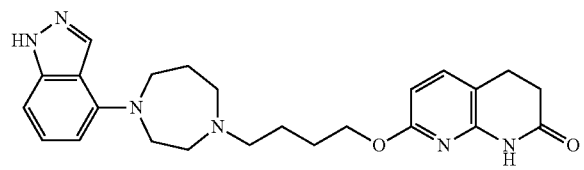
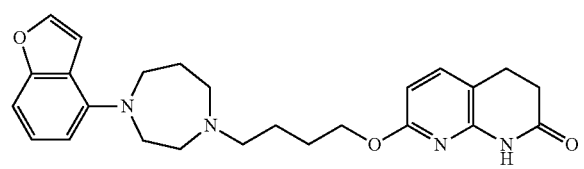
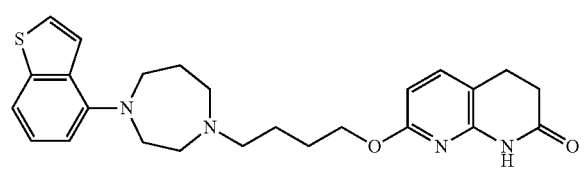
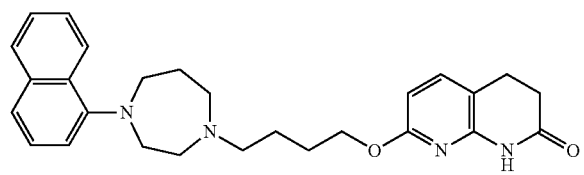
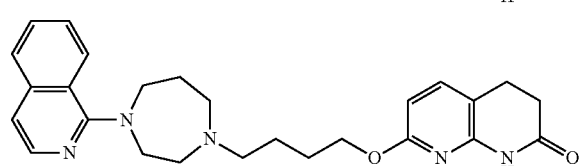
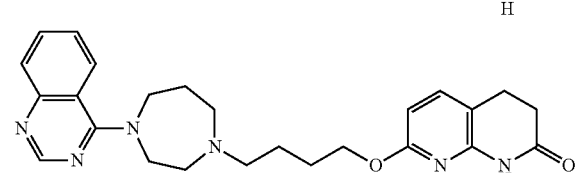
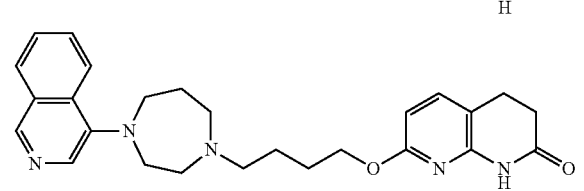
176
-continued
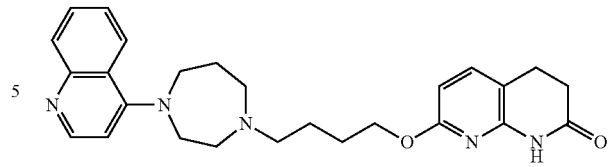
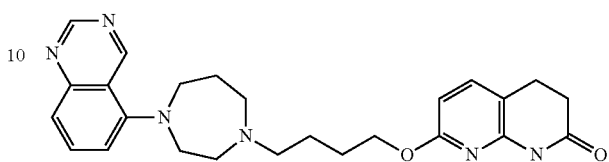
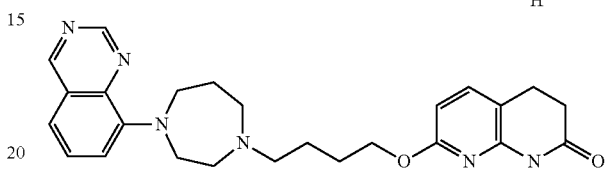
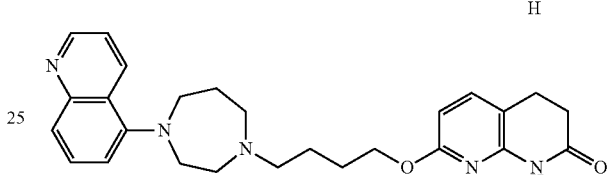
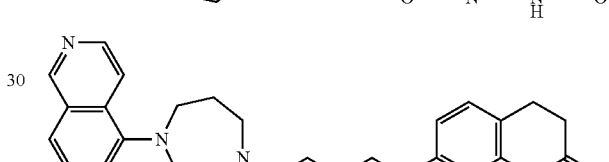
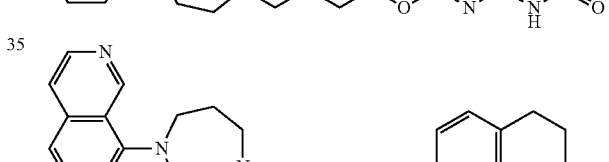
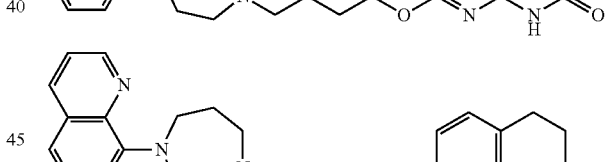
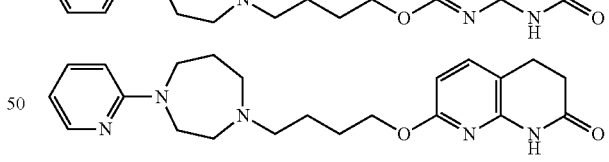
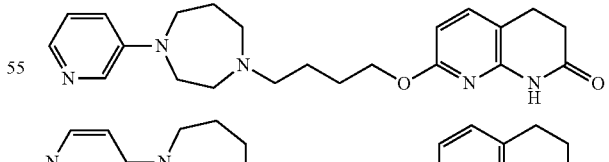
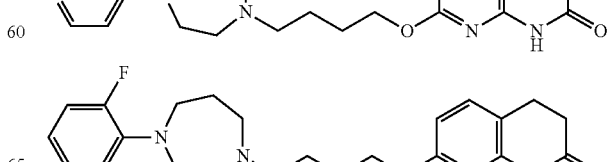

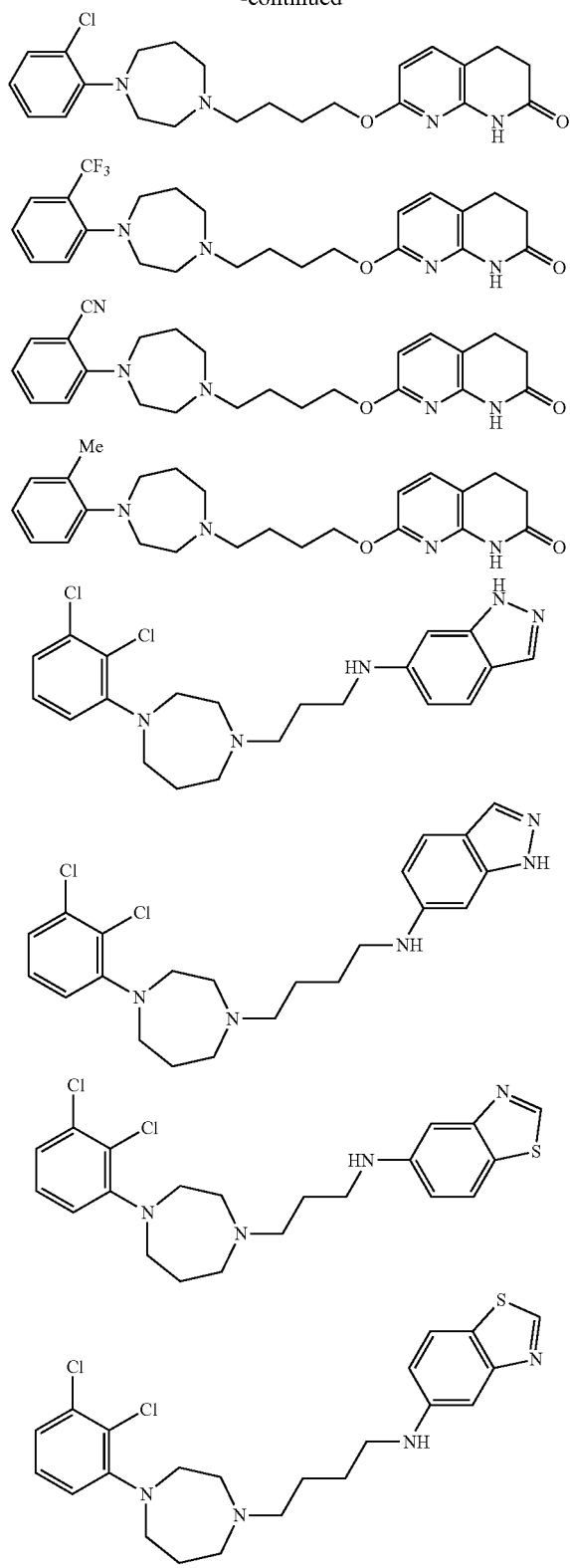

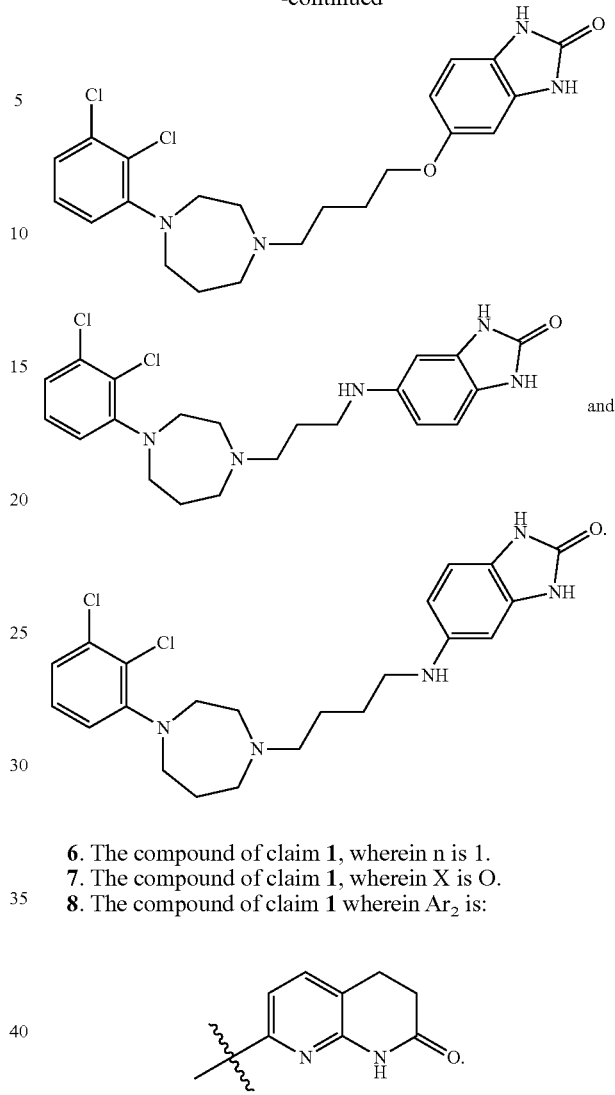

6. The compound of claim 1, wherein n is 1.
7. The compound of claim 1, wherein X is O.
8. The compound of claim 1 wherein Ar$_2$ is:

9. A pharmaceutical composition comprising the compound of claim 1 and a pharmaceutically acceptable carrier.

10. A method of treating a central nervous system disorder associated with D$_2$ dopamine receptors in a subject, comprising delivering to the subject a therapeutically effective amount of the compound of claim 1, wherein the disorder associated with D$_2$ dopamine receptors is a disorder having a psychosis component, Parkinson's disease, pituitary adenoma, prolactinoma, or galactorrhea.

11. The method of claim 10, wherein the disorder associated with D$_2$ dopamine receptors is selected from the group consisting of schizophrenia, schizoaffective disorder, schizophreniform disorder, bipolar disorder, mania, manic psychosis, Tourette's syndrome and Tourette-like disorders, obsessive-compulsive disorder, depression with psychotic features, and psychosis not otherwise specified (Psychosis NOS).

* * * * *

UNITED STATES PATENT AND TRADEMARK OFFICE
CERTIFICATE OF CORRECTION

| | |
|---|---|
| PATENT NO. | : 9,156,822 B2 |
| APPLICATION NO. | : 13/807347 |
| DATED | : October 13, 2015 |
| INVENTOR(S) | : Jin et al. |

It is certified that error appears in the above-identified patent and that said Letters Patent is hereby corrected as shown below:

In the Specification:
Column 1, Line 15: Please correct "Nos." to read -- No. --
Column 4, Line 2: Please correct "βarrestin-2" to read -- β-arrestin-2 --
Column 78, Line 45: Intermediate 2: Please correct "NaI/$K_2CO_3$" to read -- NaI/$Et_3N$ --
Column 80, Line 43: Please correct "BnO($H_2C$)$_4$O" to read -- HO($H_2C$)$_4$O --
Column 99, Line 32: Please correct "(EST)" to read -- (ESI) --
Column 108, Line 3: Please correct "$Pd_2$ $dba_3$" to read -- $Pd_2dba_3$ --
Column 117, Line 16: Please correct "$Pd_2$ $dba_3$" to read -- $Pd_2dba_3$ --
Columns 119-120, Scheme 37, Synthesis of intermediate 47: Please correct Scheme 37 below:

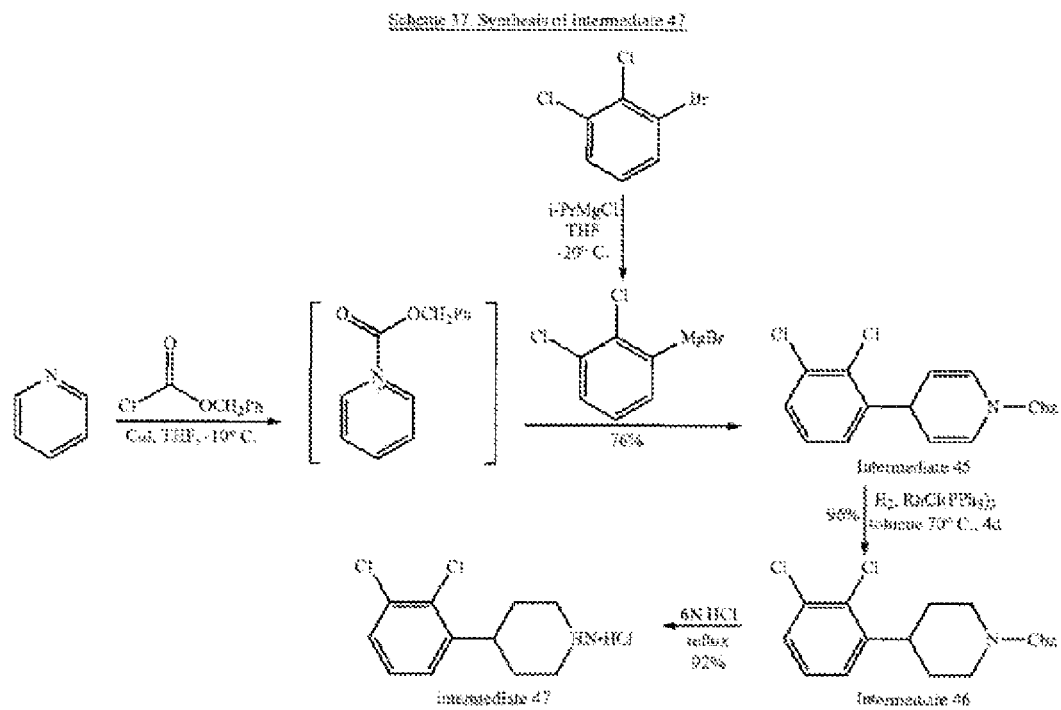

Signed and Sealed this
Ninth Day of August, 2016

Michelle K. Lee
*Director of the United States Patent and Trademark Office*

CERTIFICATE OF CORRECTION (continued)
U.S. Pat. No. 9,156,822 B2 to read as:

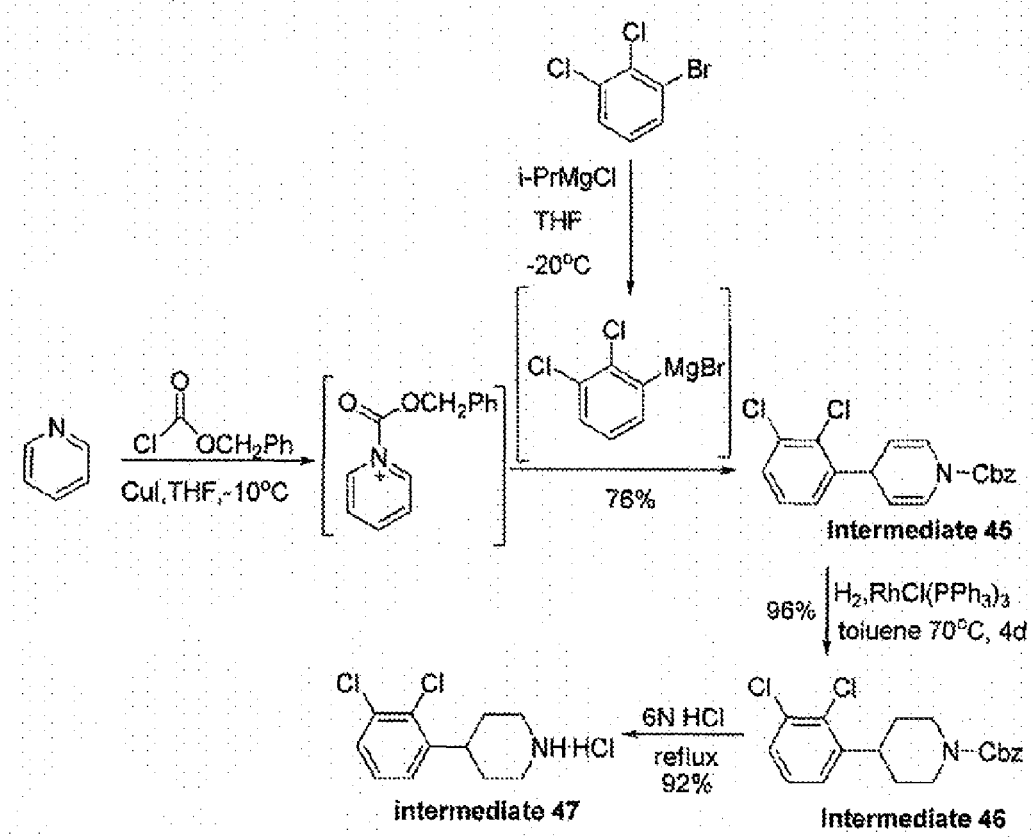

Column 122, Lines 1-10: Please correct the compound below: